(12) United States Patent
Bur et al.

(10) Patent No.: US 8,217,029 B2
(45) Date of Patent: Jul. 10, 2012

(54) OXAZOLIDINONE ANTIBIOTICS

(75) Inventors: Daniel Bur, Therwil (CH); Christian Hubschwerlen, Durmenach (FR); Georg Rueedi, Allschwil (CH); Jean-Philippe Surivet, Kembs (FR); Cornelia Zumbrunn-Acklin, Basel (CH)

(73) Assignee: Actelion Pharmaceuticals Ltd, Allschwil (CH)

( * ) Notice: Subject to any disclaimer, the term of this patent is extended or adjusted under 35 U.S.C. 154(b) by 101 days.

(21) Appl. No.: 12/595,720

(22) PCT Filed: Apr. 11, 2008

(86) PCT No.: PCT/IB2008/051374
§ 371 (c)(1),
(2), (4) Date: Oct. 13, 2009

(87) PCT Pub. No.: WO2008/126034
PCT Pub. Date: Oct. 23, 2008

(65) Prior Publication Data
US 2011/0039823 A1 Feb. 17, 2011

(30) Foreign Application Priority Data

Apr. 11, 2007 (WO) .................. PCT/IB2007/051290
Nov. 12, 2007 (WO) .................. PCT/IB2007/054587
Nov. 23, 2007 (WO) .................. PCT/IB2007/054768

(51) Int. Cl.
| | |
|---|---|
| A61K 31/397 | (2006.01) |
| A61K 31/55 | (2006.01) |
| A61K 31/54 | (2006.01) |
| A61K 31/50 | (2006.01) |
| A61K 31/497 | (2006.01) |
| A61K 31/44 | (2006.01) |
| C07D 243/08 | (2006.01) |
| C07D 279/10 | (2006.01) |
| C07D 237/26 | (2006.01) |
| C07D 401/14 | (2006.01) |
| C07D 239/72 | (2006.01) |
| C07D 471/12 | (2006.01) |
| C07D 471/22 | (2006.01) |
| C07D 215/00 | (2006.01) |

(52) U.S. Cl. ............... 514/210.21; 514/218; 514/224.2; 514/253.04; 514/266.22; 514/300; 514/248; 540/575; 544/52; 544/235; 544/284; 544/287; 544/362; 546/122; 546/174

(58) Field of Classification Search ............. 514/210.21, 514/218, 224.2, 248, 253.04, 266.02, 300; 540/575; 544/52, 235, 284, 287, 362; 546/122, 546/174
See application file for complete search history.

(56) References Cited

U.S. PATENT DOCUMENTS

| | | |
|---|---|---|
| 4,970,217 A | 11/1990 | Prucher et al. |
| 2007/0060558 A1 | 3/2007 | Sanchez et al. |

FOREIGN PATENT DOCUMENTS

| | | |
|---|---|---|
| EP | 0 300 272 | 1/1989 |
| WO | WO 93/03026 | 2/1993 |
| WO | WO 00/40554 | 7/2000 |
| WO | WO 02/08224 | 1/2002 |
| WO | WO 02/50040 | 6/2002 |
| WO | WO 03/087098 | 10/2003 |
| WO | WO 2004/002490 | 1/2004 |
| WO | WO 2004/089947 | 10/2004 |
| WO | WO 2005/019215 | 3/2005 |
| WO | WO 2006/032466 | 3/2006 |
| WO | WO 2006/081289 | 8/2006 |
| WO | WO 2007/053498 | 5/2007 |
| WO | WO 2007/081597 | 7/2007 |
| WO | WO 2007/107965 | 9/2007 |
| WO | WO 2008/003690 | 1/2008 |

OTHER PUBLICATIONS

Bal et al., Tetrahedron, Great Britain vol. 37, pp. 2091-2096 (1981).
Cha et al., Chemical Reviews—American Chemical Society, vol. 95, No. 6, pp. 1761-1795 (1995).
Chen et al., Organic Letters, vol. 8, No. 24, pp. 5609-5612, Sep. 2006.
Fox, L., Remington: The Science and Practice of Pharmacy, 21$^{st}$ Edition, Lippincott Williams & Wilkins, Index and Abstract Only, (2005).
Gould, P., International journal of Pharmaceutics, vol. 33, pp. 201-217, (1986).

(Continued)

*Primary Examiner* — Rebecca Anderson
*Assistant Examiner* — Samantha Shterengarts
(74) *Attorney, Agent, or Firm* — Hunton & Williams LLP

(57) ABSTRACT

The invention relates to compounds of formula (I) wherein U, V, W, X, R1, R2, R3, R4, R5, R6, A, B, D, E, G, m, and n are as defined in the description, to pharmaceutically acceptable salts of such compounds for use in the manufacture of a medicament for the prevention or treatment of a bacterial infection. Certain compounds of formula (I) are new and are also part of this invention.

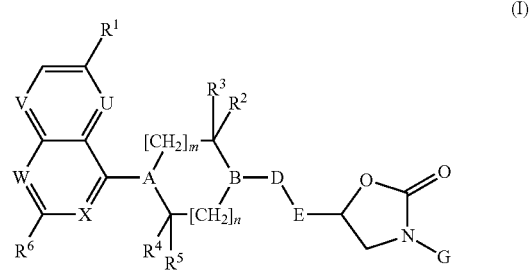

(I)

19 Claims, No Drawings

OTHER PUBLICATIONS

Greene, T.W., "Protection for the Amino Group", Protecting Groups in Organic Synthesis, 3$^{rd}$ Ed (1999), pp. 23-147, 369-441 and 494-653.

Kolb et al., Chemical Reviews—American Chemical Society, vol. 94, No. 8, pp. 2483-2547 (1994).

Larock, Comprehensive Organic Transformations—A guide to Functional Group Preparations, Index and pp. 381; 1941-1949, © 1999.

Mancuso et al., Journal of Organic Chemistry, vol. 43, No. 12 pp. 2480-2482, (1978).

Margolis et al., Journal of Organic Chemistry, vol. 72, pp. 2232-2235, Oct. 2006.

Martin, The Journal of Organic Chemistry, vol. 48, No. 22, pp. 4155-4156, Nov. 1983.

Schaus et al., Journal of the American Chemical Society, vol. 124, No. 7, pp. 1307-1315 (2002).

Shi, Accounts of Chemical Research—Articles, vol. 37, No. 8, pp. 488-496, Mar. 2004.

Tokunaga et al., Science, vol. 277, pp. 936-938, Aug. 1997, www.sciencemag.org.

Toto et al., Tetrahedron Letters, vol. 47, pp. 1181-1186 (2006) www.sciencedirect.com.

Vanrheenen et al., Tetrahedron Letters, Pergamon Press, Great Britain, No. 23, pp. 1973-1976 (1976).

Walters et al., Journal of Combinatorial Chemistry, vol. 4, No. 2, pp. 125-130 (2002).

Benz, G., "Synthesis of Amides and Related Compounds, Comprehensive Organic Synthesis." Comprehensive Organic Synthesis—Selectivity, Strategy and Efficiency in Modern Organic Chemistry, vol. 6, Section 2:2.3, edited by: Trost, Barry M.; Fleming, Ian © 1991 Elsevier, Pergamon Press, NY, p. 381-417 (1991).

Fatiadi, "The Classical Permanganate Ion: Still a Novel Oxidant in Organic Chemistry," *Synthesis*, pp. 85-127, Feb. 1987.

Greene, T.W. and Wuts, P.G.M., Protective Groups in Organic Synthesis, Cover and Content pages For 2$^{nd}$ (1991) and 3$^{rd}$ (1999) Editions, John Wiley & Sons, Inc.

Larock, et al., Section 4—Amines: "From Alkyl and Aryl Halides or Sulfonates," Comprehensive Organic Transformations: A Guide to Functional Group Preparations, 2$^{nd}$ Ed., Wiley Publishing, New York, Chichester, Weinheim, Brisbane, Singapore, Toronto, p. 779-784 (1999).

Panek & Liu, Total Synthesis of the Actin-Depolymeri zing Agent (—)-Mycalolide A: Application of Chiral Silane-Based Bond Construction Methodology, *J. Am. Chem. Soc.*, vol. 122, p. 11090-11097 (2000).

Takemoto, et al., "Synthesis of a Fluorobenzoxazine Derivative and Its Analogues," *Biosci. Biotech. Biochem.*, vol. 58(4), p. 788-789 (1994).

OXAZOLIDINONE ANTIBIOTICS

CROSS-REFERENCE TO RELATED APPLICATIONS

This application is the U.S. National Stage filing of International Application No. PCT/IB2008/051374, filed Apr. 11, 2008, which claims priority to International Application No. PCT/IB2007/051290, filed Apr. 11, 2007, International Application No. PCT/IB2007/054587, filed Nov. 12, 2007, and International Application No. PCT/IB2007/054768, filed Nov. 23, 2007, the disclosures of which are hereby incorporated by reference in their entirety.

BACKGROUND OF THE INVENTION

The intensive use of antibiotics has exerted a selective evolutionary pressure on micro-organisms to produce genetically based resistance mechanisms. Modern medicine and socio-economic behaviour exacerbates the problem of resistance development by creating slow growth situations for pathogenic microbes, e.g. in artificial joints, and by supporting long-term host reservoirs, e.g. in immuno-compromised patients.

In hospital settings, an increasing number of strains of *Staphylococcus aureus, Streptococcus pneumoniae, Enterococcus* spp., and *Pseudomonas aeruginosa*, major sources of infections, are becoming multi-drug resistant and therefore difficult if not impossible to treat:

*S. aureus* is resistant to β-lactams, quinolones and now even to vancomycin;

*S. pneumoniae* is becoming resistant to penicillin or quinolone antibiotics and even to new macrolides;

*Enteroccocci* are quinolone and vancomycin resistant and β-lactam antibiotics are inefficacious against these strains;

*Enterobacteriacea* are cephalosporin and quinolone resistant;

*P. aeruginosa* are β-lactam and quinolone resistant.

Further new emerging organisms like *Acinetobacter* spp. or *Clostridium difficile*, which have been selected during therapy with the currently used antibiotics, are becoming a real problem in hospital settings. In addition, microorganisms that are causing persistent infections are increasingly being recognized as causative agents or cofactors of severe chronic diseases like peptic ulcers or heart diseases.

Certain antibacterial agents are known from WO 2006/081289, but these agents do not contain an oxazolidinone moiety. Further antibacterial agents are disclosed in WO 2002/050040, but in these agents the piperazine ring is not directly bound to the quinoline analog moiety. Certain oxazolidinone derivatives having effects on the central nervous system are known from EP0300272.

BRIEF SUMMARY OF THE INVENTION

The present invention concerns novel antibiotic derivatives, a pharmaceutical antibacterial composition containing them and the use of these compounds in the manufacture of a medicament for the treatment of infections (e.g. bacterial infections). These compounds are useful antimicrobial agents effective against a variety of human and veterinary pathogens including among others Gram positive and Gram negative aerobic and anaerobic bacteria and mycobacteria.

DETAILED DESCRIPTION OF THE INVENTION

Various embodiments of the invention are presented hereafter:

1) A first embodiment of the present invention relates to compounds of formula (I), or pharmaceutically acceptable salts thereof,

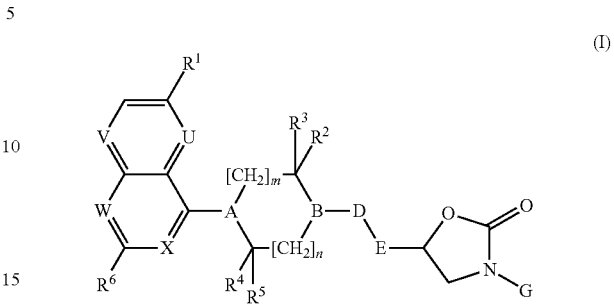

(I)

wherein $R^1$ represents hydrogen, alkoxy, halogen or cyano (preferably alkoxy);

one or two (preferably two) of U, V, W, and X (preferably of U, W, and X) represent(s) N and the remaining each represent CH, or, in the case of X, represent $CR^a$;

$R^a$ represents hydrogen or halogen;

$R^6$ represents hydrogen or $(C_1-C_4)$alkyl;

A represents N, B represents N, D represents a bond, E represents $CH_2$ or CO, $R^2$, $R^3$, $R^4$ and $R^5$ each represent H, m represents the integer 2, and n represents the integer 1; or A represents N; B represents N; D represents a bond; E represents $CH_2$ or *—$COCH_2$— wherein the asterisk indicates the bond which is attached to B; $R^2$, $R^3$, $R^4$ and $R^5$ each represent H, or $R^4$ and $R^5$ represent H and $R^2$ and $R^3$ together with the carbon atom to which they are attached to form a carbonyl group, or $R^2$ and $R^3$ represent H and $R^4$ and $R^5$ together with the carbon atom to which they are attached to form a carbonyl group, or $R^2$ and $R^4$ represent H and $R^3$ and $R^5$ together form a methylene bridge; and m and n each represent the integer 1; or A represents N, B represents C(OH), D represents a bond, E represents $CH_2$, $R^2$, $R^3$, $R^4$ and $R^5$ each represent H, and m and n each represent the integer 1; or A represents N, B represents CH, D represents $NR^b$, E represents $CH_2$, $R^2$, $R^3$, $R^4$ and $R^5$ each represent H, $R^b$ represents H or $(C_1-C_4)$alkyl, and m and n each represent the integer 1; or A represents N, B represents CH, D represents NH, E represents $CH_2$, $R^2$, $R^3$, $R^4$ and $R^5$ each represent H, m represents the integer 2, and n represents the integer 0; or A represents C(OH), B represents N, D represents a bond, E represents $CH_2$, $R^2$, $R^3$, $R^4$ and $R^5$ each represent H, and m and n each represent the integer 1; or A represents N; B represents CH; D represents $NR^c$; E represents $CH_2$, CO or $CH_2CH_2$; $R^2$, $R^3$, $R^4$ and $R^5$ each represent H and $R^c$ represents H or $(C_1-C_4)$alkyl, or $R^c$, $R^3$, $R^4$ and $R^5$ each represent H and $R^2$ represents a group selected from hydroxy, $(C_1-C_4)$alkoxy, $(C_1-C_4)$alkoxycarbonyl, and carboxy, or $R^3$, $R^4$ and $R^5$ each represent H and $R^c$ forms together with $R^2$ an ethane-1,2-diyl bridge; m represents the integer 1, and n represents the integer 0; or A represents N; B represents CH; D represents *—CH($R^d$)—N($R^e$)— wherein the asterisk indicates the bond which is attached to B; E represents $CH_2$ or CO; $R^d$, $R^2$, $R^3$, $R^4$ and $R^5$ each represent H and $R^e$ represents H or $(C_1-C_4)$alkyl, or $R^e$, $R^3$, $R^4$ and $R^5$ each represent H and $R^d$ and $R^2$ together form a bond, or $R^d$, $R^2$, $R^3$ and $R^5$ each represent H and $R^e$ and $R^4$ together form a methylene bridge, or $R^d$, $R^e$, $R^3$, $R^4$ and $R^5$ each represent H and $R^2$ represents hydroxy; m represents the integer 1, and n represents the integer 0; or A represents N, B represents CH, D represents *—CONH— wherein the asterisk indicates the bond which is attached to B, E represents $CH_2$, $R^2$, $R^3$, $R^4$ and $R^5$ each represent H, m represents the integer 1, and n represents the integer 0; or A represents N, B represents CH, D represents NH, E represents $CH_2$ or CO, $R^2$, $R^3$ and $R^5$ each represent H and $R^4$ represents hydroxymethyl, m represents the integer 0, and n represents the integer 1; or A represents N, B represents C(OH), D represents *—$CH_2$—NH— wherein the asterisk indicates the bond which is attached to B, E represents $CH_2$, $R^2$, $R^3$, $R^4$ and $R^5$ each represent H, m represents the integer 1, and n represents the integer 0; or A represents N, B represents CH, D represents *—CO—NH— wherein the asterisk indicates the bond which is attached to B, E represents $CH_2$, $R^2$, $R^3$, $R^4$ and $R^5$ each represent H, and m and n each represent the integer 0; or A represents N, B represents CH, D represents *—$CH_2$—N($R^f$)— wherein the asterisk indicates the bond which is attached to B, E represents $CH_2$, $CH_2CH_2$ or CO, $R^2$, $R^3$, $R^4$ and $R^5$ each represent H, $R^f$ represents H or $(C_1$-$C_4)$ alkyl, and m and n each represent the integer 0; or A represents N; B represents CH; D represents $NR^g$; E represents $CH_2$, $CH_2CH_2$, CO or *—$COCH_2$— wherein the asterisk indicates the bond which is attached to B; $R^2$, $R^3$, $R^4$ and $R^5$ each represent H; $R^g$ represents H, $(C_1$-$C_4)$alkyl or $(C_2$-$C_4)$alkyl which is mono- or di-substituted with hydroxy; and m and n each represent the integer 0;

G represents phenyl which is unsubstituted, mono-substituted in position 3 or 4, or disubstituted in positions 3 and 4, wherein each substituent is independently selected from the group consisting of $(C_1$-$C_4)$alkyl, $(C_1$-$C_4)$alkoxy, fluoroalkyl, fluoroalkoxy, cyano, halogen and —$NR^{N1}R^{N2}$; or G represents pyridin-2-yl which is mono-substituted in position 5, wherein the substituent is selected from the group consisting of $(C_1$-$C_4)$alkyl and fluoroalkyl; or G represents 6,7-dihydro-[1,4]dioxino[2,3-c]pyridazin-3-yl; or G represents a group selected from the group consisting of:

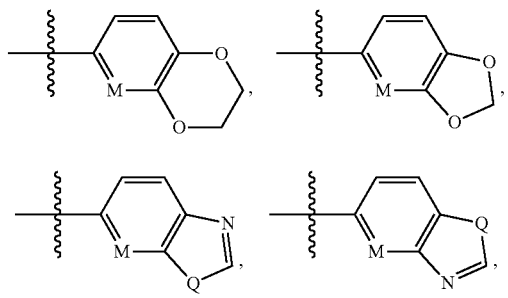

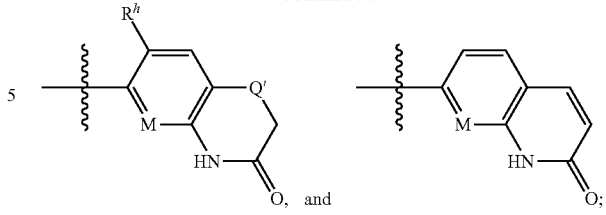

wherein
$R^h$ represents hydrogen or fluorine;
M represents CH or N; and Q and Q' independently represent O or S; and
$R^{N1}$ and $R^{N2}$ independently represent $(C_1$-$C_4)$alkyl, or together with the nitrogen that carries them form a pyrrolidine ring;
for the prevention or treatment of a bacterial infection; or
to said compounds, or pharmaceutically acceptable salts thereof, for use in the manufacture of a medicament for the prevention or treatment of a bacterial infection.

2) A further embodiment of the present invention relates to compounds of formula (I) according to embodiment 1), or pharmaceutically acceptable salts thereof, wherein
$R^6$ represents hydrogen;
A represents N, B represents N, D represents a bond, E represents $CH_2$ or CO, $R^2$, $R^3$, $R^4$ and $R^5$ each represent H, m represents the integer 2, and n represents the integer 1; or A represents N; B represents N; D represents a bond; E represents $CH_2$ or *—$COCH_2$— wherein the asterisk indicates the bond which is attached to B; $R^2$, $R^3$, $R^4$ and $R^5$ each represent H, or $R^4$ and $R^5$ represent H and $R^2$ and $R^3$ together with the carbon atom to which they are attached to form a carbonyl group, or $R^2$ and $R^3$ represent H and $R^4$ and $R^5$ together with the carbon atom to which they are attached to form a carbonyl group; and m and n each represent the integer 1; or A represents N, B represents C(OH), D represents a bond, E represents $CH_2$, $R^2$, $R^3$, $R^4$ and $R^5$ each represent H, and m and n each represent the integer 1; or A represents N, B represents CH, D represents $NR^b$, E represents $CH_2$, $R^2$, $R^3$, $R^4$ and $R^5$ each represent H, $R^b$ represents H or $(C_1$-$C_4)$alkyl, and m and n each represent the integer 1; or A represents N, B represents CH, D represents NH, E represents $CH_2$, $R^2$, $R^3$, $R^4$ and $R^5$ each represent H, m represents the integer 2, and n represents the integer 0; or A represents C(OH), B represents N, D represents a bond, E represents $CH_2$, $R^2$, $R^3$, $R^4$ and $R^5$ each represent H, and m and n each represent the integer 1; or A represents N; B represents CH; D represents $NR^c$; E represents $CH_2$, CO or $CH_2CH_2$; $R^2$, $R^3$, $R^4$ and $R^5$ each represent H and $R^c$ represents H or $(C_1$-$C_4)$alkyl, or $R^c$, $R^3$, $R^4$ and $R^5$ each represent H and $R^2$ represents a group selected from hydroxy, $(C_1$-$C_4)$alkoxy, $(C_1$-$C_4)$alkoxycarbonyl, and carboxy, or $R^3$, $R^4$ and $R^5$ each represent H and $R^c$ forms together with $R^2$ an ethane-1,2-diyl bridge; m represents the integer 1, and n represents the integer 0; or A represents N; B represents CH; D represents *—CH($R^d$)—N($R^e$)— wherein the asterisk indicates the bond which is attached to B; E represents $CH_2$ or CO; $R^d$, $R^2$, $R^3$, $R^4$ and $R^5$ each represent H and $R^e$ represents H or $(C_1$-$C_4)$alkyl, or $R^e$, $R^3$, $R^4$ and $R^5$ each represent H and $R^d$ and $R^2$ together form a bond, or $R^d$, $R^2$, $R^3$ and $R^5$ each represent H and $R^e$ and $R^4$ together form a methylene bridge, or $R^d$, $R^e$, $R^3$, $R^4$ and $R^5$ each represent H and $R^2$ represents hydroxy; m represents the integer 1, and n represents the integer 0; or A represents N, B represents CH, D represents *—CONH— wherein the asterisk indicates the bond which is attached to B, E represents $CH_2$, $R^2$, $R^3$, $R^4$ and $R^5$ each represent H, m represents the integer 1, and n represents the integer 0; or A represents N, B represents CH, D represents NH, E represents $CH_2$ or CO, $R^2$, $R^3$ and $R^5$ each represent H and $R^4$ represents hydroxymethyl, m represents the integer 0, and n represents the integer 1; or A represents N, B represents CH, D represents *—$CH_2$—N($R^f$)— wherein the asterisk indicates the bond which is attached to B, E represents $CH_2$, $CH_2CH_2$ or CO (especially $CH_2$ or CO), $R^2$, $R^3$, $R^4$ and $R^5$ each represent H, $R^1$ represents H or $(C_1-C_4)$alkyl, and m and n each represent the integer 0; or A represents N; B represents CH; D represents $NR^g$; E represents $CH_2$, $CH_2CH_2$, CO or *—$COCH_2$— wherein the asterisk indicates the bond which is attached to B; $R^2$, $R^3$, $R^4$ and $R^5$ each represent H; $R^g$ represents H, $(C_1-C_4)$alkyl or 2-hydroxyethyl; and m and n each represent the integer 0; and G represents phenyl which is unsubstituted, mono-substituted in position 3 or 4, or disubstituted in positions 3 and 4, wherein each substituent is independently selected from the group consisting of $(C_1-C_4)$alkyl, $(C_1-C_4)$alkoxy, fluoroalkyl, fluoroalkoxy, cyano, halogen and —$NR^{N1}R^{N2}$ (preferably from the group consisting of $(C_1-C_3)$alkyl, $(C_1-C_3)$alkoxy and halogen); or G represents pyridin-2-yl which is mono-substituted in position 5, wherein the substituent is selected from the group consisting of $(C_1-C_4)$alkyl and fluoroalkyl; or G represents 6,7-dihydro-[1,4]dioxino[2,3-c]pyridazin-3-yl; or G represents a group selected from the group consisting of:

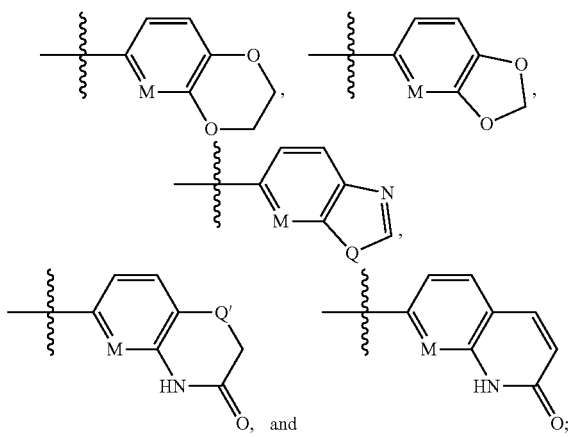

wherein

M represents CH or N; and Q and Q' independently represent O or S;

for the prevention or treatment of a bacterial infection; or to said compounds, or pharmaceutically acceptable salts thereof, for use in the manufacture of a medicament for the prevention or treatment of a bacterial infection.

3) A further embodiment of the present invention relates to compounds of formula (I) according to embodiments 1) or 2), or pharmaceutically acceptable salts thereof, wherein A represents N, B represents N, D represents a bond, E represents $CH_2$ or CO, $R^2$, $R^3$, $R^4$ and $R^5$ each represent H, m represents the integer 2, and n represents the integer 1; or A represents N; B represents N; D represents a bond; E represents $CH_2$, or *—$COCH_2$— wherein the asterisk indicates the bond which is attached to B; $R^2$, $R^3$, $R^4$ and $R^5$ each represent H; and m and n each represent the integer 1; or A represents N, B represents C(OH), D represents a bond, E represents $CH_2$, $R^2$, $R^3$, $R^4$ and $R^5$ each represent H, and m and n each represent the integer 1; or A represents N, B represents CH, D represents $NR^b$, E represents $CH_2$, $R^2$, $R^3$, $R^4$ and $R^5$ each represent H, $R^b$ represents H or $(C_1-C_4)$alkyl, and m and n each represent the integer 1; or A represents C(OH), B represents N, D represents a bond, E represents $CH_2$, $R^2$, $R^3$, $R^4$ and $R^5$ each represent H, and m and n each represent the integer 1; or A represents N; B represents CH; D represents $NR^c$; E represents $CH_2$, CO or $CH_2CH_2$; $R^2$, $R^3$, $R^4$ and $R^5$ each represent H and $R^c$ represents H or $(C_1-C_4)$alkyl, or $R^3$, $R^4$ and $R^5$ each represent H and $R^c$ forms together with $R^2$ an ethane-1,2-diyl bridge; m represents the integer 1, and n represents the integer 0; or A represents N; B represents CH; D represents *—CH($R^d$)—N($R^e$)— wherein the asterisk indicates the bond which is attached to B; E represents $CH_2$ or CO; $R^d$, $R^2$, $R^3$, $R^4$ and $R^5$ each represent H and $R^e$ represents H or $(C_1-C_4)$alkyl, or $R^e$, $R^3$, $R^4$ and $R^5$ each represent H and $R^d$ and $R^2$ together form a bond; m represents the integer 1, and n represents the integer 0; or A represents N, B represents CH, D represents *—CONH— wherein the asterisk indicates the bond which is attached to B, E represents $CH_2$, $R^2$, $R^3$, $R^4$ and $R^5$ each represent H, m represents the integer 1, and n represents the integer 0; or A represents N, B represents CH, D represents *—$CH_2$—N($R^f$)— wherein the asterisk indicates the bond which is attached to B, E represents $CH_2$, $CH_2CH_2$ or CO (especially $CH_2$ or $CH_2CH_2$), $R^2$, $R^3$, $R^4$ and $R^5$ each represent H, $R^f$ represents H or $(C_1-C_4)$alkyl, and m and n each represent the integer 0; or A represents N; B represents CH; D represents $NR^g$; E represents $CH_2$, $CH_2CH_2$ or CO; $R^2$, $R^3$, $R^4$ and $R^5$ each represent H; $R^g$ represents H, $(C_1-C_4)$alkyl or 2-hydroxyethyl; and m and n each represent the integer 0;

for the prevention or treatment of a bacterial infection; or to said compounds, or pharmaceutically acceptable salts thereof, for use in the manufacture of a medicament for the prevention or treatment of a bacterial infection.

4) A further embodiment of the present invention relates to compounds of formula (I) according to embodiment 1), which are also compounds of formula ($I_{P1}$), or pharmaceutically acceptable salts thereof,

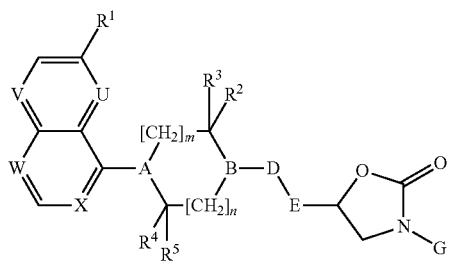

(I_{P1})

wherein
R¹ represents alkoxy, halogen or cyano (preferably alkoxy); one or two (preferably two) of U, V, W, and X (preferably of U, W, and X) represent(s) N and the remaining each represent CH, or, in the case of X, represent CR$^a$;
R$^a$ represents hydrogen or halogen (preferably hydrogen);
  A represents N, B represents N, D represents a bond, E represents CH₂, R², R³, R⁴ and R⁵ each represent H, and m and n each represent the integer 1; or
  A represents N, B represents C(OH), D represents a bond, E represents CH₂, R², R³, R⁴ and R⁵ each represent H, and m and n each represent the integer 1; or
  A represents C(OH), B represents N, D represents a bond, E represents CH₂, R², R³, R⁴ and R⁵ each represent H, and m and n each represent the integer 1; or
  A represents N, B represents CH, D represents *—CH₂—NH— wherein the asterisk indicates the bond which is attached to B, E represents CH₂ or CO, R², R³, R⁴ and R⁵ each represent H, and m and n each represent the integer 0; or
  A represents N, B represents CH, D represents NH, E represents CH₂, R², R³, R⁴ and R⁵ each represent H, m represents the integer 1, and n represents the integer 0;
G represents phenyl which is unsubstituted, mono-substituted in position 3 or 4, or disubstituted in positions 3 and 4, wherein each substituent is independently selected from the group consisting of (C₁-C₄)alkyl, (C₁-C₄)alkoxy, fluoroalkyl, fluoroalkoxy, cyano, halogen and —NR$^{N1}$R$^{N2}$ (preferably from the group consisting of (C₁-C₃)alkyl, (C₁-C₃)alkoxy and halogen); or
G represents pyridin-2-yl which is mono-substituted in position 5, wherein the substituent is selected from the group consisting of (C₁-C₄)alkyl and fluoroalkyl; or
G represents a group selected from the group consisting of:

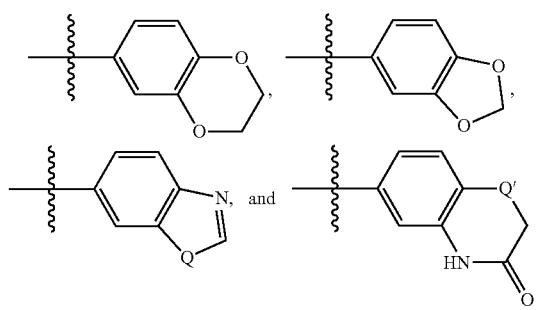

wherein
Q and Q' independently represent O or S; and
R$^{N1}$ and R$^{N2}$ independently represent (C₁-C₄)alkyl, or together with the nitrogen that carries them form a pyrrolidine ring;

for the prevention or treatment of a bacterial infection; or to said compounds, or pharmaceutically acceptable salts thereof, for use in the manufacture of a medicament for the prevention or treatment of a bacterial infection.

5) A further embodiment of the present invention relates to compounds of formula (I) according to embodiment 1), which are also compounds of formula (I_{CE-P1}), or pharmaceutically acceptable salts thereof,

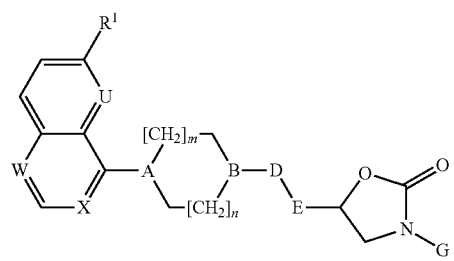

(I_{CE-P1})

wherein
R¹ represents alkoxy;
two of U, W, and X represent N and the remaining represents CH;
  A represents N, B represents N, D represents a bond, E represents CH₂, and m and n each represent the integer 1; or
  A represents N, B represents C(OH), D represents a bond, E represents CH₂, and m and n each represent the integer 1; or
  A represents C(OH), B represents N, D represents a bond, E represents CH₂, and m and n each represent the integer 1; or
  A represents N, B represents CH, D represents *—CH₂—NH— wherein the asterisk indicates the bond which is attached to B, E represents CH₂ or CO, and m and n each represent the integer 0; or
  A represents N, B represents CH, D represents NH, E represents CH₂, m represents the integer 1, and n represents the integer 0;
G represents phenyl which is unsubstituted, mono-substituted in position 3 or 4, or disubstituted in positions 3 and 4, wherein each substituent is independently selected from the group consisting of (C₁-C₄)alkyl, (C₁-C₄)alkoxy, fluoroalkyl, fluoroalkoxy, cyano, halogen and —NR$^{N1}$R$^{N2}$ (preferably from the group consisting of (C₁-C₃)alkyl, (C₁-C₃)alkoxy and halogen); or
G represents pyridin-2-yl which is mono-substituted in position 5, wherein the substituent is selected from the group consisting of (C₁-C₄)alkyl and fluoroalkyl; or
G represents a group selected from the group consisting of:

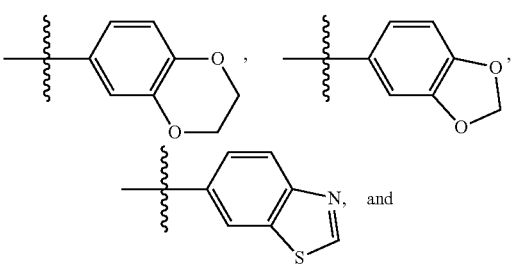

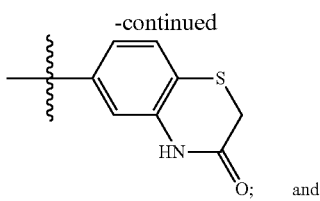
and $R^{N1}$ and $R^{N2}$ independently represent $(C_1-C_4)$alkyl, or together with the nitrogen that carries them form a pyrrolidine ring;
for the prevention or treatment of a bacterial infection; or
to said compounds, or pharmaceutically acceptable salts thereof, for use in the manufacture of a medicament for the prevention or treatment of a bacterial infection.

6) A further embodiment of the invention relates to compounds of formula (I) according to any one of embodiments 1) to 5), or pharmaceutically acceptable salts thereof, wherein A represents C(OH) and B represents N;
for the prevention or treatment of a bacterial infection; or
to said compounds, or pharmaceutically acceptable salts thereof, for use in the manufacture of a medicament for the prevention or treatment of a bacterial infection.

7) The invention further relates to a compound of formula (I) according to embodiment 1),
or a pharmaceutically acceptable salt thereof, wherein said compound is selected from the group consisting of:

(S)-3-(2,3-Dihydro-benzo[1,4]dioxin-6-yl)-5-({[1-(6-methoxy-[1,5]naphthyridin-4-yl)-azetidin-3-ylmethyl]-amino}-methyl)-oxazolidin-2-one;
(S)-3-(2,3-Dihydro-benzo[1,4]dioxin-6-yl)-2-oxo-oxazolidine-5-carboxylic acid[1-(6-methoxy-[1,5]naphthyridin-4-yl)-azetidin-3-ylmethyl]-amide;
3-(2,3-Dihydro-benzo[1,4]dioxin-6-yl)-5-[4-hydroxy-4-(6-methoxy-[1,5]naphthyridin-4-yl)-piperidin-1-ylmethyl]-oxazolidin-2-one;
3-(2,3-Dihydro-benzo[1,4]dioxin-6-yl)-5-[4-hydroxy-1-(6-methoxy-quinazolin-4-yl)-piperidin-4-ylmethyl]-oxazolidin-2-one;
3-(2,3-Dihydro-benzo[1,4]dioxin-6-yl)-5-[4-hydroxy-1-(6-methoxy-[1,5]naphthyridin-4-yl)-piperidin-4-ylmethyl]-oxazolidin-2-one;
3-(2,3-Dihydro-benzo[1,4]dioxin-6-yl)-5-[4-(6-methoxy-quinazolin-4-yl)-piperazin-1-ylmethyl]-oxazolidin-2-one;
6-{5-[4-(6-Methoxy-quinazolin-4-yl)-piperazin-1-ylmethyl]-2-oxo-oxazolidin-3-yl}-4H-benzo[1,4]thiazin-3-one;
3-(2,3-Dihydro-benzo[1,4]dioxin-6-yl)-5-[4-(6-methoxy-[1,5]naphthyridin-4-yl)-piperazin-1-ylmethyl]-oxazolidin-2-one;
(R)-3-(2,3-Dihydro-benzo[1,4]dioxin-6-yl)-5-[4-(6-methoxy-[1,5]naphthyridin-4-yl)-piperazin-1-ylmethyl]-oxazolidin-2-one;
(R)-5-[4-(6-Methoxy-[1,5]naphthyridin-4-yl)-piperazin-1-ylmethyl]-3-(3-trifluoromethoxy-phenyl)-oxazolidin-2-one;
(R)-5-[4-(6-Methoxy-[1,5]naphthyridin-4-yl)-piperazin-1-ylmethyl]-3-(4-trifluoromethoxy-phenyl)-oxazolidin-2-one;
(R)-5-[4-(6-Methoxy-[1,5]naphthyridin-4-yl)-piperazin-1-ylmethyl]-3-phenyl-oxazolidin-2-one;
(R)-3-(4-Bromo-3-fluoro-phenyl)-5-[4-(6-methoxy-[1,5]naphthyridin-4-yl)-piperazin-1-ylmethyl]-oxazolidin-2-one;
(R)-3-(3,4-Dimethoxy-phenyl)-5-[4-(6-methoxy-[1,5]naphthyridin-4-yl)-piperazin-1-ylmethyl]-oxazolidin-2-one;
(R)-3-(4-Fluoro-phenyl)-5-[4-(6-methoxy-[1,5]naphthyridin-4-yl)-piperazin-1-ylmethyl]-oxazolidin-2-one;
(R)-5-[4-(6-Methoxy-[1,5]naphthyridin-4-yl)-piperazin-1-ylmethyl]-3-(3-trifluoromethyl-phenyl)-oxazolidin-2-one;
(R)-3-(3-Chloro-4-fluoro-phenyl)-5-[4-(6-methoxy-[1,5]naphthyridin-4-yl)-piperazin-1-ylmethyl]-oxazolidin-2-one;
(R)-5-[4-(6-Methoxy-[1,5]naphthyridin-4-yl)-piperazin-1-ylmethyl]-3-(4-methyl-3-trifluoromethyl-phenyl)-oxazolidin-2-one;
(R)-3-Benzothiazol-6-yl-5-[4-(6-methoxy-[1,5]naphthyridin-4-yl)-piperazin-1-ylmethyl]-oxazolidin-2-one;
(R)-3-(4-Difluoromethoxy-phenyl)-5-[4-(6-methoxy-[1,5]naphthyridin-4-yl)-piperazin-1-ylmethyl]-oxazolidin-2-one;
3-{(R)-5-[4-(6-Methoxy-[1,5]naphthyridin-4-yl)-piperazin-1-ylmethyl]-2-oxo-oxazolidin-3-yl}-benzonitrile;
6-{(R)-5-[4-(6-Methoxy-[1,5]naphthyridin-4-yl)-piperazin-1-ylmethyl]-2-oxo-oxazolidin-3-yl}-4H-benzo[1,4]thiazin-3-one;
(R)-5-[4-(6-Methoxy-[1,5]naphthyridin-4-yl)-piperazin-1-ylmethyl]-3-(4-pyrrolidin-1-yl-phenyl)-oxazolidin-2-one;
(R)-5-[4-(6-Methoxy-[1,5]naphthyridin-4-yl)-piperazin-1-ylmethyl]-3-(3-methoxy-phenyl)-oxazolidin-2-one;
(R)-5-[4-(6-Methoxy-[1,5]naphthyridin-4-yl)-piperazin-1-ylmethyl]-3-(4-propyl-phenyl)-oxazolidin-2-one;
(R)-3-(4-Ethyl-phenyl)-5-[4-(6-methoxy-[1,5]naphthyridin-4-yl)-piperazin-1-ylmethyl]-oxazolidin-2-one;
(R)-3-(3,4-Dimethyl-phenyl)-5-[4-(6-methoxy-[1,5]naphthyridin-4-yl)-piperazin-1-ylmethyl]-oxazolidin-2-one;
(R)-3-(3-Chloro-4-methoxy-phenyl)-5-[4-(6-methoxy-[1,5]naphthyridin-4-yl)-piperazin-1-ylmethyl]-oxazolidin-2-one;
(R)-3-(3,4-Difluoro-phenyl)-5-[4-(6-methoxy-[1,5]naphthyridin-4-yl)-piperazin-1-ylmethyl]-oxazolidin-2-one;
(R)-3-(4-Fluoro-3-methyl-phenyl)-5-[4-(6-methoxy-[1,5]naphthyridin-4-yl)-piperazin-1-ylmethyl]-oxazolidin-2-one;
(R)-3-(4-Bromo-3-methyl-phenyl)-5-[4-(6-methoxy-[1,5]naphthyridin-4-yl)-piperazin-1-ylmethyl]-oxazolidin-2-one;
(R)-3-(3-Bromo-4-methyl-phenyl)-5-[4-(6-methoxy-[1,5]naphthyridin-4-yl)-piperazin-1-ylmethyl]-oxazolidin-2-one;
(R)-5-[4-(6-Methoxy-[1,5]naphthyridin-4-yl)-piperazin-1-ylmethyl]-3-(4-methoxy-3-trifluoromethyl-phenyl)-oxazolidin-2-one;
(R)-3-(3-Dimethylamino-phenyl)-5-[4-(6-methoxy-[1,5]naphthyridin-4-yl)-piperazin-1-ylmethyl]-oxazolidin-2-one;
(R)-3-Benzo[1,3]dioxol-5-yl-5-[4-(6-methoxy-[1,5]naphthyridin-4-yl)-piperazin-1-ylmethyl]-oxazolidin-2-one;
(R)-3-(3-Fluoro-4-methyl-phenyl)-5-[4-(6-methoxy-[1,5]naphthyridin-4-yl)-piperazin-1-ylmethyl]-oxazolidin-2-one;
(S)-3-(2,3-Dihydro-benzo[1,4]dioxin-6-yl)-5-[4-(6-methoxy-[1,5]naphthyridin-4-yl)-piperazin-1-ylmethyl]-oxazolidin-2-one;
(S)-3-(3-Fluoro-4-methyl-phenyl)-5-[4-(6-methoxy-[1,5]naphthyridin-4-yl)-piperazin-1-ylmethyl]-oxazolidin-2-one;
6-{(S)-5-[4-(6-Methoxy-[1,5]naphthyridin-4-yl)-piperazin-1-ylmethyl]-2-oxo-oxazolidin-3-yl}-4H-benzo[1,4]thiazin-3-one;

(S)-3-(3-Fluoro-phenyl)-5-[4-(6-methoxy-[1,5]naphthyridin-4-yl)-piperazin-1-ylmethyl]-oxazolidin-2-one;

(R)-3-(2,3-Dihydro-benzo[1,4]dioxin-6-yl)-5-{[(S)-1-(6-methoxy-[1,5]naphthyridin-4-yl)-pyrrolidin-3-ylamino]-methyl}-oxazolidin-2-one;

(R)-3-(2,3-Dihydro-benzo[1,4]dioxin-6-yl)-5-{[(R)-1-(6-methoxy-[1,5]naphthyridin-4-yl)-pyrrolidin-3-ylamino]-methyl}-oxazolidin-2-one;

5-[4-(6-Methoxy-[1,5]naphthyridin-4-yl)-piperazin-1-ylmethyl]-3-(5-methyl-pyridin-2-yl)-oxazolidin-2-one;

5-[4-(6-Methoxy-[1,5]naphthyridin-4-yl)-piperazin-1-ylmethyl]-3-(5-trifluoromethyl-pyridin-2-yl)-oxazolidin-2-one;

6-((R)-5-{[1-(3-Fluoro-6-methoxy-[1,5]naphthyridin-4-yl)-azetidin-3-ylamino]-methyl}-2-oxo-oxazolidin-3-yl)-4H-benzo[1,4]oxazin-3-one;

(R)-5-{[1-(3-Fluoro-6-methoxy-[1,5]naphthyridin-4-yl)-azetidin-3-ylamino]-methyl}-3-(3-fluoro-4-methyl-phenyl)-oxazolidin-2-one;

(R)-3-(2,3-Dihydro-benzo[1,4]dioxin-6-yl)-5-{[1-(3-fluoro-6-methoxy-[1,5]naphthyridin-4-yl)-azetidin-3-ylamino]-methyl}-oxazolidin-2-one;

6-((R)-5-{[1-(3-Fluoro-6-methoxy-[1,5]naphthyridin-4-yl)-azetidin-3-ylamino]-methyl}-2-oxo-oxazolidin-3-yl)-4H-benzo[1,4]thiazin-3-one;

6-((R)-5-{[1-(6-Methoxy-quinolin-4-yl)-azetidin-3-ylamino]-methyl}-2-oxo-oxazolidin-3-yl)-4H-benzo[1,4]thiazin-3-one;

(R)-3-(3-Fluoro-4-methyl-phenyl)-5-{[1-(6-methoxy-[1,5]naphthyridin-4-yl)-azetidin-3-ylamino]-methyl}-oxazolidin-2-one;

(R)-3-(2,3-Dihydro-benzo[1,4]dioxin-6-yl)-5-{[1-(6-methoxy-[1,5]naphthyridin-4-yl)-azetidin-3-ylamino]-methyl}-oxazolidin-2-one;

6-((R)-5-{[1-(6-Methoxy-[1,5]naphthyridin-4-yl)-azetidin-3-ylamino]-methyl}-2-oxo-oxazolidin-3-yl)-4H-benzo[1,4]oxazin-3-one;

6-((R)-5-{[1-(6-Methoxy-[1,5]naphthyridin-4-yl)-azetidin-3-ylamino]-methyl}-2-oxo-oxazolidin-3-yl)-4H-benzo[1,4]thiazin-3-one;

6-((R)-5-{[1-(6-Methoxy-quinazolin-4-yl)-azetidin-3-ylamino]-methyl}-2-oxo-oxazolidin-3-yl)-4H-benzo[1,4]oxazin-3-one;

6-((R)-5-{[1-(6-Methoxy-quinazolin-4-yl)-azetidin-3-ylamino]-methyl}-2-oxo-oxazolidin-3-yl)-4H-benzo[1,4]thiazin-3-one;

6-[(R)-5-({[1-(6-Methoxy-[1,5]naphthyridin-4-yl)-azetidin-3-yl]-methyl-amino}-methyl)-2-oxo-oxazolidin-3-yl]-4H-benzo[1,4]thiazin-3-one;

6-((S)-5-{[1-(6-Methoxy-[1,5]naphthyridin-4-yl)-azetidin-3-ylamino]-methyl}-2-oxo-oxazolidin-3-yl)-4H-benzo[1,4]thiazin-3-one;

6-(5-{2-[1-(6-Methoxy-[1,5]naphthyridin-4-yl)-azetidin-3-ylamino]-ethyl}-2-oxo-oxazolidin-3-yl)-4H-benzo[1,4]thiazin-3-one;

6-[(S)-5-({[1-(6-Methoxy-[1,5]naphthyridin-4-yl)-azetidin-3-ylmethyl]-amino}-methyl)-2-oxo-oxazolidin-3-yl]-4H-benzo[1,4]thiazin-3-one;

(S)-3-(2,3-Dihydro-benzo[1,4]dioxin-6-yl)-2-oxo-oxazolidine-5-carboxylic acid [(S)-1-(6-methoxy-[1,5]naphthyridin-4-yl)-pyrrolidin-3-yl]-amide;

(S)-3-(2,3-Dihydro-benzo[1,4]dioxin-6-yl)-2-oxo-oxazolidine-5-carboxylic acid [(R)-1-(6-methoxy-[1,5]naphthyridin-4-yl)-pyrrolidin-3-yl]-amide;

(S)-3-(3-Fluoro-4-methyl-phenyl)-2-oxo-oxazolidine-5-carboxylic acid [(R)-1-(6-methoxy-[1,5]naphthyridin-4-yl)-pyrrolidin-3-yl]-amide;

(S)-3-(3-Fluoro-4-methyl-phenyl)-2-oxo-oxazolidine-5-carboxylic acid [(S)-1-(6-methoxy-[1,5]naphthyridin-4-yl)-pyrrolidin-3-yl]-amide;

6-((R)-5-{[(S)-1-(3-Fluoro-6-methoxy-[1,5]naphthyridin-4-yl)-pyrrolidin-3-ylamino]-methyl}-2-oxo-oxazolidin-3-yl)-4H-benzo[1,4]oxazin-3-one;

6-((R)-5-{[(S)-1-(3-Fluoro-6-methoxy-[1,5]naphthyridin-4-yl)-pyrrolidin-3-ylamino]-methyl}-2-oxo-oxazolidin-3-yl)-4H-benzo[1,4]thiazin-3-one;

(R)-3-(2,3-Dihydro-benzo[1,4]dioxin-6-yl)-5-{[(S)-1-(3-fluoro-6-methoxy-[1,5]naphthyridin-4-yl)-pyrrolidin-3-ylamino]-methyl}-oxazolidin-2-one;

(R)-3-(3-Fluoro-4-methyl-phenyl)-5-{[(S)-1-(6-methoxy-[1,5]naphthyridin-4-yl)-pyrrolidin-3-ylamino]-methyl}-oxazolidin-2-one;

(R)-3-(3-Fluoro-4-methyl-phenyl)-5-{[(R)-1-(6-methoxy-[1,5]naphthyridin-4-yl)-pyrrolidin-3-ylamino]-methyl}-oxazolidin-2-one;

6-((R)-5-{[(S)-1-(6-Methoxy-[1,5]naphthyridin-4-yl)-pyrrolidin-3-ylamino]-methyl}-2-oxo-oxazolidin-3-yl)-4H-benzo[1,4]oxazin-3-one;

6-((R)-5-{[(S)-1-(6-Methoxy-[1,5]naphthyridin-4-yl)-pyrrolidin-3-ylamino]-methyl}-2-oxo-oxazolidin-3-yl)-4H-benzo[1,4]thiazin-3-one;

6-((R)-5-{[(R)-1-(6-Methoxy-[1,5]naphthyridin-4-yl)-pyrrolidin-3-ylamino]-methyl}-2-oxo-oxazolidin-3-yl)-4H-benzo[1,4]thiazin-3-one;

6-((R)-5-{[(R)-1-(6-Methoxy-[1,5]naphthyridin-4-yl)-pyrrolidin-3-ylamino]-methyl}-2-oxo-oxazolidin-3-yl)-4H-benzo[1,4]oxazin-3-one;

(3R*,4S*)-1-(6-Methoxy-[1,5]naphthyridin-4-yl)-4-{[(S)-2-oxo-3-(3-oxo-3,4-dihydro-2H-benzo[1,4]thiazin-6-yl)-oxazolidin-5-ylmethyl]-amino}-pyrrolidine-3-carboxylic acid ethyl ester;

(3R*,4S*)-1-(6-Methoxy-[1,5]naphthyridin-4-yl)-4-{[(R)-2-oxo-3-(3-oxo-3,4-dihydro-2H-benzo[1,4]thiazin-6-yl)-oxazolidin-5-ylmethyl]-amino}-pyrrolidine-3-carboxylic acid;

6-((R)-5-{[(3R*,4R*)-4-Methoxy-1-(6-methoxy-[1,5]naphthyridin-4-yl)-pyrrolidin-3-ylamino]-methyl}-2-oxo-oxazolidin-3-yl)-4H-benzo[1,4]thiazin-3-one (notably 6-((R)-5-{[(3S,4S)-4-Methoxy-1-(6-methoxy-[1,5]naphthyridin-4-yl)-pyrrolidin-3-ylamino]-methyl}-2-oxo-oxazolidin-3-yl)-4H-benzo[1,4]thiazin-3-one);

6-((R)-5-{[(3R*,4R*)-4-Hydroxy-1-(6-methoxy-[1,5]naphthyridin-4-yl)-pyrrolidin-3-ylamino]-methyl}-2-oxo-oxazolidin-3-yl)-4H-benzo[1,4]thiazin-3-one;

(R)-3-(2,3-Dihydro-benzo[1,4]dioxin-6-yl)-5-{[(3R*,4R*)-4-hydroxy-1-(6-methoxy-[1,5]naphthyridin-4-yl)-pyrrolidin-3-ylamino]-methyl}-oxazolidin-2-one;

(S)-3-(2,3-Dihydro-benzo[1,4]dioxin-6-yl)-2-oxo-oxazolidine-5-carboxylic acid [(3R,5S)-5-hydroxymethyl-1-(6-methoxy-[1,5]naphthyridin-4-yl)-pyrrolidin-3-yl]-amide;

6-((R)-5-{[(3R,5S)-5-Hydroxymethyl-1-(6-methoxy-[1,5]naphthyridin-4-yl)-pyrrolidin-3-ylamino]-methyl}-2-oxo-oxazolidin-3-yl)-4H-benzo[1,4]thiazin-3-one;

6-[(R)-5-({[1-(6-Methoxy-[1,5]naphthyridin-4-yl)-pyrrolidin-3-ylmethyl]-amino}-methyl)-2-oxo-oxazolidin-3-yl]-4H-benzo[1,4]thiazin-3-one;

(S)-3-(2,3-Dihydro-benzo[1,4]dioxin-6-yl)-2-oxo-oxazolidine-5-carboxylic acid[1-(6-methoxy-[1,5]naphthyridin-4-yl)-pyrrolidin-3-ylmethyl]-amide;

(S)-3-(3-Fluoro-4-methyl-phenyl)-2-oxo-oxazolidine-5-carboxylic acid[1-(6-methoxy-[1,5]naphthyridin-4-yl)-pyrrolidin-3-ylmethyl]-amide;

6-[(R)-5-({[4-Hydroxy-1-(6-methoxy-[1,5]naphthyridin-4-yl)-pyrrolidin-3-ylmethyl]-amino}-methyl)-2-oxo-oxazolidin-3-yl]-4H-benzo[1,4]thiazin-3-one;

1-(6-Methoxy-[1,5]naphthyridin-4-yl)-pyrrolidine-3-carboxylic acid [(R)-3-(3-fluoro-4-methyl-phenyl)-2-oxo-oxazolidin-5-ylmethyl]-amide;

1-(6-Methoxy-[1,5]naphthyridin-4-yl)-pyrrolidine-3-carboxylic acid [(R)-3-(2,3-dihydro-benzo[1,4]dioxin-6-yl)-2-oxo-oxazolidin-5-ylmethyl]-amide;

6-(5-{2-[(S)-1-(6-Methoxy-[1,5]naphthyridin-4-yl)-pyrrolidin-3-ylamino]-ethyl}-2-oxo-oxazolidin-3-yl)-4H-benzo[1,4]thiazin-3-one;

6-(5-{2-[(R)-1-(6-Methoxy-[1,5]naphthyridin-4-yl)-pyrrolidin-3-ylamino]-ethyl}-2-oxo-oxazolidin-3-yl)-4H-benzo[1,4]thiazin-3-one;

(R)-3-(3-Fluoro-4-methyl-phenyl)-5-{[(1a,5a,6a)-3-(6-methoxy-[1,5]naphthyridin-4-yl)-3-aza-bicyclo[3.1.0]hex-6-ylamino]-methyl}-oxazolidin-2-one;

6-((R)-5-{[(1a,5a,6a)-3-(6-Methoxy-[1,5]naphthyridin-4-yl)-3-aza-bicyclo[3.1.0]hex-6-ylamino]-methyl}-2-oxo-oxazolidin-3-yl)-4H-benzo[1,4]thiazin-3-one;

(R)-3-(2,3-Dihydro-benzo[1,4]dioxin-6-yl)-5-{[(3aR*,6aR*)-1-(6-methoxy-[1,5]naphthyridin-4-yl)-hexahydro-pyrrolo[3,4-b]pyrrol-5-yl]-methyl}-oxazolidin-2-one;

6-{{(R)-5-[(3aR*,6aR*)-1-(6-Methoxy-[1,5]naphthyridin-4-yl)-hexahydro-pyrrolo[3,4-b]pyrrol-5-yl]-methyl}-2-oxo-oxazolidin-3-yl}-4H-benzo[1,4]thiazin-3-one;

(S)-3-(2,3-Dihydro-benzo[1,4]dioxin-6-yl)-5-[(3aR*,6aR*)-1-(6-methoxy-[1,5]naphthyridin-4-yl)-hexahydro-pyrrolo[3,4-b]pyrrole-5-carbonyl]-oxazolidin-2-one;

6-{(R)-5-{[(3aR*,6aR*)-5-(6-Methoxy-[1,5]naphthyridin-4-yl)-hexahydro-pyrrolo[3,4-b]pyrrol-1-yl]-methyl}-2-oxo-oxazolidin-3-yl}-4H-benzo[1,4]thiazin-3-one;

(R)-3-(2,3-Dihydro-benzo[1,4]dioxin-6-yl)-5-{[(3aR*,6aR*)-5-(6-methoxy-[1,5]naphthyridin-4-yl)-hexahydro-pyrrolo[3,4-b]pyrrol-1-yl]-methyl}-oxazolidin-2-one;

(S)-3-(2,3-Dihydro-benzo[1,4]dioxin-6-yl)-5-[(3aR*,6aR*)-5-(6-methoxy-[1,5]naphthyridin-4-yl)-hexahydro-pyrrolo[3,4-b]pyrrole-1-carbonyl]-oxazolidin-2-one;

6-{(R)-5-[4-(6-Methoxy-[1,5]naphthyridin-4-yl)-piperazin-1-ylmethyl]-2-oxo-oxazolidin-3-yl}-4H-benzo[1,4]oxazin-3-one;

6-{(R)-5-[4-(3-Fluoro-6-methoxy-[1,5]naphthyridin-4-yl)-piperazin-1-ylmethyl]-2-oxo-oxazolidin-3-yl}-4H-benzo[1,4]oxazin-3-one;

6-{(R)-5-[4-(3-Fluoro-6-methoxy-[1,5]naphthyridin-4-yl)-piperazin-1-ylmethyl]-2-oxo-oxazolidin-3-yl}-4H-benzo[1,4]thiazin-3-one;

(R)-3-(2,3-Dihydro-benzo[1,4]dioxin-6-yl)-5-(4-quinolin-4-yl-piperazin-1-ylmethyl)-oxazolidin-2-one;

[3-(3-Fluoro-4-methyl-phenyl)-2-oxo-oxazolidin-5-ylmethyl]-4-(6-methoxy-[1,5]naphthyridin-4-yl)-piperazin-2-one;

6-{(R)-5-[4-(6-Methoxy-[1,5]naphthyridin-4-yl)-3-oxo-piperazin-1-ylmethyl]-2-oxo-oxazolidin-3-yl}-4H-benzo[1,4]thiazin-3-one;

(R)-3-(2,3-Dihydro-benzo[1,4]dioxin-6-yl)-5-{[1-(6-methoxy-[1,5]naphthyridin-4-yl)-piperidin-3-ylamino]-methyl}-oxazolidin-2-one;

6-{(R)-5-[4-(3-Fluoro-6-methoxy-[1,5]naphthyridin-4-yl)-[1,4]diazepan-1-ylmethyl]-2-oxo-oxazolidin-3-yl}-4H-benzo[1,4]oxazin-3-one;

6-{(R)-5-[4-(3-Fluoro-6-methoxy-[1,5]naphthyridin-4-yl)-[1,4]diazepan-1-ylmethyl]-2-oxo-oxazolidin-3-yl}-4H-benzo[1,4]thiazin-3-one;

6-{(R)-5-[4-(6-Methoxy-[1,5]naphthyridin-4-yl)-[1,4]diazepan-1-ylmethyl]-2-oxo-oxazolidin-3-yl}-4H-benzo[1,4]oxazin-3-one;

6-{(R)-5-[4-(6-Methoxy-[1,5]naphthyridin-4-yl)-[1,4]diazepan-1-ylmethyl]-2-oxo-oxazolidin-3-yl}-4H-benzo[1,4]thiazin-3-one;

(R)-3-(2,3-Dihydro-benzo[1,4]dioxin-6-yl)-5-[4-(6-methoxy-[1,5]naphthyridin-4-yl)-[1,4]diazepan-1-ylmethyl]-oxazolidin-2-one;

(R)-3-(3-Fluoro-4-methyl-phenyl)-5-[4-(6-methoxy-[1,5]naphthyridin-4-yl)-[1,4]diazepan-1-ylmethyl]-oxazolidin-2-one;

(S)-3-(2,3-Dihydro-benzo[1,4]dioxin-6-yl)-5-[4-(6-methoxy-[1,5]naphthyridin-4-yl)-[1,4]diazepane-1-carbonyl]-oxazolidin-2-one;

3-(6,7-Dihydro-[1,4]dioxino[2,3-c]pyridazin-3-yl)-5-[4-(6-methoxy-[1,5]naphthyridin-4-yl)-piperazin-1-ylmethyl]-oxazolidin-2-one;

3-(6,7-Dihydro-[1,4]dioxino[2,3-c]pyridazin-3-yl)-5-[4-(6-methoxy-[1,5]naphthyridin-4-yl)-piperazin-1-ylmethyl]-oxazolidin-2-one;

(R)-3-(2,3-Dihydro-benzo[1,4]dioxin-6-yl)-5-({[(S)-1-(6-methoxy-[1,5]naphthyridin-4-yl)-pyrrolidin-3-yl]-methyl-amino}-methyl)-oxazolidin-2-one;

6-{5-[4-(6-Methoxy-[1,5]naphthyridin-4-yl)-piperazin-1-ylmethyl]-2-oxo-oxazolidin-3-yl}-4H-pyrido[3,2-b][1,4]oxazin-3-one;

6-((R)-5-{2-[4-(6-Methoxy-[1,5]naphthyridin-4-yl)-piperazin-1-yl]-2-oxo-ethyl}-2-oxo-oxazolidin-3-yl)-4H-benzo[1,4]thiazin-3-one;

N-[1-(6-Methoxy-[1,5]naphthyridin-4-yl)-azetidin-3-yl]-2-[(R)-2-oxo-3-(3-oxo-3,4-dihydro-2H-benzo[1,4]thiazin-6-yl)-oxazolidin-5-yl]-acetamide;

(S)-3-(2,3-Dihydro-benzo[1,4]dioxin-6-yl)-2-oxo-oxazolidine-5-carboxylic acid [1-(6-methoxy-[1,5]naphthyridin-4-yl)-azetidin-3-yl]-amide;

6-[(R)-5-({[1-(6-Methoxy-[1,5]naphthyridin-4-yl)-pyrrolidin-3-ylmethyl]-methyl-amino}-methyl)-2-oxo-oxazolidin-3-yl]-4H-benzo[1,4]thiazin-3-one;

(S)-3-(2,3-Dihydro-benzo[1,4]dioxin-6-yl)-5-({[1-(6-methoxy-[1,5]naphthyridin-4-yl)-azetidin-3-ylmethyl]-methyl-amino}-methyl)-oxazolidin-2-one;

6-((R)-5-{[1-(6-Methoxy-[1,5]naphthyridin-4-yl)-piperidin-4-ylamino]-methyl}-2-oxo-oxazolidin-3-yl)-4H-benzo[1,4]thiazin-3-one;

6-((R)-5-{[1-(6-Methoxy-[1,5]naphthyridin-4-yl)-piperidin-4-ylamino]-methyl}-2-oxo-oxazolidin-3-yl)-4H-benzo[1,4]oxazin-3-one;

(R)-3-(3-Fluoro-4-methyl-phenyl)-5-{[1-(6-methoxy-[1,5]naphthyridin-4-yl)-piperidin-4-ylamino]-methyl}-oxazolidin-2-one;

6-((R)-5-{[1-(3-Fluoro-6-methoxy-[1,5]naphthyridin-4-yl)-piperidin-4-ylamino]-methyl}-2-oxo-oxazolidin-3-yl)-4H-benzo[1,4]thiazin-3-one;

6-((R)-5-{[1-(3-Fluoro-6-methoxy-[1,5]naphthyridin-4-yl)-piperidin-4-ylamino]-methyl}-2-oxo-oxazolidin-3-yl)-4H-benzo[1,4]oxazin-3-one;

6-[(R)-5-({[1-(3-Fluoro-6-methoxy-[1,5]naphthyridin-4-yl)-piperidin-4-yl]-methyl-amino}-methyl)-2-oxo-oxazolidin-3-yl]-4H-benzo[1,4]thiazin-3-one;

6-{(R)-5-[4-Hydroxy-4-(6-methoxy-quinolin-4-yl)-piperidin-1-ylmethyl]-2-oxo-oxazolidin-3-yl}-4H-benzo[1,4]thiazin-3-one;

6-{(R)-5-[4-(3-Fluoro-6-methoxy-[1,5]naphthyridin-4-yl)-4-hydroxy-piperidin-1-ylmethyl]-2-oxo-oxazolidin-3-yl}-4H-benzo[1,4]thiazin-3-one;

6-[(R)-5-({[1-(3-Fluoro-6-methoxy-[1,5]naphthyridin-4-yl)-azetidin-3-yl]-methyl-amino}-methyl)-2-oxo-oxazolidin-3-yl]-4H-benzo[1,4]oxazin-3-one; and 6-[(R)-5-({(2-Hydroxy-ethyl)-[1-(6-methoxy-[1,5]naphthyridin-4-yl)-azetidin-3-yl]-amino}-methyl)-2-oxo-oxazolidin-3-yl]-4H-benzo[1,4]thiazin-3-one; for the prevention or treatment of a bacterial infection; or to said compound, or a pharmaceutically acceptable salt thereof, for use in the manufacture of a medicament for the prevention or treatment of a bacterial infection;

wherein in the above list the first 44 compounds constitute a particular sub-embodiment.

8) In addition to the compounds listed in embodiment 7), the invention further relates to a compound of formula (I) according to embodiment 1), or a pharmaceutically acceptable salt thereof, wherein said compound is selected from the group consisting of:

6-[(R)-5-({[3-Hydroxy-1-(6-methoxy-[1,5]naphthyridin-4-yl)-pyrrolidin-3-ylmethyl]-amino}-methyl)-2-oxo-oxazolidin-3-yl]-4H-benzo[1,4]thiazin-3-one;

(S)-3-(3-Fluoro-4-methyl-phenyl)-2-oxo-oxazolidine-5-carboxylic acid[1-(6-methoxy-[1,5]naphthyridin-4-yl)-azetidin-3-ylmethyl]-amide;

6-((R)-5-{[1-(6-Methoxy-2-methyl-quinolin-4-yl)-azetidin-3-ylamino]-methyl}-2-oxo-oxazolidin-3-yl)-4H-benzo[1,4]thiazin-3-one;

6-{(R)-5-[4-Hydroxy-4-(6-methoxy-quinolin-4-yl)-piperidin-1-ylmethyl]-2-oxo-oxazolidin-3-yl}-4H-benzo[1,4]oxazin-3-one;

(R)-5-({[1-(6-Methoxy-[1,5]naphthyridin-4-yl)-azetidin-3-yl]-methyl-amino}-methyl)-3-phenyl-oxazolidin-2-one;

(R)-3-(4-Difluoromethoxy-phenyl)-5-({[1-(6-methoxy-[1,5]naphthyridin-4-yl)-azetidin-3-yl]-methyl-amino}-methyl)-oxazolidin-2-one;

(R)-5-({[1-(6-Methoxy-[1,5]naphthyridin-4-yl)-azetidin-3-yl]-methyl-amino}-methyl)-3-(4-methyl-3-trifluoromethyl-phenyl)-oxazolidin-2-one;

(R)-3-(3-Chloro-4-fluoro-phenyl)-5-({[1-(6-methoxy-[1,5]naphthyridin-4-yl)-azetidin-3-yl]-methyl-amino}-methyl)-oxazolidin-2-one;

(R)-3-(4-Ethyl-phenyl)-5-({[1-(6-methoxy-[1,5]naphthyridin-4-yl)-azetidin-3-yl]-methyl-amino}-methyl)-oxazolidin-2-one;

(R)-3-(3,4-Dimethyl-phenyl)-5-({[1-(6-methoxy-[1,5]naphthyridin-4-yl)-azetidin-3-yl]-methyl-amino}-methyl)-oxazolidin-2-one;

(R)-5-({[1-(6-Methoxy-[1,5]naphthyridin-4-yl)-azetidin-3-yl]-methyl-amino}-methyl)-3-(4-propyl-phenyl)-oxazolidin-2-one;

(R)-3-(3-Dimethylamino-phenyl)-5-({[1-(6-methoxy-[1,5]naphthyridin-4-yl)-azetidin-3-yl]-methyl-amino}-methyl)-oxazolidin-2-one;

(R)-3-(4-Bromo-3-fluoro-phenyl)-5-({[1-(6-methoxy-[1,5]naphthyridin-4-yl)-azetidin-3-yl]-methyl-amino}-methyl)-oxazolidin-2-one;

(R)-3-(3-Bromo-4-methyl-phenyl)-5-({[1-(6-methoxy-[1,5]naphthyridin-4-yl)-azetidin-3-yl]-methyl-amino}-methyl)-oxazolidin-2-one;

(R)-3-(4-Bromo-3-methyl-phenyl)-5-({[1-(6-methoxy-[1,5]naphthyridin-4-yl)-azetidin-3-yl]-methyl-amino}-methyl)-oxazolidin-2-one;

(R)-3-Benzothiazol-6-yl-5-({[1-(6-methoxy-[1,5]naphthyridin-4-yl)-azetidin-3-yl]-methyl-amino}-methyl)-oxazolidin-2-one;

(R)-3-Benzo[1,3]dioxol-5-yl-5-({[1-(6-methoxy-[1,5]naphthyridin-4-yl)-azetidin-3-yl]-methyl-amino}-methyl)-oxazolidin-2-one;

(R)-3-Benzothiazol-5-yl-5-({[1-(6-methoxy-[1,5]naphthyridin-4-yl)-azetidin-3-yl]-methyl-amino}-methyl)-oxazolidin-2-one;

(R)-3-(3-Fluoro-phenyl)-5-({[1-(6-methoxy-[1,5]naphthyridin-4-yl)-azetidin-3-yl]-methyl-amino}-methyl)-oxazolidin-2-one;

1-(6-Methoxy-[1,5]naphthyridin-4-yl)-azetidine-3-carboxylic acid [(R)-3-(3-fluoro-4-methyl-phenyl)-2-oxo-oxazolidin-5-ylmethyl]-amide;

3-(3-Fluoro-4-methyl-phenyl)-5-(2-{[1-(6-methoxy-[1,5]naphthyridin-4-yl)-azetidin-3-ylmethyl]-amino}-ethyl)-oxazolidin-2-one;

6-[(R)-5-({[1-(6-Methoxy-[1,5]naphthyridin-4-yl)-azetidin-3-yl]-methyl-amino}-methyl)-2-oxo-oxazolidin-3-yl]-4H-pyrido[3,2-b][1,4]oxazin-3-one;

6-{(R)-5-[(1S,4S)-5-(6-Methoxy-[1,5]naphthyridin-4-yl)-2,5-diaza-bicyclo[2.2.1]hept-2-ylmethyl]-2-oxo-oxazolidin-3-yl}-4H-benzo[1,4]oxazin-3-one;

6-{(R)-5-[(1S,4S)-5-(6-Methoxy-[1,5]naphthyridin-4-yl)-2,5-diaza-bicyclo[2.2.1]hept-2-ylmethyl]-2-oxo-oxazolidin-3-yl}-4H-benzo[1,4]thiazin-3-one;

(R)-3-(6,7-Dihydro-[1,4]dioxino[2,3-c]pyridazin-3-yl)-5-({[1-(6-methoxy-[1,5]naphthyridin-4-yl)-azetidin-3-yl]-methyl-amino}-methyl)-oxazolidin-2-one;

(R)-3-(3-Fluoro-4-methyl-phenyl)-5-({[1-(6-methoxy-[1,5]naphthyridin-4-yl)-azetidin-3-ylmethyl]-amino}-methyl)-oxazolidin-2-one;

7-Fluoro-6-((R)-5-{[1-(3-fluoro-6-methoxy-[1,5]naphthyridin-4-yl)-azetidin-3-ylamino]-methyl}-2-oxo-oxazolidin-3-yl)-4H-benzo[1,4]thiazin-3-one;

6-((R)-5-{[1-(6-Methoxy-quinolin-4-yl)-azetidin-3-ylamino]-methyl}-2-oxo-oxazolidin-3-yl)-4H-benzo[1,4]oxazin-3-one;

6-((R)-5-{[1-(3-Methoxy-quinolin-5-yl)-azetidin-3-ylamino]-methyl}-2-oxo-oxazolidin-3-yl)-4H-benzo[1,4]thiazin-3-one;

6-((R)-5-{[1-(2-Methoxy-quinolin-8-yl)-azetidin-3-ylamino]-methyl}-2-oxo-oxazolidin-3-yl)-4H-benzo[1,4]thiazin-3-one;

6-((R)-5-{[1-(7-Fluoro-2-methoxy-quinolin-8-yl)-azetidin-3-ylamino]-methyl}-2-oxo-oxazolidin-3-yl)-4H-benzo[1,4]thiazin-3-one;

6-((R)-5-{[1-(6-Fluoro-quinolin-4-yl)-azetidin-3-ylamino]-methyl}-2-oxo-oxazolidin-3-yl)-4H-benzo[1,4]thiazin-3-one;

4-(3-{[(R)-2-oxo-3-(3-oxo-3,4-dihydro-2H-benzo[1,4]thiazin-6-yl)-oxazolidin-5-ylmethyl]-amino}-azetidin-1-yl)-quinoline-6-carbonitrile;

6-[(R)-5-({[1-(2-Methoxy-quinolin-8-yl)-azetidin-3-ylmethyl]-amino}-methyl)-2-oxo-oxazolidin-3-yl]-4H-benzo[1,4]thiazin-3-one;

6-[(R)-5-({[1-(3-Methoxy-quinolin-5-yl)-azetidin-3-ylmethyl]-amino}-methyl)-2-oxo-oxazolidin-3-yl]-4H-benzo[1,4]thiazin-3-one;

6-((S)-5-{[(S)-1-(3-Fluoro-6-methoxy-[1,5]naphthyridin-4-yl)-pyrrolidin-3-ylamino]-methyl}-2-oxo-oxazolidin-3-yl)-4H-benzo[1,4]thiazin-3-one;

6-((S)-5-{[1-(6-Methoxy-[1,5]naphthyridin-4-yl)-piperidin-4-ylamino]-methyl}-2-oxo-oxazolidin-3-yl)-4H-benzo[1,4]thiazin-3-one;

6-{(S)-5-[4-(6-Methoxy-[1,5]naphthyridin-4-yl)-[1,4]diazepan-1-ylmethyl]-2-oxo-oxazolidin-3-yl}-4H-benzo[1,4]thiazin-3-one;

6-[(R)-5-({[(R)-1-(6-Methoxy-[1,5]naphthyridin-4-yl)-pyrrolidin-3-ylmethyl]-amino}-methyl)-2-oxo-oxazolidin-3-yl]-4H-benzo[1,4]oxazin-3-one;

6-[(R)-5-({[(S)-1-(6-Methoxy-[1,5]naphthyridin-4-yl)-pyrrolidin-3-ylmethyl]-amino}-methyl)-2-oxo-oxazolidin-3-yl]-4H-benzo[1,4]oxazin-3-one;

(R)-5-{[(S)-1-(3-Fluoro-6-methoxy-[1,5]naphthyridin-4-yl)-pyrrolidin-3-ylamino]-methyl}-3-(4-methoxy-phenyl)-oxazolidin-2-one;

(R)-3-(4-Ethoxy-phenyl)-5-{[(S)-1-(3-fluoro-6-methoxy-[1,5]naphthyridin-4-yl)-pyrrolidin-3-ylamino]-methyl}-oxazolidin-2-one;

(R)-3-(4-Difluoromethoxy-phenyl)-5-{[(S)-1-(3-fluoro-6-methoxy-[1,5]naphthyridin-4-yl)-pyrrolidin-3-ylamino]-methyl}-oxazolidin-2-one;

6-((R)-5-{[(S)-1-(6-Methoxy-quinolin-4-yl)-pyrrolidin-3-ylamino]-methyl}-2-oxo-oxazolidin-3-yl)-4H-benzo[1,4]thiazin-3-one;

6-[(R)-5-({[(S)-1-(6-Methoxy-quinolin-4-yl)-pyrrolidin-3-ylmethyl]-amino}-methyl)-2-oxo-oxazolidin-3-yl]-4H-benzo[1,4]thiazin-3-one;

(R)-5-{[1-(6-Methoxy-[1,5]naphthyridin-4-yl)-azetidin-3-ylamino]-methyl}-3-(4-methoxy-phenyl)-oxazolidin-2-one;

(R)-3-(4-Ethoxy-phenyl)-5-{[1-(6-methoxy-[1,5]naphthyridin-4-yl)-azetidin-3-ylamino]-methyl}-oxazolidin-2-one;

(R)-3-(4-Difluoromethoxy-phenyl)-5-{[1-(6-methoxy-[1,5]naphthyridin-4-yl)-azetidin-3-ylamino]-methyl}-oxazolidin-2-one;

6-((R)-5-{[(R)-1-(6-Fluoro-quinolin-4-yl)-pyrrolidin-3-ylamino]-methyl}-2-oxo-oxazolidin-3-yl)-4H-benzo[1,4]thiazin-3-one;

4-((R)-3-{[(R)-2-oxo-3-(3-oxo-3,4-dihydro-2H-benzo[1,4]thiazin-6-yl)-oxazolidin-5-ylmethyl]-amino}-pyrrolidin-1-yl)-quinoline-6-carbonitrile;

6-((R)-5-{[1-(6-Fluoro-quinolin-4-yl)-piperidin-4-ylamino]-methyl}-2-oxo-oxazolidin-3-yl)-4H-benzo[1,4]thiazin-3-one;

4-(4-{[(R)-2-oxo-3-(3-oxo-3,4-dihydro-2H-benzo[1,4]thiazin-6-yl)-oxazolidin-5-ylmethyl]-amino}-piperidin-1-yl)-quinoline-6-carbonitrile;

6-((R)-5-{[(3S,4S)-4-Methoxy-1-(6-methoxy-[1,5]naphthyridin-4-yl)-pyrrolidin-3-ylamino]-methyl}-2-oxo-oxazolidin-3-yl)-4H-benzo[1,4]oxazin-3-one;

(R)-5-{[1-(6-Methoxy-[1,5]naphthyridin-4-yl)-piperidin-4-ylamino]-methyl}-3-(4-methoxy-phenyl)-oxazolidin-2-one;

(R)-3-(4-Ethoxy-phenyl)-5-{[1-(6-methoxy-[1,5]naphthyridin-4-yl)-piperidin-4-ylamino]-methyl}-oxazolidin-2-one;

(R)-3-(4-Difluoromethoxy-phenyl)-5-{[1-(6-methoxy-[1,5]naphthyridin-4-yl)-piperidin-4-ylamino]-methyl}-oxazolidin-2-one; and 6-[(R)-5-({[1-(6-Methoxy-quinolin-4-yl)-azetidin-3-ylmethyl]-amino}-methyl)-2-oxo-oxazolidin-3-yl]-4H-benzo[1,4]thiazin-3-one;

for the prevention or treatment of a bacterial infection; or to said compound, or a pharmaceutically acceptable salt thereof, for use in the manufacture of a medicament for the prevention or treatment of a bacterial infection.

9) In another embodiment, the invention further relates to a compound of formula (I) according to embodiment 1), or a pharmaceutically acceptable salt thereof, wherein said compound is selected from the group consisting of:

(S)-3-(2,3-Dihydro-benzo[1,4]dioxin-6-yl)-5-({[1-(6-methoxy-[1,5]naphthyridin-4-yl)-azetidin-3-ylmethyl]-amino}-methyl)-oxazolidin-2-one;

(S)-3-(2,3-Dihydro-benzo[1,4]dioxin-6-yl)-2-oxo-oxazolidine-5-carboxylic acid[1-(6-methoxy-[1,5]naphthyridin-4-yl)-azetidin-3-ylmethyl]-amide;

(R)-3-(2,3-Dihydro-benzo[1,4]dioxin-6-yl)-5-[4-hydroxy-4-(6-methoxy-[1,5]naphthyridin-4-yl)-piperidin-1-ylmethyl]-oxazolidin-2-one;

(S)-3-(2,3-Dihydro-benzo[1,4]dioxin-6-yl)-5-[4-hydroxy-4-(6-methoxy-[1,5]naphthyridin-4-yl)-piperidin-1-ylmethyl]-oxazolidin-2-one;

(R)-3-(2,3-Dihydro-benzo[1,4]dioxin-6-yl)-5-[4-hydroxy-1-(6-methoxy-quinazolin-4-yl)-piperidin-4-ylmethyl]-oxazolidin-2-one;

(S)-3-(2,3-Dihydro-benzo[1,4]dioxin-6-yl)-5-[4-hydroxy-1-(6-methoxy-quinazolin-4-yl)-piperidin-4-ylmethyl]-oxazolidin-2-one;

(R)-3-(2,3-Dihydro-benzo[1,4]dioxin-6-yl)-5-[4-hydroxy-1-(6-methoxy-[1,5]naphthyridin-4-yl)-piperidin-4-ylmethyl]-oxazolidin-2-one;

(S)-3-(2,3-Dihydro-benzo[1,4]dioxin-6-yl)-5-[4-hydroxy-1-(6-methoxy-[1,5]naphthyridin-4-yl)-piperidin-4-ylmethyl]-oxazolidin-2-one;

(R)-3-(2,3-Dihydro-benzo[1,4]dioxin-6-yl)-5-[4-(6-methoxy-quinazolin-4-yl)-piperazin-1-ylmethyl]-oxazolidin-2-one;

(S)-3-(2,3-Dihydro-benzo[1,4]dioxin-6-yl)-5-[4-(6-methoxy-quinazolin-4-yl)-piperazin-1-ylmethyl]-oxazolidin-2-one;

(R)-6-{5-[4-(6-Methoxy-quinazolin-4-yl)-piperazin-1-ylmethyl]-2-oxo-oxazolidin-3-yl}-4H-benzo[1,4]thiazin-3-one;

(S)-6-{5-[4-(6-Methoxy-quinazolin-4-yl)-piperazin-1-ylmethyl]-2-oxo-oxazolidin-3-yl}-4H-benzo[1,4]thiazin-3-one;

(R)-3-(2,3-Dihydro-benzo[1,4]dioxin-6-yl)-5-[4-(6-methoxy-[1,5]naphthyridin-4-yl)-piperazin-1-ylmethyl]-oxazolidin-2-one;

(S)-3-(2,3-Dihydro-benzo[1,4]dioxin-6-yl)-5-[4-(6-methoxy-[1,5]naphthyridin-4-yl)-piperazin-1-ylmethyl]-oxazolidin-2-one;

(R)-3-(2,3-Dihydro-benzo[1,4]dioxin-6-yl)-5-[4-(6-methoxy-[1,5]naphthyridin-4-yl)-piperazin-1-ylmethyl]-oxazolidin-2-one;

(R)-5-[4-(6-Methoxy-[1,5]naphthyridin-4-yl)-piperazin-1-ylmethyl]-3-(3-trifluoromethoxy-phenyl)-oxazolidin-2-one;

(R)-5-[4-(6-Methoxy-[1,5]naphthyridin-4-yl)-piperazin-1-ylmethyl]-3-(4-trifluoromethoxy-phenyl)-oxazolidin-2-one;

(R)-5-[4-(6-Methoxy-[1,5]naphthyridin-4-yl)-piperazin-1-ylmethyl]-3-phenyl-oxazolidin-2-one;

(R)-3-(4-Bromo-3-fluoro-phenyl)-5-[4-(6-methoxy-[1,5]naphthyridin-4-yl)-piperazin-1-ylmethyl]-oxazolidin-2-one;

(R)-3-(3,4-Dimethoxy-phenyl)-5-[4-(6-methoxy-[1,5]naphthyridin-4-yl)-piperazin-1-ylmethyl]-oxazolidin-2-one;

(R)-3-(4-Fluoro-phenyl)-5-[4-(6-methoxy-[1,5]naphthyridin-4-yl)-piperazin-1-ylmethyl]-oxazolidin-2-one;

(R)-5-[4-(6-Methoxy-[1,5]naphthyridin-4-yl)-piperazin-1-ylmethyl]-3-(3-trifluoromethyl-phenyl)-oxazolidin-2-one;

(R)-3-(3-Chloro-4-fluoro-phenyl)-5-[4-(6-methoxy-[1,5]naphthyridin-4-yl)-piperazin-1-ylmethyl]-oxazolidin-2-one;

(R)-5-[4-(6-Methoxy-[1,5]naphthyridin-4-yl)-piperazin-1-ylmethyl]-3-(4-methyl-3-trifluoromethyl-phenyl)-oxazolidin-2-one;

(R)-3-Benzothiazol-6-yl-5-[4-(6-methoxy-[1,5]naphthyridin-4-yl)-piperazin-1-ylmethyl]-oxazolidin-2-one;

(R)-3-(4-Difluoromethoxy-phenyl)-5-[4-(6-methoxy-[1,5]naphthyridin-4-yl)-piperazin-1-ylmethyl]-oxazolidin-2-one;

3-{(R)-5-[4-(6-Methoxy-[1,5]naphthyridin-4-yl)-piperazin-1-ylmethyl]-2-oxo-oxazolidin-3-yl}-benzonitrile;

6-{(R)-5-[4-(6-Methoxy-[1,5]naphthyridin-4-yl)-piperazin-1-ylmethyl]-2-oxo-oxazolidin-3-yl}-4H-benzo[1,4]thiazin-3-one;

(R)-5-[4-(6-Methoxy-[1,5]naphthyridin-4-yl)-piperazin-1-ylmethyl]-3-(4-pyrrolidin-1-yl-phenyl)-oxazolidin-2-one;

(R)-5-[4-(6-Methoxy-[1,5]naphthyridin-4-yl)-piperazin-1-ylmethyl]-3-(3-methoxy-phenyl)-oxazolidin-2-one;

(R)-5-[4-(6-Methoxy-[1,5]naphthyridin-4-yl)-piperazin-1-ylmethyl]-3-(4-propyl-phenyl)-oxazolidin-2-one;

(R)-3-(4-Ethyl-phenyl)-5-[4-(6-methoxy-[1,5]naphthyridin-4-yl)-piperazin-1-ylmethyl]-oxazolidin-2-one;

(R)-3-(3,4-Dimethyl-phenyl)-5-[4-(6-methoxy-[1,5]naphthyridin-4-yl)-piperazin-1-ylmethyl]-oxazolidin-2-one;

(R)-3-(3-Chloro-4-methoxy-phenyl)-5-[4-(6-methoxy-[1,5]naphthyridin-4-yl)-piperazin-1-ylmethyl]-oxazolidin-2-one;

(R)-3-(3,4-Difluoro-phenyl)-5-[4-(6-methoxy-[1,5]naphthyridin-4-yl)-piperazin-1-ylmethyl]-oxazolidin-2-one;

(R)-3-(4-Fluoro-3-methyl-phenyl)-5-[4-(6-methoxy-[1,5]naphthyridin-4-yl)-piperazin-1-ylmethyl]-oxazolidin-2-one;

(R)-3-(4-Bromo-3-methyl-phenyl)-5-[4-(6-methoxy-[1,5]naphthyridin-4-yl)-piperazin-1-ylmethyl]-oxazolidin-2-one;

(R)-3-(3-Bromo-4-methyl-phenyl)-5-[4-(6-methoxy-[1,5]naphthyridin-4-yl)-piperazin-1-ylmethyl]-oxazolidin-2-one;

(R)-5-[4-(6-Methoxy-[1,5]naphthyridin-4-yl)-piperazin-1-ylmethyl]-3-(4-methoxy-3-trifluoromethyl-phenyl)-oxazolidin-2-one;

(R)-3-(3-Dimethylamino-phenyl)-5-[4-(6-methoxy-[1,5]naphthyridin-4-yl)-piperazin-1-ylmethyl]-oxazolidin-2-one;

(R)-3-Benzo[1,3]dioxol-5-yl-5-[4-(6-methoxy-[1,5]naphthyridin-4-yl)-piperazin-1-ylmethyl]-oxazolidin-2-one;

(R)-3-(3-Fluoro-4-methyl-phenyl)-5-[4-(6-methoxy-[1,5]naphthyridin-4-yl)-piperazin-1-ylmethyl]-oxazolidin-2-one;

(S)-3-(2,3-Dihydro-benzo[1,4]dioxin-6-yl)-5-[4-(6-methoxy-[1,5]naphthyridin-4-yl)-piperazin-1-ylmethyl]-oxazolidin-2-one;

(S)-3-(3-Fluoro-4-methyl-phenyl)-5-[4-(6-methoxy-[1,5]naphthyridin-4-yl)-piperazin-1-ylmethyl]-oxazolidin-2-one;

6-{(S)-5-[4-(6-Methoxy-[1,5]naphthyridin-4-yl)-piperazin-1-ylmethyl]-2-oxo-oxazolidin-3-yl}-4H-benzo[1,4]thiazin-3-one;

(S)-3-(3-Fluoro-phenyl)-5-[4-(6-methoxy-[1,5]naphthyridin-4-yl)-piperazin-1-ylmethyl]-oxazolidin-2-one;

(R)-3-(2,3-Dihydro-benzo[1,4]dioxin-6-yl)-5-{[(S)-1-(6-methoxy-[1,5]naphthyridin-4-yl)-pyrrolidin-3-ylamino]-methyl}-oxazolidin-2-one;

(R)-3-(2,3-Dihydro-benzo[1,4]dioxin-6-yl)-5-{[(R)-1-(6-methoxy-[1,5]naphthyridin-4-yl)-pyrrolidin-3-ylamino]-methyl}-oxazolidin-2-one;

(R)-5-[4-(6-Methoxy-[1,5]naphthyridin-4-yl)-piperazin-1-ylmethyl]-3-(5-methyl-pyridin-2-yl)-oxazolidin-2-one;

(S)-5-[4-(6-Methoxy-[1,5]naphthyridin-4-yl)-piperazin-1-ylmethyl]-3-(5-methyl-pyridin-2-yl)-oxazolidin-2-one;

(R)-5-[4-(6-Methoxy-[1,5]naphthyridin-4-yl)-piperazin-1-ylmethyl]-3-(5-trifluoromethyl-pyridin-2-yl)-oxazolidin-2-one;

(S)-5-[4-(6-Methoxy-[1,5]naphthyridin-4-yl)-piperazin-1-ylmethyl]-3-(5-trifluoromethyl-pyridin-2-yl)-oxazolidin-2-one;

6-((R)-5-{[1-(3-Fluoro-6-methoxy-[1,5]naphthyridin-4-yl)-azetidin-3-ylamino]-methyl}-2-oxo-oxazolidin-3-yl)-4H-benzo[1,4]oxazin-3-one;

(R)-5-{[1-(3-Fluoro-6-methoxy-[1,5]naphthyridin-4-yl)-azetidin-3-ylamino]-methyl}-3-(3-fluoro-4-methyl-phenyl)-oxazolidin-2-one;

(R)-3-(2,3-Dihydro-benzo[1,4]dioxin-6-yl)-5-{[1-(3-fluoro-6-methoxy-[1,5]naphthyridin-4-yl)-azetidin-3-ylamino]-methyl}-oxazolidin-2-one;

6-((R)-5-{[1-(3-Fluoro-6-methoxy-[1,5]naphthyridin-4-yl)-azetidin-3-ylamino]-methyl}-2-oxo-oxazolidin-3-yl)-4H-benzo[1,4]thiazin-3-one;

6-((R)-5-{[1-(6-Methoxy-quinolin-4-yl)-azetidin-3-ylamino]-methyl}-2-oxo-oxazolidin-3-yl)-4H-benzo[1,4]thiazin-3-one;

(R)-3-(3-Fluoro-4-methyl-phenyl)-5-{[1-(6-methoxy-[1,5]naphthyridin-4-yl)-azetidin-3-ylamino]-methyl}-oxazolidin-2-one;

(R)-3-(2,3-Dihydro-benzo[1,4]dioxin-6-yl)-5-{[1-(6-methoxy-[1,5]naphthyridin-4-yl)-azetidin-3-ylamino]-methyl}-oxazolidin-2-one;

6-((R)-5-{[1-(6-Methoxy-[1,5]naphthyridin-4-yl)-azetidin-3-ylamino]-methyl}-2-oxo-oxazolidin-3-yl)-4H-benzo[1,4]oxazin-3-one;

6-((R)-5-{[1-(6-Methoxy-[1,5]naphthyridin-4-yl)-azetidin-3-ylamino]-methyl}-2-oxo-oxazolidin-3-yl)-4H-benzo[1,4]thiazin-3-one;

6-((R)-5-{[1-(6-Methoxy-quinazolin-4-yl)-azetidin-3-ylamino]-methyl}-2-oxo-oxazolidin-3-yl)-4H-benzo[1,4]oxazin-3-one;

6-((R)-5-{[1-(6-Methoxy-quinazolin-4-yl)-azetidin-3-ylamino]-methyl}-2-oxo-oxazolidin-3-yl)-4H-benzo[1,4]thiazin-3-one;

6-[(R)-5-({[1-(6-Methoxy-[1,5]naphthyridin-4-yl)-azetidin-3-yl]-methyl-amino}-methyl)-2-oxo-oxazolidin-3-yl]-4H-benzo[1,4]thiazin-3-one;

6-((S)-5-{[1-(6-Methoxy-[1,5]naphthyridin-4-yl)-azetidin-3-ylamino]-methyl}-2-oxo-oxazolidin-3-yl)-4H-benzo[1,4]thiazin-3-one;

(R)-6-(5-{2-[1-(6-Methoxy-[1,5]naphthyridin-4-yl)-azetidin-3-ylamino]-ethyl}-2-oxo-oxazolidin-3-yl)-4H-benzo[1,4]thiazin-3-one;

(S)-6-(5-{2-[1-(6-Methoxy-[1,5]naphthyridin-4-yl)-azetidin-3-ylamino]-ethyl}-2-oxo-oxazolidin-3-yl)-4H-benzo[1,4]thiazin-3-one;

6-[(S)-5-({[1-(6-Methoxy-[1,5]naphthyridin-4-yl)-azetidin-3-ylmethyl]-amino}-methyl)-2-oxo-oxazolidin-3-yl]-4H-benzo[1,4]thiazin-3-one;

(S)-3-(2,3-Dihydro-benzo[1,4]dioxin-6-yl)-2-oxo-oxazolidine-5-carboxylic acid [(S)-1-(6-methoxy-[1,5]naphthyridin-4-yl)-pyrrolidin-3-yl]-amide;

(S)-3-(2,3-Dihydro-benzo[1,4]dioxin-6-yl)-2-oxo-oxazolidine-5-carboxylic acid [(R)-1-(6-methoxy-[1,5]naphthyridin-4-yl)-pyrrolidin-3-yl]-amide;

(S)-3-(3-Fluoro-4-methyl-phenyl)-2-oxo-oxazolidine-5-carboxylic acid [(R)-1-(6-methoxy-[1,5]naphthyridin-4-yl)-pyrrolidin-3-yl]-amide;

(S)-3-(3-Fluoro-4-methyl-phenyl)-2-oxo-oxazolidine-5-carboxylic acid [(S)-1-(6-methoxy-[1,5]naphthyridin-4-yl)-pyrrolidin-3-yl]-amide;

6-((R)-5-{[(S)-1-(3-Fluoro-6-methoxy-[1,5]naphthyridin-4-yl)-pyrrolidin-3-ylamino]-methyl}-2-oxo-oxazolidin-3-yl)-4H-benzo[1,4]oxazin-3-one;

6-((R)-5-{[(S)-1-(3-Fluoro-6-methoxy-[1,5]naphthyridin-4-yl)-pyrrolidin-3-ylamino]-methyl}-2-oxo-oxazolidin-3-yl)-4H-benzo[1,4]thiazin-3-one;

(R)-3-(2,3-Dihydro-benzo[1,4]dioxin-6-yl)-5-{[(S)-1-(3-fluoro-6-methoxy-[1,5]naphthyridin-4-yl)-pyrrolidin-3-ylamino]-methyl}-oxazolidin-2-one;

(R)-3-(3-Fluoro-4-methyl-phenyl)-5-{[(S)-1-(6-methoxy-[1,5]naphthyridin-4-yl)-pyrrolidin-3-ylamino]-methyl}-oxazolidin-2-one;

(R)-3-(3-Fluoro-4-methyl-phenyl)-5-{[(R)-1-(6-methoxy-[1,5]naphthyridin-4-yl)-pyrrolidin-3-ylamino]-methyl}-oxazolidin-2-one;

6-((R)-5-{[(S)-1-(6-Methoxy-[1,5]naphthyridin-4-yl)-pyrrolidin-3-ylamino]-methyl}-2-oxo-oxazolidin-3-yl)-4H-benzo[1,4]oxazin-3-one;

6-((R)-5-{[(S)-1-(6-Methoxy-[1,5]naphthyridin-4-yl)-pyrrolidin-3-ylamino]-methyl}-2-oxo-oxazolidin-3-yl)-4H-benzo[1,4]thiazin-3-one;

6-((R)-5-{[(R)-1-(6-Methoxy-[1,5]naphthyridin-4-yl)-pyrrolidin-3-ylamino]-methyl}-2-oxo-oxazolidin-3-yl)-4H-benzo[1,4]thiazin-3-one;

6-((R)-5-{[(R)-1-(6-Methoxy-[1,5]naphthyridin-4-yl)-pyrrolidin-3-ylamino]-methyl}-2-oxo-oxazolidin-3-yl)-4H-benzo[1,4]oxazin-3-one;

(3S,4R)-1-(6-Methoxy-[1,5]naphthyridin-4-yl)-4-{[(S)-2-oxo-3-(3-oxo-3,4-dihydro-2H-benzo[1,4]thiazin-6-yl)-oxazolidin-5-ylmethyl]-amino}-pyrrolidine-3-carboxylic acid ethyl ester;

(3R,4S)-1-(6-Methoxy-[1,5]naphthyridin-4-yl)-4-{[(S)-2-oxo-3-(3-oxo-3,4-dihydro-2H-benzo[1,4]thiazin-6-yl)-oxazolidin-5-ylmethyl]-amino}-pyrrolidine-3-carboxylic acid ethyl ester;

(3S,4R)-1-(6-Methoxy-[1,5]naphthyridin-4-yl)-4-{[(R)-2-oxo-3-(3-oxo-3,4-dihydro-2H-benzo[1,4]thiazin-6-yl)-oxazolidin-5-ylmethyl]-amino}-pyrrolidine-3-carboxylic acid;

(3R,4S)-1-(6-Methoxy-[1,5]naphthyridin-4-yl)-4-{[(R)-2-oxo-3-(3-oxo-3,4-dihydro-2H-benzo[1,4]thiazin-6-yl)-oxazolidin-5-ylmethyl]-amino}-pyrrolidine-3-carboxylic acid;

6-((R)-5-{[(3S,4S)-4-Methoxy-1-(6-methoxy-[1,5]naphthyridin-4-yl)-pyrrolidin-3-ylamino]-methyl}-2-oxo-oxazolidin-3-yl)-4H-benzo[1,4]thiazin-3-one;

6-((R)-5-{[(3R,4R)-4-Methoxy-1-(6-methoxy-[1,5]naphthyridin-4-yl)-pyrrolidin-3-ylamino]-methyl}-2-oxo-oxazolidin-3-yl)-4H-benzo[1,4]thiazin-3-one;

6-((R)-5-{[(3S,4S)-4-Hydroxy-1-(6-methoxy-[1,5]naphthyridin-4-yl)-pyrrolidin-3-ylamino]-methyl}-2-oxo-oxazolidin-3-yl)-4H-benzo[1,4]thiazin-3-one;

6-((R)-5-{[(3R,4R)-4-Hydroxy-1-(6-methoxy-[1,5]naphthyridin-4-yl)-pyrrolidin-3-ylamino]-methyl}-2-oxo-oxazolidin-3-yl)-4H-benzo[1,4]thiazin-3-one;

(R)-3-(2,3-Dihydro-benzo[1,4]dioxin-6-yl)-5-{[(3S,4S)-4-hydroxy-1-(6-methoxy-[1,5]naphthyridin-4-yl)-pyrrolidin-3-ylamino]-methyl}-oxazolidin-2-one;

(R)-3-(2,3-Dihydro-benzo[1,4]dioxin-6-yl)-5-{[(3R,4R)-4-hydroxy-1-(6-methoxy-[1,5]naphthyridin-4-yl)-pyrrolidin-3-ylamino]-methyl}-oxazolidin-2-one;

(S)-3-(2,3-Dihydro-benzo[1,4]dioxin-6-yl)-2-oxo-oxazolidine-5-carboxylic acid [(3R,5S)-5-hydroxymethyl-1-(6-methoxy-[1,5]naphthyridin-4-yl)-pyrrolidin-3-yl]-amide;

6-((R)-5-{[(3R,5S)-5-Hydroxymethyl-1-(6-methoxy-[1,5]naphthyridin-4-yl)-pyrrolidin-3-ylamino]-methyl}-2-oxo-oxazolidin-3-yl)-4H-benzo[1,4]thiazin-3-one;

6-[(R)-5-({[(S)-1-(6-Methoxy-[1,5]naphthyridin-4-yl)-pyrrolidin-3-ylmethyl]-amino}-methyl)-2-oxo-oxazolidin-3-yl]-4H-benzo[1,4]thiazin-3-one;

6-[(R)-5-({[(R)-1-(6-Methoxy-[1,5]naphthyridin-4-yl)-pyrrolidin-3-ylmethyl]-amino}-methyl)-2-oxo-oxazolidin-3-yl]-4H-benzo[1,4]thiazin-3-one;

(S)-3-(2,3-Dihydro-benzo[1,4]dioxin-6-yl)-2-oxo-oxazolidine-5-carboxylic acid [(S)-1-(6-methoxy-[1,5]naphthyridin-4-yl)-pyrrolidin-3-ylmethyl]-amide;

(S)-3-(2,3-Dihydro-benzo[1,4]dioxin-6-yl)-2-oxo-oxazolidine-5-carboxylic acid [(R)-1-(6-methoxy-[1,5]naphthyridin-4-yl)-pyrrolidin-3-ylmethyl]-amide;

(S)-3-(3-Fluoro-4-methyl-phenyl)-2-oxo-oxazolidine-5-carboxylic acid [(S)-1-(6-methoxy-[1,5]naphthyridin-4-yl)-pyrrolidin-3-ylmethyl]-amide;

(S)-3-(3-Fluoro-4-methyl-phenyl)-2-oxo-oxazolidine-5-carboxylic acid [(R)-1-(6-methoxy-[1,5]naphthyridin-4-yl)-pyrrolidin-3-ylmethyl]-amide;

6-[(R)-5-({[(3S,4S)-4-Hydroxy-1-(6-methoxy-[1,5]naphthyridin-4-yl)-pyrrolidin-3-ylmethyl]-amino}-methyl)-2-oxo-oxazolidin-3-yl]-4H-benzo[1,4]thiazin-3-one;

6-[(R)-5-({[(3S,4R)-4-Hydroxy-1-(6-methoxy-[1,5]naphthyridin-4-yl)-pyrrolidin-3-ylmethyl]-amino}-methyl)-2-oxo-oxazolidin-3-yl]-4H-benzo[1,4]thiazin-3-one;

6-[(R)-5-({[(3R,4S)-4-Hydroxy-1-(6-methoxy-[1,5]naphthyridin-4-yl)-pyrrolidin-3-ylmethyl]-amino}-methyl)-2-oxo-oxazolidin-3-yl]-4H-benzo[1,4]thiazin-3-one;

6-[(R)-5-({[(3R,4R)-4-Hydroxy-1-(6-methoxy-[1,5]naphthyridin-4-yl)-pyrrolidin-3-ylmethyl]-amino}-methyl)-2-oxo-oxazolidin-3-yl]-4H-benzo[1,4]thiazin-3-one;

(S)-1-(6-Methoxy-[1,5]naphthyridin-4-yl)-pyrrolidine-3-carboxylic acid [(R)-3-(3-fluoro-4-methyl-phenyl)-2-oxo-oxazolidin-5-ylmethyl]-amide;

(R)-1-(6-Methoxy-[1,5]naphthyridin-4-yl)-pyrrolidine-3-carboxylic acid [(R)-3-(3-fluoro-4-methyl-phenyl)-2-oxo-oxazolidin-5-ylmethyl]-amide;

(S)-1-(6-Methoxy-[1,5]naphthyridin-4-yl)-pyrrolidine-3-carboxylic acid [(R)-3-(2,3-dihydro-benzo[1,4]dioxin-6-yl)-2-oxo-oxazolidin-5-ylmethyl]-amide;

(R)-1-(6-Methoxy-[1,5]naphthyridin-4-yl)-pyrrolidine-3-carboxylic acid [(R)-3-(2,3-dihydro-benzo[1,4]dioxin-6-yl)-2-oxo-oxazolidin-5-ylmethyl]-amide;

6-((R)-5-{2-[(S)-1-(6-Methoxy-[1,5]naphthyridin-4-yl)-pyrrolidin-3-ylamino]-ethyl}-2-oxo-oxazolidin-3-yl)-4H-benzo[1,4]thiazin-3-one;

6-((S)-5-{2-[(S)-1-(6-Methoxy-[1,5]naphthyridin-4-yl)-pyrrolidin-3-ylamino]-ethyl}-2-oxo-oxazolidin-3-yl)-4H-benzo[1,4]thiazin-3-one;

6-((R)-5-{2-[(R)-1-(6-Methoxy-[1,5]naphthyridin-4-yl)-pyrrolidin-3-ylamino]-ethyl}-2-oxo-oxazolidin-3-yl)-4H-benzo[1,4]thiazin-3-one;

6-((S)-5-{2-[(R)-1-(6-Methoxy-[1,5]naphthyridin-4-yl)-pyrrolidin-3-ylamino]-ethyl}-2-oxo-oxazolidin-3-yl)-4H-benzo[1,4]thiazin-3-one;

(R)-3-(3-Fluoro-4-methyl-phenyl)-5-{[(1a,5a,6a)-3-(6-methoxy-[1,5]naphthyridin-4-yl)-3-aza-bicyclo[3.1.0]hex-6-ylamino]-methyl}-oxazolidin-2-one;

6-((R)-5-{[(1a,5a,6a)-3-(6-Methoxy-[1,5]naphthyridin-4-yl)-3-aza-bicyclo[3.1.0]hex-6-ylamino]-methyl}-2-oxo-oxazolidin-3-yl)-4H-benzo[1,4]thiazin-3-one;

(R)-3-(2,3-Dihydro-benzo[1,4]dioxin-6-yl)-5-{[(3aS,6aS)-1-(6-methoxy-[1,5]naphthyridin-4-yl)-hexahydro-pyrrolo[3,4-b]pyrrol-5-yl]-methyl}-oxazolidin-2-one;

(R)-3-(2,3-Dihydro-benzo[1,4]dioxin-6-yl)-5-{[(3aR,6aR)-1-(6-methoxy-[1,5]naphthyridin-4-yl)-hexahydro-pyrrolo[3,4-b]pyrrol-5-yl]-methyl}-oxazolidin-2-one;

6-{{(R)-5-[(3aS,6aS)-1-(6-Methoxy-[1,5]naphthyridin-4-yl)-hexahydro-pyrrolo[3,4-b]pyrrol-5-yl]-methyl}-2-oxo-oxazolidin-3-yl]-4H-benzo[1,4]thiazin-3-one;

6-{{(R)-5-[(3aR,6aR)-1-(6-Methoxy-[1,5]naphthyridin-4-yl)-hexahydro-pyrrolo[3,4-b]pyrrol-5-yl]-methyl}-2-oxo-oxazolidin-3-yl}-4H-benzo[1,4]thiazin-3-one;

(S)-3-(2,3-Dihydro-benzo[1,4]dioxin-6-yl)-5-[(3aS,6aS)-1-(6-methoxy-[1,5]naphthyridin-4-yl)-hexahydro-pyrrolo[3,4-b]pyrrole-5-carbonyl]-oxazolidin-2-one;

(S)-3-(2,3-Dihydro-benzo[1,4]dioxin-6-yl)-5-[(3aR,6aR)-1-(6-methoxy-[1,5]naphthyridin-4-yl)-hexahydro-pyrrolo[3,4-b]pyrrole-5-carbonyl]-oxazolidin-2-one;

6-{(R)-5-{[(3aR,6aR)-5-(6-Methoxy-[1,5]naphthyridin-4-yl)-hexahydro-pyrrolo[3,4-b]pyrrol-1-yl]-methyl}-2-oxo-oxazolidin-3-yl}-4H-benzo[1,4]thiazin-3-one;

6-{(R)-5-{[(3aS,6aS)-5-(6-Methoxy-[1,5]naphthyridin-4-yl)-hexahydro-pyrrolo[3,4-b]pyrrol-1-yl]-methyl}-2-oxo-oxazolidin-3-yl}-4H-benzo[1,4]thiazin-3-one;

(R)-3-(2,3-Dihydro-benzo[1,4]dioxin-6-yl)-5-{[(3aR,6aR)-5-(6-methoxy-[1,5]naphthyridin-4-yl)-hexahydro-pyrrolo[3,4-b]pyrrol-1-yl]-methyl}-oxazolidin-2-one;

(R)-3-(2,3-Dihydro-benzo[1,4]dioxin-6-yl)-5-{[(3aS,6aS)-5-(6-methoxy-[1,5]naphthyridin-4-yl)-hexahydro-pyrrolo[3,4-b]pyrrol-1-yl]-methyl}-oxazolidin-2-one;

(S)-3-(2,3-Dihydro-benzo[1,4]dioxin-6-yl)-5-[(3aR,6aR)-5-(6-methoxy-[1,5]naphthyridin-4-yl)-hexahydro-pyrrolo[3,4-b]pyrrole-1-carbonyl]-oxazolidin-2-one;

(S)-3-(2,3-Dihydro-benzo[1,4]dioxin-6-yl)-5-[(3aS,6aS)-5-(6-methoxy-[1,5]naphthyridin-4-yl)-hexahydro-pyrrolo[3,4-b]pyrrole-1-carbonyl]-oxazolidin-2-one;

6-{(R)-5-[4-(6-Methoxy-[1,5]naphthyridin-4-yl)-piperazin-1-ylmethyl]-2-oxo-oxazolidin-3-yl}-4H-benzo[1,4]oxazin-3-one;

6-{(R)-5-[4-(3-Fluoro-6-methoxy-[1,5]naphthyridin-4-yl)-piperazin-1-ylmethyl]-2-oxo-oxazolidin-3-yl}-4H-benzo[1,4]oxazin-3-one;

6-{(R)-5-[4-(3-Fluoro-6-methoxy-[1,5]naphthyridin-4-yl)-piperazin-1-ylmethyl]-2-oxo-oxazolidin-3-yl}-4H-benzo[1,4]thiazin-3-one;

(R)-3-(2,3-Dihydro-benzo[1,4]dioxin-6-yl)-5-(4-quinolin-4-yl-piperazin-1-ylmethyl)-oxazolidin-2-one;

[(S)-3-(3-Fluoro-4-methyl-phenyl)-2-oxo-oxazolidin-5-ylmethyl]-4-(6-methoxy-[1,5]naphthyridin-4-yl)-piperazin-2-one;

[(R)-3-(3-Fluoro-4-methyl-phenyl)-2-oxo-oxazolidin-5-ylmethyl]-4-(6-methoxy-[1,5]naphthyridin-4-yl)-piperazin-2-one;

6-{(R)-5-[4-(6-Methoxy-[1,5]naphthyridin-4-yl)-3-oxo-piperazin-1-ylmethyl]-2-oxo-oxazolidin-3-yl}-4H-benzo[1,4]thiazin-3-one;

(R)-3-(2,3-Dihydro-benzo[1,4]dioxin-6-yl)-5-{[(R)-1-(6-methoxy-[1,5]naphthyridin-4-yl)-piperidin-3-ylamino]-methyl}-oxazolidin-2-one;

(R)-3-(2,3-Dihydro-benzo[1,4]dioxin-6-yl)-5-{[(S)-1-(6-methoxy-[1,5]naphthyridin-4-yl)-piperidin-3-ylamino]-methyl}-oxazolidin-2-one;

6-{(R)-5-[4-(3-Fluoro-6-methoxy-[1,5]naphthyridin-4-yl)-[1,4]diazepan-1-ylmethyl]-2-oxo-oxazolidin-3-yl}-4H-benzo[1,4]oxazin-3-one;

6-{(R)-5-[4-(3-Fluoro-6-methoxy-[1,5]naphthyridin-4-yl)-[1,4]diazepan-1-ylmethyl]-2-oxo-oxazolidin-3-yl}-4H-benzo[1,4]thiazin-3-one;

6-{(R)-5-[4-(6-Methoxy-[1,5]naphthyridin-4-yl)-[1,4]diazepan-1-ylmethyl]-2-oxo-oxazolidin-3-yl}-4H-benzo[1,4]oxazin-3-one;

6-{(R)-5-[4-(6-Methoxy-[1,5]naphthyridin-4-yl)-[1,4]diazepan-1-ylmethyl]-2-oxo-oxazolidin-3-yl}-4H-benzo[1,4]thiazin-3-one;

(R)-3-(2,3-Dihydro-benzo[1,4]dioxin-6-yl)-5-[4-(6-methoxy-[1,5]naphthyridin-4-yl)-[1,4]diazepan-1-ylmethyl]-oxazolidin-2-one;

(R)-3-(3-Fluoro-4-methyl-phenyl)-5-[4-(6-methoxy-[1,5]naphthyridin-4-yl)-[1,4]diazepan-1-ylmethyl]-oxazolidin-2-one;

(S)-3-(2,3-Dihydro-benzo[1,4]dioxin-6-yl)-5-[4-(6-methoxy-[1,5]naphthyridin-4-yl)-[1,4]diazepane-1-carbonyl]-oxazolidin-2-one;

(R)-3-(6,7-Dihydro-[1,4]dioxino[2,3-c]pyridazin-3-yl)-5-[4-(6-methoxy-[1,5]naphthyridin-4-yl)-piperazin-1-ylmethyl]-oxazolidin-2-one;

(S)-3-(6,7-Dihydro-[1,4]dioxino[2,3-c]pyridazin-3-yl)-5-[4-(6-methoxy-[1,5]naphthyridin-4-yl)-piperazin-1-ylmethyl]-oxazolidin-2-one;

(R)-3-(6,7-Dihydro-[1,4]dioxino[2,3-c]pyridazin-3-yl)-5-[4-(6-methoxy-[1,5]naphthyridin-4-yl)-piperazin-1-ylmethyl]-oxazolidin-2-one;

(S)-3-(6,7-Dihydro-[1,4]dioxino[2,3-c]pyridazin-3-yl)-5-[4-(6-methoxy-[1,5]naphthyridin-4-yl)-piperazin-1-ylmethyl]-oxazolidin-2-one;

(R)-3-(2,3-Dihydro-benzo[1,4]dioxin-6-yl)-5-({[(S)-1-(6-methoxy-[1,5]naphthyridin-4-yl)-pyrrolidin-3-yl]-methyl-amino}-methyl)-oxazolidin-2-one;

(R)-6-{5-[4-(6-Methoxy-[1,5]naphthyridin-4-yl)-piperazin-1-ylmethyl]-2-oxo-oxazolidin-3-yl}-4H-pyrido[3,2-b][1,4]oxazin-3-one;

(S)-6-{5-[4-(6-Methoxy-[1,5]naphthyridin-4-yl)-piperazin-1-ylmethyl]-2-oxo-oxazolidin-3-yl}-4H-pyrido[3,2-b][1,4]oxazin-3-one;

6-((R)-5-{2-[4-(6-Methoxy-[1,5]naphthyridin-4-yl)-piperazin-1-yl]-2-oxo-ethyl}-2-oxo-oxazolidin-3-yl)-4H-benzo[1,4]thiazin-3-one;

N-[1-(6-Methoxy-[1,5]naphthyridin-4-yl)-azetidin-3-yl]-2-[(R)-2-oxo-3-(3-oxo-3,4-dihydro-2H-benzo[1,4]thiazin-6-yl)-oxazolidin-5-yl]-acetamide;

(S)-3-(2,3-Dihydro-benzo[1,4]dioxin-6-yl)-2-oxo-oxazolidine-5-carboxylic acid[1-(6-methoxy-[1,5]naphthyridin-4-yl)-azetidin-3-yl]-amide;

6-[(R)-5-({[(S)-1-(6-Methoxy-[1,5]naphthyridin-4-yl)-pyrrolidin-3-ylmethyl]-methyl-amino}-methyl)-2-oxo-oxazolidin-3-yl]-4H-benzo[1,4]thiazin-3-one;

6-[(R)-5-({[(R)-1-(6-Methoxy-[1,5]naphthyridin-4-yl)-pyrrolidin-3-ylmethyl]-methyl-amino}-methyl)-2-oxo-oxazolidin-3-yl]-4H-benzo[1,4]thiazin-3-one;

(S)-3-(2,3-Dihydro-benzo[1,4]dioxin-6-yl)-5-({[1-(6-methoxy-[1,5]naphthyridin-4-yl)-azetidin-3-ylmethyl]-methyl-amino}-methyl)-oxazolidin-2-one;

6-((R)-5-{[1-(6-Methoxy-[1,5]naphthyridin-4-yl)-piperidin-4-ylamino]-methyl}-2-oxo-oxazolidin-3-yl)-4H-benzo[1,4]thiazin-3-one;

6-((R)-5-{[1-(6-Methoxy-[1,5]naphthyridin-4-yl)-piperidin-4-ylamino]-methyl}-2-oxo-oxazolidin-3-yl)-4H-benzo[1,4]oxazin-3-one;

(R)-3-(3-Fluoro-4-methyl-phenyl)-5-{[1-(6-methoxy-[1,5]naphthyridin-4-yl)-piperidin-4-ylamino]-methyl}-oxazolidin-2-one;

6-((R)-5-{[1-(3-Fluoro-6-methoxy-[1,5]naphthyridin-4-yl)-piperidin-4-ylamino]-methyl}-2-oxo-oxazolidin-3-yl)-4H-benzo[1,4]thiazin-3-one;

6-((R)-5-{[1-(3-Fluoro-6-methoxy-[1,5]naphthyridin-4-yl)-piperidin-4-ylamino]-methyl}-2-oxo-oxazolidin-3-yl)-4H-benzo[1,4]oxazin-3-one;

6-[(R)-5-({[1-(3-Fluoro-6-methoxy-[1,5]naphthyridin-4-yl)-piperidin-4-yl]-methyl-amino}-methyl)-2-oxo-oxazolidin-3-yl]-4H-benzo[1,4]thiazin-3-one;

6-{(R)-5-[4-Hydroxy-4-(6-methoxy-quinolin-4-yl)-piperidin-1-ylmethyl]-2-oxo-oxazolidin-3-yl}-4H-benzo[1,4]thiazin-3-one;

6-{(R)-5-[4-(3-Fluoro-6-methoxy-[1,5]naphthyridin-4-yl)-4-hydroxy-piperidin-1-ylmethyl]-2-oxo-oxazolidin-3-yl}-4H-benzo[1,4]thiazin-3-one;

6-[(R)-5-({[1-(3-Fluoro-6-methoxy-[1,5]naphthyridin-4-yl)-azetidin-3-yl]-methyl-amino}-methyl)-2-oxo-oxazolidin-3-yl]-4H-benzo[1,4]oxazin-3-one; and 6-[(R)-5-({(2-Hydroxy-ethyl)-[1-(6-methoxy-[1,5]naphthyridin-4-yl)-azetidin-3-yl]-amino}-methyl)-2-oxo-oxazolidin-3-yl]-4H-benzo[1,4]thiazin-3-one;

for the prevention or treatment of a bacterial infection; or to said compound, or a pharmaceutically acceptable salt thereof, for use in the manufacture of a medicament for the prevention or treatment of a bacterial infection;

wherein in the above list the first 52 compounds constitute a particular sub-embodiment.

10) In addition to the compounds listed in embodiment 9), the invention further relates to a compound of formula (I) according to embodiment 1), or a pharmaceutically acceptable salt thereof, wherein said compound is selected from the group consisting of:

6-[(R)-5-({[(R)-3-Hydroxy-1-(6-methoxy-[1,5]naphthyridin-4-yl)-pyrrolidin-3-ylmethyl]-amino}-methyl)-2-oxo-oxazolidin-3-yl]-4H-benzo[1,4]thiazin-3-one;

6-[(R)-5-({[(S)-3-Hydroxy-1-(6-methoxy-[1,5]naphthyridin-4-yl)-pyrrolidin-3-ylmethyl]-amino}-methyl)-2-oxo-oxazolidin-3-yl]-4H-benzo[1,4]thiazin-3-one;

(S)-3-(3-Fluoro-4-methyl-phenyl)-2-oxo-oxazolidine-5-carboxylic acid[1-(6-methoxy-[1,5]naphthyridin-4-yl)-azetidin-3-ylmethyl]-amide;

6-((R)-5-{[1-(6-Methoxy-2-methyl-quinolin-4-yl)-azetidin-3-ylamino]-methyl}-2-oxo-oxazolidin-3-yl)-4H-benzo[1,4]thiazin-3-one;

6-{(R)-5-[4-Hydroxy-4-(6-methoxy-quinolin-4-yl)-piperidin-1-ylmethyl]-2-oxo-oxazolidin-3-yl}-4H-benzo[1,4]oxazin-3-one;

(R)-5-({[1-(6-Methoxy-[1,5]naphthyridin-4-yl)-azetidin-3-yl]-methyl-amino}-methyl)-3-phenyl-oxazolidin-2-one;

(R)-3-(4-Difluoromethoxy-phenyl)-5-({[1-(6-methoxy-[1,5]naphthyridin-4-yl)-azetidin-3-yl]-methyl-amino}-methyl)-oxazolidin-2-one;

(R)-5-({[1-(6-Methoxy-[1,5]naphthyridin-4-yl)-azetidin-3-yl]-methyl-amino}-methyl)-3-(4-methyl-3-trifluoromethyl-phenyl)-oxazolidin-2-one;

(R)-3-(3-Chloro-4-fluoro-phenyl)-5-({[1-(6-methoxy-[1,5]naphthyridin-4-yl)-azetidin-3-yl]-methyl-amino}-methyl)-oxazolidin-2-one;

(R)-3-(4-Ethyl-phenyl)-5-({[1-(6-methoxy-[1,5]naphthyridin-4-yl)-azetidin-3-yl]-methyl-amino}-methyl)-oxazolidin-2-one;

(R)-3-(3,4-Dimethyl-phenyl)-5-({[1-(6-methoxy-[1,5]naphthyridin-4-yl)-azetidin-3-yl]-methyl-amino}-methyl)-oxazolidin-2-one;

(R)-5-({[1-(6-Methoxy-[1,5]naphthyridin-4-yl)-azetidin-3-yl]-methyl-amino}-methyl)-3-(4-propyl-phenyl)-oxazolidin-2-one;

(R)-3-(3-Dimethylamino-phenyl)-5-({[1-(6-methoxy-[1,5]naphthyridin-4-yl)-azetidin-3-yl]-methyl-amino}-methyl)-oxazolidin-2-one;

(R)-3-(4-Bromo-3-fluoro-phenyl)-5-({[1-(6-methoxy-[1,5]naphthyridin-4-yl)-azetidin-3-yl]-methyl-amino}-methyl)-oxazolidin-2-one;

(R)-3-(3-Bromo-4-methyl-phenyl)-5-({[1-(6-methoxy-[1,5]naphthyridin-4-yl)-azetidin-3-yl]-methyl-amino}-methyl)-oxazolidin-2-one;

(R)-3-(4-Bromo-3-methyl-phenyl)-5-({[1-(6-methoxy-[1,5]naphthyridin-4-yl)-azetidin-3-yl]-methyl-amino}-methyl)-oxazolidin-2-one;

(R)-3-Benzothiazol-6-yl-5-({[1-(6-methoxy-[1,5]naphthyridin-4-yl)-azetidin-3-yl]-methyl-amino}-methyl)-oxazolidin-2-one;

(R)-3-Benzo[1,3]dioxol-5-yl-5-({[1-(6-methoxy-[1,5]naphthyridin-4-yl)-azetidin-3-yl]-methyl-amino}-methyl)-oxazolidin-2-one;

(R)-3-Benzothiazol-5-yl-5-({[1-(6-methoxy-[1,5]naphthyridin-4-yl)-azetidin-3-yl]-methyl-amino}-methyl)-oxazolidin-2-one;

(R)-3-(3-Fluoro-phenyl)-5-({[1-(6-methoxy-[1,5]naphthyridin-4-yl)-azetidin-3-yl]-methyl-amino}-methyl)-oxazolidin-2-one;

1-(6-Methoxy-[1,5]naphthyridin-4-yl)-azetidine-3-carboxylic acid [(R)-3-(3-fluoro-4-methyl-phenyl)-2-oxo-oxazolidin-5-ylmethyl]-amide;

(R)-3-(3-Fluoro-4-methyl-phenyl)-5-(2-{[1-(6-methoxy-[1,5]naphthyridin-4-yl)-azetidin-3-ylmethyl]-amino}-ethyl)-oxazolidin-2-one;

(S)-3-(3-Fluoro-4-methyl-phenyl)-5-(2-{[1-(6-methoxy-[1,5]naphthyridin-4-yl)-azetidin-3-ylmethyl]-amino}-ethyl)-oxazolidin-2-one;

6-[(R)-5-({[1-(6-Methoxy-[1,5]naphthyridin-4-yl)-azetidin-3-yl]-methyl-amino}-methyl)-2-oxo-oxazolidin-3-yl]-4H-pyrido[3,2-b][1,4]oxazin-3-one;

6-{(R)-5-[(1S,4S)-5-(6-Methoxy-[1,5]naphthyridin-4-yl)-2,5-diaza-bicyclo[2.2.1]hept-2-ylmethyl]-2-oxo-oxazolidin-3-yl}-4H-benzo[1,4]oxazin-3-one;

6-{(R)-5-[(1S,4S)-5-(6-Methoxy-[1,5]naphthyridin-4-yl)-2,5-diaza-bicyclo[2.2.1]hept-2-ylmethyl]-2-oxo-oxazolidin-3-yl}-4H-benzo[1,4]thiazin-3-one;

(R)-3-(6,7-Dihydro-[1,4]dioxino[2,3-c]pyridazin-3-yl)-5-({[1-(6-methoxy-[1,5]naphthyridin-4-yl)-azetidin-3-yl]-methyl-amino}-methyl)-oxazolidin-2-one;

(R)-3-(3-Fluoro-4-methyl-phenyl)-5-({[1-(6-methoxy-[1,5]naphthyridin-4-yl)-azetidin-3-ylmethyl]-amino}-methyl)-oxazolidin-2-one;

7-Fluoro-6-((R)-5-{[1-(3-fluoro-6-methoxy-[1,5]naphthyridin-4-yl)-azetidin-3-ylamino]-methyl}-2-oxo-oxazolidin-3-yl)-4H-benzo[1,4]thiazin-3-one;

6-((R)-5-{[1-(6-Methoxy-quinolin-4-yl)-azetidin-3-ylamino]-methyl}-2-oxo-oxazolidin-3-yl)-4H-benzo[1,4]oxazin-3-one;

6-((R)-5-{[1-(3-Methoxy-quinolin-5-yl)-azetidin-3-ylamino]-methyl}-2-oxo-oxazolidin-3-yl)-4H-benzo[1,4]thiazin-3-one;

6-((R)-5-{[1-(2-Methoxy-quinolin-8-yl)-azetidin-3-ylamino]-methyl}-2-oxo-oxazolidin-3-yl)-4H-benzo[1,4]thiazin-3-one;

6-((R)-5-{[1-(7-Fluoro-2-methoxy-quinolin-8-yl)-azetidin-3-ylamino]-methyl}-2-oxo-oxazolidin-3-yl)-4H-benzo[1,4]thiazin-3-one;

6-((R)-5-{[1-(6-Fluoro-quinolin-4-yl)-azetidin-3-ylamino]-methyl}-2-oxo-oxazolidin-3-yl)-4H-benzo[1,4]thiazin-3-one;

4-(3-{[(R)-2-oxo-3-(3-oxo-3,4-dihydro-2H-benzo[1,4]thiazin-6-yl)-oxazolidin-5-ylmethyl]-amino}-azetidin-1-yl)-quinoline-6-carbonitrile;

6-[(R)-5-({[1-(2-Methoxy-quinolin-8-yl)-azetidin-3-ylmethyl]-amino}-methyl)-2-oxo-oxazolidin-3-yl]-4H-benzo[1,4]thiazin-3-one;

6-[(R)-5-({[1-(3-Methoxy-quinolin-5-yl)-azetidin-3-ylmethyl]-amino}-methyl)-2-oxo-oxazolidin-3-yl]-4H-benzo[1,4]thiazin-3-one;

6-((S)-5-{[(S)-1-(3-Fluoro-6-methoxy-[1,5]naphthyridin-4-yl)-pyrrolidin-3-ylamino]-methyl}-2-oxo-oxazolidin-3-yl)-4H-benzo[1,4]thiazin-3-one;

6-((S)-5-{[1-(6-Methoxy-[1,5]naphthyridin-4-yl)-piperidin-4-ylamino]-methyl}-2-oxo-oxazolidin-3-yl)-4H-benzo[1,4]thiazin-3-one;

6-{(S)-5-[4-(6-Methoxy-[1,5]naphthyridin-4-yl)-[1,4]diazepan-1-ylmethyl]-2-oxo-oxazolidin-3-yl}-4H-benzo[1,4]thiazin-3-one;

6-[(R)-5-({[(R)-1-(6-Methoxy-[1,5]naphthyridin-4-yl)-pyrrolidin-3-ylmethyl]-amino}-methyl)-2-oxo-oxazolidin-3-yl]-4H-benzo[1,4]oxazin-3-one;

6-[(R)-5-({[(S)-1-(6-Methoxy-[1,5]naphthyridin-4-yl)-pyrrolidin-3-ylmethyl]-amino}-methyl)-2-oxo-oxazolidin-3-yl]-4H-benzo[1,4]oxazin-3-one;

(R)-5-{[(S)-1-(3-Fluoro-6-methoxy-[1,5]naphthyridin-4-yl)-pyrrolidin-3-ylamino]-methyl}-3-(4-methoxy-phenyl)-oxazolidin-2-one;

(R)-3-(4-Ethoxy-phenyl)-5-{[(S)-1-(3-fluoro-6-methoxy-[1,5]naphthyridin-4-yl)-pyrrolidin-3-ylamino]-methyl}-oxazolidin-2-one;

(R)-3-(4-Difluoromethoxy-phenyl)-5-{[(S)-1-(3-fluoro-6-methoxy-[1,5]naphthyridin-4-yl)-pyrrolidin-3-ylamino]-methyl}-oxazolidin-2-one;

6-((R)-5-{[(S)-1-(6-Methoxy-quinolin-4-yl)-pyrrolidin-3-ylamino]-methyl}-2-oxo-oxazolidin-3-yl)-4H-benzo[1,4]thiazin-3-one;

6-[(R)-5-({[(S)-1-(6-Methoxy-quinolin-4-yl)-pyrrolidin-3-ylmethyl]-amino}-methyl)-2-oxo-oxazolidin-3-yl]-4H-benzo[1,4]thiazin-3-one;

(R)-5-{[1-(6-Methoxy-[1,5]naphthyridin-4-yl)-azetidin-3-ylamino]-methyl}-3-(4-methoxy-phenyl)-oxazolidin-2-one;

(R)-3-(4-Ethoxy-phenyl)-5-{[1-(6-methoxy-[1,5]naphthyridin-4-yl)-azetidin-3-ylamino]-methyl}-oxazolidin-2-one;

(R)-3-(4-Difluoromethoxy-phenyl)-5-{[1-(6-methoxy-[1,5]naphthyridin-4-yl)-azetidin-3-ylamino]-methyl}-oxazolidin-2-one;

6-((R)-5-{[(R)-1-(6-Fluoro-quinolin-4-yl)-pyrrolidin-3-ylamino]-methyl}-2-oxo-oxazolidin-3-yl)-4H-benzo[1,4]thiazin-3-one;

4-((R)-3-{[(R)-2-Oxo-3-(3-oxo-3,4-dihydro-2H-benzo[1,4]thiazin-6-yl)-oxazolidin-5-ylmethyl]-amino}-pyrrolidin-1-yl)-quinoline-6-carbonitrile;

6-((R)-5-{[1-(6-Fluoro-quinolin-4-yl)-piperidin-4-ylamino]-methyl}-2-oxo-oxazolidin-3-yl)-4H-benzo[1,4]thiazin-3-one;

4-(4-{[(R)-2-oxo-3-(3-oxo-3,4-dihydro-2H-benzo[1,4]thiazin-6-yl)-oxazolidin-5-ylmethyl]-amino}-piperidin-1-yl)-quinoline-6-carbonitrile;

6-((R)-5-{[(3S,4S)-4-Methoxy-1-(6-methoxy-[1,5]naphthyridin-4-yl)-pyrrolidin-3-ylamino]-methyl}-2-oxo-oxazolidin-3-yl)-4H-benzo[1,4]oxazin-3-one;

(R)-5-{[1-(6-Methoxy-[1,5]naphthyridin-4-yl)-piperidin-4-ylamino]-methyl}-3-(4-methoxy-phenyl)-oxazolidin-2-one;

(R)-3-(4-Ethoxy-phenyl)-5-{[1-(6-methoxy-[1,5]naphthyridin-4-yl)-piperidin-4-ylamino]-methyl}-oxazolidin-2-one;

(R)-3-(4-Difluoromethoxy-phenyl)-5-{[1-(6-methoxy-[1,5]naphthyridin-4-yl)-piperidin-4-ylamino]-methyl}-oxazolidin-2-one; and 6-[(R)-5-({[1-(6-Methoxy-quinolin-4-yl)-azetidin-3-ylmethyl]-amino}-methyl)-2-oxo-oxazolidin-3-yl]-4H-benzo[1,4]thiazin-3-one;

for the prevention or treatment of a bacterial infection; or
to said compound, or a pharmaceutically acceptable salt thereof, for use in the manufacture of a medicament for the prevention or treatment of a bacterial infection.

11) The present invention also relates to novel antibiotic compounds of formula ($I_N$),

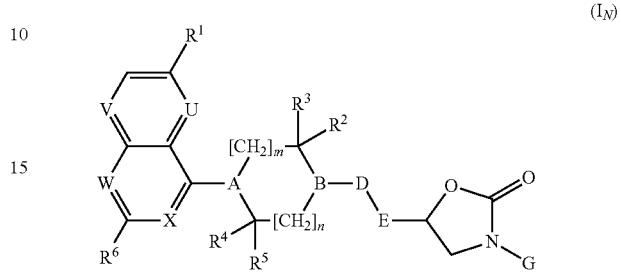

wherein $R^1$ represents hydrogen, alkoxy, halogen or cyano (preferably alkoxy);

one or two (preferably two) of U, V, W, and X (preferably of U, W, and X) represent(s) N and the remaining each represent CH, or, in the case of X, represent $CR^a$;

$R^a$ represents hydrogen or halogen;

$R^6$ represents hydrogen or $(C_1-C_4)$alkyl;

A represents N;

B represents N, D represents a bond, E represents $CH_2$ or CO, $R^2$, $R^3$, $R^4$ and $R^5$ each represent H, m represents the integer 2, and n represents the integer 1; or B represents N; D represents a bond; E represents $CH_2$ or *—$COCH_2$— wherein the asterisk indicates the bond which is attached to B; $R^2$, $R^3$, $R^4$ and $R^5$ each represent H, or $R^4$ and $R^5$ represent H and $R^2$ and $R^3$ together with the carbon atom to which they are attached to form a carbonyl group, or $R^2$ and $R^3$ represent H and $R^4$ and $R^5$ together with the carbon atom to which they are attached to form a carbonyl group, or $R^2$ and $R^4$ represent H and $R^3$ and $R^5$ together form a methylene bridge; and m and n each represent the integer 1; or B represents C(OH), D represents a bond, E represents $CH_2$, $R^2$, $R^3$, $R^4$ and $R^5$ each represent H, and m and n each represent the integer 1; or B represents CH, D represents $NR^b$, E represents $CH_2$, $R^2$, $R^3$, $R^4$ and $R^5$ each represent H, $R^b$ represents H or $(C_1-C_4)$alkyl, and m and n each represent the integer 1; or B represents CH, D represents NH, E represents $CH_2$, $R^2$, $R^3$, $R^4$ and $R^5$ each represent H, m represents the integer 2, and n represents the integer 0; or B represents CH; D represents $NR^c$; E represents $CH_2$, CO or $CH_2CH_2$; $R^2$, $R^3$, $R^4$ and $R^5$ each represent H and $R^c$ represents H or $(C_1-C_4)$alkyl, or $R^c$, $R^3$, $R^4$ and $R^5$ each represent H and $R^2$ represents a group selected from hydroxy, $(C_1-C_4)$alkoxy, $(C_1-C_4)$alkoxy-carbonyl, and carboxy, or $R^3$, $R^4$ and $R^5$ each represent H and $R^c$ forms together with $R^2$ an ethane-1,2-diyl bridge; m represents the integer 1, and n represents the integer 0; or B represents CH; D represents *—$CH(R^d)$—$N(R^e)$— wherein the asterisk indicates the bond which is attached to B; E represents $CH_2$ or CO; $R^d$, $R^2$, $R^3$, $R^4$ and $R^5$ each represent H and $R^e$ represents H or $(C_1-C_4)$alkyl, or $R^e$, $R^3$, $R^4$ and $R^5$ each represent H and $R^d$ and $R^2$ together form a bond, or $R^d$, $R^2$, $R^3$ and $R^5$ each represent H and $R^e$ and $R^4$ together form a methylene bridge, or $R^d$, $R^e$, $R^3$, $R^4$ and $R^5$ each represent H and $R^2$ represents hydroxy; m represents the integer 1, and n represents the integer 0; or B represents CH, D represents *—CONH— wherein the asterisk indicates the bond which is attached to B, E represents $CH_2$, $R^2$, $R^3$, $R^4$ and $R^5$ each represent H, m represents the integer 1, and n represents the integer 0; or B represents CH, D represents NH, E represents $CH_2$ or CO, $R^2$, $R^3$ and $R^5$ each represent H and $R^4$ represents hydroxymethyl, m represents the integer 0, and n represents the integer 1; or B represents C(OH), D represents *—$CH_2$—NH— wherein the asterisk indicates the bond which is attached to B, E represents $CH_2$, $R^2$, $R^3$, $R^4$ and $R^5$ each represent H, m represents the integer 1, and n represents the integer 0; or B represents CH, D represents *—CO—NH— wherein the asterisk indicates the bond which is attached to B, E represents $CH_2$, $R^2$, $R^3$, $R^4$ and $R^5$ each represent H, and m and n each represent the integer 0; or B represents CH, D represents *—$CH_2$—N(R)— wherein the asterisk indicates the bond which is attached to B, E represents $CH_2$, $CH_2CH_2$ or CO, $R^2$, $R^3$, $R^4$ and $R^5$ each represent H, $R^f$ represents H or $(C_1-C_4)$alkyl, and m and n each represent the integer 0; or B represents CH; D represents $NR^g$; E represents $CH_2$, $CH_2CH_2$, CO or *—$COCH_2$—wherein the asterisk indicates the bond which is attached to B; $R^2$, $R^3$, $R^4$ and $R^5$ each represent H; $R^g$ represents H, $(C_1-C_4)$alkyl or $(C_2-C_4)$alkyl which is mono- or di-substituted with hydroxy; and m and n each represent the integer 0;

G represents phenyl which is unsubstituted, mono-substituted in position 3 or 4, or disubstituted in positions 3 and 4, wherein each substituent is independently selected from the group consisting of $(C_1-C_4)$alkyl, $(C_1-C_4)$alkoxy, fluoroalkyl, fluoroalkoxy, cyano, halogen and —$NR^{N1}R^{N2}$; or G represents pyridin-2-yl which is mono-substituted in position 5, wherein the substituent is selected from the group consisting of $(C_1-C_4)$alkyl and fluoroalkyl; or G represents 6,7-dihydro-[1,4]dioxino[2,3-c]pyridazin-3-yl; or G represents a group selected from the group consisting of:

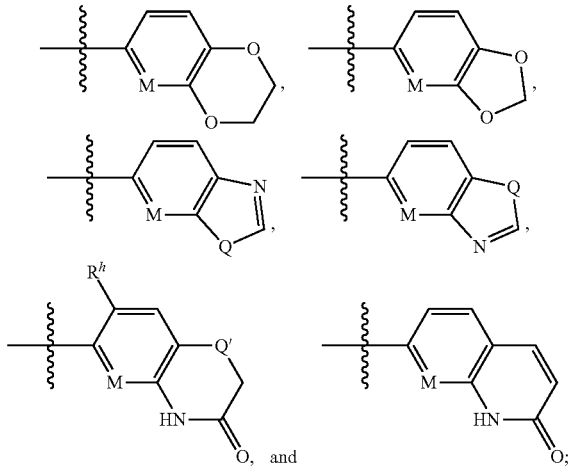

$R^h$ represents hydrogen or fluorine;
M represents CH or N; and Q and Q' independently represent O or S; and $R^{N1}$ and $R^{N2}$ independently represent $(C_1-C_4)$alkyl, or together with the nitrogen that carries them form a pyrrolidine ring.

12) A further embodiment of the invention relates to novel antibiotic compounds of formula ($I_N$) according to embodiment 11), wherein $R^6$ represents hydrogen;

B represents N, D represents a bond, E represents $CH_2$ or CO, $R^2$, $R^3$, $R^4$ and $R^5$ each represent H, m represents the integer 2, and n represents the integer 1; or B represents N; D represents a bond; E represents $CH_2$ or *—$COCH_2$— wherein the asterisk indicates the bond which is attached to B; $R^2$, $R^3$, $R^4$ and $R^5$ each represent H, or $R^4$ and $R^5$ represent H and $R^2$ and $R^3$ together with the carbon atom to which they are attached to form a carbonyl group, or $R^2$ and $R^3$ represent H and $R^4$ and $R^5$ together with the carbon atom to which they are attached to form a carbonyl group; and m and n each represent the integer 1; or B represents C(OH), D represents a bond, E represents $CH_2$, $R^2$, $R^3$, $R^4$ and $R^5$ each represent H, and m and n each represent the integer 1; or B represents CH, D represents $NR^b$, E represents $CH_2$, $R^2$, $R^3$, $R^4$ and $R^5$ each represent H, $R^b$ represents H or $(C_1-C_4)$alkyl, and m and n each represent the integer 1; or B represents CH, D represents NH, E represents $CH_2$, $R^2$, $R^3$, $R^4$ and $R^5$ each represent H, m represents the integer 2, and n represents the integer 0; or B represents CH; D represents $NR^c$; E represents $CH_2$, CO or $CH_2CH_2$; $R^2$, $R^3$, $R^4$ and $R^5$ each represent H and $R^c$ represents H or $(C_1-C_4)$alkyl, or $R^c$, $R^3$, $R^4$ and $R^5$ each represent H and $R^2$ represents a group selected from hydroxy, $(C_1-C_4)$alkoxy, $(C_1-C_4)$alkoxy-carbonyl, and carboxy, or $R^3$, $R^4$ and $R^5$ each represent H and $R^c$ forms together with $R^2$ an ethane-1,2-diyl bridge; m represents the integer 1, and n represents the integer 0; or B represents CH; D represents *—CH($R^d$)—N($R^e$)— wherein the asterisk indicates the bond which is attached to B; E represents $CH_2$ or CO; $R^d$, $R^2$, $R^3$, $R^4$ and $R^5$ each represent H and $R^e$ represents H or $(C_1-C_4)$alkyl, or $R^e$, $R^3$, $R^4$ and $R^5$ each represent H and $R^d$ and $R^2$ together form a bond, or $R^d$, $R^2$, $R^3$ and $R^5$ each represent H and $R^e$ and $R^4$ together form a methylene bridge, or $R^d$, $R^e$, $R^3$, $R^4$ and $R^5$ each represent H and $R^2$ represents hydroxy; m represents the integer 1, and n represents the integer 0; or B represents CH, D represents *—CONH— wherein the asterisk indicates the bond which is attached to B, E represents $CH_2$, $R^2$, $R^3$, $R^4$ and $R^5$ each represent H, m represents the integer 1, and n represents the integer 0; or B represents CH, D represents NH, E represents $CH_2$ or CO, $R^2$, $R^3$ and $R^5$ each represent H and $R^4$ represents hydroxymethyl, m represents the integer 0, and n represents the integer 1; or B represents CH, D represents *—$CH_2$—N($R^f$)— wherein the asterisk indicates the bond which is attached to B, E represents $CH_2$, $CH_2CH_2$ or CO (especially $CH_2$ or CO), $R^2$, $R^3$, $R^4$ and $R^5$ each represent H, $R^1$ represents H or $(C_1-C_4)$alkyl, and m and n each represent the integer 0; or B represents CH; D represents $NR^g$; E represents $CH_2$, $CH_2CH_2$, CO or *—$COCH_2$— wherein the asterisk indicates the bond which is attached to B; $R^2$, $R^3$, $R^4$ and $R^5$ each represent H; $R^g$ represents H, $(C_1-C_4)$alkyl or 2-hydroxyethyl; and m and n each represent the integer 0; and G represents phenyl which is unsubstituted, mono-substituted in position 3 or 4, or disubstituted in positions 3 and 4, wherein each substituent is independently selected from the group consisting of $(C_1\text{-}C_4)$alkyl, $(C_1\text{-}C_4)$alkoxy, fluoroalkyl, fluoroalkoxy, cyano, halogen and $-NR^{N1}R^{N2}$ (preferably from the group consisting of $(C_1\text{-}C_3)$alkyl, $(C_1\text{-}C_3)$alkoxy and halogen); or G represents pyridin-2-yl which is mono-substituted in position 5, wherein the substituent is selected from the group consisting of $(C_1\text{-}C_4)$alkyl and fluoroalkyl; or G represents 6,7-dihydro-[1,4]dioxino[2,3-c]pyridazin-3-yl; or G represents a group selected from the group consisting of:

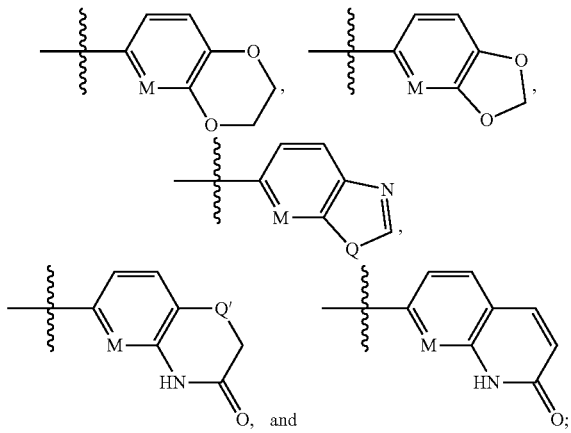

wherein
M represents CH or N; and Q and Q' independently represent O or S.

13) A further embodiment of the invention relates to novel antibiotic compounds of formula $(I_N)$ according to embodiment 11), which are also compounds of formula $(I_{N\text{-}P1})$,

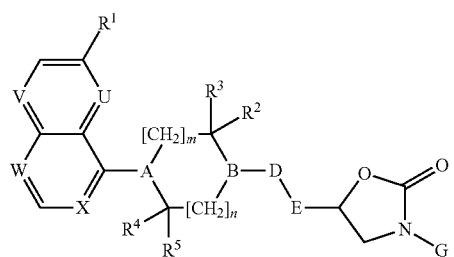

(I$_{N\text{-}P1}$)

wherein
$R^1$ represents alkoxy, halogen or cyano (preferably alkoxy); one or two (preferably two) of U, V, W, and X (preferably of U, W, and X) represent(s) N and the remaining each represent CH, or, in the case of X, represent $CR^a$;
$R^a$ represents hydrogen or halogen (preferably hydrogen);
A represents N;
  B represents N, D represents a bond, E represents $CH_2$, $R^2$, $R^3$, $R^4$ and $R^5$ each represent H, and m and n each represent the integer 1; or
  B represents C(OH), D represents a bond, E represents $CH_2$, $R^2$, $R^3$, $R^4$ and $R^5$ each represent H, and m and n each represent the integer 1; or
  B represents CH, D represents *—$CH_2$—NH— wherein the asterisk indicates the bond which is attached to B, E represents $CH_2$ or CO, $R^2$, $R^3$, $R^4$ and $R^5$ each represent H, and m and n each represent the integer 0; or
  B represents CH, D represents NH, E represents $CH_2$, $R^2$, $R^3$, $R^4$ and $R^5$ each represent H, m represents the integer 1, and n represents the integer 0;

G represents phenyl which is unsubstituted, mono-substituted in position 3 or 4, or disubstituted in positions 3 and 4, wherein each substituent is independently selected from the group consisting of $(C_1\text{-}C_4)$alkyl, $(C_1\text{-}C_4)$alkoxy, fluoroalkyl, fluoroalkoxy, cyano, halogen and $-NR^{N1}R^{N2}$ (preferably from the group consisting of $(C_1\text{-}C_3)$alkyl, $(C_1\text{-}C_3)$alkoxy and halogen); or G represents pyridin-2-yl which is mono-substituted in position 5, wherein the substituent is selected from the group consisting of $(C_1\text{-}C_4)$alkyl and fluoroalkyl; or G represents a group selected from the group consisting of:

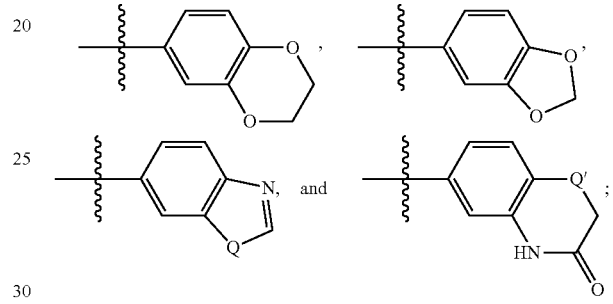

wherein
Q and Q' independently represent O or S; and
$R^{N1}$ and $R^{N2}$ independently represent $(C_1\text{-}C_4)$alkyl, or together with the nitrogen that carries them form a pyrrolidine ring.

The following paragraphs provide definitions of the various chemical moieties for the compounds according to the invention and are intended to apply uniformly throughout the specification and claims, unless an otherwise expressly set out definition provides a broader or narrower definition.

In this patent application, a bond interrupted by a wavy line shows the point of attachment of the radical drawn. For example, the radical drawn below

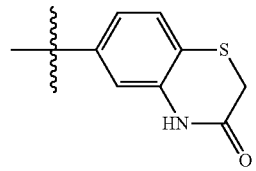

is the 4H-benzo[1,4]thiazin-3-on-6-yl group.

The term "halogen" refers to fluorine, chlorine, bromine or iodine; especially to fluorine, chlorine or bromine; preferably to fluorine or chlorine. In another embodiment, the term halogen as used for the substituents $R^a$ and $R^1$ preferably refers to fluorine.

The term "alkyl", used alone or in combination, refers to a straight or branched chain alkyl group containing one to four carbon atoms. The term "$(C_x\text{-}C_y)$alkyl" (x and y each being an integer), refers to an alkyl group as defined before containing x to y carbon atoms. For example a $(C_1\text{-}C_4)$alkyl group contains from one to four carbon atoms. Representative examples of alkyl groups include methyl, ethyl, n-propyl, iso-propyl, n-butyl, iso-butyl, sec-butyl and tert-butyl. Preferred are methyl, ethyl, n-propyl and iso-propyl. Most preferred are ethyl and methyl.

The term "$(C_2-C_4)$alkyl which is mono- or di-substituted with hydroxy" means a $(C_2-C_4)$alkyl group as defined before, wherein one or two hydrogen atoms have been replaced by hydroxy. Examples of such groups are 2-hydroxyethyl, 3-hydroxypropyl, 1,3-dihydroxy-propan-2-yl and 2,3-dihydroxypropan-1-yl. Preferred is 2-hydroxyethyl.

The term "alkoxy", used alone or in combination, refers to an alkyl-O— group wherein the alkyl group is as defined before. The term "$(C_x-C_y)$alkoxy" (x and y each being an integer) refers to an alkoxy group as defined before containing x to y carbon atoms. For example a $(C_1-C_4)$alkoxy group contains from one to four carbon atoms. Representative examples of alkoxy groups include methoxy, ethoxy, n-propoxy, iso-propoxy, n-butoxy, iso-butoxy, sec-butoxy and tert-butoxy. Preferred are ethoxy and methoxy. Most preferred is methoxy.

The term "fluoroalkyl" refers to an alkyl group as defined before containing one to three carbon atoms in which one or more (and possibly all) hydrogen atoms have been replaced with fluorine. The term "$(C_x-C_y)$fluoroalkyl" (x and y each being an integer) refers to a fluoroalkyl group as defined before containing x to y carbon atoms. For example a $(C_1-C_3)$ fluoroalkyl group contains from one to three carbon atoms in which one to seven hydrogen atoms have been replaced with fluorine. Representative examples of fluoroalkyl groups include trifluoromethyl and 2,2,2-trifluoroethyl. Preferred is trifluoromethyl.

The term "fluoroalkoxy" refers to an alkoxy group as defined before containing one to three carbon atoms in which one or more (and possibly all) hydrogen atoms have been replaced with fluorine. The term "$(C_x-C_y)$fluoroalkoxy" (x and y each being an integer) refers to a fluoroalkoxy group as defined before containing x to y carbon atoms. For example a $(C_1-C_3)$ fluoroalkoxy group contains from one to three carbon atoms in which one to seven hydrogen atoms have been replaced with fluorine. Representative examples of fluoroalkoxy groups include trifluoromethoxy, difluoromethoxy and 2,2,2-trifluoroethoxy. Preferred are $(C_1)$ fluoroalkoxy groups such as trifluoromethoxy and difluoromethoxy. Most preferred is trifluoromethoxy.

Examples of G representing "phenyl which is unsubstituted, mono-substituted in position 3 or 4, or disubstituted in positions 3 and 4", wherein the substituents are as defined for formula (I) and/or formula $(I_N)$, are selected from the group consisting of phenyl, 3-trifluoromethoxy-phenyl, 4-trifluoromethoxy-phenyl, 4-bromo-3-fluoro-phenyl, 3,4-dimethoxy-phenyl, 4-fluoro-phenyl, 3-trifluoromethyl-phenyl, 3-chloro-4-fluoro-phenyl, 4-methyl-3-trifluoromethyl-phenyl, 4-(difluoromethoxy)-phenyl, 3-cyano-phenyl, 4-(pyrrolidin-1-yl)-phenyl, 3-methoxy-phenyl, 4-n-propyl-phenyl, 4-ethyl-phenyl, 3,4-dimethyl-phenyl, 3-chloro-4-methoxy-phenyl, 3,4-difluoro-phenyl, 4-fluoro-3-methyl-phenyl, 4-bromo-3-methyl-phenyl, 3-bromo-4-methyl-phenyl, 4-methoxy-3-trifluoromethyl-phenyl, 3-dimethylamino-phenyl and 3-fluoro-4-methyl-phenyl. In addition to the above groups, a further example is 3-fluoro-phenyl. Preferred groups are mono-substituted in position 3 or 4, or disubstituted in positions 3 and 4, wherein the substituents are as defined for formula (I) and/or formula $(I_N)$.

Preferably the substituents are independently selected from the group consisting of $(C_1-C_3)$alkyl, $(C_1-C_3)$alkoxy and halogen.

Examples of G representing "pyridin-2-yl which is mono-substituted in position 5, wherein the substituent is selected from the group consisting of $(C_1-C_4)$alkyl and fluoroalkyl" are 3-methyl-pyridin-6-yl and 3-trifluoromethyl-pyridin-6-yl.

Examples of G representing "a group selected from the group consisting of:

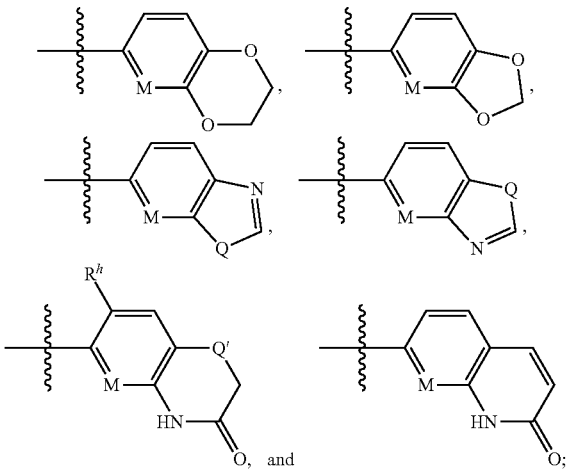

wherein
$R^h$ represents hydrogen or fluorine;
M represents CH or N; and Q and Q' independently represent O or S",
as used for formula (I) and/or formula $(I_N)$, are 2,3-dihydro-benzo[1,4]dioxin-6-yl, benzo[1,3]dioxol-5-yl, 3-oxo-3,4-dihydro-2H-benzo[1,4]oxazin-6-yl, 3-oxo-3,4-dihydro-2H-benzo[1,4]thiazin-6-yl, 3-oxo-3,4-dihydro-2H-pyrido[3,2-b][1,4]oxazin-6-yl, 7-fluoro-3-oxo-3,4-dihydro-2H-benzo[1,4]thiazin-6-yl, 2-oxo-1,2-dihydro-quinolin-7-yl, benzothiazol-6-yl, benzothiazol-5-yl and benzooxazol-6-yl. In another embodiment, examples are 2,3-dihydro-benzo[1,4]dioxin-6-yl, benzo[1,3]dioxol-5-yl, 3-oxo-3,4-dihydro-2H-benzo[1,4]oxazin-6-yl, 3-oxo-3,4-dihydro-2H-benzo[1,4]thiazin-6-yl, 3-oxo-3,4-dihydro-2H-pyrido[3,2-b][1,4]oxazin-6-yl, 2-oxo-1,2-dihydro-quinolin-7-yl, benzothiazol-6-yl and benzooxazol-6-yl. In yet another embodiment, examples are 2,3-dihydro-benzo[1,4]dioxin-6-yl, benzo[1,3]dioxol-5-yl, 3-oxo-3,4-dihydro-2H-benzo[1,4]oxazin-6-yl, 3-oxo-3,4-dihydro-2H-benzo[1,4]thiazin-6-yl, 3-oxo-3,4-dihydro-2H-pyrido[3,2-b][1,4]oxazin-6-yl, 2-oxo-1,2-dihydro-quinolin-7-yl and benzothiazol-6-yl. Preferred are 2,3-dihydro-benzo[1,4]dioxin-6-yl, 3-oxo-3,4-dihydro-2H-benzo[1,4]oxazin-6-yl, 3-oxo-3,4-dihydro-2H-benzo[1,4]thiazin-6-yl, 3-oxo-3,4-dihydro-2H-pyrido[3,2-b][1,4]oxazin-6-yl and 2-oxo-1,2-dihydro-quinolin-7-yl. In yet another embodiment, preferred are 3-oxo-3,4-dihydro-2H-benzo[1,4]oxazin-6-yl, 3-oxo-3,4-dihydro-2H-benzo[1,4]thiazin-6-yl, 3-oxo-3,4-dihydro-2H-pyrido[3,2-b][1,4]oxazin-6-yl, and 7-fluoro-3-oxo-3,4-dihydro-2H-benzo[1,4]thiazin-6-yl.

Further examples of such groups are the following groups [as used for the substituent G in formula $(I_{P1})$, $(I_{N-P1})$ and/or formula $(I_{CE-P1})$], wherein G represents "a group selected from the group consisting of:

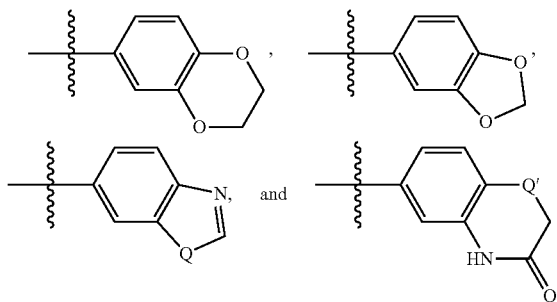

wherein Q and Q' independently represent O or S".

Preferred examples of such groups are 2,3-dihydro-benzo[1,4]dioxin-6-yl, benzo[1,3]dioxol-5-yl, 3-oxo-3,4-dihydro-2H-benzo[1,4]oxazin-6-yl, 3-oxo-3,4-dihydro-2H-benzo[1,4]thiazin-6-yl, benzothiazol-6-yl and benzooxazol-6-yl. More preferred are 2,3-dihydro-benzo[1,4]dioxin-6-yl, benzo[1,3]dioxol-5-yl, 3-oxo-3,4-dihydro-2H-benzo[1,4]thiazol-5-yl and benzothiazol-6-yl.

An example of $R^2$ representing $(C_1-C_4)$alkoxy-carbonyl is ethoxy-carbonyl.

Examples of —$NR^{N1}R^{N2}$ groups are dimethylamino and pyrrolidin-1-yl.

In case a compound of formula (I) or ($I_N$) according to embodiments i) or viii) contains a fragment

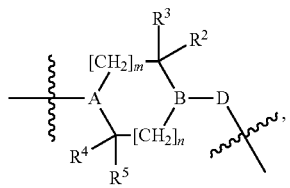

that is such that:

A represents N; B represents CH; D represents $NR^c$; $R^3$, $R^4$ and $R^5$ each represent H and $R^c$ forms together with $R^2$ an ethane-1,2-diyl bridge; m represents the integer 1, and n represents the integer 0;
then such fragment is a hexahydro-pyrrolo[3,4-b]pyrrol-1,5-diyl group (preferably a (3aR*,6aR*)-hexahydro-pyrrolo[3,4-b]pyrrol-1,5-diyl group), wherein A corresponds to the nitrogen atom in position 5;

A represents N; B represents CH; D represents *—CH($R^d$)—N($R^e$)— wherein the asterisk indicates the bond which is attached to B; $R^e$, $R^3$, $R^4$ and $R^5$ each represent H and $R^d$ and $R^2$ together form a bond; m represents the integer 1, and n represents the integer 0;
then such fragment is 6-N($R^e$)-3-aza-bicyclo[3.1.0]hexan-3-yl (preferably 6-N($R^e$)—(1α,5α,6α)-3-aza-bicyclo[3.1.0]hexan-3-yl), wherein A corresponds to the nitrogen atom in position 3;

A represents N; B represents CH; D represents *—CH($R^d$)—N($R^e$)— wherein the asterisk indicates the bond which is attached to B; $R^d$, $R^2$, $R^3$ and $R^5$ each represent H and $R^e$ and $R^4$ together form a methylene bridge; m represents the integer 1, and n represents the integer 0;
then such fragment is a hexahydro-pyrrolo[3,4-b]pyrrol-1,5-diyl group (preferably a (3aR*,6aR*)-hexahydro-pyrrolo[3,4-b]pyrrol-1,5-diyl group), wherein A corresponds to the nitrogen atom in position 1;

A represents N; B represents N; D represents a bond; $R^2$ and $R^4$ represent H and $R^3$ and $R^5$ together form a methylene bridge; and m and n each represent the integer 1;
then such fragment is a 2,5-diaza-bicyclo[2.2.1]hept-2,5-diyl group (preferably a (1S,4S)-2,5-diaza-bicyclo[2.2.1]hept-2,5-diyl group), wherein A corresponds to the nitrogen atom in position 5.

In the following, further embodiments of the invention are described:

14) A further embodiment of the invention relates to compounds according to any one of embodiments 11) to 13), wherein the stereocenter at position 5 of the oxazolidin-2-one ring is in (R)-configuration:

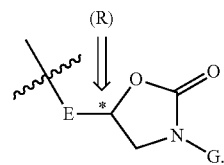

15) A further embodiment of the invention relates to compounds according to any one of embodiments 11) to 13), wherein the stereocenter at position 5 of the oxazolidin-2-one ring is in (S)-configuration:

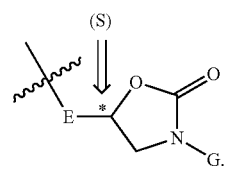

16) A further embodiment of the invention relates to compounds according to any one of embodiments 11), 14) or 15), wherein one of U, V, W, and X (preferably one of U, V and W, and notably W) represents N and the remaining each represent CH or, in the case of X, represent $CR^a$; $R^1$ represents hydrogen, alkoxy, halogen or cyano (notably hydrogen or alkoxy); and $R^6$ represents hydrogen or $(C_1-C_4)$alkyl (especially methyl).

17) A further embodiment of the invention relates to compounds according to any one of embodiments 11) or 14) to 16), wherein $R^6$ represents hydrogen.

18) A further embodiment of the invention relates to compounds according to any one of embodiments 11) to 17), wherein $R^1$ represents alkoxy (especially methoxy).

19) A further embodiment of the invention relates to compounds according to any one of embodiments 11) to 17), wherein two of U, W, and X (preferably U and W or W and X) represent N and the remaining and V each represent CH, or, in the case of X, represent $CR^a$; wherein $R^a$ represents hydrogen or fluorine.

20) A further embodiment of the invention relates to compounds according to any one of embodiments 11) to 17), wherein U and W each represent N; V represents CH and X represents $CR^a$; wherein $R^a$ represents hydrogen or fluorine (especially fluorine).

21) A further embodiment of the invention relates to compounds according to any one of embodiments 11) to 17), wherein W and X each represent N; and U and V each represent CH.

22) A further embodiment of the invention relates to compounds according to any one of embodiments 11) to 17), 19) or 20) wherein $R^a$ represents hydrogen.

23) A further embodiment of the invention relates to compounds according to any one of embodiments 11), 12) or 14) to 22), wherein A represents N; and
- B represents N, D represents a bond, E represents $CH_2$ or CO, $R^2$, $R^3$, $R^4$ and $R^5$ each represent H, m represents the integer 2, and n represents the integer 1; or
- B represents N; D represents a bond; E represents $CH_2$ or *—$COCH_2$— wherein the asterisk indicates the bond which is attached to B; $R^2$, $R^3$, $R^4$ and $R^5$ each represent H; and m and n each represent the integer 1; or
- B represents C(OH), D represents a bond, E represents $CH_2$, $R^2$, $R^3$, $R^4$ and $R^5$ each represent H, and m and n each represent the integer 1; or
- B represents CH, D represents $NR^b$, E represents $CH_2$, $R^2$, $R^3$, $R^4$ and $R^5$ each represent H, $R^b$ represents H or $(C_1$-$C_4)$alkyl, and m and n each represent the integer 1; or
- B represents CH; D represents $NR^c$; E represents $CH_2$, CO or $CH_2CH_2$; $R^2$, $R^3$, $R^4$ and $R^5$ each represent H and $R^c$ represents H or $(C_1$-$C_4)$alkyl, or $R^3$, $R^4$ and $R^5$ each represent H and $R^c$ forms together with $R^2$ an ethane-1,2-diyl bridge; m represents the integer 1, and n represents the integer 0; or
- B represents CH; D represents *—$CH(R^d)$—$N(R^e)$— wherein the asterisk indicates the bond which is attached to B; E represents $CH_2$ or CO; $R^d$, $R^2$, $R^3$, $R^4$ and $R^5$ each represent H and $R^e$ represents H or $(C_1$-$C_4)$alkyl, or $R^e$, $R^3$, $R^4$ and $R^5$ each represent H and $R^d$ and $R^2$ together form a bond; m represents the integer 1, and n represents the integer 0; or
- B represents CH, D represents *—CONH— wherein the asterisk indicates the bond which is attached to B, E represents $CH_2$, $R^2$, $R^3$, $R^4$ and $R^5$ each represent H, m represents the integer 1, and n represents the integer 0; or
- B represents CH, D represents *—$CH_2$—$N(R^f)$— wherein the asterisk indicates the bond which is attached to B, E represents $CH_2$, $CH_2CH_2$ or CO (especially $CH_2$ or $CH_2CH_2$), $R^2$, $R^3$, $R^4$ and $R^5$ each represent H, $R^f$ represents H or $(C_1$-$C_4)$alkyl, and m and n each represent the integer 0; or
- B represents CH; D represents $NR^g$; E represents $CH_2$, $CH_2CH_2$ or CO; $R^2$, $R^3$, $R^4$ and $R^5$ each represent H; $R^g$ represents H, $(C_1$-$C_4)$alkyl or 2-hydroxyethyl; and m and n each represent the integer 0.

24) A further embodiment of the invention relates to compounds according to any one of embodiments 11), 12) or 14) to 22), wherein A represents N; and
- B represents CH; D represents $NR^c$; E represents $CH_2$, CO or $CH_2CH_2$; $R^3$, $R^4$ and $R^5$ each represent H and $R^c$ forms together with $R^2$ an ethane-1,2-diyl bridge; m represents the integer 1, and n represents the integer 0; or
- B represents CH; D represents *—$CH(R^d)$—$N(R^e)$— wherein the asterisk indicates the bond which is attached to B; E represents $CH_2$ or CO; $R^e$, $R^3$, $R^4$ and $R^5$ each represent H and $R^d$ and $R^2$ together form a bond, or $R^d$, $R^2$, $R^3$ and $R^5$ each represent H and $R^e$ and $R^4$ together form a methylene bridge; m represents the integer 1, and n represents the integer 0.

25) A further embodiment of the invention relates to compounds according to any one of embodiments 11) to 23), wherein $R^2$, $R^3$, $R^4$ and $R^5$ each represent H.

26) A further embodiment of the invention relates to compounds according to any one of embodiments 11), 12) or 14) to 25), wherein E represents $CH_2$ or $CH_2CH_2$.

27) A further embodiment of the invention relates to compounds according to any one of embodiments 11) to 25), wherein E represents $CH_2$.

28) A further embodiment of the invention relates to compounds according to any one of embodiments 11) to 25), wherein E represents CO.

29) A further embodiment of the invention relates to compounds according to any one of embodiments 11) to 28), wherein A represents N and B represents N.

30) A further embodiment of the invention relates to compounds according to any one of embodiments 11) to 28), wherein A represents N and B represents CH or C(OH).

31) A further embodiment of the invention relates to compounds according to any one of embodiments 11) to 28) or 30), wherein m represents the integer 0 or 1, and n represents the integer 0.

32) A further embodiment of the invention relates to compounds according to any one of embodiments 11) to 28) or 30), wherein m represents the integer 1, and n represents the integer 0 or 1.

33) A further embodiment of the invention relates to compounds according to any one of embodiments 11), 12), 14) to 23), 25), or 27) to 29) wherein the ring

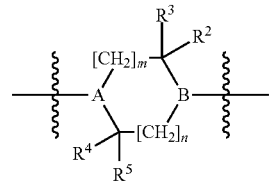

is a seven-membered ring, i.e. the sum of the integers m and n is 3 (especially m represents the integer 2 and n represents the integer 1).

34) A further embodiment of the invention relates to compounds according to any one of embodiments 11) to 23), 25), or 27) to 30), wherein the ring

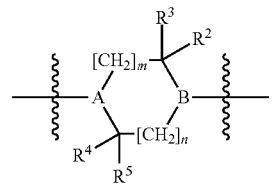

is a six-membered ring, i.e. the sum of the integers m and n is 2 (especially m and n each represent the integer 1).

35) A further embodiment of the invention relates to compounds according to any one of embodiments 11) to 28), wherein the ring

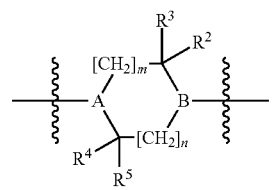

is a five-membered ring, i.e. the sum of the integers m and n is 1 (especially m represents the integer 1 and n represents the integer 0). In one variant of the invention, in case B is a stereocenter and represents CH, the absolute configuration at the stereocenter B of said five-membered ring is (R). In another variant of the invention, the absolute configuration at said stereocenter B of said five-membered ring is (S).

36) A further embodiment of the invention relates to compounds according to any one of embodiments 11) to 28), wherein the ring

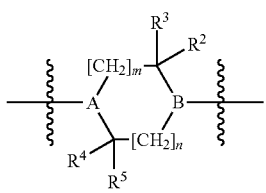

is a four-membered ring, i.e. m and n each represent the integer 0.

37) A further embodiment of the invention relates to compounds according to any one of embodiments 11) or 14) to 36), wherein
G represents phenyl which is mono-substituted in position 3 or 4, or disubstituted in positions 3 and 4, wherein each substituent is independently selected from the group consisting of $(C_1-C_4)$alkyl, $(C_1-C_4)$alkoxy, fluoroalkyl, fluoroalkoxy and halogen; or
G represents 6,7-dihydro-[1,4]dioxino[2,3-c]pyridazin-3-yl; or
G represents a group selected from the group consisting of:

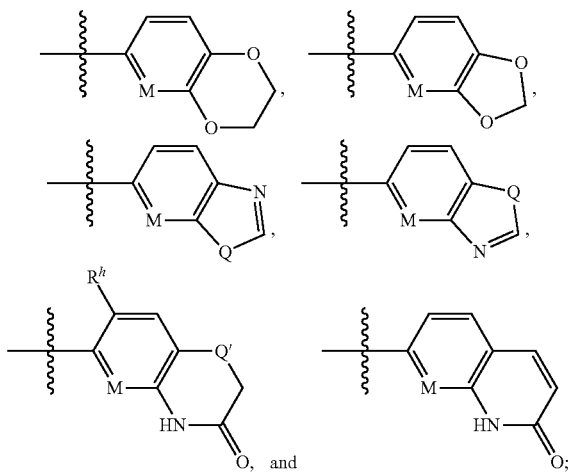

wherein
$R^h$ represents hydrogen or fluorine;
M represents CH or N; and Q and Q' independently represent O or S.

38) A further embodiment of the invention relates to compounds according to any one of embodiments 11), 12) or 14) to 37), wherein
G represents phenyl which is mono-substituted in position 3 or 4, or disubstituted in positions 3 and 4, wherein each substituent is independently selected from the group consisting of $(C_1-C_4)$alkyl, $(C_1-C_4)$alkoxy, fluoroalkyl, fluoroalkoxy and halogen; or
G represents 6,7-dihydro-[1,4]dioxino[2,3-c]pyridazin-3-yl; or
G represents a group selected from the group consisting of:

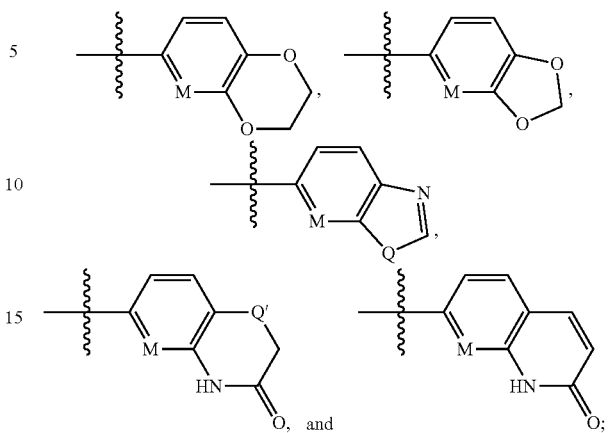

wherein
M represents CH or N; and Q and Q' independently represent O or S.

39) A further embodiment of the invention relates to compounds according to any one of embodiments 11) to 38), wherein
G represents phenyl which is mono-substituted in position 3 or 4, or disubstituted in positions 3 and 4, wherein each substituent is independently selected from the group consisting of $(C_1-C_4)$alkyl, $(C_1-C_4)$alkoxy, fluoroalkyl, fluoroalkoxy and halogen; or
G represents a group selected from the group consisting of:

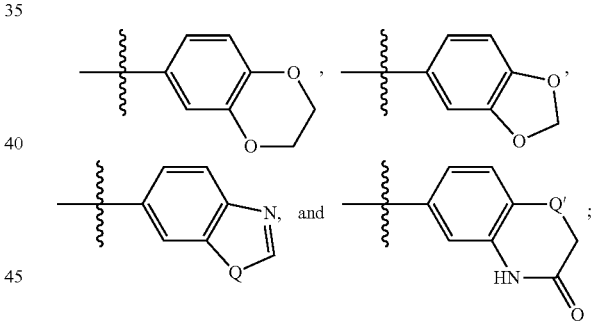

wherein Q and Q' independently represent O or S.

40) A further embodiment of the invention relates to compounds according to any one of embodiments 11) to 39), wherein G represents phenyl which is mono-substituted in position 3 or 4, or disubstituted in positions 3 and 4, wherein each substituent is independently selected from the group consisting of $(C_1-C_4)$alkyl, $(C_1-C_4)$alkoxy, fluoroalkyl, fluoroalkoxy and halogen.

41) A further embodiment of the invention relates to compounds according to any one of embodiments 11) to 40), wherein G represents phenyl which is mono-substituted in position 4, or disubstituted in positions 3 and 4, wherein each substituent is independently selected from the group consisting of $(C_1-C_3)$alkyl, $(C_1-C_3)$alkoxy, fluoroalkyl, fluoroalkoxy and halogen.

42) A further embodiment of the invention relates to compounds according to any one of embodiments 11) to 41), wherein G represents phenyl which is mono-substituted in position 4, or disubstituted in positions 3 and 4, wherein the substituent in position 4 is selected from the group consisting of $(C_1-C_3)$alkyl (especially methyl and ethyl), methoxy, trifluoromethyl, $(C_1)$ fluoroalkoxy and halogen.

43) A further embodiment of the invention relates to compounds according to any one of embodiments 11) or 14) to 37), wherein
G represents 6,7-dihydro-[1,4]dioxino[2,3-c]pyridazin-3-yl; or
G represents a group selected from the group consisting of:

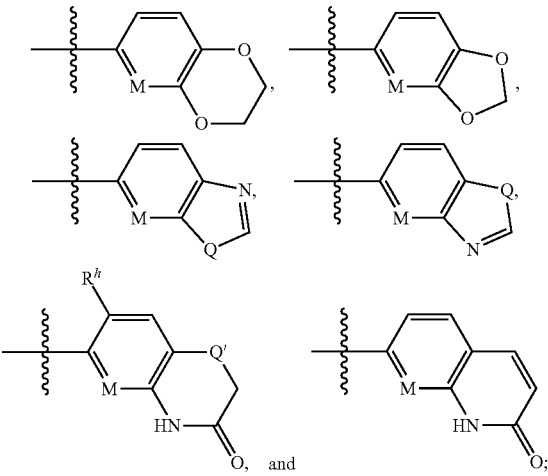

wherein
$R^h$ represents hydrogen or fluorine;
M represents CH or N; and Q and Q' independently represent O or S.

44) A further embodiment of the invention relates to compounds according to any one of embodiments 11), 12) or 14) to 38), wherein
G represents 6,7-dihydro-[1,4]dioxino[2,3-c]pyridazin-3-yl; or
G represents a group selected from the group consisting of:

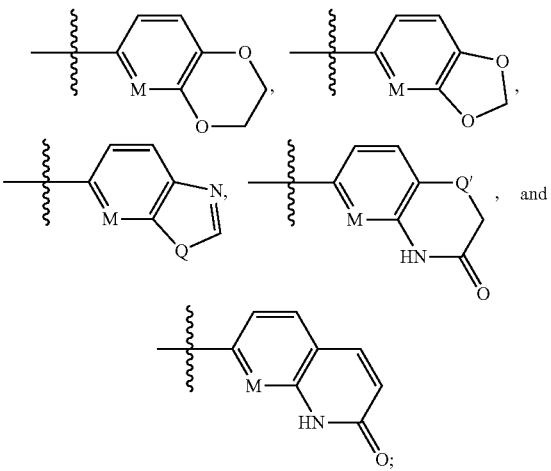

wherein
M represents CH or N; and Q and Q' independently represent O or S.

45) A further embodiment of the invention relates to compounds according to any one of embodiments 11) to 39), 43) or 44), wherein
G represents a group selected from the group consisting of:

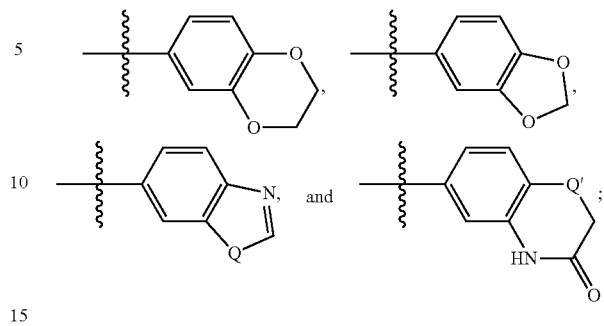

wherein Q and Q' independently represent O or S.

46) A further embodiment of the invention relates to compounds according to any one of embodiments 11), 14) to 37) or 43) wherein G represents a fused benzene or pyridine ring of the formula

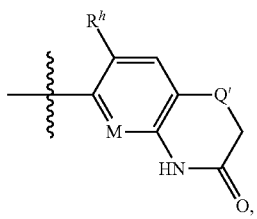

wherein
$R^h$ represents hydrogen or fluorine;
M represents CH or N; and Q' represents O or S.

47) A further embodiment of the invention relates to compounds according to any one of embodiments 11), 12), 14) to 38), 43), 44) or 46) wherein G represents a fused benzene or pyridine ring of the formula

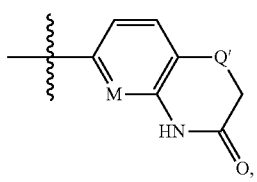

wherein M represents CH or N; and Q' represents O or S.

48) A further embodiment of the invention relates to compounds according to any one of embodiments 11), 12), 14) to 38), 43), 44), 46) or 47), wherein M represents CH.

49) A further embodiment of the invention relates to compounds according to any one of embodiments 11), 12), 14) to 38), 43), 44), 46) or 47), wherein M represents N.

50) A further embodiment of the invention relates to compounds according to any one of embodiments 11) to 39) or 43) to 49), wherein Q' represents S.

51) A further embodiment of the invention relates to compounds according to any one of embodiments 11) to 39) or 43) to 49), wherein Q' represents O.

52) A further embodiment of the invention relates to compounds according to any one of embodiments 11), 37), 43), 46), 48) or 50), wherein $R^h$ represents hydrogen.

53) A further embodiment of the invention relates to compounds according to any one of embodiments 11) to 39), 43) to 45) or 48), wherein Q represents S.

54) A further embodiment of the invention relates to compounds according to any one of embodiments 11) to 38), 43) or 44), wherein G represents 2,3-dihydro-benzo[1,4]dioxin-6-yl, 3-oxo-3,4-dihydro-2H-benzo[1,4]oxazin-6-yl, 3-oxo-3,4-dihydro-2H-benzo[1,4]thiazin-6-yl, 3-oxo-3,4-dihydro-2H-pyrido[3,2-b][1,4]oxazin-6-yl or 2-oxo-1,2-dihydro-quinolin-7-yl.

55) A further embodiment of the invention relates to compounds according to any one of embodiments 11), 14) to 37), 43) or 46), wherein G represents 3-oxo-3,4-dihydro-2H-benzo[1,4]oxazin-6-yl, 3-oxo-3,4-dihydro-2H-benzo[1,4]thiazin-6-yl, 3-oxo-3,4-dihydro-2H-pyrido[3,2-b][1,4]oxazin-6-yl, or 7-fluoro-3-oxo-3,4-dihydro-2H-benzo[1,4]thiazin-6-yl.

56) The invention also relates to compounds of formula (I) according to embodiment 1), or pharmaceutically acceptable salts thereof, wherein the meanings of the substituents or groups are replaced by the meaning(S) given for said substituents or groups in any one of embodiments 11) to 55); for the prevention or treatment of a bacterial infection; or to said compounds, or pharmaceutically acceptable salts thereof, for use in the manufacture of a medicament for the prevention or treatment of a bacterial infection.

57) Preferred compounds of formula ($I_N$) as defined in embodiment 11) are selected from the compounds given in embodiment 7), with the exception of:
3-(2,3-Dihydro-benzo[1,4]dioxin-6-yl)-5-[4-hydroxy-4-(6-methoxy-[1,5]naphthyridin-4-yl)-piperidin-1-ylmethyl]-oxazolidin-2-one;
6-{(R)-5-[4-Hydroxy-4-(6-methoxy-quinolin-4-yl)-piperidin-1-ylmethyl]-2-oxo-oxazolidin-3-yl}-4H-benzo[1,4]thiazin-3-one; and
6-{(R)-5-[4-(3-Fluoro-6-methoxy-[1,5]naphthyridin-4-yl)-4-hydroxy-piperidin-1-ylmethyl]-2-oxo-oxazolidin-3-yl}-4H-benzo[1,4]thiazin-3-one.

58) In addition to the compounds of embodiment 57), additional preferred compounds of formula ($I_N$) as defined in embodiment 11) are selected from the compounds given in embodiment 8), with the exception of:
6-{(R)-5-[4-Hydroxy-4-(6-methoxy-quinolin-4-yl)-piperidin-1-ylmethyl]-2-oxo-oxazolidin-3-yl}-4H-benzo[1,4]oxazin-3-one.

59) In another embodiment, preferred compounds of formula ($I_N$) as defined in embodiment 11) are selected from the compounds given in embodiment 9), with the exception of:
(R)-3-(2,3-Dihydro-benzo[1,4]dioxin-6-yl)-5-[4-hydroxy-4-(6-methoxy-[1,5]naphthyridin-4-yl)-piperidin-1-ylmethyl]-oxazolidin-2-one;
(S)-3-(2,3-Dihydro-benzo[1,4]dioxin-6-yl)-5-[4-hydroxy-4-(6-methoxy-[1,5]naphthyridin-4-yl)-piperidin-1-ylmethyl]-oxazolidin-2-one;
6-{(R)-5-[4-Hydroxy-4-(6-methoxy-quinolin-4-yl)-piperidin-1-ylmethyl]-2-oxo-oxazolidin-3-yl}-4H-benzo[1,4]thiazin-3-one; and
6-{(R)-5-[4-(3-Fluoro-6-methoxy-[1,5]naphthyridin-4-yl)-4-hydroxy-piperidin-1-ylmethyl]-2-oxo-oxazolidin-3-yl}-4H-benzo[1,4]thiazin-3-one.

60) In addition to the compounds of embodiment 59), additional preferred compounds of formula ($I_N$) as defined in embodiment 11) are selected from the compounds given in embodiment 10), with the exception of:
6-{(R)-5-[4-Hydroxy-4-(6-methoxy-quinolin-4-yl)-piperidin-1-ylmethyl]-2-oxo-oxazolidin-3-yl}-4H-benzo[1,4]oxazin-3-one.

61) The invention also relates to compounds of formula (I), wherein A represents C(OH) and B represents N, which are selected from:
3-(2,3-Dihydro-benzo[1,4]dioxin-6-yl)-5-[4-hydroxy-4-(6-methoxy-[1,5]naphthyridin-4-yl)-piperidin-1-ylmethyl]-oxazolidin-2-one;
6-{(R)-5-[4-Hydroxy-4-(6-methoxy-quinolin-4-yl)-piperidin-1-ylmethyl]-2-oxo-oxazolidin-3-yl}-4H-benzo[1,4]thiazin-3-one; and
6-{(R)-5-[4-(3-Fluoro-6-methoxy-[1,5]naphthyridin-4-yl)-4-hydroxy-piperidin-1-ylmethyl]-2-oxo-oxazolidin-3-yl}-4H-benzo[1,4]thiazin-3-one; and
6-{(R)-5-[4-Hydroxy-4-(6-methoxy-quinolin-4-yl)-piperidin-1-ylmethyl]-2-oxo-oxazolidin-3-yl}-4H-benzo[1,4]oxazin-3-one.

61) The invention also relates to compounds of formula (I), wherein A represents C(OH) and B represents N, which are selected from:
(R)-3-(2,3-Dihydro-benzo[1,4]dioxin-6-yl)-5-[4-hydroxy-4-(6-methoxy-[1,5]naphthyridin-4-yl)-piperidin-1-ylmethyl]-oxazolidin-2-one;
(S)-3-(2,3-Dihydro-benzo[1,4]dioxin-6-yl)-5-[4-hydroxy-4-(6-methoxy-[1,5]naphthyridin-4-yl)-piperidin-1-ylmethyl]-oxazolidin-2-one;
6-{(R)-5-[4-Hydroxy-4-(6-methoxy-quinolin-4-yl)-piperidin-1-ylmethyl]-2-oxo-oxazolidin-3-yl}-4H-benzo[1,4]thiazin-3-one;
6-{(R)-5-[4-(3-Fluoro-6-methoxy-[1,5]naphthyridin-4-yl)-4-hydroxy-piperidin-1-ylmethyl]-2-oxo-oxazolidin-3-yl}-4H-benzo[1,4]thiazin-3-one; and
6-{(R)-5-[4-Hydroxy-4-(6-methoxy-quinolin-4-yl)-piperidin-1-ylmethyl]-2-oxo-oxazolidin-3-yl}-4H-benzo[1,4]oxazin-3-one.

The compounds of formula (I), ($I_{P1}$), ($I_{CE-P1}$), ($I_N$) and/or formula ($I_{N-P1}$) according to embodiments 1), 4), 5), 11) and/or 13) may contain one or more stereogenic or asymmetric centers, such as one or more asymmetric carbon atoms. The compounds of formula (I), ($I_{P1}$), ($I_{CE-P1}$), ($I_N$) and/or formula ($I_{N-P1}$) may thus be present as mixtures of stereoisomers or preferably as pure stereoisomers. Mixtures of stereoisomers may be separated in a manner known to a person skilled in the art.

The relative configuration of stereoisomers is denoted as follows: for example, 6-{(R)-5-{[(3aR*,6aR*)-5-(6-methoxy-[1,5]naphthyridin-4-yl)-hexahydro-pyrrolo[3,4-b]pyrrol-1-yl]-methyl}-2-oxo-oxazolidin-3-yl}-4H-benzo[1,4]thiazin-3-one denominates 6-{(R)-5-{[(3aR,6aR)-5-(6-methoxy-[1,5]naphthyridin-4-yl)-hexahydro-pyrrolo[3,4-b]pyrrol-1-yl]-methyl}-2-oxo-oxazolidin-3-yl}-4H-benzo[1,4]thiazin-3-one, or 6-{(R)-5-{[(3aS,6aS)-5-(6-methoxy-[1,5]naphthyridin-4-yl)-hexahydro-pyrrolo[3,4-b]pyrrol-1-yl]-methyl}-2-oxo-oxazolidin-3-yl}-4H-benzo[1,4]thiazin-3-one, or mixtures of these two stereoisomers.

Compounds of formula (I), ($I_{P1}$), ($I_{CE-P1}$), ($I_N$) and/or formula ($I_{N-P1}$) according to embodiments 1), 4), 5), 11) and/or 13) are suitable for the use as chemotherapeutic active compounds in human and veterinary medicine and as substances for preserving inorganic and organic materials in particular all types of organic materials for example polymers, lubricants, paints, fibres, leather, paper and wood.

These compounds according to the invention are particularly active against bacteria and bacteria-like organisms. They are therefore particularly suitable in human and veterinary medicine for the prophylaxis and chemotherapy of local and systemic infections caused by these pathogens as well as disorders related to bacterial infections comprising pneumonia, otitis media, sinusitis, bronchitis, tonsillitis, and mastoiditis related to infection by *Streptococcus pneumoniae*, *Haemophilus influenzae*, *Moraxella catarrhalis*, *Staphylococcus aureus*, *Enterococcus faecalis*, *E. faecium*, *E. cas-*

*seliflavus, S. epidermidis, S. haemolyticus,* or *Peptostreptococcus* spp.; pharyngitis, rheumatic fever, and glomerulonephritis related to infection by *Streptococcus pyogenes,* Groups C and G streptococci, *Corynebacterium diphtheriae,* or *Actinobacillus haemolyticum;* respiratory tract infections related to infection by *Mycoplasma pneumoniae, Legionella pneumophila, Streptococcus pneumoniae, Haemophilus influenzae,* or *Chlamydia pneumoniae;* blood and tissue infections, including endocarditis and osteomyelitis, caused by *S. aureus, S. haemolyticus, E. faecalis, E. faecium, E. durans,* including strains resistant to known antibacterials such as, but not limited to, beta-lactams, vancomycin, aminoglycosides, quinolones, chloramphenicol, tetracyclines and macrolides; uncomplicated skin and soft tissue infections and abscesses, and puerperal fever related to infection by *Staphylococcus aureus,* coagulase-negative staphylococci (i.e., *S. epidermidis, S. haemolyticus,* etc.), *Streptococcus pyogenes, Streptococcus agalactiae,* Streptococcal groups C-F (minute colony streptococci), viridans streptococci, *Corynebacterium minutissimum, Clostridium* spp., or *Bartonella henselae;* uncomplicated acute urinary tract infections related to infection by *Staphylococcus aureus,* coagulase-negative *staphylococcal* species, or *Enterococcus* spp.; urethritis and cervicitis; sexually transmitted diseases related to infection by *Chlamydia trachomatis, Haemophilus ducreyi, Treponema pallidum, Ureaplasma urealyticum,* or *Neiserria gonorrheae;* toxin diseases related to infection by *S. aureus* (food poisoning and toxic shock syndrome), or Groups A, B, and C streptococci; ulcers related to infection by *Helicobacter pylori;* systemic febrile syndromes related to infection by *Borrelia recurrentis;* Lyme disease related to infection by *Borrelia burgdorferi;* conjunctivitis, keratitis, and dacrocystitis related to infection by *Chlamydia trachomatis, Neisseria gonorrhoeae, S. aureus, S. pneumoniae, S. pyogenes, H. influenzae,* or *Listeria* spp.; disseminated *Mycobacterium avium* complex (MAC) disease related to infection by *Mycobacterium avium,* or *Mycobacterium intracellulare;* infections caused by *Mycobacterium tuberculosis, M. leprae, M. paratuberculosis, M. kansasii,* or *M. chelonei;* gastroenteritis related to infection by *Campylobacter jejuni;* intestinal protozoa related to infection by *Cryptosporidium* spp.; odontogenic infection related to infection by viridans streptococci; persistent cough related to infection by *Bordetella pertussis;* gas gangrene related to infection by *Clostridium perfringens* or *Bacteroides* spp.; and atherosclerosis or cardiovascular disease related to infection by *Helicobacter pylori* or *Chlamydia pneumoniae.*

Compounds of formula (I), ($I_{P1}$), ($I_{CE-P1}$), ($I_N$) and/or formula ($I_{N-P1}$) according to embodiments 1), 4), 5), 11) and/or 13) are further useful for the preparation of a medicament for the treatment of infections that are mediated by bacteria such as *E. coli, Klebsiella pneumoniae* and other Enterobacteriaceae, *Acinetobacter* spp., *Stenothrophomonas maltophilia, Neisseria meningitidis, Bacillus cereus, Bacillus anthracis, Clostridium difficile, Corynebacterium* spp., *Propionibacterium acnes* and *bacteroide* spp.

Compounds of formula (I), ($I_{P1}$), ($I_{CE-P1}$), ($I_N$) and/or formula ($I_{N-P1}$) according to embodiments 1), 4), 5), 11) and/or 13) are further useful to treat protozoal infections caused by *Plasmodium malaria, Plasmodium falciparum, Toxoplasma gondii, Pneumocystis carinii, Trypanosoma brucei* and *Leishmania* spp.

The present list of pathogens is to be interpreted merely as examples and in no way as limiting.

One aspect of this invention therefore relates to the use of a compound of formula (I), ($I_{P1}$), ($I_{CE-P1}$), ($I_N$) and/or formula ($I_{N-P1}$) according to embodiments 1), 4), 5), 11) and/or 13), or of a pharmaceutically acceptable salt thereof, for the manufacture of a medicament for the prevention or treatment of a bacterial infection.

As well as in humans, bacterial infections can also be treated using compounds of formula (I), ($I_{P1}$), ($I_{CE-P1}$), ($I_N$) and/or formula ($I_{N-P1}$) according to embodiments 1), 4), 5), 11) and/or 13) (or pharmaceutically acceptable salts thereof) in other species like pigs, ruminants, horses, dogs, cats and poultry.

The present invention also relates to pharmacologically acceptable salts and to compositions and formulations of compounds of formula (I), ($I_{P1}$), ($I_{CE-P1}$), ($I_N$) and/or formula ($I_{N-P1}$) according to embodiments 1), 4), 5), 11) and/or 13).

Any reference to a compound of formula (I), ($I_{P1}$), and/or formula ($I_{CE-P1}$), according to embodiments 1), 4), and/or 5) is to be understood as referring also to the pharmaceutically acceptable salts of such compounds, as appropriate and expedient.

Any reference to a compound of formula ($I_N$) and/or formula ($I_{N-P1}$) according to embodiments 11) and/or 13) is to be understood as referring also to the salts (and especially the pharmaceutically acceptable salts) of such compounds, as appropriate and expedient.

The term "pharmaceutically acceptable salts" refers to non-toxic, inorganic or organic acid and/or base addition salts. Reference can be made to "Salt selection for basic drugs", Int. J. Pharm. (1986), 33, 201-217.

A pharmaceutical composition according to the present invention contains at least one compound of formula (I), ($I_{P1}$), ($I_{CE-P1}$), ($I_N$) and/or formula ($I_{N-P1}$) according to embodiments 1), 4), 5), 11) and/or 13) (or a pharmaceutically acceptable salt thereof) as the active agent and optionally carriers and/or diluents and/or adjuvants, and may also contain additional known antibiotics.

As mentioned above, therapeutically useful agents that contain compounds of formula (I), ($I_{P1}$), ($I_{CE-P1}$), ($I_N$) and/or formula ($I_{N-P1}$) according to embodiments 1), 4), 5), 11) and/or 13), their salts and formulations thereof are also comprised in the scope of the present invention.

The compounds of formula (I), ($I_{P1}$), ($I_{CE-P1}$), ($I_N$) and/or formula ($I_{N-P1}$) according to embodiments 1), 4), 5), 11) and/or 13) and their pharmaceutically acceptable salts can be used as medicaments, e.g. in the form of pharmaceutical compositions for enteral or parenteral administration.

The production of the pharmaceutical compositions can be effected in a manner which will be familiar to any person skilled in the art (see for example Remington, *The Science and Practice of Pharmacy,* 21st Edition (2005), Part 5, "Pharmaceutical Manufacturing" [published by Lippincott Williams & Wilkins]) by bringing the described compounds of formula (I) or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Another aspect of the invention concerns a method for the prevention or the treatment of a bacterial infection in a patient comprising the administration to said patient of a pharmaceutically active amount of a compound according to formula (I), ($I_{P1}$), ($I_{CE-P1}$), ($I_N$) and/or formula ($I_{N-P1}$) according to embodiments 1), 4), 5), 11) and/or 13), or a pharmaceutically acceptable salt thereof.

Besides, any preferences indicated for the compounds of formula (I) (whether for the compounds themselves, salts thereof, compositions containing the compounds or salts thereof, uses of the compounds or salts thereof, etc.) apply mutatis mutandis to compounds of formula ($I_{P1}$) and/or formula ($I_{CE-P1}$).

Further, any preferences indicated for the compounds of formula ($I_N$) (whether for the compounds themselves, salts thereof, compositions containing the compounds or salts thereof, uses of the compounds or salts thereof, etc.) apply mutatis mutandis to compounds of formula (I), ($I_{P1}$) ($I_{CE-P1}$) and/or formula ($I_{N-P1}$).

Moreover, the compounds of formula (I), ($I_{P1}$), ($I_{CE-P1}$), ($I_N$) and/or formula ($I_{N-P1}$) according to embodiments 1), 4), 5), 11) and/or 13) may also be used for cleaning purposes, e.g. to remove pathogenic microbes and bacteria from surgical instruments or to make a room or an area aseptic. For such purposes, the compounds of formula (I), ($I_{P1}$), ($I_{CE-P1}$), ($I_N$) and/or formula ($I_{N-P1}$) could be contained in a solution or in a spray formulation.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" placed before a temperature "Y" refers in the current application to an interval extending from the temperature Y minus 10° C. to Y plus 10° C., and preferably to an interval extending from Y minus 5° C. to Y plus 5° C. Besides, the term "room temperature" (rt) as used herein refers to a temperature of about 25° C.

Preparation of Compounds of Formula (I)

The compounds of formula (I), ($I_{P1}$), ($I_{CE-P1}$), ($I_N$) and/or formula ($I_{N-P1}$) can be manufactured by the methods given below, by the methods given in the examples or by analogous methods. Optimum reaction conditions may vary with the particular reactants or solvents used, but such conditions can be determined by a person skilled in the art by routine optimisation procedures.

Sections a) to h) hereafter describe general methods for preparing compounds of formula (I). The preparation of elaborated intermediates and basic building blocks is described thereafter. General synthetic methods used repeatedly throughout the schemes below are referenced to and described in the end of this section. If not indicated otherwise, the generic groups or integers U, V, W, X, $R^1$, $R^2$, $R^3$, $R^4$, $R^5$, $R^6$, $R^a$, $R^b$, $R^c$, $R^d$, $R^e$, $R^f$, $R^g$, $R^h$, A, B, D, E, G, m and n are as defined for formula (I). Other abbreviations used are defined in the experimental section. In some instances the generic groups $R^2$, $R^3$, $R^4$, $R^5$, $R^6$, $R^a$, $R^b$, $R^c$, $R^d$, $R^f$, $R^g$, $R^h$, A, B, D or E might be incompatible with the assembly illustrated in the schemes below and so will require the use of protecting groups (PG). The use of protecting groups is well known in the art (see for example "Protective Groups in Organic Synthesis", T. W. Greene, P. G. M. Wuts, Wiley-Interscience, 1999). For the purposes of this discussion, it will be assumed that such protecting groups as are necessary are in place.

a) Compounds of formula (I) can be obtained by reacting a compound of formula (II)

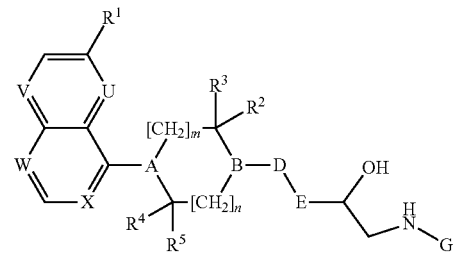

with a carbonic acid derivative of formula (III),

wherein $L^0$ and $L^{00}$ both represent chloro, $OCCl_3$, imidazolyl or succinimidyloxy, or $L^0$ represents chloro and $L^{00}$ represents $OCCl_3$. This reaction is preferably carried out in a dry aprotic solvent such as DCM or THF in presence of an organic base such as TEA or pyridine and at a temperature range between −30° C. and +80° C. In case there is one or two free amino or alcohol functions on A, B, D or E, these functional groups are protected [see general synthetic method 1 and 2] prior to the reaction and the protecting groups removed thereafter [see general synthetic method 3 and 10].

b) Compounds of formula (I) can be obtained by reacting a compound of formula (IV)

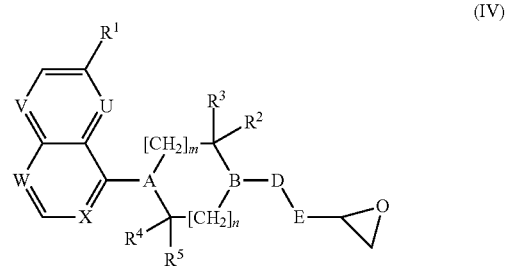

with the anion generated from compound of formula (V),

wherein R represents alkyl or benzyl, with a base such as KHMDS. This reaction is performed following [general synthetic method 4].

c) Compounds of formula (I) wherein A represents N can be obtained by reacting a compound of formula (VI)

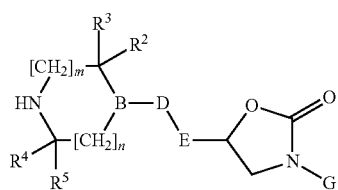
(VI)

with a compound of formula (VII)

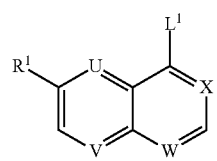
(VII)

wherein L¹ represents chloro, bromo or OTf, in a solvent such as dioxane or EtOH between about +20° C. and about +120° C. as described in Procedure F in the experimental part, or in presence of a catalyst as described in [general synthetic method 5].

d) Compounds of formula (I) wherein A represents C(OH) can be obtained by reacting a compound of formula (VIII)

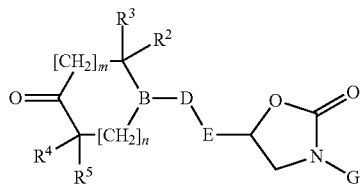
(VIII)

with a compound of formula (VII) wherein L¹ represents Li, MgCl, MgBr or MgI following [general synthetic method 6].

e) Compounds of formula (I) wherein B represents N, D represents a bond, and E represents $CH_2$ can be obtained by coupling compounds of formula (IX)

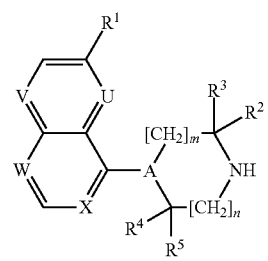
(IX)

with a compound of formula (X), wherein o represents the integer 0 or 1, and L² represents O-Ms, O-Tf, O-Ts, chloro, bromo, iodo or hydroxy following [general synthetic methods 7 and/or 11].

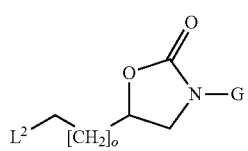
(X)

f) Compounds of formula (I) can be obtained as shown in scheme 1. Compounds of formula (I) wherein B represents CH, D represents NH, $NR^b$, $NR^c$, *—$CH_2$—$N(R^e)$—, *—$CH_2$—$N(R^f)$—, or $NR^g$, wherein the asterisks indicate the bond which is attached to B, and E represents $CH_2$, $CH_2CH_2$, CO or *—$COCH_2$— can be obtained by reacting a compound of formula (XI), wherein p represents the integer 0 or 1 and $R^z$ represents hydrogen, $R^b$, $R^c$, $R^e$, $R^f$ or $R^g$, with a compound of formula (X), wherein L² is as above following [general synthetic methods 7 and/or 11], or with an acid of formula (XII) wherein o represents the integer 0 or 1 following [general synthetic method 8]. In case $R^z$ represents hydrogen, the nitrogen atom may subsequently be further alkylated following [general synthetic method 11] or, preferably, using standard reductive amination procedures.

Scheme 1

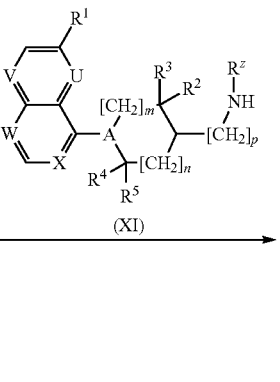

In scheme 1, $R^z$ represents hydrogen, $R^b$, $R^c$, $R^e$, $R^f$ or $R^g$ as defined for formula (I), represents the integer 0 or 1 and p represents the integer 0 or 1.

g) Compounds of formula (I) wherein B represents CH, D represents *—CONH— wherein the asterisk indicates the bond which is attached to B, and E represents $CH_2$ or $CH_2$—$CH_2$ can be obtained according to scheme 2 by reacting a compound of formula ($XI_A$) with a compound of formula ($X_A$), wherein o represents the integer 0 or 1 following [general synthetic method 8].

Scheme 2

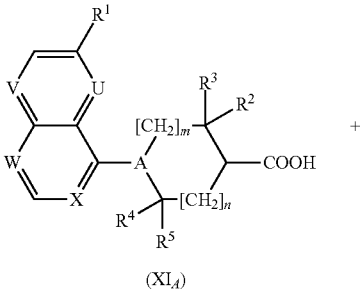
($XI_A$)

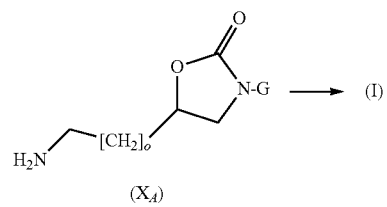
($X_A$)

h) Compounds of formula (I) can be obtained by reacting a compound of formula (IV$_A$)

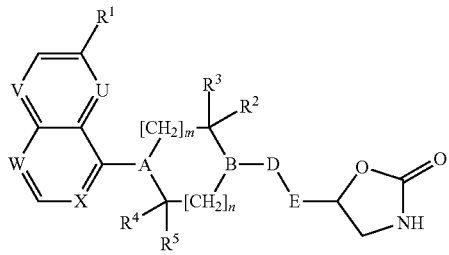

with a compound of formula L$^1$-G, wherein L$^1$ represents OTf or halogen such as bromine or iodine. This reaction is performed under conditions described for the metal catalyzed N-arylation of 2-oxazolidinones or amides. In particular by using CuI and 1,1,1-tris(hydroxymethyl)ethane in presence of CsCO$_3$ (Org. Let. 2006, 8, 5609-5612), or Pd(OAc)$_2$ and DPEphos in presence of K$_3$PO$_4$. In case G represents 2-pyridinyl, the reaction is performed in presence of a NaH.

Elaborated Intermediates

Compounds of formulae (II) and (IV) can be obtained as described in scheme 3.

Alternatively, the chiral epoxides can also be obtained from the ethylenic derivatives of formula (XIII) through either Shi chiral epoxidation using a chiral ketone as described *Acc. Chem. Res.* 2004, 37, 488-496 or through chiral cis-dihydroxylation using AD mixtures in presence of methanesulfonamide in a water/2-methyl-2-propanol mixture as described in *Chem. Rev.* 1994, 94, 2483. The sense of induction relies on the chiral ligand contained in the mixture, either a dihydroquinine-based ligand in AD-mix α or a dihydroquinidine-based ligand in AD-mix β [see general synthetic method 9]

In the particular case wherein the group -D-E- represents —CH$_2$—NH—CH$_2$— or —NH—CH$_2$—, the epoxide of formula (IV) can also be obtained by reacting the amines of formula (XI) with epichlorhydrin, or optionally with one of the two enantiomers of epichlorhydrin, followed by protection of the amine function with a benzyloxycarbonyl or a tert-butoxycarbonyl group following [general synthetic method 1], epoxide formation after basic treatment and removal of the transient amino protecting group following [general synthetic method 10].

The epoxides of formula (IV) are reacted with amines of formula G-NH$_2$ affording compounds of formula (II).

Intermediates of formula (IV$_A$) are obtained by reacting the epoxides of formula (IV) with sodium azide followed by Scheme 3

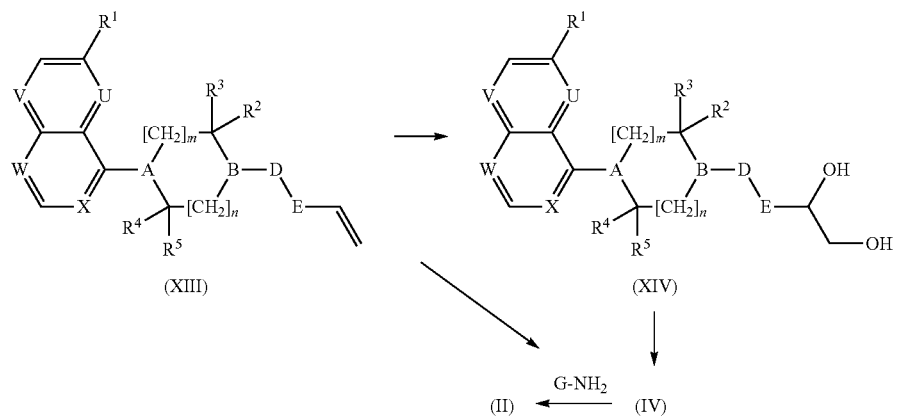

The vinyl derivatives of formula (XIII) are transformed into the corresponding epoxides of formula (IV) either through direct epoxidation of the terminal double bond with a peracide such as mCPBA or H$_2$O$_2$ in presence of an inorganic base such as NaOH, NaHCO$_3$ or urea or via cis-dihydroxylation with OsO$_4$/NMO following [general synthetic method 9], or as described in *Tetrahedron Lett.* 1976, 23, 1973-76, followed by conversion into the corresponding epoxides after mesylation or tosylation, and ring closure under basic conditions such as K$_2$CO$_3$ or NaOMe. In case chiral epoxides are required, they can be obtained by hydrolytic kinetic resolution (HKR) catalyzed by chiral (salen)—Co(III) complex (e.g. [(R,R)—N,N'-bis(3,5-di-tert-butylsalicylidene)-1,2-cyclohexanediaminato (2-)]cobalt(III) of the racemic mixture of epoxides as described by Jacobsen et al in *J. Am. Chem. Soc.* 2002, 124, 1307-1315 and *Science*, 1997, 277, 936-938.

hydrogenation over a noble metal catalyst such as Pd on charcoal and subsequent transformation into their corresponding carbamates with CbzCl or BOC$_2$O. The oxazolidinone ring is formed by subsequent reaction with NaH.

Compounds of formula (XIII) are obtained as shown in scheme 4. Compounds of formula (XIII), wherein B represents N or CH are obtained by reacting amines of formulae (IX) or (XI) with an allyl halogenide (q represents the integer 1) following [general synthetic method 11]. Compounds of formula (XIII) wherein B represents C(OH), and R$^2$ and R$^3$ represent H are obtained by reacting a ketone of formula (XV) with allyl magnesium bromide following [general synthetic method 6]. Compounds of formula (XIII) wherein B represents CH, D represents NH or *—CH$_2$NH$_2$— and E represents CO are obtained by reacting amines of formula (XI) with acrylic acid following [general synthetic method 8].

Scheme 4

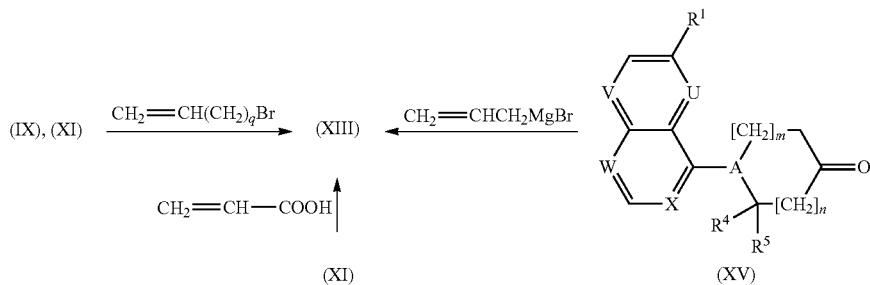

Compounds of formulae (IX) and (XI) are obtained by reacting derivatives of formula (VII) wherein $L^1$ represents bromine or OTf with amines of formula (XVI) or amines of formula (XVII), wherein p represents the integer 0 or 1, $R^z$ represents hydrogen, $R^b$, $R^c$, $R^e$, $R^f$ or $R^g$; and PG represents a nitrogen protecting group such as benzyloxycarbonyl or tert-butoxycarbonyl,

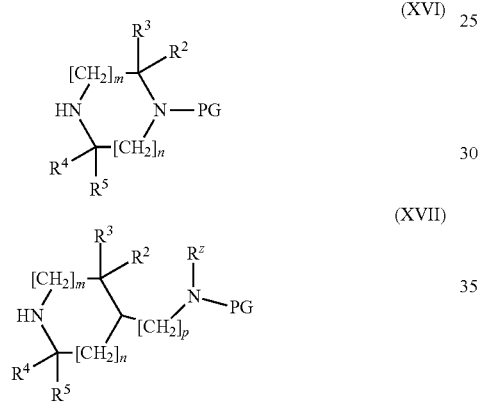

using the same methodology as described in c) followed by removal of the nitrogen protecting group following [general synthetic method 10].

Compounds of formula (XV) wherein A represents N are obtained by reacting derivatives of formula (VII) wherein $L^1$ represents bromine or OTf with compounds of formula (XVIII) using the same methodology as described in c). Compounds of formula (XI$_A$) are prepared in analogy.

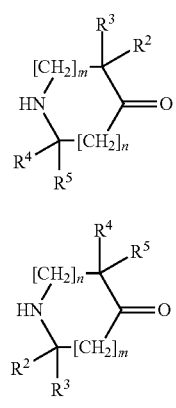

Compounds of formula (XV) wherein A represents C(OH) are obtained by reacting derivatives of formula (VII) wherein $L^1$ represents MgCl, MgBr, MgI or Li on ketones of formula (XIX) or (XIX') wherein both $R^x$ represent alkyl or both $R^x$ together form an ethane-1,2-diyl or a propane-1,3-diyl linker.

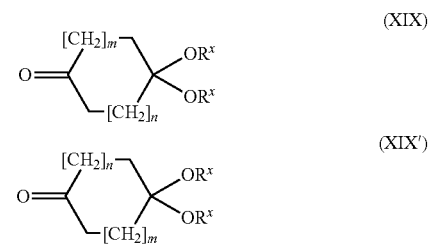

The intermediate ketals are transformed into the corresponding ketone following [general synthetic method 12].

Compounds of formula (IX) wherein A is CH(OH) are obtained by reacting derivatives of formula (VII) wherein $L^1$ represents MgCl, MgBr, MgI or Li on ketones of formula (XIX") wherein PG represents an amino protecting group such as Cbz or BOC, followed by removal of the amino protecting group following [general synthetic method 10].

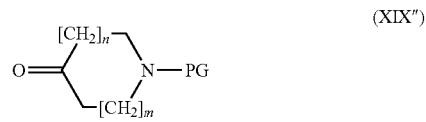

Compounds of formula (VI) are obtained as described in scheme 5.

Scheme 5

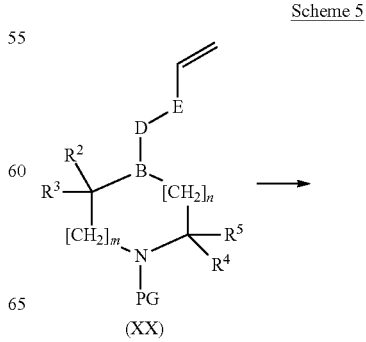

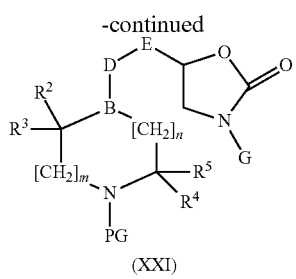

(XXI)

The vinyl derivatives (XX), wherein PG represents a nitrogen protecting group such as benzyloxycarbonyl or tert-butoxycarbonyl, are transformed into the oxazolidinones (XXI) using one of the methods described in a) or b). The protecting group of compounds of formula (XXI) are removed to afford compounds of formula (VI) following [general synthetic method 10].

Basic Building Blocks

Compounds of formula (XX) wherein B represents N, D represents a bond, E represents $CH_2$, and $R^2$ and $R^3$ represent H are prepared by alkylation of compounds of formula (XXII)

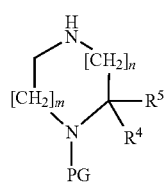

(XXII)

wherein PG represents a nitrogen protecting group such as benzyloxycarbonyl or tert-butoxycarbonyl, with allyl bromide following [general synthetic method 11].

Compounds of formula (XX) wherein B represents C(OH), D represents a bond, E represents $CH_2$, and $R^2$ and $R^3$ each represent H are prepared by alkylation of compounds of formula (XXIII)

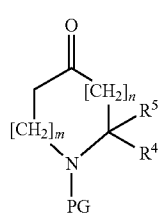

(XXIII)

wherein PG represents a nitrogen protecting group such as benzyloxycarbonyl or tert-butoxycarbonyl, with $CH_2$=$CHCH_2MgBr$.

Compounds of formula (VIII) are obtained from the corresponding vinyl derivatives of formula (XXIV)

(XXIV)

using one of the methods described in a) or b). In case D represents *—$CH_2$—NH— or NH the nitrogen may be protected using an appropriate protecting group as described before.

Compounds of formula (XXIV) wherein B represents N, D represents a bond and E represents $CH_2$ are obtained by alkylation of the compounds of formula (XVIII') with allylbromide. Compounds of formula (XXIV) wherein B represents C(OH), D represents a bond, E represents $CH_2$, and $R^2$, $R^3$, $R^4$, $R^5$ represent hydrogen are obtained by reaction of compounds of formula (XIX'), wherein both $R^x$ represent alkyl or both $R^x$ together form an ethane-1,2-diyl or a propane-1,3-diyl linker, with $CH_2$=$CHCH_2MgBr$, followed by deprotection of the ketal group following [general synthetic method 12].

Compounds of formula (X) wherein o represents the integer 0 or 1, $L^2$ represents O-Ms, O-Tf, O-Ts, chloro, bromo or iodo are obtained from the corresponding alcohol derivatives of formula (XXVI) following [general synthetic method 7], the latter being obtained as shown in scheme 6. Compounds of formula (X) can in turn be transformed to the corresponding amines of formula ($X_A$) via reaction with sodium azide and subsequent hydrogenation in presence of a noble metal catalyst. PG represents —C(O)R, wherein R represents alkyl, or a silyl protecting group such as tert-butyldimethylsilyl-.

Scheme 6

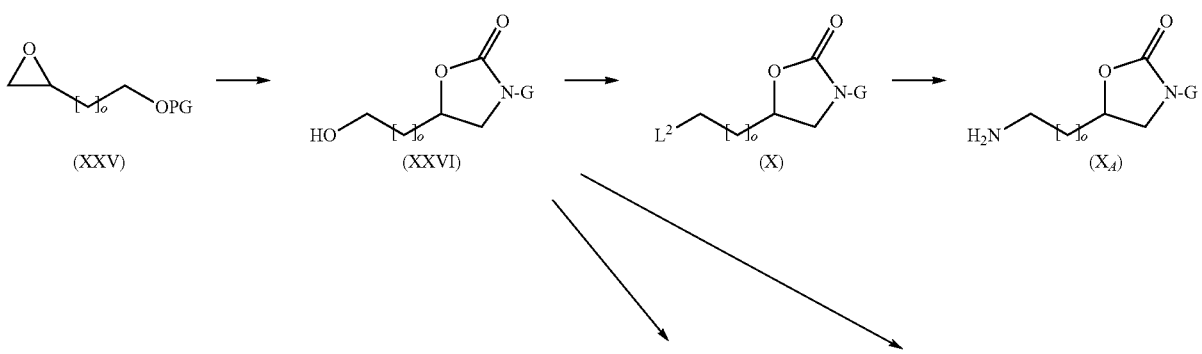

-continued

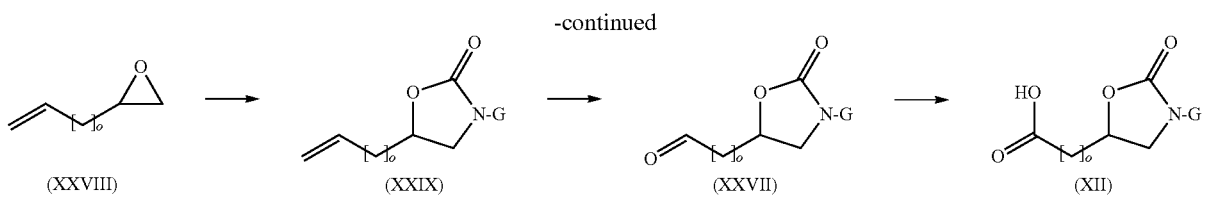

(XXVIII) (XXIX) (XXVII) (XII)

The known epoxide derivatives (XXV), wherein PG represents —C(O)R and o represents the integer 0, are reacted with the anion of the carbamate of formula (V) generated by the action of a strong base such as n-BuLi between −80° C. and −30° C., affording the alcohols of formula (XXVI). Alternatively, alcohols of formula (XXVI) are obtained, after final deprotection, by reaction of known epoxide derivatives (XXV), wherein PG represents a silyl protecting group and o represents the integer 1, with compounds of formula G-NH$_2$ according to the methods described in a) and scheme 3 above. Acids of formula (XII) can be obtained by oxidation of either the corresponding alcohol of formula (XXVI) or of the aldehyde of formula (XXVII) following [general synthetic method 13]. Aldehydes of formula (XXVII) are obtained from alkenes of formula (XXIX) after tandem cis-dihydroxylation with OsO$_4$ and periodic cleavage, or, alternatively, from the corresponding alcohol of formula (XXVIII) following [general synthetic method 14]. Alkenes of formula (XXIX) are obtained from the known epoxides of formula (XXVIII) after ring opening with the amines of formula G-NH$_2$, followed by oxazolidinone formation as described before.

Compounds of formula (XVI) wherein m and n represent the integer 1, $R^2$, $R^3$, $R^4$ and $R^5$ represent H and PG represents benzyloxycarbonyl or tert-butoxycarbonyl are commercially available. Compounds of formula (XVII) wherein m and n represent the integer 0, p represents the integer 1, $R^2$, $R^3$, $R^4$ and $R^5$ represent H and PG represents tert-butoxycarbonyl are commercially available. Compounds of formula (XVII) wherein m represents the integer 1 and n represents the integer 0, p represents the integer 0, $R^2$, $R^3$, $R^4$, $R^5$ and $R^z$ represent H and PG represents tert-butoxycarbonyl are commercially available. Compounds of formula (XVII) wherein $R^z$ represents (C$_1$-C$_4$)alkyl are obtained from the known alcohol of formula (XXX) wherein m, n and p represent independently the integer 1 or 0 by transformation of the alcohol into the corresponding amine by reaction with the amine of formula $R^z$—NH$_2$ wherein $R^z$ represents (C$_1$-C$_4$)alkyl, following [general synthetic method 7], protection of the amine function with a BOC group following [general synthetic method 1] and removal of the Cbz protecting group following [general synthetic method 10].

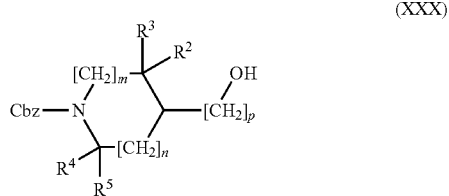

(XXX)

Compounds of formula (XVIII) wherein m and n represent the integer 1, m and n represent the integer 0, or m represents the integer 1 and n represents the integer 0, and $R^2$, $R^3$, $R^4$ and $R^5$ represent H are commercially available. Compounds of formula (XIX) and (XIX') wherein m and n represent the integer 1, and both $R^a$ together form an ethane-1,2-diyl linker are commercially available. Compounds of formula (XIX") wherein m and n represent independently the integer 1 or 0 and PG represents BOC or Cbz are commercially available. Compounds of formula (XXII) wherein m and n represent the integer 1, $R^4$ and $R^5$ represent H and PG represents benzyloxycarbonyl or tert-butoxycarbonyl are commercially available. Compounds of formula (XXIII) wherein m and n represent the integer 1, $R^4$ and $R^5$ represent H and PG represents benzyloxycarbonyl or tert-butoxycarbonyl are commercially available Carbamates of formula (V) are prepared from commercially available amines G-NH$_2$ following [general synthetic method 1]

The required quinoline, [1,5]-naphthyridine, quinazoline and quinoxaline derivatives of formula (VII) wherein $L^1$ represents OTf are prepared from the corresponding derivatives of formula (VII) wherein $L^1$ represents OH following procedures analogous to those described in WO 2000/40554, WO 2002/008224 and WO 2004/002490.

The required quinoline, [1,5]-naphthyridine, quinazoline and quinoxaline derivatives of formula (VII) wherein $L^1$ represents Br are either commercially available or prepared following literature procedures. For example, compounds wherein $L^1$=Br, W=N and X=V=U=CH are prepared according to WO 2003/087098, compounds wherein $L^1$=Br, W=V=N and X=U=CH are prepared according to WO 2006/032466, compounds wherein $L^1$=Br, X=N and U=V=W=CH or wherein $L^1$=Cl, W=N and X=V=U=CH are prepared according to WO 2004/089947, and compounds wherein $L^1$=Cl, V=N and X=W=U=CH are prepared according to WO 2005/019215. Compounds of formula (VII) wherein $L^1$=OH are reacted with PBr$_3$ in DMF at 40° C. and provide derivatives of formula (VII) wherein $L^1$=Br.

Derivatives of formula (VII) wherein $L^1$ represents Li can be prepared from the corresponding derivatives of formula (VII) wherein $L^1$ represents Br after reaction with n-BuLi between −80° C. and −30° C. in a solvent such as THF or ether.

General Synthetic Methods
General Synthetic Method 1: Amine Protection

Amines are usually protected as carbamates such as Alloc, Cbz, BOC or FMOC. They are obtained by reacting the amine with allyl or benzyl chloroformate, di tert-butyl dicarbonate or FMOC-Cl in presence of a base such as NaOH, TEA, DMAP or imidazole. They can also be protected as N-benzyl derivatives by reaction with benzyl bromide or chloride in presence of a base such as sodium carbonate or TEA. Alternatively, N-benzyl derivatives can be obtained through reductive amination in presence of benzaldehyde and a borohydride reagent such as NaBH$_4$, NaBH$_3$CN or NaBH(OAc)$_3$ in a solvent such as MeOH, DCE or THF. Further strategies to introduce other amine protecting groups have been described in Protecting Groups in Organic Synthesis, 3rd Ed (1999), 494-653; T. W. Greene, P. G. M. Wuts; (Publisher: John Wiley and Sons, Inc., New York, N.Y.).

General Synthetic Method 2: Protection of Alcohols

The alcohols are protected as silyl ether (usually TBDMS or TBDPS). The alcohol is reacted with the required silyl chloride reagent (TBDMS-Cl or TBDPS-Cl) in presence of a base such as imidazole or TEA in a solvent such as DCM or DMF between +10° C. and +40° C. Further strategies to introduce other alcohol protecting groups have been described in Protecting Groups in Organic Synthesis $3^{rd}$ Ed; 1999, 23-147; T. W. Greene, P. G. M. Wuts; (Publisher: John Wiley and Sons, Inc., New York, N.Y.).

General Synthetic Method 3: Hydroxy Deprotection

The silyl ether groups are removed either using fluoride anion sources such as tetrabutyl ammonium fluoride in THF between 0° C. and +40° C. or HF in MeCN between 0° C. and +40° C. or using acidic conditions such as AcOH in THF/MeOH or HCl in MeOH. Further methods to remove the TBDMS and TBDPS groups are given in Protecting Groups in Organic Synthesis $3^{rd}$ Ed; 1999, 133-139 and 142-143 respectively; T. W. Greene, P. G. M. Wuts; (Publisher: John Wiley and Sons, Inc., New York, N.Y.). Further general methods to remove alcohol protecting groups are described in Protecting Groups in Organic Synthesis $3^{rd}$ Ed; 1999, 23-147; T. W. Greene, P. G. M. Wuts; (Publisher: John Wiley and Sons, Inc., New York, N.Y.).

General Synthetic Method 4: Oxazolidinones Via Glycidyl Esters

The carbamate of formula (V) is reacted in a dry solvent such as THF with a strong organic base such as n-BuLi between −100° C. and −30° C. or with lithium or potassium tert-butoxide or KHMDS between −100° C. and −30° C. The anion is reacted at these temperatures with the required epoxide and allowed to reach room temperature.

General Synthetic Method 5: Buchwald Hartwig Amination

The aromatic halide or the triflate is reacted with the corresponding amine in presence of a palladium catalyst such as palladium (II) acetate, in presence of a ligand such as DPEphos and in presence of a base such as $K_3PO_4$, between +20° C. and +100° C., as described in *J. Org. Chem.* 2007, 72, 2232-2235.

In the Goldberg variant, the reaction is performed between an aromatic halide or triflate and a lactam in presence of CuI, an inorganic base such as $K_2CO_3$ or $K_3PO_4$ between +40° C. and +110° C., as described in *Tetrahedron Letters* 2006, 47, 1181-86.

General Synthetic Method 6: Addition of Metal-Organic Reagents to Ketones

Grignard reagents are prepared by reacting the halide in a dry aprotic solvent such as THF or ether with magnesium. The reaction is initiated by the addition of a trace of $I_2$. Lithium reagents are prepared by reacting the halide in a dry aprotic solvent such as THF or ether with a butyl-lithium reagent. The resulting metal-organic reagent is reacted with the corresponding ketone between −80° C. and +60° C. in a dry aprotic solvent such as THF or ether.

General Synthetic Method 7: Substitution

The alcohol is reacted with Ms-Cl, Tf-Cl or Ts-Cl in presence of a base such as TEA in a dry aprotic solvent such as pyridine, THF or DCM between −30° C. and +50° C. In the case of the trifluoromethanesulfonate or methanesulfonate, $Tf_2O$ or $Ms_2O$ can also be used. These sulfonates can be reacted with sodium iodide in acetone or DMF between +40° C. and +120° C. delivering the corresponding iodo derivatives. Once activated (either as a sulfonate or a iodo derivative), the alcohol reacts with an amine as described in [general synthetic method 11].

General Synthetic Method 8: Amide Coupling

The carboxylic acid is reacted with the amine in presence of an activating agent such as DCC, EDC, HOBT, n-propylphosphonic cyclic anhydride, HATU or di-(N-succinimidyl)-carbonate, in a dry aprotic solvent such as DCM, MeCN or DMF between −20° C. and +60° C. (see G. Benz in *Comprehensive Organic Synthesis*, B. M. Trost, I. Fleming, Eds; Pergamon Press: New York (1991), vol. 6, p. 381). Alternatively, the carboxylic acid can be activated by conversion into its corresponding acid chloride by reaction with oxalyl chloride or thionyl chloride neat or in a solvent like DCM between −20° and +60° C. Further activating agents can be found in *Comprehensive Organic Transformations. A guide to Functional Group Preparations;* $2^{nd}$ Edition, R. C. Larock, Wiley-V C; New York, Chichester, Weinheim, Brisbane, Singapore, Toronto, 1999. Section nitriles, carboxylic acids and derivatives p. 1941-1949.

General Synthetic Method 9: Cis-Dihydroxylation

The diol is obtained by dihydroxylation of the corresponding ethylenic derivative using a catalytic amount of osmium tetroxide in the presence a co-oxidant such as NMO in aq. solvent such as an acetone—water or DCM—water mixture (see Cha, J. K. *Chem. Rev.* 1995, 95, 1761-1795). The chiral cis-diols are obtained by using AD-mix α or AD-mix β in presence of methanesulfonamide in a water/2-methyl-2 propanol mixture as described in *Chem. Rev.* (1994), 94, 2483. The sense of induction relies on the chiral ligand contained in the AD mixture, either a dihydroquinine-based ligand in AD-mix α or a dihydroquinidine-based ligand in AD-mix β.

General Synthetic Method 10: Amino Deprotection

The benzyl carbamates are deprotected by hydrogenolysis over a noble catalyst (e.g. Pd/C or Pd(OH)$_2$/C). The Boc group is removed under acidic conditions such as HCl in an organic solvent such as MeOH or dioxane, or TFA neat or diluted in a solvent such DCM. Further general methods to remove amine protecting groups have been described in *Protecting Groups in Organic Synthesis,* $3^{rd}$ Ed (1999), 494-653; T. W. Greene, P. G. M. Wuts; (Publisher: John Wiley and Sons, Inc., New York, N.Y.).

General Synthetic Method 11: Alkylation

The amine derivative is reacted with a compound of formula alkyl-$L^2$, wherein $L^2$ represents O-Ms, O-Tf, O-Ts, Cl, Br or I, a compound of formula (X) wherein $L^2$ represents O-Ms, O-Tf, O-Ts, Cl, Br or I, or an allyl- or homoallyl halogenide in presence of an inorganic base such as $K_2CO_3$ or an organic base such as TEA in a solvent such as THF between 0° C. and +80° C. Further details can be found in *Comprehensive Organic Transformations. A guide to Functional Group Preparations;* $2^{nd}$ Edition, R. C. Larock, Wiley-V C; New York, Chichester, Weinheim, Brisbane, Singapore, Toronto, (1999). Section Amines p. 779.

General Synthetic Method 12: Ketal Deprotection

The ketal is converted into its corresponding ketone under acidic conditions such as diluted aq. HCl in MeOH, diluted aq. AcOH or by using an acidic resin such as Amberlite IR120H or DOWEX 50W8 in a water-solvent mixture such as MeOH/water or THF/water.

General Synthetic Method 13: Oxidation of Alcohols/Aldehydes into Acids

Aldehydes can be oxidized into their corresponding acids by a variety of methods as described in *Comprehensive Organic Transformations. A guide to Functionnal Group Preparations;* $2^{nd}$ Edition, R. C. Larock, Wiley-V C; New York, Chichester, Weinheim, Brisbane, Singapore, Toronto, 1999. Section nitriles, carboxylic acids and derivatives p. 1653-1655. Among them, potassium permanganate in an acetone-water mixture (see *Synthesis* 1987, 85) or sodium chlorite in 2-methyl-2-propanol in presence of 2-methyl-2-butene (see *Tetrahedron* 1981, 37, 2091-2096) are frequently used.

Alcohols can be directly oxydized into their corresponding acids by a variety of methods as described in *Comprehensive Organic Transformations. A guide to Functionnal Group Preparations*; 2$^{nd}$ Edition, R. C. Larock, Wiley-V C; New York, Chichester, Weinheim, Brisbane, Singapore, Toronto, 1999. Section nitriles, carboxylic acids and derivatives p. 1646-1648. Among them, [bis(acetoxy)iodo]benzene in presence of TEMPO, the Jones reagents ($CrO_3/H_2SO_4$), $NaIO_4$ in presence of $RuCl_3$, $KMnO_4$ or pyridine $H_2Cr_2O_7$ are frequently used.

General Synthetic Method 14: Formation of Aldehydes

The alcohols can be transformed into their corresponding aldehydes through oxidation under Swern (see D. Swern et al., J. Org. Chem. 1978, 43, 2480-2482) or Dess Martin (see D. B. Dess and J. C. Martin, J. Org. Chem. 1983, 48, 4155) conditions, respectively Alternatively the esters can be transformed into their corresponding aldehydes by controlled reduction with a bulky hydride reagent such as DIBAH.

General Synthetic Method 15: Hydrolysis of Ester into Carboxylic Acids

When the ester side chain is a linear alkyl, the hydrolysis is usually performed by treatment with an alkali hydroxide such as LiOH, KOH or NaOH in a water-dioxane or water—THF mixture between 0° C. and +80° C. When the ester side chain is tert-butyl, the hydrolysis can also be performed in neat TFA or diluted TFA or HCl in an organic solvent such as ether or THF. When the ester side chain is the allyl group, the reaction is performed in presence of tetrakis(triphenylphosphine)palladium(0) in presence of an 11-allyl cation scavenger such as morpholine, dimedone or tributyltin hydride between 0° C. and +50° C. in a solvent such as THF. When the ester side chain is benzyl, the reaction is performed under hydrogen in presence of a noble metal catalyst such as Pd/C in a solvent such as MeOH, THF or EA. Further strategies to introduce other acid protecting groups and general methods to remove them have been described in Protecting Groups in Organic Synthesis 3$^{rd}$ Ed; 1999, 369-441; T. W. Greene, P. G. M. Wuts; (Publisher: John Wiley and Sons, Inc., New York, N.Y.).

The compounds of formula (I), ($I_{P1}$), ($I_{CE-P1}$), ($I_N$) and/or formula ($I_{N-P1}$) obtained according to the abovementioned general preparation methods may then, if desired, be converted into their salts, and notably into their pharmaceutically acceptable salts.

Whenever the compounds of formula (I), ($I_{P1}$), ($I_{CE-P1}$), ($I_N$) and/or formula ($I_{N-P1}$) are obtained in the form of mixtures of enantiomers, the enantiomers can be separated using methods known to one skilled in the art: e.g. by formation and separation of diastereomeric salts or by HPLC over a chiral stationary phase such as a Regis Whelk-O 1 (R,R) (10 μm) column, a Daicel ChiralCel OD-H (5-10 μm) column, or a Daicel ChiralPak IA (10 μm) or AD-H (5 μm) column. Typical conditions of chiral HPLC are an isocratic mixture of eluent A (EtOH, in presence or absence of an amine such as triethylamine, diethylamine) and eluent B (hexane), at a flow rate of 0.8 to 150 mL/min.

Particular embodiments of the invention are described in the following examples, which serve to illustrate the invention in more detail without limiting its scope in any way.

EXPERIMENTAL SECTION

Abbreviations (as Used Herein and in the Description Above)

| | |
|---|---|
| AcOH | acetic acid |
| AD-mix α | 1,4-bis(dihydroquinine)phthalazine, $K_3Fe(CN)_6$, $K_2CO_3$ and $K_2OsO_4$•$2H_2O$ |
| AD-mix β | 1,4-bis(dihydroquinidine)phthalazine, $K_3Fe(CN)_6$, $K_2CO_3$ and $K_2OsO_4$•$2H_2O$ |
| alloc | allyloxycarbonyl- |
| aq. | aqueous. |
| BINAP | 2,2'-bis(diphenylphosphino)-1,1'-binaphthyl |
| BOC | tert-butoxycarbonyl- |
| $BOC_2O$ | tert-butyl dicarbonate |
| n-BuLi | n-butyl lithium |
| Cbz | benzyloxycarbonyl- |
| CC | column chromatography over $SiO_2$ |
| CDI | 1,1'-carbonyldiimidazole |
| d | day(s) |
| DCM | dichloromethane |
| DCC | N,N'-dicyclohexylcarbodiimide |
| DCE | 1,2-dichloroethane |
| DPEphos | bis(2-diphenylphosphinophenyl)ether |
| DHQD | dihydroquinidine |
| DIBAH | diisobutylaluminium hydride |
| DIPEA | N,N-diisopropylethylamine |
| DMA | N,N-dimethylacetamide |
| DMAP | 4-dimethylaminopyridine |
| DMF | N,N-dimethylformamide |
| DMSO | dimethylsulfoxide |
| EA | ethyl acetate |
| EDCI | 1-(3-dimethylaminopropyl)-3-ethylcarbodiimide |
| eq. | equivalent(s) |
| ESI | Electron Spray Ionisation |
| Et | ethyl |
| ether | diethylether |
| EtOH | ethanol |
| $Et_3SiH$ | triethylsilane |
| FMOC | 9-fluorenylmethyloxycarbonyl- |
| h | hour(s) |
| HATU | (O-(7-azabenzotriazol-1-yl)-1,1,3,3-tetramethyl-uronium hexafluorphoshate |
| hex | hexane |
| HOBT | hydroxybenzotriazole |
| KHMDS | potassium bis(trimethylsilyl)amide |
| KOtBu | potassium tert. butoxide |
| LiOtBu | lithium tert. butoxide |
| mCPBA | m-chloroperbenzoic acid |
| Me | methyl |
| MeCN | acetonitrile |
| MeOH | methanol |
| min | minutes |
| Ms | methanesulfonyl- |
| MS | Mass Spectroscopy |
| $Ms_2O$ | methansulfonic acid anhydride |
| MS 3A | molecular sieves (3 Å) |
| NaOMe | sodium methylate |
| NMO | N-methylmorpholine N-oxide |
| NMP | N-methylpyrrolidone |
| OAc | acetate |
| org. | organic |
| PHAL | phtalazine |
| rt | room temperature |
| sat. | saturated |
| TBAF | tetrabutylammonium fluoride |
| TBDMS | tert-butyldimethylsilyl- |
| TBDPS | tert-butyldiphenylsilyl- |
| TBME | tert-butyl-methyl-ether |
| TEA | triethylamine |
| TEMPO | 2,2,4,4-tetramethylpiperidine 1-oxyl |
| Tf | trifluoromethanesulfonyl- |
| $Tf_2O$ | trifluoromethanesulfonic acid anhydride |
| TFA | trifluoroacetic acid |
| THF | tetrahydrofuran |
| Ts | p-toluenesulfonyl- |

All temperatures are stated in ° C. Compounds are characterized by $^1$H-NMR (300 MHz) (Varian Oxford); or by $^1$H-NMR (400 MHz) (Bruker Advance 400). Chemical shifts are given in ppm relative to the solvent used; multiplicities: s=singlet, d=doublet, t=triplet, q=quadruplet, p=pentuplet, hex=hexet, hept=heptet, m=multiplet, br=broad, coupling constants are given in Hz. Alternatively compounds are characterized by LC-MS (Sciex API 2000 with Agilent 1100 Binary Pump and DAD, using RP-C18 based columns); by TLC (TLC-plates from Merck, Silica gel 60 $F_{254}$); or by melting point. Compounds are purified by chromatography on Silica gel 60A. $NH_4OH$ as used for CC is 25% aq. Racemates can be separated into their enantiomers as described before. Preferred conditions of chiral HPLC are: ChiralPak AD (4.6×250 mm, 5 μm) column, using an isocratic mixture (eg. at a ratio of 10/90) of eluent A (EtOH, in presence of diethylamine in an amount of eg. 0.1%) and eluent B (hexane), at rt, at a flow rate of eg. 0.8 mL/min.

General Procedures:

Procedure A: Epoxide Opening

A solution of the epoxide (1 mmol) and the amine (1 mmol) in $EtOH/H_2O$ (9:1, 1 mL) is heated at 80° C. for 12 h. The volatiles are removed under reduced pressure and the residue purified by CC.

Procedure B: Oxazolidinone Formation with CDI

A solution of the amino alcohol (1 mmol) and CDI (1-2 eq) in THF (2 mL) is heated at 50° C. until completion of the reaction. The mixture is partitioned between EA (20 mL) and water (20 mL), the org. phase washed with brine (20 mL), dried over $MgSO_4$ and concentrated.

Procedure C: Cbz-Protection of Amines

A mixture of amine (1 mmol), sat. aq. $NaHCO_3$ (2 mL) and acetone (2 mL) is treated drop wise with benzyl chloroformate (1.05 eq). After $CO_2$ evolution ceased, the mixture is partitioned between EA and sat. aq. $NaHCO_3$, the org. layer dried over $MgSO_4$ and concentrated under reduced pressure.

Procedure D: Oxazolidinone Formation

A solution of the 1-chloro-2-hydroxy-propan-3-yl derivative (or chlorohydrine) (0.5 mmol) and the Cbz-protected amine (0.5 mmol, prepared according to procedure C) in DMF (2 mL) is treated with LiOtBu (0.68 mL of a 2.2 M solution in THF, 3 eq). The mixture is stirred at rt until completion of reaction, diluted with EA and washed with water. The org. layer is concentrated. Purification is achieved by CC (EA/MeOH 9:1+1% $NH_4OH$).

Procedure E: BOC Deprotection

The BOC protected amine (1 mmol) is dissolved in DCM (5 mL) and treated with TFA (2 mL). The mixture is stirred at rt for 1 h, concentrated in vacuo and taken up in DCM/aq. $NH_4OH$. The org. layer is washed with water, dried over $MgSO_4$ and concentrated.

Procedure F: Nucleophilic Aromatic Substitution

A mixture of the aryl halide or the aryl triflate (1 mmol), amine (1 mmol) and DIPEA (1.2 mmol) in NMP (4 mL) was heated at 70-80° C. until completion of the reaction. Water was added and the mixture was extracted with EA. The combined org. layers were washed with water (3×), brine, dried over $MgSO_4$ and concentrated under reduced pressure. The residue was purified by CC.

Procedure G: Hydrogenation of Cbz-Group

A suspension of the benzyl carbamate (1 mmol) in MeOH (6 mL) was hydrogenated over 5 or 10% Pd/C (200 mg) for 2 h. The catalyst was filtered and the filter cake was washed thoroughly with MeOH and DCM. The filtrate was concentrated under reduced pressure.

Procedure H: Alkylation of Amines with Mesylates

A solution of the amine (1.8-2.3 mmol) and the mesylate (1 mmol) in dry DMSO was heated to 70° C. until completion of the reaction (2-5 d). After cooling water and EA were added and the phases were separated. The aq. layer was extracted two more times with EA and the combined org. layers were washed with water (3×) and brine, dried over $MgSO_4$ and concentrated under reduced pressure. The residue was purified by CC. Alternatively the reaction can also be performed with 1 mmol amine in presence of 1.1 mmol of DIPEA.

Procedure I: Alkylation of Amines with Iodides

A solution of amine (1 mmol), iodide (1 mmol) and DIPEA (1.1 mmol) in dry DMSO was heated to 70° C. until completion of the reaction (1-3 d). After cooling water and EA were added and the phases were separated. The aq. layer was extracted two more times with EA and the combined org. layers were washed with water (3×) and brine, dried over $MgSO_4$ and concentrated under reduced pressure. The residue was purified by CC.

Procedure J: Amide Coupling with HATU

To a solution of the amine (1 mmol), the acid (1 mmol) and DIPEA (4 mmol) in DMF (2 mL) was added HATU (2 mmol) at rt. The resulting mixture was stirred at rt until completion of the reaction. Water and EA were added, the phases were separated and the aq. phase was extracted with EA. The combined org. layers were washed several times with water and brine, dried over $MgSO_4$ and concentrated under reduced pressure. The residue was purified by CC.

Procedure K: Amide Coupling with EDCI

To a solution of the amine (1 mmol), the acid (1 mmol) and DIPEA (3 mmol) in DMF (2 mL) were added HOBT (1.1 mmol) and EDCI (1.5 mmol) at rt. The resulting mixture was stirred at rt until completion of the reaction. Water and EA were added, the phases were separated and the aq. phase was extracted with EA. The combined org. layers were washed several times with water and brine, dried over $MgSO_4$ and concentrated under reduced pressure. The residue was purified by CC.

Procedure L: Buchwald Coupling

An oven-dried vial was charged with the aryl bromide (1 mmol), palladium(II) acetate (0.04 mmol), BINAP (0.08 mmol) or bis((2-diphenylphosphino)phenyl)ether (0.08 mmol), $K_3PO_4$ (2.5 mmol) and amine (1 mmol). The resulting mixture was purged with argon for several min. Dioxane (1 mL) was then added via a syringe and the resulting suspension was purged with argon for 3 min. The mixture was then heated at 85° C. until completion of the reaction. The solvent was removed under reduced pressure and the residue was extracted with EA/water. The org. layer was washed with brine, dried over $MgSO_4$ and concentrated under reduced pressure. The residue was purified by CC.

Method M: Methylation Via Reductive Amination

To a solution of amine (1 mmol) in MeOH (20 mL) and a few drops of DCE was added a 37% aqueous solution of formaldehyde (2 mmol). After 10 min, $NaBH(OAc)_3$ (3 mmol) was added and stirring was continued until completion of the reaction. The mixture was poured into 0.1M HCl to quench the reaction. The mixture was made basic by adding 25% $NH_4OH$ and extracted with EA (2×). The org. layers were washed with brine, dried over $MgSO_4$ and concentrated. The residue was purified by CC.

Procedure N: Amide Coupling with Propylphosphonic Anhydride Solution

To a solution of amine (1 mmol), acid (1 mmol), and DIPEA (2-4 mmol) in DMF (2 mL) was added propylphosphonic anhydride solution (50% in EA, 1.1 mmol) at rt. The resulting mixture was stirred at rt until completion of the reaction. Water and EA were added, the phases were separated and the aq. phase was extracted with EA. The combined org. layers were washed several times with water and brine, dried over MgSO$_4$ and concentrated under reduced pressure. The residue was purified by CC.

PREPARATION OF EXAMPLES

Example 1

(S)-3-(2,3-Dihydro-benzo[1,4]dioxin-6-yl)-5-({[1-(6-methoxy-[1,5]naphthyridin-4-yl)-azetidin-3-ylmethyl]-amino}-methyl)-oxazolidin-2-one 1.i) [1-(6-Methoxy-[1,5]naphthyridin-4-yl)-azetidin-3-ylmethyl]-carbamic acid tert-butyl ester A mixture of 8-bromo-2-methoxy-[1,5]naphthyridine (495 mg, 2.07 mmol, prepared as in WO 2006/032466) and tert-butyl-[(azetidin-3-yl)methyl]carbamate (405 mg, 1.05 eq) in pentanol (2 mL) was heated at 80° C. overnight. The majority of the solvent was removed in vacuo at elevated temperature (50-60° C.). The residue was triturated with ether to form the desired intermediate as beige solid (300 mg, 42%).
MS (ESI, m/z): 345.5 [M+H$^+$].

1.ii) C-[1-(6-Methoxy-[1,5]naphthyridin-4-yl)-azetidin-3-yl]-methylamine

To a solution of intermediate 1.i) (290 mg, 0.842 mmol) in DCM (5 mL) were added Et$_3$SiH (0.294 mL, 2.2 eq) and TFA (3 mL). The resulting solution was stirred for 30 min at rt. The solution was concentrated to dryness, then diluted with DCM and basified with aq. NH$_4$OH. The aq. layer was extracted twice with 9:1 DCM/MeOH. The combined org. layers were dried over Na$_2$SO$_4$, filtered and concentrated to dryness to afford the desired intermediate as yellow oil (180 mg, 88%).
MS (ESI, m/z): 245.1 [M+H$^+$].

1.iii) (R)-3-(2,3-Dihydro-benzo[1,4]dioxin-6-yl)-5-hydroxymethyl-oxazolidin-2-one A solution of (2,3-dihydro-benzo[1,4]dioxin-6-yl)-carbamic acid benzyl ester (3.0 g, 10.5 mmol, prepared according to procedure C in THF (60 mL) was cooled to −78° C. before the drop wise addition of n-BuLi (5.1 mL of a 2.5 M solution in hex, 1.2 eq). The mixture was stirred at −78° C. for 1 h and then warmed to −15° C. At this temperature (R)-glycidyl butyrate (1.98 g, 1.2 eq) was added drop wise. The mixture was stirred at rt overnight. Cs$_2$CO$_3$ (tip of a spatula) was added and the mixture heated at 40° C. until complete conversion. The mixture was diluted with EA and washed with sat. NH$_4$Cl solution and water. The org. layer was dried over MgSO$_4$ and concentrated. CC (hex/EA 2:1 to 1:1) gave the desired intermediate as beige solid (1.09 g, 41%).
$^1$H NMR (DMSO d6) δ: 7.13 (d, J=2.5 Hz, 1H), 6.96 (dd, J=2.5, 8.9 Hz, 1H), 6.86 (d, J=8.9 Hz, 1H), 5.16 (t, J=5.8, 1H), 4.70-4.50 (m, 1H), 4.30-4.10 (m, 4H), 4.10-3.90 (m, 1H), 4.80-4.70 (m, 1H), 4.70-4.60 (m, 1H), 4.60-4.50 (m, 1H).

1 Iv) Methanesulfonic acid (R)-3-(2,3-dihydro-benzo[1,4]dioxin-6-yl)-2-oxo-oxazolidin-5-ylmethyl ester A solution of intermediate 1.iii) (1 g, 4 mmol) in DCM (20 mL) was cooled to 0° C. DIPEA (0.62 g, 1.2 eq) and Ms-Cl (0.502 g, 1.1 eq) were added and the mixture stirred at 0° C. for 1 h. The mixture was diluted with DCM and washed with water. The org. phase was dried over MgSO$_4$ and concentrated to give the desired intermediate (1.26 g, 97%) as colourless solid, which was used in the next step without further purification.
MS (ESI, m/z): 329.8 [M+H$^+$].

1 v) (S)-3-(2,3-Dihydro-benzo[1,4]dioxin-6-yl)-5-({[1-(6-methoxyl-1,5]naphthyridin-4-yl)-azetidin-3-ylmethyl]-amino}-methyl)-oxazolidin-2-one A solution of intermediate 1 Iv) (57 mg, 0.173 mmol) and intermediate 1.ii) (85 mg, 2 eq) in dry DMSO (1.5 mL) was heated at 70° C. for 3 d. After cooling to rt water was added and the mixture was extracted with EA. The combined org. layers were washed with brine, dried over MgSO$_4$ and concentrated and the residue was purified by CC (DCM-MeOH—NH$_4$OH 1000:50:4) to afford the title compound as colourless foam (16 mg, 19%).
$^1$H NMR (CDCl$_3$) δ: 8.33 (d, J=5.3 Hz, 1H), 8.04 (d, J=9.1 Hz, 1H), 7.07 (d, J=2.6 Hz, 1H), 7.00 (m, 2H), 6.85 (m, 1H), 6.21 (d, J=5.3 Hz, 1H), 4.74 (m, 1H), 4.55 (m, 2H), 4.25 (s, 4H), 4.14 (m, 2H), 3.99 (m, 4H), 3.81 (dd, J=8.8, 7.0 Hz, 1H), 2.98 (m, 5H).
MS (ESI, m/z): 478.3 [M+H$^+$].

Example 2

(S)-3-(2,3-Dihydro-benzo[1,4]dioxin-6-yl)-2-oxo-oxazolidine-5-carboxylic acid[1-(6-methoxy-[1,5]naphthyridin-4-yl)-azetidin-3-ylmethyl]-amide 2.i) (S)-3-(2,3-Dihydro-benzo[1,4]dioxin-6-yl)-2-oxo-oxazolidine-5-carboxylic acid To a solution of (S)-3-(2,3-dihydro-benzo[1,4]dioxin-6-yl)-5-hydroxymethyl-oxazolidin-2-one (enantiomeric antipode of intermediate 1.iii), prepared from (S)-glycidyl butyrate, 985 mg, 3.92 mmol) in 1:1 water/MeCN (20 mL) cooled to 0° C. was added diacetoxyiodobenzene (2.83 g, 2.2 eq) and TEMPO (122 mg, 0.2 eq). The mixture was stirred at 0° C. for 30 min and at rt overnight. EA and sat. Na$_2$CO$_3$ were added and the phases separated. The aq. layer was washed once more with EA and then carefully acidified with 1M aq. HCl. The aq. phase was then extracted 2× with EA. The combined org. layers were washed with brine and dried over MgSO$_4$ and concentrated to afford the desired intermediate as colourless solid (847 mg, 81%).
MS (ESI, m/z): 266.3 [M+H$^+$].

2.ii) (S)-3-(2,3-Dihydro-benzo[1,4]dioxin-6-yl)-2-oxo-oxazolidine-5-carboxylic acid[1-(6-methoxy-[1,5]naphthyridin-4-yl)-azetidin-3-ylmethyl]-amide To a solution of intermediate 1.ii) (100 mg, 0.41 mmol), intermediate 2.i) (103 mg, 0.40 mmol) and DIPEA (0.27 mL, 4 eq) in DMF (4 mL) was added HATU (311 mg, 2 eq). The resulting solution was stirred at rt for 4 h. EA and water were added and the phases were separated. The aq. phase was extracted with EA and the combined org. extracts were washed with brine/water (3×), dried over MgSO$_4$, concentrated under reduced pressure. The residue was crystallized from ether-DCM-MeOH to afford the title compound (41 mg, 20%) as beige solid.
MS (ESI, m/z): 492.2 [M+H$^+$].

Example 3

(RS)-3-(2,3-Dihydro-benzo[1,4]dioxin-6-yl)-5-[4-hydroxy-4-(6-methoxy-[1,5]naphthyridin-4-yl)-piperidin-1-ylmethyl]-oxazolidin-2-one

3.i) 4-Hydroxy-4-(6-methoxy-[1,5]naphthyridin-4-yl)-piperidine-1-carboxylic acid tert-butyl ester To a solution of 8-bromo-2-methoxy-[1,5]naphthyridine (1 g, 4.18 mmol, prepared as in WO 2006/032466) in dry THF (20 mL) at −78° C. was added dropwise n-BuLi (2.5 M in hex, 5 mL, 1.2 eq). The mixture was stirred at −78° C. for 1 h before the dropwise addition of 4-oxo-piperidine-1-carboxylic acid tert-butyl ester (0.833 g, 4.2 mmol) in THF (5 mL). The mixture was stirred at −78° C. for another h and then slowly warmed to rt. The mixture was quenched by the addition of sat. aq. $NH_4Cl$ solution (10 mL) and extracted with EA. The combined org. layers were dried over $Na_2SO_4$, filtered and concentrated in vacuo. The residue was purified by CC (hex/EA 1:1 to EA) to give the desired intermediate (1.0 g, 66.5%) as yellow oil.

$^1$H NMR ($CDCl_3$) δ: 8.78 (d, J=4.74 Hz, 1H), 8.34 (d, J=9.1 Hz, 1H), 7.47 (d, J=4.74 Hz, 1H), 7.20-7.10 (m, 2H), 4.05 (br, 1H), 4.08 (s, 3H), 3.50-3.30 (m, 2H), 2.30-1.95 (m, 4H), 1.51 (s, 9H).

MS (ESI, m/z): 359.9 [M+H$^+$].

3.ii) 4-(6-Methoxy-[1,5]naphthyridin-4-yl)-piperidin-4-ol

A solution of intermediate 3.i) (1 g, 2.78 mmol) in DCM (10 mL) was added TFA (3 mL). The mixture was stirred at rt for 2 h, concentrated in vacuo and partitioned between DCM and aq. $NH_4OH$. The org. layer was dried over $MgSO_4$ and concentrated to give the desired intermediate (0.69 g, 95%) as yellowish oil.

MS (ESI, m/z): 260.0 [M+H$^+$].

3.iii) (RS)-1-(3-Chloro-2-hydroxy-propyl)-4-(6-methoxyl-[1,5]-naphthyridin-4-yl)-piperidin-4-ol Epichlorohydrin (0.21 mL, 2.66 mmol) was added to a solution of intermediate 3.ii) (0.69 g, 2.66 mmol) and TEA (0.37 mL, 2.66 mmol) in DCM (15 mL). The mixture was stirred at rt overnight, partitioned between water and DCM. The aq. phase was extracted with DCM and the combined org. phases dried over $MgSO_4$ and concentrated under reduced pressure. The residue was purified by CC (EA/MeOH 9:1+1% $NH_4OH$) to give the desired intermediate (0.25 g) as yellow oil.

MS (ESI, m/z): 352.3 [M+H$^+$].

3.iv) (RS)-1-[3-(2,3-Dihydro-benzo[1,4]dioxin-6-ylamino)-2-hydroxy-propyl]-4-(6-methoxyl-[1,5]naphthyridin-4-yl)-piperidin-4-ol A solution of intermediate 3.iii) (0.25 g, 0.8 mmol) and 2,3-dihydro-benzo[1,4]dioxin-6-ylamine (120 mg, 0.8 mmol) in EtOH (2 mL) was heated at reflux overnight. The volatiles were removed under reduced pressure and the residue purified by CC (DCM/MeOH 19:1+0.5% $NH_4OH$) to give the desired intermediate (0.24 g, 65%) as beige foam.

$^1$H NMR (DMSO d6) δ: 8.79 (d, J=4.74 Hz, 1H), 8.29 (d, J=9.1 Hz, 1H), 7.88 (d, J=4.74 Hz, 1H), 7.28 (d, J=9.1 Hz, 1H), 6.20-6.10 (m, 2H), 4.20-3.90 (m, 5H), 3.20-2.60 (m, 8H).

3.v) (RS)-3-(2,3-Dihydro-benzo[1,4]dioxin-6-yl)-5-[4-hydroxy-4-(6-methoxy-[1,5]-naphthyridin-4-yl)-piperidin-1-ylmethyl]-oxazolidin-2-one CDI (0.073 mg, 0.45 mmol) was added to a solution of intermediate 3.iv) (0.21 g, 0.45 mmol) in DCM. The mixture was stirred at 45° C. for 2 h, CDI (40 mg) was added and stirring continued for another 2 h. The volatiles were removed under reduced pressure and the residue purified by CC (DCM/MeOH 19:1+0.5% $NH_4OH$) to give the title compound (0.048 g, 22%) as beige foam.

MS (ESI, m/z): 492.7 [M+H$^+$].

Example 4

(RS)-3-(2,3-Dihydro-benzo[1,4]dioxin-6-yl)-5-[4-hydroxy-1-(6-methoxy-quinazolin-4-yl)-piperidin-4-ylmethyl]-oxazolidin-2-one

4.i) 4-Hydroxy-4-oxiranylmethyl-piperidine-1-carboxylic acid tert-butyl ester A solution of 4-allyl-4-hydroxy-piperidine-1-carboxylic acid tert-butyl ester (3.1 g, 12.8 mmol, prepared according to J. Comb. Chem. 2002, 4, 125) in DCM and 0.3 M phosphate buffer (pH 8, 150 mL) was treated with mCPBA (3.5 g, 1.1 eq, 70%) and the mixture vigorously stirred at rt overnight. Further 3.5 g of mCPBA were added. After a total of 24 h, the phases were separated, the org. phase dried over $MgSO_4$ and concentrated. CC (hex/EA 2:1 to 1:1 to EA) gave the desired intermediate as colourless oil (0.88 g, 26%).

$^1$H NMR ($CDCl_3$) δ: 3.90-3.70 (m, 2H), 3.30-3.10 (m, 3H), 2.83 (dd, J=4.1, 4.9 Hz, 1H), 2.51 (dd, J=2.7, 4.9 Hz, 1H), 1.89 (dd, J=3.8, 14.5 Hz, 1H), 1.80-1.40 (m, 4H), 1.47 (s, 9H).

4.ii) (RS)-4-[3-(2,3-Dihydro-benzo[1,4]dioxin-6-ylamino)-2-hydroxy-propyl]-4-hydroxy-piperidine-1-carboxylic acid tert-butyl ester According to procedure A starting from intermediate 4.i) (0.88 g, 3.4 mmol) and 2,3-dihydro-benzo[1,4]dioxin-6-ylamine (517 mg, 3.4 mmol) the desired intermediate was isolated after CC (hex/EA 2:1 to 1:1) as colourless oil (1.12 g, 80%)

MS (ESI, m/z): 408.9 [M+H$^+$].

4.iii) (RS)-4-[3-(2,3-Dihydro-benzo[1,4]dioxin-6-yl)-2-oxo-oxazolidin-5-ylmethyl]-4-hydroxy-piperidine-1-carboxylic acid tert-butyl ester A solution of intermediate 4.ii) (1.13 g, 3 mmol) in DCM (50 mL) at 0° C. was treated with TEA (1.35 mL, 3 eq) and a solution of triphosgene (0.335 g, 0.3 eq) in DCM (5 mL). The mixture was stirred at rt for 2 h. The mixture was partitioned between DCM and sat. aq. $NaHCO_3$ solution, the org. phase was dried over $MgSO_4$ and concentrated. CC (hex/EA 2:1) gave the desired intermediate (0.42 g, 30%) as colourless foam.

MS (ESI, m/z): 434.9 [M+H$^+$].

4.iv) (RS)-3-(2,3-Dihydro-benzo[1,4]dioxin-6-yl)-5-(4-hydroxy-piperidin-4-ylmethyl)-oxazolidin-2-one According to procedure E and starting from intermediate 4.iii) (0.422 g, 0.97 mmol) the desired intermediate was isolated as beige foam (0.24 g, 75%).

MS (ESI, m/z): 334.8 [M+H$^+$].

4 v) (RS)-3-(2,3-Dihydro-benzo[1,4]dioxin-6-yl)-5,4-hydroxy-1-(6-methoxy-quinazolin-4-yl)-piperidin-4-ylmethyl]-oxazolidin-2-one A mixture of intermediate 4.iv) (0.12 g, 0.35 mmol) and 4-chloro-6-methoxy-quinazoline (0.07 g, 0.35 mmol) and DIPEA (0.123 mL, 2 eq) in i-PrOH/DMA (1:1, 3 mL) was heated in a sealed flask for 2 h at 100° C. The mixture was cooled to rt, poured into water and extracted with EA. The org. extracts were washed with brine, dried over MgSO$_4$ and concentrated. CC (DCM/MeOH 19:1) gave the title compound (0.07 g, 40%) as beige foam.

$^1$H NMR (DMSO d6) δ: 8.55 (s, 1H), 7.75 (d, J=9.1 Hz, 1H), 7.49 (dd, J=2.8, 9.1 Hz, 1H), 7.22 (d, J=2.8 Hz, 1H), 7.11 (d, J=2.6 Hz, 1H), 6.97 (dd, J=2.6, 8.8 Hz, 1H), 6.85 (d, J=8.8 Hz, 1H), 5.0-4.8 (m, 1H), 4.72 (s, 1H), 4.30-4.05 (m, 5H), 4.00-3.90 (m, 5H), 3.80-3.60 (m, 1H), 3.6-3.40 (m, 2H), 2.20-1.60 (m, 6H).

MS (ESI, m/z): 492.6 [M+H$^+$].

Example 5

(RS)-3-(2,3-Dihydro-benzo[1,4]dioxin-6-yl)-5-[4-hydroxy-1-(6-methoxy-[1,5]naphthyridin-4-yl)-piperidin-4-ylmethyl]-oxazolidin-2-one The title compound was obtained starting from intermediate 4.iv) (0.12 g, 0.35 mmol) and 8-bromo-2-methoxy-[1,5]naphthyridine (0.07 g, 1 eq) and following the procedure of example 4 step v) as beige foam (30 mg, 17%).

MS (ESI, m/z): 492.6 [M+H$^+$].

Example 6

(RS)-3-(2,3-Dihydro-benzo[1,4]dioxin-6-yl)-5-[4-(6-methoxy-quinazolin-4-yl)-piperazin-1-ylmethyl]-oxazolidin-2-one 6.i) 6-Methoxy-4-piperazin-1-yl-quinazoline Piperazine (1.1 g, 12.8 mmol) was added to a solution of 4-chloro-6-methoxy-quinazoline (0.5 g, 2.6 mmol) in DMF (5 mL). The mixture was stirred at rt for 1 h, partitioned between chloroform and aq. ammonia. The org. phase was washed with water, dried over MgSO$_4$ and concentrated. Purification by CC (DCM/MeOH 19:1+0.5% NH$_4$OH) gave the desired intermediate (0.57 g, 91%) as yellow oil.

$^1$H NMR (CDCl$_3$) δ: 8.73 (s, 1H), 7.86 (d, J=9.2 Hz, 1H), 7.44 (dd, J=2.8, 9.2 Hz, 1H), 7.17 (d, J=2.8 Hz, 1H), 3.94 (s, 3H), 3.75-3.70 (m, 4H), 3.20-3.10 (m, 4H).

MS (ESI, m/z): 245.0 [M+H$^+$].

6.ii) (RS)-1-Chloro-3-[4-(6-methoxy-quinazolin-4-yl)-piperazin-1-yl]-propan-2-ol A solution of intermediate 6.i) (0.57 g, 2.3 mmol) in DCM (10 mL) was treated with TEA (0.32 mL, 1 eq) and epichlorohydrin (0.18 mL, 1 eq). The mixture was stirred at rt over night. Further epichlorohydrin (0.18 mL) was added and the mixture stirred at 40° C. for 24 h. The mixture was partitioned between DCM and aq. NH$_4$OH, the org. phase dried over MgSO$_4$ and concentrated. Purification by CC (DCM/MeOH 19:1+0.5% NH$_4$OH) gave the desired intermediate (0.4 g, 51%) as yellow oil.

MS (ESI, m/z): 337.0 [M+H$^+$].

6.iii) (RS)-1-(2,3-Dihydro-benzo[1,4]dioxin-6-ylamino)-3-[4-(6-methoxy-quinazolin-4-yl)-piperazin-1-yl]-propan-2-ol According to procedure A starting from intermediate 6.ii) (0.2 g, 0.59 mmol) and 2,3-dihydro-benzo[1,4]dioxin-6-ylamine (0.09 g, 0.59 mmol) the desired intermediate was obtained after CC (DCM/MeOH 19:1+0.5% NH$_4$OH) as brownish oil (0.1 g, 38%).

MS (ESI, m/z): 451.9 [M+H$^+$].

6.iv) (RS)-3-(2,3-Dihydro-benzo[1,4]dioxin-6-yl)-5-[4-(6-methoxy-quinazolin-4-yl)-piperazin-1-ylmethyl]-oxazolidin-2-one According to procedure B starting from intermediate 6.iii) (0.1 g, 0.22 mmol) the title compound was obtained after CC (DCM/MeOH 19:1+0.5% NH$_4$OH) as brownish oil (0.09 g, 85%).

MS (ESI, m/z): 477.8 [M+H$^+$].

Example 7

(RS)-6-{5-[4-(6-Methoxy-quinazolin-4-yl)-piperazin-1-ylmethyl]-2-oxo-oxazolidin-3-yl}-4H-benzo[1,4]thiazin-3-one 7.i) (RS)-6-{2-Hydroxy-3-[4-(6-methoxy-quinazolin-4-yl)-piperazin-1-yl]-propylamino}-4H-benzo[1,4]thiazin-3-one A solution of intermediate 6.ii) (0.7 g, 2.08 mmol) and 6-amino-4H-benzo[1,4]thiazin-3-one (0.375 g, 2.08 mmol) and TEA (0.3 mL, 1 eq) in EtOH (10 mL) was heated at 80° C. over night. The mixture was concentrated and partitioned between chloroform and aq. ammonia. The org. phase was dried over MgSO$_4$ and concentrated. The residue was crystallized from EA/ether to give the desired intermediate (0.31 g, 31%) as browhish solid.

MS (ESI, m/z): 481.2 [M+H$^+$].

7.ii) (RS)-6-{5-[4-(6-Methoxy-quinazolin-4-yl)-piperazin-1-ylmethyl]-2-oxo-oxazolidin-3-yl}-4H-benzo[1,4]thiazin-3-one A solution of intermediate 7.i) (0.31 g, 0.65 mmol) in pyridine (5 mL) at 0° C. was treated with triphosgene (0.19 g, 1 eq). The mixture was stirred at 0° C. for 30 min and at rt for 4 h. The mixture was diluted with EA (30 mL) and washed with water (5×20 mL), dried over MgSO$_4$ and concentrated. Purification by CC (DCM/MeOH 19:1+0.5% NH$_4$OH) gave the title compound as brownish solid (0.019 g, 6%).

MS (ESI, m/z): 506.6 [M+H$^+$].

Example 8

(RS)-3-(2,3-Dihydro-benzo[1,4]dioxin-6-yl)-5-[4-(6-methoxy-[1,5]naphthyridin-4-yl)-piperazin-1-ylmethyl]-oxazolidin-2-one 8.i) 2-Methoxy-8-piperazin-1-yl-[1,5]-naphthyridine A solution of 8-bromo-2-methoxy-[1,5]naphthyridine (4.78 g, 20 mmol, prepared as in WO 2006/032466) and piperazine (8.6 g, 100 mmol) in 1-pentanol (20 mL) was heated at 80° C. over night. The mixture was cooled and the precipitate filtered off. The filtrate was diluted with EA (100 mL) and washed with water (20 mL). The aq. phase contains some product, which was extracted with DCM/MeOH 9:1 (3×30 mL). The org. phases were combined, dried over MgSO$_4$ and concentrated under reduced pressure. The residue was purified by CC (EA/MeOH 4:1 to MeOH) to give the desired intermediate (4.7 g, 96%) as yellow oil.

$^1$H NMR (DMSO d6) δ: 8.43 (d, J=5.3 Hz, 1H), 8.11 (d, J=9.1 Hz, 1H), 7.14 (d, J=9.1 Hz, 1H), 6.88 (d, J=5.3 Hz, 1H), 3.95 (s, 3H), 3.40-3.60 (m, 4H), 2.90-3.00 (m, 4H).

MS (ESI, m/z): 245.2 [M+H$^+$].

8.ii) (RS)-1-Chloro-3-[4-(6-methoxy-[1,5]-naphthyridin-4-yl)-piperazin-1-yl]-propan-2-ol Starting from intermediate 8.i) (0.43 g, 1.76 mmol) and following the procedures from example 6, step ii) the desired intermediate was isolated as yellow oil (0.24 g, 40%).

MS (ESI, m/z): 336.8 [M+H$^+$].

8.iii) (RS)-3-(2,3-Dihydro-benzo[1,4]dioxin-6-yl)-5,4-(6-methoxyl-[1,5]-naphthyridin-4-yl)-piperazin-1-ylmethyl]-oxazolidin-2-one In analogy to Example 6, steps iii) and iv) the title compound was obtained starting from intermediate 8.ii) (0.24 g) as colourless foam (0.14 g).

$^1$H NMR (CDCl$_3$) δ: 8.54 (d, J=5.1, 1H), 8.15 (d, J=9.1 Hz, 1H), 7.1-7.0 (m, 3H), 6.9-6.8 (m, 2H), 5.90-5.75 (m, 1H), 4.3-4.20 (m, 4H), 4.05 (s, 3H), 4.10-4.00 (m, 1H), 4.90-4.80 (m, 1H), 4.80-4.60 (m, 4H), 3.00-2.80 (m, 6H).

MS (ESI, m/z): 478.2 [M+H$^+$].

Example 9

(R)-3-(2,3-Dihydro-benzo[1,4]dioxin-6-yl)-5-[4-(6-methoxy-[1,5]naphthyridin-4-yl)-piperazin-1-ylmethyl]-oxazolidin-2-one

9.i) (R)-1-Chloro-3,4-(6-methoxy-[1,5]naphthyridin-4-yl)-piperazin-1-yl]-propan-2-ol A solution of intermediate 8.i) (4.7 g, 19 mmol) in dry MeOH (100 mL) was treated with MgSO$_4$ (anhydrous, 5 g) and (R)-epichlorohydrin (3.8 mL, 2.5 eq). The mixture was stirred at 35° C. over night, filtered over Celite and concentrated in vacuo. The residue was taken up in DCM and washed with water, dried over MgSO$_4$ and concentrated. The product was purified by CC (EA/MeOH 9:1+1% NH$_4$OH) to give 4.8 g (75%) of the desired intermediate as yellowish oil.

MS (ESI, m/z): 337.4 [M+H$^+$].

9.ii) (5R)-3-(2,3-Dihydro-benzo[1,4]dioxin-6-yl)-5,4-(6-methoxy-[1,5]naphthyridin-4-yl)-piperazin-1-ylmethyl]-oxazolidin-2-one According to procedure D starting from intermediate 9.i) (0.17 g, 0.5 mmol) and (2,3-dihydro-benzo[1,4]dioxin-6-yl)-carbamic acid benzyl ester (0.143 g, 0.5 mmol) the title compound was obtained as colourless foam (0.13 g, 54%).

$^1$H NMR (CDCl$_3$) δ: 8.54 (d, J=5.1, 1H), 8.15 (d, J=9.1 Hz, 1H), 7.1-7.0 (m, 3H), 6.9-6.8 (m, 2H), 5.90-5.75 (m, 1H), 4.3-4.20 (m, 4H), 4.05 (s, 3H), 4.10-4.00 (m, 1H), 4.90-4.80 (m, 1H), 4.80-4.60 (m, 4H), 3.00-2.80 (m, 6H).

MS (ESI, m/z): 478.2 [M+H$^+$].

The following examples were prepared from intermediate 8l) using the appropriate configurational isomer of epichlorohydrin and the appropriate carbamic acid benzyl ester in analogy to Example 9:

| Example | Chemical name | Yield | MS (ESI) [M + H$^+$] |
|---|---|---|---|
| 10 | (R)-5-[4-(6-Methoxy-[1,5]naphthyridin-4-yl)-piperazin-1-ylmethyl]-3-(3-trifluoromethoxy-phenyl)-oxazolidin-2-one | 24% | 503.9 |
| 11 | (R)-5-[4-(6-Methoxy-[1,5]naphthyridin-4-yl)-piperazin-1-ylmethyl]-3-(4-trifluoromethoxy-phenyl)-oxazolidin-2-one | 51% | 503.9 |
| 12 | (R)-5-[4-(6-Methoxy-[1,5]naphthyridin-4-yl)-piperazin-1-ylmethyl]-3-phenyl-oxazolidin-2-one | 64% | 420.3 |
| 13 | (R)-3-(4-Bromo-3-fluoro-phenyl)-5-[4-(6-methoxy-[1,5]naphthyridin-4-yl)-piperazin-1-ylmethyl]-oxazolidin-2-one | 51% | 518.2 |
| 14 | (R)-3-(3,4-Dimethoxy-phenyl)-5-[4-(6-methoxy-[1,5]naphthyridin-4-yl)-piperazin-1-ylmethyl]-oxazolidin-2-one | 56% | 480.1 |
| 15 | (R)-3-(4-Fluoro-phenyl)-5-[4-(6-methoxy-[1,5]naphthyridin-4-yl)-piperazin-1-ylmethyl]-oxazolidin-2-one | 41% | 438.4 |
| 16 | (R)-5-[4-(6-Methoxy-[1,5]naphthyridin-4-yl)-piperazin-1-ylmethyl]-3-(3-trifluoromethyl-phenyl)-oxazolidin-2-one | 63% | 488.3 |
| 17 | (R)-3-(3-Chloro-4-fluoro-phenyl)-5-[4-(6-methoxy-[1,5]naphthyridin-4-yl)-piperazin-1-ylmethyl]-oxazolidin-2-one | 39% | 472.5 |
| 18 | (R)-5-[4-(6-Methoxy-[1,5]naphthyridin-4-yl)-piperazin-1-ylmethyl]-3-(4-methyl-3-trifluoromethyl-phenyl)-oxazolidin-2-one | 29% | 502.1 |
| 19 | (R)-3-Benzothiazol-6-yl-5-[4-(6-methoxy-[1,5]naphthyridin-4-yl)-piperazin-1-ylmethyl]-oxazolidin-2-one | 27% | 477.2 |
| 20 | (R)-3-(4-Difluoromethoxy-phenyl)-5-[4-(6-methoxy-[1,5]naphthyridin-4-yl)-piperazin-1-ylmethyl]-oxazolidin-2-one | 42% | 486.1 |

| Example | Chemical name | Yield | MS (ESI) [M + H⁺] |
|---|---|---|---|
| 21 | 3-{(R)-5-[4-(6-Methoxy-[1,5]naphthyridin-4-yl)-piperazin-1-ylmethyl]-2-oxo-oxazolidin-3-yl}-benzonitrile | 29% | 445.1 |
| 22 | 6-{(R)-5-[4-(6-Methoxy-[1,5]naphthyridin-4-yl)-piperazin-1-ylmethyl]-2-oxo-oxazolidin-3-yl}-4H-benzo[1,4]thiazin-3-one | 11% | 507.2 |
| 23 | (R)-5-[4-(6-Methoxy-[1,5]naphthyridin-4-yl)-piperazin-1-ylmethyl]-3-(4-pyrrolidin-1-yl-phenyl)-oxazolidin-2-one | 44% | 489.4 |
| 24 | (R)-5-[4-(6-Methoxy-[1,5]naphthyridin-4-yl)-piperazin-1-ylmethyl]-3-(3-methoxy-phenyl)-oxazolidin-2-one | 52% | 450.5 |
| 25 | (R)-5-[4-(6-Methoxy-[1,5]naphthyridin-4-yl)-piperazin-1-ylmethyl]-3-(4-propyl-phenyl)-oxazolidin-2-one | 48% | 462.3 |
| 26 | (R)-3-(4-Ethyl-phenyl)-5-[4-(6-methoxy-[1,5]naphthyridin-4-yl)-piperazin-1-ylmethyl]-oxazolidin-2-one | 60% | 448.1 |
| 27 | (R)-3-(3,4-Dimethyl-phenyl)-5-[4-(6-methoxy-[1,5]naphthyridin-4-yl)-piperazin-1-ylmethyl]-oxazolidin-2-one | 62% | 448.4 |
| 28 | (R)-3-(3-Chloro-4-methoxy-phenyl)-5-[4-(6-methoxy-[1,5]naphthyridin-4-yl)-piperazin-1-ylmethyl]-oxazolidin-2-one | 41% | 483.9 |
| 29 | (R)-3-(3,4-Difluoro-phenyl)-5-[4-(6-methoxy-[1,5]naphthyridin-4-yl)-piperazin-1-ylmethyl]-oxazolidin-2-one | 43% | 456 |
| 30 | (R)-3-(4-Fluoro-3-methyl-phenyl)-5-[4-(6-methoxy-[1,5]naphthyridin-4-yl)-piperazin-1-ylmethyl]-oxazolidin-2-one | 60% | 452.2 |
| 31 | (R)-3-(4-Bromo-3-methyl-phenyl)-5-[4-(6-methoxy-[1,5]naphthyridin-4-yl)-piperazin-1-ylmethyl]-oxazolidin-2-one | 48% | 514 |
| 32 | (R)-3-(3-Bromo-4-methyl-phenyl)-5-[4-(6-methoxy-[1,5]naphthyridin-4-yl)-piperazin-1-ylmethyl]-oxazolidin-2-one | 52% | 514.2 |
| 33 | (R)-5-[4-(6-Methoxy-[1,5]naphthyridin-4-yl)-piperazin-1-ylmethyl]-3-(4-methoxy-3-trifluoromethyl-phenyl)-oxazolidin-2-one | 44% | 518.3 |
| 34 | (R)-3-(3-Dimethylamino-phenyl)-5-[4-(6-methoxy-[1,5]naphthyridin-4-yl)-piperazin-1-ylmethyl]-oxazolidin-2-one | 44% | 463.3 |
| 35 | (R)-3-Benzo[1,3]dioxol-5-yl-5-[4-(6-methoxy-[1,5]naphthyridin-4-yl)-piperazin-1-ylmethyl]-oxazolidin-2-one | 53% | 464.3 |
| 36 | (R)-3-(3-Fluoro-4-methyl-phenyl)-5-[4-(6-methoxy-[1,5]naphthyridin-4-yl)-piperazin-1-ylmethyl]-oxazolidin-2-one | 58% | 452.2 |
| 37 | (S)-3-(2,3-Dihydro-benzo[1,4]dioxin-6-yl)-5-[4-(6-methoxy-[1,5]naphthyridin-4-yl)-piperazin-1-ylmethyl]-oxazolidin-2-one | 34% | 478.0 |
| 38 | (S)-3-(3-Fluoro-4-methyl-phenyl)-5-[4-(6-methoxy-[1,5]naphthyridin-4-yl)-piperazin-1-ylmethyl]-oxazolidin-2-one | 22% | 452.2 |
| 39 | 6-{(S)-5-[4-(6-Methoxy-[1,5]naphthyridin-4-yl)-piperazin-1-ylmethyl]-2-oxo-oxazolidin-3-yl}-4H-benzo[1,4]thiazin-3-one | 11% | 507.1 |
| 40 | (S)-3-(3-Fluoro-phenyl)-5-[4-(6-methoxy-[1,5]naphthyridin-4-yl)-piperazin-1-ylmethyl]-oxazolidin-2-one | 25% | 438.3 |

Example 41

(R)-3-(2,3-Dihydro-benzo[1,4]dioxin-6-yl)-5-{[(S)-1-(6-methoxy-[1,5]naphthyridin-4-yl)-pyrrolidin-3-ylamino]-methyl}-oxazolidin-2-one

41.i) [(S)-1-(6-Methoxy-[1,5]naphthyridin-4-yl)-pyrrolidin-3-yl]-carbamic acid tert-butyl ester A mixture of 8-bromo-2-methoxy-[1,5]naphthyridine (1.50 g, 6.27 mmol, prepared as in WO 2006/032466) and (S)-(−)-3-(tert-butoxycarbonylamino)pyrrolidine (1.17 g, 6.27 mmol) in pentanol (5 mL) and DIPEA (1.24 mL, 1.2 eq) was heated at 80° C. over night. The majority of the solvent was removed in vacuo at elevated temperature (50-60° C.). The residue was triturated with ether to remove residual amine. The mother liquor was concentrated and the residue was chromatographed over $SiO_2$ (DCM-MeOH—$NH_4OH$ 1000:50:4) to afford the desired intermediate as a beige foam (1.86 g, 86%).

MS (ESI, m/z): 345.2 [M+H⁺].

41.ii) (S)-1-(6-Methoxyl-1,5]naphthyridin-4-yl)-pyrrolidin-3-ylamine

To a solution of intermediate 41.i) (913 mg, 2.65 mmol) in DCM (5 mL) were added $Et_3SiH$ (0.463 mL, 1.1 eq) and TFA (5 mL). The resulting solution was stirred for 30 min at rt. The solution was concentrated to dryness, then diluted with DCM and basified with aq. NH₄OH. The aq. layer was extracted twice with 9:1 DCM/MeOH. The combined org. layers were dried over Na₂SO₄, filtered and concentrated to dryness to afford the desired intermediate as a brown solid (535 mg, 83%).

MS (ESI, m/z): 245.2 [M+H⁺].

41.iii) (R)-3-(2,3-Dihydro-benzo[1,4]dioxin-6-yl)-5-{[(S)-1-(6-methoxy-[1,5]-naphthyridin-4-yl)-pyrrolidin-3-ylamino]-methyl}-oxazolidin-2-one A solution of intermediate 41.ii) (50 mg, 0.152 mmol) and methanesulfonic acid (S)-3-(2,3-dihydro-benzo[1,4]dioxin-6-yl)-2-oxo-oxazolidin-5-ylmethyl ester (enantiomeric antipode of intermediate 11v), prepared from (S)-glycidyl butyrate in analogy to example 1, steps iii) and iv), 111 mg, 3 eq) in dry DMSO (1.5 mL) was heated at 70° C. for 3 d. After cooling to rt water was added and the mixture was extracted with EA. The combined org. layers were washed with brine, dried over MgSO₄ and concentrated and the residue was purified by CC (DCM-MeOH—NH₄OH 1000:50:4) to afford the title compound as pale yellow foam (18 mg, 25%).

¹H NMR (CDCl₃) δ: 8.32 (d, J=5.3 Hz, 1H), 8.05 (d, J=9.1 Hz, 1H), 7.01 (m, 3H), 6.82 (m, 1H), 6.39 (d, J=5.6 Hz, 1H), 4.72 (m, 1H), 4.19 (m, 5H), 3.96 (m, 6H), 3.79 (m, 2H), 3.52 (m, 1H), 2.99 (m, 2H), 2.19 (m, 1H), 1.89 (m, 1H).

MS (ESI, m/z): 478.0 [M+H⁺].

Example 42

(R)-3-(2,3-Dihydro-benzo[1,4]dioxin-6-yl)-5-{[(R)-1-(6-methoxy-[1,5]naphthyridin-4-yl)-pyrrolidin-3-ylamino]-methyl}-oxazolidin-2-one The title compound was obtained from (R)-(+)-3-(tert-butoxycarbonylamino)pyrrolidine in analogy to Example 41 as a colorless foam (150 mg, 25%).

MS (ESI, m/z): 478.0 [M+H⁺].

Example 43

(RS)-5-[4-(6-Methoxy-[1,5]naphthyridin-4-yl)-piperazin-1-ylmethyl]-3-(5-methyl-pyridin-2-yl)-oxazolidin-2-one

43.i) (RS)—Oxiranylmethyl-carbamic acid benzyl ester

A solution of allyl-carbamic acid benzyl ester (9.6 g, 50 mmol) in DCM (250 mL) was treated with mCPBA (11.55 g, 50 mmol, 75% purity) and the mixture was stirred at rt for 4 h. The pH of the mixture was adjusted to 9 by addition of 1M aq. NaOH. The phases were separated and the org. phase dried over MgSO₄ and concentrated. The residue was purified by CC (hex/EA 2:1) to give the desired intermediate (7.4 g, 71% yield) as a colourless oil.

¹H NMR (CDCl₃) δ: 7.35 (m, 5H), 5.11 (s, 2H), 4.97 (s, 1H), 3.62 (m, 1H), 3.27 (m, 1H), 3.09 (m, 1H), 2.78 (t, J=4.4 Hz, 1H), 2.59 (dd, J=4.4, 2.6 Hz, 1H).

43.ii) (RS)-{2-Hydroxy-3,4-(6-methoxyl-[1,5]-naphthyridin-4-yl)-piperazin-1-yl]-propyl}-carbamic acid benzyl ester A solution of intermediate 8.i) (1.22 g, 5 mmol) and intermediate 43.i) (1.03 g, 5 mmol) in EtOH/H₂O (9:1, 30 ml) was heated at 80° C. overnight. The mixture was concentrated in vacuo and purified by CC (EA/MeOH 9:1) to give the desired intermediate (1.72 g, 76% yield) as a yellowish foam.

¹H NMR (CDCl₃) δ: 8.54 (d, J=5.0 Hz, 1H), 8.15 (d, J=9.1 Hz, 1H), 7.35 (m, 5H), 7.07 (d, J=9.1 Hz, 1H), 6.82 (d, J=5.3 Hz, 1H), 5.25 (dd, J=1.8, 0.6 Hz, 1H), 5.12 (s, 2H), 4.02 (s, 3H), 3.88 (m, 1H), 3.66 (m, 5H), 3.18 (m, 1H), 2.94 (m, 2H), 2.70 (m, 2H), 2.47 (m, 2H).

MS (ESI, m/z): 452.3 [M+H⁺].

43.iii) (RS)-5,4-(6-Methoxy-[1,5]naphthyridin-4-yl)-piperazin-1-ylmethyl]-oxazolidin-2-one A solution of intermediate 43.ii) (1.6 g, 3.5 mmol) in DMF (20 mL) was treated with NaH dispersion (0.17 g, 1 eq., 50%). The mixture was stirred at rt for 1.5 h, diluted with water and the pH was adjusted to 5 by addition of 1M aq. HCl. The aq. phase was extracted several times with EA and DCM. The combined org. layers were dried over MgSO₄ and concentrated. The residue was triturated with ether and filtered to give the desired intermediate (0.98 g, 80% yield) as a colourless solid.

MS (ESI, m/z): 344.5 [M+H⁺].

43.iv) (RS)-5,4-(6-Methoxyl-[1,5]-naphthyridin-4-yl)-piperazin-1-ylmethyl]-3-(5-methyl-pyridin-2-yl)-oxazolidin-2-one A mixture of intermediate 43.iii) (0.1 g, 0.29 mmol), Cs₂CO₃ (0.116 g), tris(dibenzylidenacetone)dipalladium (0) chloroform complex (5.2 mg) and (BINAP) (13 mg) in dioxane (4.5 mL) was sonicated for 10 min. The mixture turned from red to orange. 2-Bromo-5-methylpyridine (0.05 g, 0.29 mmol) was added and the mixture heated at 100° C. over night. The mixture was cooled and partitioned between water and EA. The org. extracts were washed with sat. NH₄Cl solution, dried over MgSO₄ and concentrated. The residue was triturated with ether and filtered to give the title compound (0.053 g, 42% yield) as a reddish solid.

¹H NMR (CDCl₃) δ: 8.54 (d, J=5.0 Hz, 1H), 8.14 (m, 3H), 7.53 (m, 1H), 7.07 (d, J=9.1 Hz, 1H), 6.83 (d, J=5.3 Hz, 1H), 4.85 (m, 1H), 4.35 (m, 1H), 4.03 (m, 4H), 3.68 (m, 4H), 2.90 (m, 6H), 2.30 (s, 3H).

MS (ESI, m/z): 435.4 [M+H⁺].

Example 44

(RS)-5-[4-(6-Methoxy-[1,5]naphthyridin-4-yl)-piperazin-1-ylmethyl]-3-(5-trifluoromethyl-pyridin-2-yl)-oxazolidin-2-one A solution of intermediate 43.iii) (0.1 g, 0.29 mmol) and 2-chloro-5-trifluoromethyl-pyridine (0.053 g, 0.29 mmol) in DMF (1.5 mL) was treated with NaH dispersion (0.013 g, 1 eq, 50%). The mixture was stirred at rt for 1 h and heated at 60° C. for 3.5 h. The mixture was cooled and partitioned between water and EA. The org. extracts were dried over MgSO₄ and concentrated. The residue was purified by purified by CC (EA/MeOH 9:1+1% NH₄OH) to give the title compound (0.03 g, 21% yield) as a yellowish oil.

¹H NMR (CDCl₃) δ: 8.60 (m, 1H), 8.54 (m, 1H), 8.39 (m, 1H), 8.16 (d, J=8.8 Hz, 1H), 7.92 (m, 1H), 7.08 (d, J=9.1 Hz, 1H), 6.83 (m, 1H), 4.89 (m, 1H), 4.40 (m, 1H), 4.09 (m, 1H), 4.04 (m, 3H), 3.69 (m, 4H), 2.90 (m, 8H).

MS (ESI, m/z): 489.2 [M+H⁺].

Example 45

6-((R)-5-{[1-(3-Fluoro-6-methoxy-[1,5]naphthyridin-4-yl)-azetidin-3-ylamino]-methyl}-2-oxo-oxazolidin-3-yl)-4H-benzo[1,4]oxazin-3-one

45.i) [1-(3-Fluoro-6-methoxy-[1,5]naphthyridin-4-yl)-azetidin-3-yl]-carbamic acid benzyl ester An oven-dried vial was charged with 8-bromo-7-fluoro-2-methoxy-[1,5]naphthyridine (commercial; 2.0 g, 7.78 mmol), palladium(II) acetate (70 mg, 0.31 mmol), DPEphos (335 mg, 0.62 mmol), $K_3PO_4$ (4.13 g, 19.45 mmol) and azetidin-3-yl-carbamic acid benzyl ester (1.68 g, 8.17 mmol). The resulting mixture was purged with argon for several min. Dioxane (25 mL) was then added via syringe and the resulting suspension was purged with argon for 3 min. The mixture was then heated at 85° C. overnight. The solvent was removed in vacuo and the residue was extracted with EA/water. The org. layer was washed with brine, dried over $MgSO_4$ and concentrated. To the resulting solid TBME and a few drops of DCM and MeOH were added and the mixture was sonicated for 5 min and filtered to afford the title intermediate as a beige solid (2.53 g, 85%).

MS (ESI, m/z): 338.1 [M+H$^+$].

45.ii) 1-(3-Fluoro-6-methoxy-[1,5]naphthyridin-4-yl)-azetidin-3-ylamine

According to procedure G and starting from intermediate 45.i), the desired intermediate was isolated as a colorless solid (1.13 g, 70%).

MS (ESI, m/z): 249.5 [M+H$^+$].

45.iii) 6-[(S)-3-(tert-Butyl-dimethyl-silanyloxy)-2-hydroxy-propylamino]-4H-benzo[1,4]oxazin-3-one To a solution of tert-butyl-dimethyl-((S)-1-oxiranylmethoxy)-silane (commercial; 13.0 g, 69 mmol) in MeCN (220 mL) was added $LiClO_4$ (22 g, 207 mmol). 6-Amino-4H-benzo[1,4]oxazin-3-one (commercial; 11.45 g, 64 mmol) was added and the mixture was stirred at 50° C. for 6 h. The solvent was removed in vacuo and the residue was purified by CC (DCM/MeOH/NH$_4$OH 1000/25/2->1000/100/2) to afford the title compound as a pale brown foam (11.16 g, 44%).

MS (ESI, m/z): 353.3 [M+H$^+$].

45.iv) 6-[(S)-5-(tert-Butyl-dimethyl-silanyloxymethyl)-2-oxo-oxazolidin-3-yl]-4H-benzo[1,4]oxazin-3-one A solution of intermediate 45.iii) (11.16 g, 30 mmol) and CDI (5.57 g, 33 mmol) in THF (130 mL) was heated at 50° C. for 2 h; the mixture was concentrated in vacuo and partitioned between EA and water. Some crystallized product was filtered and washed with $H_2O$ and EA to give 5.21 g. The org. layer was washed with brine, dried over $MgSO_4$ and concentrated under reduced pressure. The residue was purified by purified by CC (DCM/MeOH 1000:50:4) to give additional 2.28 g as a colorless solid (7.49 g, 63%).

MS (ESI, m/z): 379.2 [M+H$^+$].

45.v) 6-((S)-5-Hydroxymethyl-2-oxo-oxazolidin-3-yl)-4H-benzo[1,4]oxazin-3-one A suspension of intermediate 45.iv) (11.49 g, 29.1 mmol) in THF (30 mL) was treated with TBAF (1M in THF, 29.1 mL). The yellow solution was stirred at 0° C. for 3 h and then partitioned between water and EA. Some crystallized product was filtered and washed with $H_2O$ and EA to give 6.49 g. The aq. phase was extracted with EA (3×). The combined org. layers were washed with brine, dried over $MgSO_4$, filtered and concentrated under reduced pressure. The crude product was triturated with EA to give 1.23 g (overall 7.72 g, 95% as an off-white solid).

MS (ESI, m/z): 265.5 [M+H$^+$].

45.vi) Methanesulfonic acid (S)-2-oxo-3-(3-oxo-3,4-dihydro-2H-benzo[1,4]oxazin-6-yl)-oxazolidin-5-ylmethyl ester In analogy to the preparation of intermediate 1.iv), the title compound was obtained from intermediate 45.v as an off-white solid (1.40 g, 44%).

$^1$H NMR (DMSO-d6) δ: 10.72 (s, 1H), 7.29 (dd, J=2.1, 0.6 Hz, 1H), 6.94 (m, 2H), 4.95 (m, 1H), 4.52 (s, 2H), 4.49 (m, 2H), 4.11 (t, J=9.1 Hz, 1H), 3.73 (m, 2H), 3.23 (s, 3H).

MS (ESI, m/z): 343.2 [M+H$^+$].

45.vii) 6-((R)-5-{[1-(3-Fluoro-6-methoxy-[1,5]naphthyridin-4-yl)-azetidin-3-ylamino]-methyl}-2-oxo-oxazolidin-3-yl)-4H-benzo[1,4]oxazin-3-one According to procedure H and starting from intermediates 45.ii) and 45.vi), the title compound was isolated as a pale yellow solid (49 mg, 28%).

MS (ESI, m/z): 495.1 [M+H$^+$].

Example 46

(R)-5-{[1-(3-Fluoro-6-methoxy-[1,5]naphthyridin-4-yl)-azetidin-3-ylamino]-methyl}-3-(3-fluoro-4-methyl-phenyl)-oxazolidin-2-one

46.i) (S)-3-(3-Fluoro-4-methyl-phenyl)-5-hydroxymethyl-oxazolidin-2-one

Starting from (3-fluoro-4-methyl-phenyl)-carbamic acid benzyl ester (prepared from 3-fluoro-4-methyl-aniline and CbzCl according to procedure C) and (S)-glycidyl butyrate and following the procedure described for the preparation of intermediate 1.iii)(procedure D), the title compound was obtained as a yellow solid (4.16 g, 65%).

MS (ESI, m/z): 226.0 [M+H$^+$].

46.ii) Methanesulfonic acid (S)-3-(3-fluoro-4-methyl-phenyl)-2-oxo-oxazolidin-5-ylmethyl ester In analogy to example 1.iv), the title compound was obtained from intermediate 46.i and Ms-Cl as a yellow solid (1.62 g, 100%).

$^1$H NMR (DMSO-d6) δ: 7.44 (dd, J=12.3, 2.1 Hz, 1H), 7.24 (m, 2H), 4.98 (m, 1H), 4.47 (m, 2H), 4.16 (t, J=9.4 Hz, 1H), 3.80 (m, 1H), 3.23 (s, 3H), 2.19 (d, J=1.5 Hz, 3 H).

46.iii) (S)-3-(3-Fluoro-4-methyl-phenyl)-5-iodomethyl-oxazolidin-2-one

A mixture of intermediate 46.ii) (640 mg, 2.11 mmol) and NaI (1.27 g, 8.44 mmol) in acetone (12 mL) was heated at reflux for 3 h. The solvent was evaporated and the residue extracted with water/DCM. The org. layer was washed with brine, dried over MgSO₄ and concentrated under reduced pressure to afford the title compound as a yellow solid (600 mg, 85%).

MS (ESI, m/z): 335.9 [M+H⁺].

46.iv) (R)-5-{[1-(3-Fluoro-6-methoxy-[1,5]naphthyridin-4-yl)-azetidin-3-ylamino]-methyl}-3-(3-fluoro-4-methyl-phenyl)-oxazolidin-2-one According to procedure I and starting from intermediate 45.0 and intermediate 46.iii), the title compound was isolated as a colorless solid (45 mg, 35%).

¹H NMR (CDCl₃) δ: 8.30 (d, J=4.7 Hz, 1H), 8.01 (d, J=9.1 Hz, 1H), 7.36 (m, 1H), 7.14 (m, 2H), 6.95 (d, J=9.1 Hz, 1H), 4.94 (m, 2H), 4.75 (m, 1H), 4.42 (m, 2H), 3.96 (m, 6H), 3.05 (m, 1H), 2.93 (m, 1H), 2.24 (d, J=1.8 Hz, 3H).

MS (ESI, m/z): 456.6 [M+H⁺].

Example 47

(R)-3-(2,3-Dihydro-benzo[1,4]dioxin-6-yl)-5-{[1-(3-fluoro-6-methoxy-[1,5]naphthyridin-4-yl)-azetidin-3-ylamino]-methyl}-oxazolidin-2-one

47.i) Methanesulfonic acid (S)-3-(2,3-dihydro-benzo[1,4]dioxin-6-yl)-2-oxo-oxazolidin-5-ylmethyl ester The title compound was prepared from the (S) enantiomer of intermediate 1iii) as described in example 1) step 1.iv) and isolated as a colourless material (1.11 g, 50%).

MS (ESI, m/z): 330.1 [M+H⁺].

47.ii) (S)-3-(2,3-Dihydro-benzo[1,4]dioxin-6-yl)-5-iodomethyl-oxazolidin-2-one The title compound was obtained as a colorless solid (393 mg, 70%) starting from intermediate 473) and NaI following the procedure described in example 46 step 46.iii).

¹H NMR (CDCl₃) δ: 7.07 (d, J=2.6 Hz, 1H), 6.98 (dd, J=9.1, 2.6 Hz, 1H), 6.85 (d, J=8.9 Hz, 1H), 4.68 (m, 1H), 4.24 (s, 4H), 4.10 (t, J=9.1 Hz, 1H), 3.72 (dd, J=9.1, 5.9 Hz, 1H), 3.46 (m, 1H), 3.33 (m, 1H).

MS (ESI, m/z): 362.1 [M+H⁺].

47.iii) (R)-3-(2,3-Dihydro-benzo[1,4]dioxin-6-yl)-5-{[1-(3-fluoro-6-methoxy-[1,5]naphthyridin-4-yl)-azetidin-3-ylamino]-methyl}-oxazolidin-2-one The title compound was isolated as a colorless solid (50 mg, 45%) starting from intermediates 45.ii) and 47.ii) following the procedure I.

MS (ESI, m/z): 482.2 [M+H⁺].

Example 48

6-((R)-5-{[1-(3-Fluoro-6-methoxy-[1,5]naphthyridin-4-yl)-azetidin-3-ylamino]-methyl}-2-oxo-oxazolidin-3-yl)-4H-benzo[1,4]thiazin-3-one

48.i) 6-[(S)-3-(tert-Butyl-dimethyl-silanyloxy)-2-hydroxy-propylamino]-4H-benzo[1,4]thiazin-3-one In analogy to the preparation of intermediate 45.v) and starting from 6-amino-4H-benzo[1,4]thiazin-3-one (commercial), the title compound was obtained as a pale brown foam (11.16 g, 44%).

MS (ESI, m/z): 369.3 [M+H⁺].

48.ii) 6-[(S)-5-(tert-Butyl-dimethyl-silanyloxymethyl)-2-oxo-oxazolidin-3-yl]-4H-benzo[1,4]thiazin-3-one In analogy to the preparation of intermediate 45.iv), the title compound was obtained from intermediate 48.0 as an off-white solid (7.49 g, 63%).

MS (ESI, m/z): 395.1 [M+H⁺].

48.iii) 6-((S)-5-Hydroxymethyl-2-oxo-oxazolidin-3-yl)-4H-benzo[1,4]thiazin-3-one In analogy to the preparation of intermediate 45.iii), the title compound was obtained from intermediate 48.ii) as a colorless solid (7.72 g, 95%).

MS (ESI, m/z): 281.3 [M+H⁺].

48.iv) Toluene-4-sulfonic acid (S)-2-oxo-3-(3-oxo-3,4-dihydro-2H-benzo[1,4]thiazin-6-yl)-oxazolidin-5-ylmethyl ester To a solution of intermediate 48.iii) (3.2 g, 11.5 mmol) and DMAP (1.40 g, 11.5 mmol) in DCM (80 mL) cooled to 0° C. were added TEA (4.6 mL, 33.3 mmol) and a solution of p-Ts-Cl (2.2 g, 11.5 mmol) in DCM (15 mL). The mixture was stirred at rt over night after which water was added. The resulting solid was filtered to afford the title compound as beige solid (4.19 g, 84%).

MS (ESI, m/z): 435.2 [M+H⁺].

48.v) 6-((S)-5-Iodomethyl-2-oxo-oxazolidin-3-yl)-4H-benzo[1,4]thiazin-3-one

A suspension of intermediate 48.iv) (4.19 g, 9.64 mmol) and NaI (5.78 g, 38.57 mmol) in acetone (70 mL) was refluxed for 5 h. The solvent was evaporated and the residue extracted with water/DCM. Thereby the desired product precipitated as a pale pink solid (3.39 g, 90%).

¹H NMR (DMSO-d6) δ: 10.54 (s, 1H), 7.30 (m, 2H), 7.11 (dd, J=8.5, 2.1 Hz, 1H), 4.69 (m, 1H), 4.13 (t, J=9.1 Hz, 1H), 3.57 (m, 3H), 3.43 (s, 2H).

MS (ESI, m/z): 391.1 [M+H⁺].

48.vi) 6-((R)-5-{[1-(3-Fluoro-6-methoxy-[1,5]naphthyridin-4-yl)-azetidin-3-ylamino]-methyl}-2-oxo-oxazolidin-3-yl)-4H-benzo[1,4]thiazin-3-one According to procedure I and starting from intermediate 45.ii) and intermediate 48.v) the title compound was isolated as a yellow solid (40 mg, 24%).

¹H NMR (CDCl₃) δ: 8.47 (s, 1H), 8.29 (d, J=4.7 Hz, 1H), 8.00 (d, J=9.1 Hz, 1H), 7.49 (d, J=2.3 Hz, 1H), 7.24 (m, 1H), 6.95 (d, J=8.5 Hz, 1H), 6.87 (dd, J=8.5, 2.3 Hz, 1H), 4.92 (m, 2H), 4.76 (m, 1H), 4.42 (m, 2H), 4.03 (t, J=8.8 Hz, 1H), 3.89 (m, 5H), 3.36 (s, 2H), 3.06 (dd, J=12.9, 4.1 Hz, 1H), 2.90 (dd, J=12.9, 5.6 Hz, 1H).

MS (ESI, m/z): 511.2 [M+H⁺].

Example 49

6-((R)-5-{[1-(6-Methoxy-quinolin-4-yl)-azetidin-3-ylamino]-methyl}-2-oxo-oxazolidin-3-yl)-4H-benzo[1,4]thiazin-3-one

49.i) [1-(6-Methoxy-quinolin-4-yl)-azetidin-3-yl]-carbamic acid benzyl ester According to procedure F and starting from trifluoromethanesulfonic acid 6-methoxy-quinolin-4-yl ester (prepared according to WO2000040554) and azetidin-3-yl-carbamic acid benzyl ester (commercial), the desired intermediate was isolated after CC (DCM/MeOH/NH$_4$OH: 100/50/4) as a yellow solid (1.25 g, 35%).
MS (ESI, m/z): 364.3 [M+H$^+$].

49.ii) 1-(6-Methoxy-quinolin-4-yl)-azetidin-3-ylamine

According to procedure G but using Pd(OH)$_2$ instead of Pd/C and starting from intermediate 493) the desired intermediate was isolated as a yellow solid (248 mg, 33%).
MS (ESI, m/z): 230.4 [M+H$^+$].

49.iii) 6-((R)-5-{[1-(6-Methoxy-quinolin-4-yl)-azetidin-3-ylamino-]-methyl}-2-oxo-oxazolidin-3-yl)-4H-benzo[1,4]thiazin-3-one According to procedure I and starting from intermediate 49.ii) and intermediate 48.v) the title compound was isolated as a yellow solid (17 mg, 15%).
MS (ESI, m/z): 492.0 [M+H$^+$].

Example 50

(R)-3-(3-Fluoro-4-methyl-phenyl)-5-{[1-(6-methoxy-[1,5]naphthyridin-4-yl)-azetidin-3-ylamino]-methyl}-oxazolidin-2-one 50.i) [1-(6-Methoxy-[1,5]naphthyridin-4-yl)-azetidin-3-yl]-carbamic acid benzyl ester According to procedure F and starting from trifluoromethanesulfonic acid 6-methoxy-[1,5]naphthyridin-4-yl ester (prepared according to WO 02/008224) and azetidin-3-yl-carbamic acid benzyl ester the desired intermediate was isolated after trituration with ether as a colorless solid (5.05 g, 71%).
MS (ESI, m/z): 365.2 [M+H$^+$].

50.ii) 1-(6-Methoxy-[1,5]naphthyridin-4-yl)-azetidin-3-ylamine

According to procedure G and starting from intermediate 503) the desired intermediate was isolated as a colorless solid (1.55 g, 59%).
MS (ESI, m/z): 231.6 [M+H$^+$].

50.iii) (R)-3-(3-Fluoro-4-methyl-phenyl)-5-{[1-(6-methoxy-[1,5]naphthyridin-4-yl)-azetidin-3-ylamino]-methyl}-oxazolidin-2-one According to procedure I and starting from intermediate 50.ii) and intermediate 46.iii the title compound was isolated as a colorless solid (33 mg, 25%).
MS (ESI, m/z): 438.3 [M+H$^+$].

Example 51

(R)-3-(2,3-Dihydro-benzo[1,4]dioxin-6-yl)-5-{[1-(6-methoxy-[1,5]naphthyridin-4-yl)-azetidin-3-ylamino]-methyl}-oxazolidin-2-one According to procedure I and starting from intermediate 50.0 and intermediate 47.ii) the title compound was isolated as a colorless solid (39 mg, 30%).

$^1$H NMR (CDCl$_3$) δ: 8.31 (d, J=5.3 Hz, 1H), 8.02 (d, J=9.1 Hz, 1H), 7.07 (s, 1H), 7.00 (m, 2H), 6.82 (m, 1H), 6.20 (d, J=5.3 Hz, 1H), 4.67 (m, 3H), 4.22 (s, 4H), 4.11 (m, 3H), 3.98 (s, 3H), 3.83 (m, 2H), 3.02 (m, 1H), 2.92 (m, 1H), 2.04 (m, 1H).
MS (ESI, m/z): 464.3 [M+H$^+$].

Example 52

6-((R)-5-{[1-(6-Methoxy-[1,5]naphthyridin-4-yl)-azetidin-3-ylamino]-methyl}-2-oxo-oxazolidin-3-yl)-4H-benzo[1,4]oxazin-3-one According to procedure H and starting from intermediate 50.0 and intermediate 45.vi), the title compound was isolated as a pale yellow solid (22 mg, 18%).
MS (ESI, m/z): 477.0 [M+H$^+$].
Alternatively, the title compound was synthesized according to steps 52.i) to 52.iii) below.

52.i) 3-{[(R)-2-oxo-3-(3-oxo-3,4-dihydro-2H-benzo[1,4]oxazin-6-yl)-oxazolidin-5-ylmethyl]-amino}-azetidine-1-carboxylic acid tert-butyl ester According to procedure H and starting from 3-amino-azetidine-1-carboxylic acid tert-butyl ester (commercial) and intermediate 45.vi), the title compound was isolated as a pale beige solid (960 mg, 52%).
MS (ESI, m/z): 419.2 [M+H$^+$].

52.ii) 6-[(R)-5-(Azetidin-3-ylaminomethyl)-2-oxo-oxazolidin-3-yl]-4H-benzo[1,4]oxazin-3-one According to procedure E and starting from intermediate 52.i), the title compound was isolated as a pale beige solid (552 mg, 100%).
MS (ESI, m/z): 319.1 [M+H$^+$].

52.iii) 6-((R)-5-{[1-(6-Methoxy-[1,5]naphthyridin-4-yl)-azetidin-3-ylamino]-methyl}-2-oxo-oxazolidin-3-yl)-4H-benzo[1,4]oxazin-3-one According to procedure F and starting from trifluoromethanesulfonic acid 6-methoxy-[1,5]naphthyridin-4-yl ester (prepared according to WO 02/008224) and intermediate 52.ii) the title compound was isolated as a colorless solid (270 mg, 38%).
$^1$H NMR (CDCl$_3$) δ: 8.35 (d, J=5.0 Hz, 1H), 8.06 (m, 2H), 7.49 (m, 1H), 7.00 (d, J=9.1 Hz, 1H), 6.94 (m, 1H), 6.75 (m, 1H), 6.24 (d, J=5.3 Hz, 1H), 4.72 (m, 3H), 4.57 (s, 2H), 4.15 (m, 1H), 4.00 (m, 5H), 3.49 (m, 2H), 3.05 (m, 1H), 2.94 (m, 1H).
MS (ESI, m/z): 477.0 [M+H$^+$].

Example 53

6-((R)-5-{[1-(6-Methoxy-[1,5]naphthyridin-4-yl)-azetidin-3-ylamino]-methyl}-2-oxo-oxazolidin-3-yl)-4H-benzo[1,4]thiazin-3-one According to procedure I and starting from intermediate 50.0 and intermediate 48.v), the title compound was isolated as a colorless solid (252 mg, 33%).
$^1$H NMR (CDCl$_3$) δ: 9.08 (m, 1H), 8.32 (d, J=5.0 Hz, 1H), 8.03 (d, J=9.1 Hz, 1H), 7.52 (d, J=2.1 Hz, 1H), 7.23 (m, 1H), 6.97 (d, J=8.8 Hz, 1H), 6.83 (m, 1H), 6.19 (m, 1H), 4.68 (m, 3H), 4.13 (m, 2H), 3.92 (m, 6H), 3.33 (s, 2H), 3.05 (m, 1H), 2.90 (m, 1H).
MS (ESI, m/z): 493.0 [M+H$^+$].

Example 54

6-((R)-5-{[1-(6-Methoxy-quinazolin-4-yl)-azetidin-3-ylamino]-methyl}-2-oxo-oxazolidin-3-yl)-4H-benzo[1,4]oxazin-3-one 54.i) [1-(6-Methoxy-quinazolin-4-yl)-azetidin-3-yl]-carbamic acid benzyl ester According to procedure F and starting from 4-chloro-6-methoxy-quinazoline (commercial) and azetidin-3-yl-carbamic acid benzyl ester, the desired intermediate was isolated as a colorless solid (0.62 g, 59%).
MS (ESI, m/z): 365.2 [M+H$^+$].

54.ii) 1-(6-Methoxy-quinazolin-4-yl)-azetidin-3-ylamine

According to procedure G and starting from intermediate 54.i) the desired intermediate was isolated as a colorless solid (0.31 g, 82%).
MS (ESI, m/z): 231.4 [M+H$^+$].

54.iii) 6-((R)-5-{[1-(6-Methoxy-quinazolin-4-yl)-azetidin-3-ylamino]-methyl}-2-oxo-oxazolidin-3-yl)-4H-benzo[1,4]oxazin-3-one According to procedure H and starting from intermediate 54.ii) and intermediate 45. vi), the title compound was isolated as a colorless solid (5 mg, 5%).
MS (ESI, m/z): 476.9 [M+H$^+$].

Example 55

6-((R)-5-{[1-(6-Methoxy-quinazolin-4-yl)-azetidin-3-ylamino]-methyl}-2-oxo-oxazolidin-3-yl)-4H-benzo[1,4]thiazin-3-one 55.i) Methanesulfonic acid (S)-2-oxo-3-(3-oxo-3,4-dihydro-2H-benzo[1,4]thiazin-6-yl)-oxazolidin-5-ylmethyl ester A solution of intermediate 48.iii) (2.77 g, 9.88 mmol) in anhydrous DCM (100 mL) and DIPEA (4.7 mL, 28.2 mmol) was cooled to 0° C. and Ms-Cl (1.07 mL, 13.8 mmol) was added dropwise. The resulting mixture was stirred at 0° C. for 1 h. Water was added and the mixture was extracted with DCM and the combined org. layers were washed with water. The yellow residue was triturated with EA/DCM/ether to afford the title compound as a colorless solid (2.45 g, 69%).
$^1$H NMR (DMSO-d6) δ: 10.57 (s, 1H), 7.31 (m, 2H), 7.10 (dd, J=8.5, 2.3 Hz, 1H), 4.98 (m, 1H), 4.48 (m, 2H), 4.13 (t, J=9.4 Hz, 1H), 3.75 (dd, J=9.4, 6.4 Hz, 1H), 3.43 (s, 2H), 3.23 (s, 3H).
MS (ESI, m/z): 359.3 [M+H$^+$].

55.ii) 6-((R)-5-{[1-(6-Methoxy-quinazolin-4-yl)-azetidin-3-ylamino]-methyl}-2-oxo-oxazolidin-3-yl)-4H-benzo[1,4]thiazin-3-one According to procedure H and starting from intermediate 54.ii) and intermediate 553), the title compound was isolated as a colorless solid (10 mg, 10%).
MS (ESI, m/z): 493.1 [M+H$^+$].

Example 56

6-[(R)-5-({[1-(6-Methoxy-[1,5]naphthyridin-4-yl)-azetidin-3-yl]-methyl-amino}-methyl)-2-oxo-oxazolidin-3-yl]-4H-benzo[1,4]thiazin-3-one To a solution of example 53 in MeOH (1.5 mL) and a few drops of DCE was added a 37% aq. solution of formaldehyde. After 10 min, NaBH$_3$CN was added and the mixture was stirred at rt for 1 h. The reaction was quenched by the addition of 0.1M HCl. EA was added and the mixture basified using NH$_4$OH. The aq. layer was extracted with EA (2×) and the combined org. layers were washed with water and brine, dried over MgSO$_4$ and concentrated under reduced pressure. The residue was purified by CC (DCM-MeOH—NH$_4$OH 1000-50-4) to afford the title compound as a colorless solid (14 mg, 91%).
$^1$H NMR (CDCl$_3$) δ: 8.35 (m, 2H), 8.06 (d, J=9.1 Hz, 1H), 7.41 (d, J=2.3 Hz, 1H), 7.24 (m, 1H), 7.00 (m, 1H), 6.90 (dd, J=8.5, 2.3 Hz, 1H), 6.25 (d, J=5.3 Hz, 1H), 4.79 (m, 1H), 4.22 (m, 2H), 4.03 (m, 2H), 3.95 (m, 1H), 3.94 (s, 3H), 3.80 (dd, J=9.1, 7.0 Hz, 1H), 3.63 (m, 1H), 3.39 (s, 2H), 2.77 (m, 2H), 2.39 (s, 3H).
MS (ESI, m/z): 507.1 [M+H$^+$].

Example 57

6-((S)-5-{[1-(6-Methoxy-[1,5]naphthyridin-4-yl)-azetidin-3-ylamino]-methyl}-2-oxo-oxazolidin-3-yl)-4H-benzo[1,4]thiazin-3-one 57.i) Toluene-4-sulfonic acid (R)-2-oxo-3-(3-oxo-3,4-dihydro-2H-benzo[1,4]thiazin-6-yl)-oxazolidin-5-ylmethyl ester The title compound was prepared according to the procedure described for intermediate 48.iv) starting from the enantiomer of intermediate 48.iii) obtained from tert-butyl-dimethyl-((R)-1-oxiranylmethoxy)-silane as an off-white solid (400 mg, 30%).
MS (ESI, m/z): 435.3 [M+H$^+$].

57.ii) 6-((R)-5-Iodomethyl-2-oxo-oxazolidin-3-yl)-4H-benzo[1,4]thiazin-3-one

The title compound was prepared from intermediate 57.i) according to the procedure described for example 46 step 46.iii). It was obtained as an off-white solid (120 mg, 33%).
MS (ESI, m/z): 391.1 [M+H$^+$].

57.iii) 6-((S)-5-{[1-(6-Methoxy-[1,5]naphthyridin-4-yl)-azetidin-3-ylamino]-methyl}-2-oxo-oxazolidin-3-yl)-4H-benzo[1,4]thiazin-3-one According to procedure I and starting from intermediate 50.0 and intermediate 57.ii), the title compound was isolated as a yellow solid (19 mg, 13%).
MS (ESI, m/z): 493.0 [M+H$^+$].

Example 58

(RS)-6-(5-{2-[1-(6-Methoxy-[1,5]naphthyridin-4-yl)-azetidin-3-ylamino]-ethyl}-2-oxo-oxazolidin-3-yl)-4H-benzo[1,4]thiazin-3-one 58.i) (RS)-6,4-(tert-Butyl-dimethyl-silanyloxy)-2-hydroxy-butylamino]-4H-benzo[1,4]thiazin-3-one A solution of (RS)-tert-butyl-dimethyl-(2-oxiranyl-ethoxy)-silane (4 g, 20 mmol, prepared according to Heterocycles (1987), 25(1), 329-32) and 6-amino-4H-benzo[1,4] thiazin-3-one (4 g, 20 mmol) in EtOH/water 9:1 (140 mL) was heated at 80° C. for 2 d. The mixture was concentrated under reduced pressure and the residue was purified by CC (DCM/MeOH/NH$_4$OH 1000:50:4) to afford the title intermediate as a brown oil (2.2 g, 29%).
MS (ESI, m/z): 383.2 [M+H$^+$].

58.ii) (RS)-6-{5-[2-(tert-Butyl-dimethyl-silanyloxy)-ethyl]-2-oxo-oxazolidin-3-yl}-4H-benzo[1,4]thiazin-3-one According to procedure B the title intermediate was obtained from intermediate 58.i) and isolated as an orange solid (1.53 g, 65%) after CC (DCM/MeOH/NH$_4$OH 1000:50:4).
MS (ESI, m/z): 409.4 [M+H$^+$].

58.iii) (RS)-6-[5-(2-Hydroxy-ethyl)-2-oxo-oxazolidin-3-yl]-4H-benzo[1,4]thiazin-3-one A solution of intermediate 58.0 (1.50 g, 3.67 mmol) in THF (10 mL) was treated with TBAF solution (1M in THF, 1 eq.). The solution was stirred at 0° C. for 2 h, after which water and EA were added. The aq. phase was extracted with EA. The combined org. layers were washed with brine, dried over MgSO$_4$, filtered and concentrated under reduced pressure. The residue was recrystallized from ether/EA to afford the title intermediate as a beige solid (730 mg, 68%).
MS (ESI, m/z): 295.1 [M+H$^+$].

58.iv) (RS)-Methanesulfonic acid 2-oxo-3-(3-oxo-3,4-dihydro-2H-benzo[1,4]thiazin-6-yl)-oxazolidin-5-yl]-ethyl ester A solution of intermediate 58.iii) (700 mg, 2.34 mmol) in anhydrous DCM (12 mL) and DIPEA (1.1 mL, 6.8 mmol) was cooled to 0° C. and Ms-Cl (0.23 mL, 2.9 mmol) was added dropwise. The resulting mixture was stirred at 0° C. for 1 h. Water was added and the mixture was extracted with DCM and the combined org. layers were washed with water. The yellow residue was purified by CC (DCM/MeOH/NH$_4$OH 1000:50:4) to afford the title intermediate as a beige (795 mg, 90%).
MS (ESI, m/z): 373.1 [M+H$^+$].

58.v) (RS)-6-(5-{2-[1-(6-Methoxy-[1,5]naphthyridin-4-yl)-azetidin-3-ylamino]-ethyl}-2-oxo-oxazolidin-3-yl)-4H-benzo[1,4]thiazin-3-one According to procedure H and starting from intermediate 50.ii) and intermediate 58.iv), the title compound was isolated as an off-white solid (38 mg, 25%).
MS (ESI, m/z): 507.1 [M+H$^+$].

Example 59

6-[(S)-5-({[1-(6-Methoxy-[1,5]naphthyridin-4-yl)-azetidin-3-ylmethyl]-amino}-methyl)-2-oxo-oxazolidin-3-yl]-4H-benzo[1,4]thiazin-3-one According to procedure H and starting from intermediate 1.ii) and intermediate 57.i), the title compound was isolated as a pale yellow solid (8 mg, 9%).
MS (ESI, m/z): 507.0 [M+H$^+$].

Example 60

(S)-3-(2,3-Dihydro-benzo[1,4]dioxin-6-yl)-2-oxo-oxazolidine-5-carboxylic acid [(S)-1-(6-methoxy-[1,5]naphthyridin-4-yl)-pyrrolidin-3-yl]-amide According to procedure J and starting from intermediate 41.0 and intermediate 23) the title compound was isolated as a pale colorless solid (8 mg, 9%).
MS (ESI, m/z): 492.3 [M+H$^+$].

Example 61

(S)-3-(2,3-Dihydro-benzo[1,4]dioxin-6-yl)-2-oxo-oxazolidine-5-carboxylic acid [(R)-1-(6-methoxy-[1,5]naphthyridin-4-yl)-pyrrolidin-3-yl]-amide 61.i) (R)-1-(6-Methoxy-[1,5]-naphthyridin-4-yl)-pyrrolidin-3-ylamine The title compound was obtained from (R)-(+)-3-(tert-butoxycarbonylamino)pyrrolidine (commercial) in analogy to Example 41 (steps 41.i) and 41.ii)) as a colorless solid (627 mg, 54% over two steps).
MS (ESI, m/z): 245.2 [M+H$^+$].

61.ii) (S)-3-(2,3-Dihydro-benzo[1,4]dioxin-6-yl)-2-oxo-oxazolidine-5-carboxylic acid

[(R)-1-(6-methoxyl-[1,5]-naphthyridin-4-yl)-pyrrolidin-3-yl]-amide
The title compoud was obtained from intermediate 61.i) and intermediate 2.i) following procedure J and isolated as a colorless foam (20 mg, 34%).
MS (ESI, m/z): 492.2 [M+H$^+$].

Example 62

(S)-3-(3-Fluoro-4-methyl-phenyl)-2-oxo-oxazolidine-5-carboxylic acid [(R)-1-(6-methoxy-[1,5]naphthyridin-4-yl)-pyrrolidin-3-yl]-amide 62.i) (S)-3-(3-Fluoro-4-methyl-phenyl)-2-oxo-oxazolidine-5-carboxylic acid Prepared according to the procedure described for intermediate 2.i) starting from intermediate 46.i). The title compound was obtained as a colorless solid (1.01 g, 79%).
MS (ESI, m/z): 240.3 [M+H$^+$].

62.ii) (S)-3-(3-Fluoro-4-methyl-phenyl)-2-oxo-oxazolidine-5-carboxylic acid [(R)-1-(6-methoxy-[1,5]naphthyridin-4-yl)-pyrrolidin-3-yl]-amide The title compound was obtained from intermediate 62.0 and intermediate 61.1) following procedure J, and isolated as a beige solid (41 mg, 67%).
MS (ESI, m/z): 466.2 [M+H$^+$].

Example 63

(S)-3-(3-Fluoro-4-methyl-phenyl)-2-oxo-oxazolidine-5-carboxylic acid [(S)-1-(6-methoxy-[1,5]naphthyridin-4-yl)-pyrrolidin-3-yl]-amide The title compound was obtained from intermediate 62.0 and 41.0, in analogy to Example 60 as a beige solid (34 mg, 55%).

¹H NMR (CDCl₃) δ: 8.35 (m, 1H), 8.07 (d, J=9.1 Hz, 1H), 7.36 (dd, J=11.7, 2.3 Hz, 1H), 7.16 (t, J=8.5 Hz, 1H), 7.04 (m, 3H), 6.42 (m, 1H), 4.95 (dd, J=9.1, 6.7 Hz, 1H), 4.66 (m, 1H), 4.25 (m, 3H), 4.01 (m, 6H), 2.33 (m, 1H), 2.26 (m, 3H), 2.09 (m, 1H).
MS (ESI, m/z): 466.3 [M+H⁺].

Example 64

6-((R)-5-{[(S)-1-(3-Fluoro-6-methoxy-[1,5]naphthyridin-4-yl)-pyrrolidin-3-ylamino]-methyl}-2-oxo-oxazolidin-3-yl)-4H-benzo[1,4]oxazin-3-one 64.i) [(S)-1-(3-Fluoro-6-methoxy-[1,5]naphthyridin-4-yl)-pyrrolidin-3-yl]-carbamic acid tert-butyl ester According to procedure F and starting from 8-bromo-7-fluoro-2-methoxy-[1,5]naphthyridine and (S)-(−)-3-(tert-butoxycarbonylamino)pyrrolidine the title intermediate was isolated as a yellow oil (304 mg, 48%).
MS (ESI, m/z): 363.1 [M+H⁺].

64.ii) (S)-1-(3-Fluoro-6-methoxy-[1,5]naphthyridin-4-yl)-pyrrolidin-3-ylamine

According to procedure E and starting from intermediate 64.0 the title intermediate was isolated as a pale yellow solid (176 mg, 81%).
MS (ESI, m/z): 263.3 [M+H⁺].

64.iii) 6-((R)-5-{[(S)-1-(3-Fluoro-6-methoxy-[1,5]naphthyridin-4-yl)-pyrrolidin-3-ylamino]-methyl}-2-oxo-oxazolidin-3-yl)-4H-benzo[1,4]oxazin-3-one According to procedure H and starting from intermediate 64.ii) and intermediate 45. vi), the title compound was isolated as a pale yellow solid (12 mg, 32%).
MS (ESI, m/z): 509.1 [M+H⁺].

Example 65

6-((R)-5-{[(S)-1-(3-Fluoro-6-methoxy-[1,5]naphthyridin-4-yl)-pyrrolidin-3-ylamino]-methyl}-2-oxo-oxazolidin-3-yl)-4H-benzo[1,4]thiazin-3-one According to procedure H and starting from intermediate 64.ii) and intermediate 55.i), the title compound was isolated as a pale yellow solid (71 mg, 54%).
MS (ESI, m/z): 525.1 [M+H⁺].

Example 66

(R)-3-(2,3-Dihydro-benzo[1,4]dioxin-6-yl)-5-{[(5)-1-(3-fluoro-6-methoxy-[1,5]naphthyridin-4-yl)-pyrrolidin-3-ylamino]-methyl}-oxazolidin-2-one According to procedure H and starting from intermediate 64.0 and intermediate 47.0, the title compound was isolated as a pale yellow solid (3 mg, 10%).
MS (ESI, m/z): 496.3 [M+H⁺].

Example 67

(R)-3-(3-Fluoro-4-methyl-phenyl)-5-{[(S)-1-(6-methoxy-[1,5]naphthyridin-4-yl)-pyrrolidin-3-ylamino]-methyl}-oxazolidin-2-one According to procedure H and starting from intermediate 41.0 and intermediate 46.0, the title compound was isolated as a pale yellow solid (15 mg, 29%).
MS (ESI, m/z): 452.2 [M+H⁺].

Example 68

(R)-3-(3-Fluoro-4-methyl-phenyl)-5-{[(R)-1-(6-methoxy-[1,5]naphthyridin-4-yl)-pyrrolidin-3-ylamino]-methyl}-oxazolidin-2-one The title compound was obtained from intermediate 61.i) and intermediate 46.ii) following procedure H, and isolated as a colorless foam (22 mg, 25%).
MS (ESI, m/z): 452.3[M+H⁺].

Example 69

6-((R)-5-{[(S)-1-(6-Methoxy-[1,5]naphthyridin-4-yl)-pyrrolidin-3-ylamino]-methyl}-2-oxo-oxazolidin-3-yl)-4H-benzo[1,4]oxazin-3-one According to procedure H and starting from intermediate 41.ii) and intermediate 45.vi), the title compound was isolated as a pale yellow solid (15 mg, 26%).
¹H NMR (CDCl₃) δ: 9.29 (br. s, 1H), 8.30 (m, 1H), 8.06 (m, 1H), 7.25 (m, 1H), 6.97 (d, J=8.8 Hz, 1H), 6.86 (m, 1H), 6.74 (dd, J=8.8, 2.6 Hz, 1H), 6.37 (d, J=5.9 Hz, 1H), 4.70 (m, 1H), 4.51 (m, 2H), 4.12 (dd, J=11.4, 5.6 Hz, 1H), 3.91 (m, 7H), 3.72 (dd, J=8.5, 6.7 Hz, 1H), 3.51 (m, 1H), 3.00 (d, J=5.0 Hz, 2H), 2.19 (m, 1H), 1.90 (m, 1H).
MS (ESI, m/z): 491.0 [M+H⁺].

Example 70

6-((R)-5-{[(S)-1-(6-Methoxy-[1,5]naphthyridin-4-yl)-pyrrolidin-3-ylamino]-methyl}-2-oxo-oxazolidin-3-yl)-4H-benzo[1,4]thiazin-3-one According to procedure H and starting from intermediate 41.ii) and intermediate 55.i), the title compound was isolated as a pale yellow solid (19 mg, 19%).
¹H NMR (CDCl₃) δ: 9.18 (s, 1H), 8.28 (d, J=5.6 Hz, 1H), 8.02 (d, J=9.1 Hz, 1H), 7.28 (m, 1H), 7.15 (m, 1H), 6.95 (d, J=9.1 Hz, 1H), 6.82 (dd, J=8.8, 2.3 Hz, 1H), 6.34 (d, J=5.6 Hz, 1H), 4.71 (m, 1H), 4.10 (dd, J=11.5, 5.3 Hz, 1H), 3.91 (m, 7H), 3.74 (dd, J=8.5, 6.7 Hz, 1H), 3.51 (m, 1H), 3.33 (s, 2H), 3.01 (m, 1H), 2.16 (m, 1H), 1.90 (m, 1H).
MS (ESI, m/z): 506.9 [M+H⁺].

Example 71

6-((R)-5-{[(R)-1-(6-Methoxy-[1,5]naphthyridin-4-yl)-pyrrolidin-3-ylamino]-methyl}-2-oxo-oxazolidin-3-yl)-4H-benzo[1,4]thiazin-3-one The title compound was obtained from intermediate 55.i) and intermediate 61.i) following procedure H, and isolated as a pale yellow solid (18 mg, 30%).
MS (ESI, m/z): 507.0 [M+H⁺].

Example 72

6-((R)-5-{[(R)-1-(6-Methoxy-[1,5]naphthyridin-4-yl)-pyrrolidin-3-ylamino]-methyl}-2-oxo-oxazolidin-3-yl)-4H-benzo[1,4]oxazin-3-one The title compound was obtained from intermediate 45.vi) and intermediate 61.i) following procedure H, and isolated, as a pale yellow solid (20 mg, 35%).
MS (ESI, m/z): 490.9 [M+H⁺].

Example 73

(3R*,4S*)-1-(6-Methoxy-[1,5]naphthyridin-4-yl)-4-{[(S)-2-oxo-3-(3-oxo-3,4-dihydro-2H-benzo[1,4]thiazin-6-yl)-oxazolidin-5-ylmethyl]amino}-pyrrolidine-3-carboxylic acid ethyl ester

73.i) (3R*,4S*)-4-Benzylamino-pyrrolidine-1,3-dicarboxylic acid 1-tert-butyl ester 3-ethyl ester To a solution of (RS)-4-oxo-pyrrolidine-1,3-dicarboxylic acid 1-tert-butyl ester 3-ethyl ester (commercial; 1 g, 3.9 mmol) in EtOH (15 mL) were added benzylamine (0.85 mL, 7.77 mmol) and AcOH (0.45 mL, 7.77 mmol) and the mixture was stirred 3 h at rt. Sodium cyanoborohydride (0.98 g, 15.5 mmol) was then added at rt and the mixture was heated to 75° C. for 5 h, then 15 h to 50° C. and again 1 h to 75° C. The mixture was concentrated under reduced pressure, water was added and the mixture extracted 3× with EA. The combined org. extracts were washed with brine dried over MgSO$_4$ and concentrated under reduced pressure. The residue was purified by CC (Hep/EA from 2:1 to 1:1) to afford the title intermediate as a yellow oil (0.73 g, 54%).
MS (ESI, m/z): 349.2 [M+H$^+$].

73.ii) (3R*,4P)-4-Benzylamino-pyrrolidine-3-carboxylic acid ethyl ester

According to procedure E and starting from intermediate 73.0 the title intermediate was isolated as a brown solid (434 mg, 85%).
MS (ESI, m/z): 249.4 [M+H$^+$].

73.iii) (3R*,4S*)-4-Benzylamino-1-(6-methoxy-[1,5]naphthyridin-4-yl)-pyrrolidine-3-carboxylic acid ethyl ester According to procedure F and starting from 8-bromo-2-methoxy-[1,5]naphthyridine (commercial) and intermediate 73.ii), the desired intermediate was isolated as a yellow oil (331 mg, 47%).
MS (ESI, m/z): 407.4 [M+H$^+$].

73.iv) (3R*,4S*)-4-Amino-1-(6-methoxy-[1,5]naphthyridin-4-yl)-pyrrolidine-3-carboxylic acid ethyl ester A solution of intermediate 73.iii) (331 mg, 0.81 mmol) in EtOH (7 mL) and AcOH (1 eq.) was hydrogenated over Pd(OH)$_2$ (64 mg) for 48 h. The catalyst was filtered off and the filtrate concentrated under reduced pressure. Sat. aq. NH$_4$OH was added and the mixture extracted with DCM-MeOH 9:1 (3×). The combined org. layers were washed with brine, dried over MgSO$_4$, filtered, concentrated under reduced pressure and purified by CC (DCM/MeOH/NH$_4$OH 1000:100:8) to afford the title intermediate as a yellow oil (137 mg, 53%).
MS (ESI, m/z): 317.3 [M+H$^+$].

73.v) (3R*,4S*)-1-(6-Methoxy-[1,5]naphthyridin-4-yl)-4-{[(S)-2-oxo-3-(3-oxo-3,4-dihydro-2H-benzo[1,4]thiazin-6-yl)-oxazolidin-5-ylmethyl]amino}-pyrrolidine-3-carboxylic acid ethyl ester According to procedure H and starting from intermediate 73.iv) and intermediate 57.i), the title compound was isolated as a pale yellow solid (15 mg, 12%).
MS (ESI, m/z): 579.2 [M+H$^+$].

Example 74

(3R*,4S*)-1-(6-Methoxy-[1,5]naphthyridin-4-yl)-4-{[(R)-2-oxo-3-(3-oxo-3,4-dihydro-2H-benzo[1,4]thiazin-6-yl)-oxazolidin-5-ylmethyl]-amino}-pyrrolidine-3-carboxylic acid To a solution of intermediate 73.v) (12 mg, 0.021 mmol) in dioxane (1 mL) was added HCl 37% (0.029 mL) and the mixture was stirred at rt for 48 h. The resulting suspension was concentrated under reduced pressure and the residue was triturated with MeOH and EA, filtered and washed with EA to afford the title compound hydrochloride as a pale brown solid (12 mg, 99%).
MS (ESI, m/z): 551.4 [M+H$^+$].

Example 75

6-((R)-5-{[(3R*,4R*)-4-Methoxy-1-(6-methoxy-[1,5]naphthyridin-4-yl)-pyrrolidin-3-ylamino]-methyl}-2-oxo-oxazolidin-3-yl)-4H-benzo[1,4]thiazin-3-one

75.i) (3R*,4R*)-4-Azido-1-(6-methoxy-[1,5]naphthyridin-4-yl)-pyrrolidin-3-ol According to procedure F and starting from (3R*,4R*)-4-azido-pyrrolidin-3-ol (prepared according to WO2007053498) and 8-bromo-2-methoxy-[1,5]naphthyridine, the title intermediate was isolated as a beige solid (1.53 g, 51%).
MS (ESI, m/z): 287.3 [M+H$^+$].

75.ii) 8-((3R*,4R*)-3-Azido-4-methoxy-pyrrolidin-1-yl)-2-methoxy-1,5]naphthyridine To a solution of intermediate 75.i) (386 mg, 1.35 mmol) in dry DMF (8 mL) were added NaH (60% in mineral oil, 65 mg, 1.62 mmol) and MeI (0.13 mL, 2.02 mmol) at rt and the mixture was stirred at rt for 1 h. Water and EA were added and the mixture extracted with EA. The combined org. layers were washed with water (2×) and brine dried over MgSO$_4$, filtered and concentrated under reduced pressure. The residue was purified by CC (DCM/MeOH/NH$_4$OH 1000:50:4) to afford the title intermediate as a pale yellow solid (128 mg, 32%).
MS (ESI, m/z): 301.4 [M+H$^+$].

75.iii) (3R*,4R*)-4-Methoxy-1-(6-methoxy-[1,5]naphthyridin-4-yl)-pyrrolidin-3-ylamine A solution of intermediate 75.ii) (128 mg, 0.43 mmol) in EtOH (5 mL) was hydrogenated over Pd(OH)$_2$ (23 mg) for 2 h. The catalyst was filtered off and the filtrate was concentrated under reduced pressure to afford the title intermediate as a dark yellow oil (110 mg, 94%).
MS (ESI, m/z): 275.4 [M+H$^+$].

75.iv) 6-((R)-5-{[(3R*,4R*)-4-Methoxy-1-(6-methoxy-[1,5]naphthyridin-4-yl)-pyrrolidin-3-ylamino]-methyl}-2-oxo-oxazolidin-3-yl)-4H-benzo[1,4]thiazin-3-one According to procedure H and starting from intermediate 75.iii) and intermediate 55.i), the title compound was isolated as a pale yellow solid (15 mg, 17%).
MS (ESI, m/z): 537.3 [M+H$^+$].

Example 76

6-((R)-5-{[(3R*,4R*)-4-Hydroxy-1-(6-methoxy-[1,5]naphthyridin-4-yl)-pyrrolidin-3-ylamino]-methyl}-2-oxo-oxazolidin-3-yl)-4H-benzo[1,4]thiazin-3-one

76.i) (3R*,4R*)-4-Amino-1-(6-methoxy-[1,5]naphthyridin-4-yl)-pyrrolidin-3-ol A solution of intermediate 75.i) (518 mg, 1.81 mmol) in EtOH (20 mL) was hydrogenated over Pd(OH)$_2$ (23 mg) for 2 h. The catalyst was filtered off and the filtrate was concentrated to afford the title intermediate as a pale yellow foam (510 mg), which was used immediately in the next step without further purification.
MS (ESI, m/z): 261.2 [M+H$^+$].

76.ii) 6-((R)-5-{[(3R*,4R*)-4-Hydroxy-1-(6-methoxy-[1,5]naphthyridin-4-yl)-pyrrolidin-3-ylamino]-methyl}-2-oxo-oxazolidin-3-yl)-4H-benzo[1,4]thiazin-3-one According to procedure H and starting from intermediate 76.i) and intermediate 55.i), the title compound was isolated as a pale yellow solid (37 mg, 32%).
MS (ESI, m/z): 523.1 [M+H$^+$].

Example 77

(R)-3-(2,3-Dihydro-benzo[1,4]dioxin-6-yl)-5-{[(3R*,4R*)-4-hydroxy-1-(6-methoxy-[1,5]naphthyridin-4-yl)-pyrrolidin-3-ylamino]-methyl}-oxazolidin-2-one According to procedure H and starting from intermediate 76.0 and intermediate 47.i), the title compound was isolated as a pale yellow solid (22 mg, 32%).
$^1$H NMR (CDCl$_3$) δ: 8.11 (dd, J=5.3, 1.5 Hz, 1H), 7.97 (dd, J=8.8, 1.5 Hz, 1H), 7.02 (m, 1H), 6.83 (m, 3H), 6.13 (d, J=4.7, Hz, 1H), 4.68 (m, 1H), 4.14 (m, 7H), 3.92 (m, 5H), 3.72 (m, 1H), 3.61 (m, 1H), 3.35 (m, 1H), 3.07 (m, 1H), 2.95 (m, 1H).
MS (ESI, m/z): 494.2 [M+H$^+$].

Example 78

(S)-3-(2,3-Dihydro-benzo[1,4]dioxin-6-yl)-2-oxo-oxazolidine-5-carboxylic acid [(3R,5S)-5-hydroxymethyl-1-(6-methoxy-[1,5]naphthyridin-4-yl)-pyrrolidin-3-yl]-amide

78.i) (2S,4R)-4-Benzylamino-2-(2,2-dimethyl-propionyloxymethyl)-pyrrolidine-1-carboxylic acid tert-butyl ester To a solution of 2-(2,2-dimethyl-propionyloxymethyl)-4-oxo-pyrrolidine-1-carboxylic acid tert-butyl ester (prepared according to WO2007017828, 8.0 g, 26.7 mmol) and benzylamine (2.9 mL, 1 eq) in DCE (100 mL) were added NaBH(OAc)$_3$ (7.9 g, 1.4 eq) and AcOH (1.53 mL, 1 eq) and the resulting solution was stirred at rt for 1 h. The mixture was quenched by adding NH$_4$OH and the aq. layer was extracted with EA. The combined org. layers were washed with brine, dried over Na$_2$SO$_4$ and concentrated under reduced pressure. The residue was purified by CC (DCM/MeOH/NH$_4$OH 1000:25:2) to afford the title intermediate as a yellow oil (10.2 g, 98%).
MS (ESI, m/z): 391.7 [M+H$^+$].

78.ii) (2S,4R)-4-Benzylamino-2-hydroxymethyl-pyrrolidine-1-carboxylic acid tert-butyl ester NaOMe (1.44 mL, 26.6 mmol) was added to a solution of intermediate 78.ii) (9.91 g, 25.4 mmol) ester in MeOH (100 mL) at rt. The reaction mixture was stirred at rt for 20 h. The reaction was quenched by the addition of 10% citric acid. and diluted with EA. The layers were separated and the aq. layer was extracted with EA. The combined org. layers were washed with brine, dried over MgSO$_4$, filtered and concentrated under reduced pressure to afford the title intermediate as a dark oil (7.43 g, 96%).
MS (ESI, m/z): 307.5 [M+H$^+$].

78.iii) ((2S,4R)-4-Benzylamino-pyrrolidin-2-yl)-methanol

According to procedure E and starting from intermediate 78.ii), the title compound was isolated as a dark oil (5.93 g, 100%).
MS (ESI, m/z): 206.9 [M+H$^+$].

78.iv) [(2S,4R)-4-Benzylamino-1-(6-methoxy-[1,5]naphthyridin-4-yl)-pyrrolidin-2-yl]-methanol According to procedure F and starting from intermediate 78.iii) and 8-bromo-2-methoxy-[1,5]naphthyridine the title intermediate was isolated as a brown foam (2.48 g, 27%).
MS (ESI, m/z): 365.1 [M+H$^+$].

78.v) [(2S,4R)-4-Amino-1-(6-methoxy-[1,5]naphthyridin-4-yl)-pyrrolidin-2-yl]-methanol A solution intermediate 78.iv) (640 mg, 1.76 mmol) and AcOH (0.10 mL, 1 eq) in MeOH (15 mL) was hydrogenated over Pd(OH)$_2$ (140 mg) overnight. The catalyst was filtered off and the filtrate concentrated. NH$_4$OH was added and the mixture was extracted with DCM-MeOH 9-1 (3×). The combined org. layer were washed with brine, dried over MgSO$_4$, filtered and concentrated under reduced pressure to afford the title intermediate as a dark brown viscous oil (436 mg, 91%).
MS (ESI, m/z): 275.4 [M+H$^+$].

78.vi) (S)-3-(2,3-Dihydro-benzo[1,4]dioxin-6-yl)-2-oxo-oxazolidine-5-carboxylic acid [(3R,5S)-5-hydroxymethyl-1-(6-methoxy-[1,5]naphthyridin-4-yl)-pyrrolidin-3-yl]-amide According to procedure J and starting from intermediate 78.v) and intermediate 2.i), the title compound was isolated as a colorless solid (21 mg, 18%).
MS (ESI, m/z): 522.2 [M+H$^+$].

Example 79

6-((R)-5-{[(3R,5S)-5-Hydroxymethyl-1-(6-methoxy-[1,5]naphthyridin-4-yl)-pyrrolidin-3-ylamino]-methyl}-2-oxo-oxazolidin-3-yl)-4H-benzo[1,4]thiazin-3-one According to procedure H and starting from intermediate 78.v) and intermediate 55.i), the title compound was isolated as a pale yellow solid (22 mg, 21%).
$^1$H NMR (DMSO-d6) δ: 8.79 (d, J=7.0 Hz, 1H), 8.29 (d, J=5.3 Hz, 1H), 8.05 (d, J=9.1 Hz, 1H), 7.11 (m, 2H), 6.98 (dd, J=8.8, 2.6 Hz, 1H), 6.85 (m, 1H), 6.65 (m, 1H), 4.98 (m, 3H), 4.38 (m, 1H), 4.22 (s, 4H), 4.05-3.80 (m, 6H), 3.52 (m, 2H), 3.16 (d, J=5.3 Hz, 1H), 2.42 (m, 1H), 2.06 (m, 1H).
MS (ESI, m/z): 537.3 [M+H$^+$].

Example 80

6-[(R)-5-({[(RS)-1-(6-Methoxy-[1,5]naphthyridin-4-yl)-pyrrolidin-3-ylmethyl]-amino}-methyl)-2-oxo-oxazolidin-3-yl]-4H-benzo[1,4]thiazin-3-one

80.i) (RS)-[1-(6-Methoxy-[1,5]naphthyridin-4-yl)-pyrrolidin-3-ylmethyl]-carbamic acid tert-butyl ester According to procedure F and starting from (RS)-pyrrolidin-3-ylmethyl-carbamic acid tert-butyl ester (commercial) and 8-bromo-2-methoxy-[1,5]naphthyridine, the title intermediate was isolated as a yellow oil (1.01 g, 45%).
$^1$H NMR (CDCl$_3$) δ: 9.37 (br. s, 1H), 8.28 (d, J=5.3 Hz, 1H), 8.05 (d, J=9.1 Hz, 1H), 7.40 (dd, J=4.7, 2.3 Hz, 1H), 7.22 (m, 1H), 6.93 (m, 2H), 6.32 (dd, J=5.6, 2.3 Hz, 1 H), 4.73 (m, 1H), 3.94 (m, 7H), 3.78 (m, 1H), 3.61 (m, 1H), 3.38 (s, 2H), 2.87 (m, 3H), 2.42 (m, 1H), 2.13 (m, 2H), 1.71 (m, 1H).
MS (ESI, m/z): 359.4 [M+H$^+$].

80.ii) (RS)-1-(6-Methoxyl-[1,5]-naphthyridin-4-yl)-pyrrolidin-3-yl]-methylamine According to procedure E and starting from intermediate 80.i), the title intermediate was isolated as a slightly red oil (320 mg) and was directly submitted in the next step without further purification.

80.iii) 6-[(R)-5-({[S)-1-(6-Methoxy-[1,5]naphthyridin-4-yl)-pyrrolidin-3-ylmethyl]-amino}-methyl)-2-oxo-oxazolidin-3-yl]-4H-benzo[1,4]thiazin-3-one According to procedure H and starting from intermediate 80.ii) and intermediate 55.i), the title compound was isolated as a pale yellow solid (47 mg, 46%).
MS (ESI, m/z): 521.4 [M+H$^+$].

Example 81

(S)-3-(2,3-Dihydro-benzo[1,4]dioxin-6-yl)-2-oxo-oxazolidine-5-carboxylic acid [(RS)-1-(6-methoxy-[1,5]naphthyridin-4-yl)-pyrrolidin-3-ylmethyl]-amide According to procedure J and starting from intermediate 80.ii) and intermediate 2.i), the title compound was isolated as a pale colorless solid (12 mg, 20%).
MS (ESI, m/z): 506.3 [M+H$^+$].

Example 82

(S)-3-(3-Fluoro-4-methyl-phenyl)-2-oxo-oxazolidine-5-carboxylic acid [(RS)-1-(6-methoxy-[1,5]naphthyridin-4-yl)-pyrrolidin-3-ylmethyl]-amide According to procedure J and starting from intermediate 80.0 and intermediate 62.i), the title compound was isolated as a pale beige solid (33 mg, 52%).
MS (ESI, m/z): 480.4 [M+H$^+$].

Example 83

6-[(R)-5-({[(3RS)-(4RS)-4-Hydroxy-1-(6-methoxy-[1,5]naphthyridin-4-yl)-pyrrolidin-3-ylmethyl]-amino}-methyl)-2-oxo-oxazolidin-3-yl]-4H-benzo[1,4]thiazin-3-one

83.i) (3RS)-(4RS)-3-Azidomethyl-4-hydroxy-pyrrolidine-1-carboxylic acid tert-butyl ester Ms-Cl (0.38 mL, 2.6 eq) was added to a solution of 3-hydroxy-4-hydroxymethyl-pyrrolidine-1-carboxylic acid tert-butyl ester (mixture of stereoisomers, prepared according to WO9303026, 410 mg, 1.89 mmol) in pyridine (3.5 mL) at 0° C. The reaction mixture was stirred at 0° C. for 1 h. Then DCM was added and the mixture was washed with sat. aq. NaHCO$_3$, dried over MgSO$_4$, concentrated under reduced pressure and dried at HV. The crude mesylate was dissolved in DMF (18 mL), treated with NaN$_3$ (1.23 g, 10 eq) and stirred at 95° C. for 1.5 h. After cooling to rt the mixture was concentrated to dryness and dissolved in DCM. The org. layer was washed with water, dried over MgSO$_4$, concentrated under reduced pressure and the residue was purified by CC (DCM to DCM/MeOH 95:5) to afford the title intermediate as a yellow oil (390 mg, 85%).
$^1$H NMR (CDCl$_3$) δ: 4.20-3.00 (m, 7H), 2.50-2.15 (m, 1H), 1.47 (m, 9H).

83.ii) (3RS)-(4RS)-4-Azidomethyl-pyrrolidin-3-ol

According to procedure E and starting from intermediate 83.i), the title compound was isolated as a yellow oil (257 mg, 100%).

83.iii) (3RS)-(4RS)-4-Azidomethyl-1-(6-methoxy-[1,5]-naphthyridin-4-yl)-pyrrolidin-3-ol According to procedure F and starting from intermediate 83.ii) and 8-bromo-2-methoxy-[1,5]naphthyridine, the title intermediate was isolated as a yellow oil (213 mg), which was directly submitted to the next step without further purification.

83.iv) (3RS)-(4RS)-4-Aminomethyl-1-(6-methoxy-[1,5]naphthyridin-4-yl)-pyrrolidin-3-ol A solution intermediate 83.iii) (213 mg, 0.71 mmol) in EtOH (8 mL) was hydrogenated over Pd(OH)$_2$ (38 mg) for 2 h. The catalyst was filtered off and the filtrate was concentrated under reduced pressure to afford the title intermediate as a yellow oil (174 mg, 89%).
MS (ESI, m/z): 274.3 [M+H$^+$].

83.v) 6-[(R)-5-({[(3RS)-(4RS)-4-Hydroxy-1-(6-methoxy-[1,5]naphthyridin-4-yl)-pyrrolidin-3-ylmethyl]-amino}-methyl)-2-oxo-oxazolidin-3-yl]-4H-benzo[1,4]thiazin-3-one According to procedure H and starting from intermediate 83.iv) and intermediate 55.i), the title compound was isolated as a pale yellow solid (14 mg, 14%).
MS (ESI, m/z): 536.5 [M+H$^+$].

Example 84

(RS)-1-(6-Methoxy-[1,5]naphthyridin-4-yl)-pyrrolidine-3-carboxylic acid [(R)-3-(3-fluoro-4-methyl-phenyl)-2-oxo-oxazolidin-5-ylmethyl]-amide

84.i) (3-Fluoro-4-methyl-phenyl)-carbamic acid benzyl ester

The title compound was obtained from Cbz-Cl (1.41 mL, 10 mmol) and 4-fluoro-3-methyl-phenylamine (1.15 mL, 10 mmol) following procedure C. The yield was 94% (colorless solid).
$^1$H NMR (CDCl$_3$) δ: 7.42-7.20 (m, 6H), 7.07 (m, 1H), 6.92 (dd, J=8.2, 2.3 Hz, 1H), 6.63 (br. s, 1H), 5.20 (s, 2H), 2.21 (d, J=2.1 Hz, 3H).

84.ii) (R)-5-Aminomethyl-3-(3-fluoro-4-methyl-phenyl)-oxazolidin-2-one

LiOtBu (6.8 mL, 2.2M) was added dropwise to a solution of (R)-tert-butyl 3-chloro-2-hydroxypropylcarbamate (1.57 g, 7.5 mmol) and intermediate 84.ii) (1.30 g, 5 mmol) in DMF (10 mL) at rt. The mixture was stirred at rt for 2d. The mixture was partitioned between EA and water. The org. phase was washed with water (5×50 ml) and brine, dried over MgSO$_4$ and concentrated under reduced pressure. The residue was purified by CC (hex/EA 2:1, 1:1) to afford a yellowish solid (1.32 g) which was reacted to the free amine according to procedure E to afford the title intermediate as yellowish solid (0.80 g, 71%).

$^1$H NMR (CDCl$_3$) δ: 7.40-7.20 (m, 8H), 4.66 (m, 1H), 4.01 (t, J=8.8 Hz, 1H), 3.81 (dd, J=8.8, 6.7 Hz, 1H), 3.10 (m, 1H), 2.97 (m, 1H), 2.24 (d, J=1.8 Hz, 3H).

84.iii) (RS)-3-{[(R)-3-(3-Fluoro-4-methyl-phenyl)-2-oxo-oxazolidin-5-ylmethyl]-carbamoyl}-pyrrolidine-1-carboxylic acid tert-butyl ester The title intermediate was obtained from intermediates 84.ii) and (RS)-1-Boc-pyrrolidine-3-carboxylic acid (commercial), according to procedure J as a pale pink solid (310 mg, 29%).

MS (ESI, m/z): 422.4 [M+H$^+$].

84.iv) (RS)-Pyrrolidine-3-carboxylic acid [(R)-3-(3-fluoro-4-methyl-phenyl)-2-oxo-oxazolidin-5-ylmethyl]-amide The title intermediate was obtained from intermediate 84.iii), according to procedure E as an orange solid (223 mg, 97%).

MS (ESI, m/z): 322.3 [M+H$^+$].

84.v) (RS)-1-(6-Methoxy-[1,5]naphthyridin-4-yl)-pyrrolidine-3-carboxylic acid [(R)-3-(3-fluoro-4-methyl-phenyl)-2-oxo-oxazolidin-5-ylmethyl]-amide The title compound was obtained from intermediate 84.iv) and 8-bromo-2-methoxy-[1,5]naphthyridine according to procedure F as a brown solid (46 mg, 31%).

MS (ESI, m/z): 480.3 [M+H$^+$].

Example 85

(RS)-1-(6-Methoxy-[1,5]naphthyridin-4-yl)-pyrrolidine-3-carboxylic acid [(R)-3-(2,3-dihydro-benzo[1,4]dioxin-6-yl)-2-oxo-oxazolidin-5-ylmethyl]-amide

85.i) (S)-5-azidomethyl-3-(2,3-dihydro-benzo[1,4]dioxin-6-yl)-oxazolidin-2-one A solution of intermediate 47.i) (1.26 g, 3.8 mmol) in DMF (20 mL) was treated with NaN$_3$ (0.3 g, 1.2 eq.) and the mixture heated at 80° C. overnight. The mixture was cooled and partitioned between ether and water. The org. phase was washed with water and brine, dried over MgSO$_4$ and concentrated under reduced pressure to give the desired azide as a colourless solid (0.95 g, 90% yield).

MS (ESI, m/z): 277.1 [M+H$^+$].

85.ii) (R)-5-aminomethyl-3-(2,3-dihydro-benzo[1,4]dioxin-6-yl)-oxazolidin-2-one A solution of intermediate 85.ii) (0.95 g, 3.4 mmol) in EtOH/THF (1:1, 40 mL) was hydrogenated over Pd(OH)$_2$ (0.18 g, 0.1 eq.) under 1 bar of H$_2$ for 3 h. The catalyst was filtered off and the filtrate concentrated in vacuo to give the desired amine as a colourless solid (0.62 g, 72% yield).

$^1$H NMR (DMSO d6) δ: 7.12 (d, J=2.5 Hz, 1H), 6.98 (dd, J=2.5, 8.9 Hz, 1H), 6.86 (d, J=8.9 Hz, 1H), 4.60-4.50 (m, 1H), 4.30-4.10 (m, 4H), 3.99 (t, J=8.8 Hz, 1H), 3.79 (dd, J=6.5, 8.8 Hz, 1H), 3.90-3.75 (m, 2H).

MS (ESI, m/z): 251.0 [M+H$^+$].

85.iii) (RS)-3-{[(R)-3-(2,3-Dihydro-benzo[1,4]dioxin-6-yl)-2-oxo-oxazolidin-5-ylmethyl]-carbamoyl}-pyrrolidine-1-carboxylic acid tert-butyl ester The title intermediate was obtained from intermediates 85.ii) and (RS)-1-Boc-pyrrolidine-3-carboxylic acid (commercial), according to procedure J as a pink solid (810 mg, 91%).

$^1$H NMR (CDCl$_3$) δ: 7.05 (d, J=2.6 Hz, 1H), 6.84 (m, 1H), 6.93 (m, 1H), 6.22 (m, 1H), 4.73 (m, 1H), 4.24 (2, 4H), 4.00 (t, J=8.8 Hz, 1H), 3.80-3.30 (m, 6H), 2.87 (m, 1H), 2.05 (m, 2H), 1.44 (m, 9H).

MS (ESI, m/z): 448.5 [M+H$^+$].

85.iv) (RS)-Pyrrolidine-3-carboxylic acid [(R)-3-(2,3-dihydro-benzo[1,4]dioxin-6-yl)-2-oxo-oxazolidin-5-ylmethyl]-amide The title intermediate was obtained from intermediate 85.iii) according to procedure E as pale pink solid (580 mg, 93%).

MS (ESI, m/z): 348.1 [M+H$^+$].

85.v) (RS)-1-(6-Methoxy-[1,5]naphthyridin-4-yl)-pyrrolidine-3-carboxylic acid [(R)-3-(2,3-dihydro-benzo[1,4]dioxin-6-yl)-2-oxo-oxazolidin-5-ylmethyl]-amide The title compound was obtained from intermediate 85.iv) and 8-bromo-2-methoxy-[1,5]naphthyridine according to procedure F as a colorless solid (55 mg, 38%).

MS (ESI, m/z): 506.3 [M+H$^+$].

Example 86

6-((RS)-5-{2-[(S)-1-(6-Methoxy-[1,5]naphthyridin-4-yl)-pyrrolidin-3-ylamino]-ethyl}-2-oxo-oxazolidin-3-yl)-4H-benzo[1,4]thiazin-3-one According to procedure H and starting from intermediate 41.ii) and intermediate 58.iv), the title compound was isolated as an off-white solid (25 mg, 17%).

MS (ESI, m/z): 521.4 [M+H$^+$].

Example 87

6-((RS)-5-{2-[(R)-1-(6-Methoxy-[1,5]naphthyridin-4-yl)-pyrrolidin-3-ylamino]-ethyl}-2-oxo-oxazolidin-3-yl)-4H-benzo[1,4]thiazin-3-one According to procedure H and starting intermediate 61.i) and intermediate 58.iv), the title compound was isolated as an off-white solid (9 mg, 6%).

MS (ESI, m/z): 521.4 [M+H$^+$].

Example 88

(R)-3-(3-Fluoro-4-methyl-phenyl)-5-{[(1a,5a,6a)-3-(6-methoxy-[1,5]naphthyridin-4-yl)-3-aza-bicyclo[3.1.0]hex-6-ylamino]-methyl}-oxazolidin-2-one

88.i) [(1α,5α,6α)-3-(6-Methoxy-[1, 5]naphthyridin-4-yl)-3-aza-bicyclo[3.1.0]hex-6-yl]-carbamic acid tert-butyl ester The title compound was obtained from (1α,5α,6α)-(3-aza-bicyclo[3.1.0]hex-6-yl)-carbamic acid tert-butyl ester (commercial, CAS-Registry No: 155475-25-5) and 8-bromo-2-methoxy-[1,5]naphthyridine according to procedure F as a beige solid (210 mg, 61%).
MS (ESI, m/z): 357.3 [M+H$^+$].

88.ii) (1α,5α, 6α)-3-(6-Methoxyl-[1,5]naphthyridin-4-yl)-3-aza-bicyclo[3.1.0]hex-6-ylamine The title intermediate was obtained from intermediate 88.0 according to procedure E as dark yellow oil (161 mg, 100%).
MS (ESI, m/z): 257.5 [M+H$^+$].

88.iii) (R)-3-(3-Fluoro-4-methyl-phenyl)-5-{[(1α,5α,6α)-3-(6-methoxy-[1,5]naphthyridin-4-yl)-3-aza-bicyclo[3.1.0]hex-6-ylamino]-methyl}-oxazolidin-2-one According to procedure H the title compound was obtained from intermediates 88.ii and 46.ii and isolated as colorless foam (23 mg, 29%).
MS (ESI, m/z): 464.4 [M+H$^+$].

Example 89

6-((R)-5-{[(1α,5α,6α)-3-(6-Methoxy-[1,5]naphthyridin-4-yl)-3-aza-bicyclo[3.1.0]hex-6-ylamino]-methyl}-2-oxo-oxazolidin-3-yl)-4H-benzo[1,4]thiazin-3-one According to procedure H the title compound was obtained from intermediates 88.0 and 55.i) and isolated as colorless solid (9 mg, 10%).
$^1$H NMR (CDCl$_3$) δ: 8.55 (s, 1H), 8.32 (d, J=5.3 Hz, 1H), 8.06 (d, J=9.1 Hz, 1H), 7.44 (s, 1H), 7.27 (m, 1H), 7.00 (d, J=9.1 Hz, 1H), 6.93 (d, J=8.5 Hz, 1H), 6.36 (d, J=5.0 Hz, 1H), 4.77 (m, 1H), 4.35 (m, 2H), 4.03 (m, 3H), 3.81 (m, 3H), 3.44 (m, 4H), 3.06 (m, 2H), 2.09 (m, 1H), 1.80 (m, 1H).
MS (ESI, m/z): 519.5 [M+H$^+$].

Example 90

(R)-3-(2,3-Dihydro-benzo[1,4]dioxin-6-yl)-5-{[(3aR*,6aR*)-1-(6-methoxy-[1,5]naphthyridin-4-yl)-hexahydro-pyrrolo[3,4-b]pyrrol-5-yl]-methyl}-oxazolidin-2-one

90.i) (3aR*,6aR*)-1-(6-Methoxy-[1,5]naphthyridin-4-yl)-hexahydro-pyrrolo[3,4-b]pyrrole-5-carboxylic acid tert-butyl ester The title intermediate was obtained from (3aR*,6aR*)-hexahydro-pyrrolo[3,4-b]pyrrole-5-carboxylic acid tert-butyl ester (racemic, commercial) and 8-bromo-2-methoxy-[1,5]naphthyridine according to procedure F as a brown oil (5.30 g, 61%).
MS (ESI, m/z): 371.4 [M+H$^+$].

90.ii) 8-(3aR*,6aR*)-Hexahydro-pyrrolo[3,4-b]pyrrol-1-yl-2-methoxy-[1,5]naphthyridine The title intermediate was obtained from intermediate 90.i) according to procedure E as dark yellow oil (2.60 g, 96%).
MS (ESI, m/z): 271.2 [M+H$^+$].

90.iii) (R)-3-(2,3-Dihydro-benzo[1,4]dioxin-6-yl)-5-{[(3aR*,6aR*)-1-(6-methoxy-[1,5]naphthyridin-4-yl)-hexahydro-pyrrolo[3,4-b]pyrrol-5-yl]-methyl}-oxazolidin-2-one According to procedure H the title compound was obtained from intermediates 47.i. and 90.ii) and isolated as a pale yellow foam (47 mg, 31%).
$^1$H NMR (CDCl$_3$) δ: 8.36 (t, J=6.2 Hz, 1H), 8.11 (d, J=8.8 Hz, 1H), 7.05-6.80 (m, 4H), 6.52 (d, J=5.6 Hz, 0.5H), 6.37 (d, J=5.3 Hz, 0.5H), 5.59 (m, 1H), 4.58 (m, 1H), 4.26 (m, 4H), 3.98 (m, 3H), 3.91 (m, 1H), 3.80-3.65 (m, 3H), 3.03 (m, 1H), 2.80-2.48 (m, 5H), 2.16 (m, 1H), 1.93 (m, 1H).
MS (ESI, m/z): 504.6 [M+H$^+$].

Example 91

6-{{(R)-5-[(3aR*,6aR*)-1-(6-Methoxy-[1,5]naphthyridin-4-yl)-hexahydro-pyrrolo[3,4-b]pyrrol-5-yl]-methyl}-2-oxo-oxazolidin-3-yl}-4H-benzo[1,4]thiazin-3-one According to procedure H the title compound was obtained from intermediates 55.0 and 90.ii) and isolated as a pale yellow foam (48 mg, 32%).
MS (ESI, m/z): 533.3 [M+H$^+$].

Example 92

(S)-3-(2,3-Dihydro-benzo[1,4]dioxin-6-yl)-5-[(3aR*,6aR*)-1-(6-methoxy-[1,5]naphthyridin-4-yl)-hexahydro-pyrrolo[3,4-b]pyrrole-5-carbonyl]-oxazolidin-2-one According to procedure K the title compound was obtained from intermediates 2.0 and 90.0 and isolated as a pale yellow foam (83 mg, 52%).
MS (ESI, m/z): 518.5 [M+H$^+$].

Example 93

6-{(R)-5-{[(3aR*,6aR*)-5-(6-Methoxy-[1,5]naphthyridin-4-yl)-hexahydro-pyrrolo[3,4-b]pyrrol-1-yl]-methyl}-2-oxo-oxazolidin-3-yl}-4H-benzo[1,4]thiazin-3-one

93.i) 8-((3aR*,6aR*)-1-benzyl-hexahydro-pyrrolo[3,4-b]pyrrol-5-yl)-2-methoxy-[1,5]naphthyridine The title intermediate was obtained from (3aR*,6aR*)-1-benzyl-octahydro-pyrrolo[3,4-b]pyrrole (racemic, commercial) and 8-bromo-2-methoxy-[1,5]naphthyridine according to procedure F as a brown oil (4.95 g, 69%).
MS (ESI, m/z): 361.3 [M+H$^+$].

93.ii) 8-(3aR*, 6aR*)-hexahydro-pyrrolo[3,4-b]pyrrol-5-yl-2-methoxy-[1,5]naphthyridine A solution of intermediate 933). (4.95 g, 13.7 mmol) in MeOH (110 mL) and AcOH (1 eq.) was hydrogenated over Pd(OH)$_2$ (1.1 g) for 18 h. The catalyst was filtered off and the filtrate concentrated under reduced pressure. Sat. aq. NH$_4$OH was added and the mixture extracted with DCM-MeOH 9:1 (3×). The combined org. layers were washed with brine, dried over MgSO$_4$, filtered and concentrated under reduced pressure to afford the title intermediate as a yellow oil (3.54 g, 95%).

MS (ESI, m/z): 271.3 [M+H$^+$].

93.iii) 6-{(R)-5-{[(3aR*, 6aR*)-5-(6-Methoxy-[1,5]naphthyridin-4-yl)-hexahydro-pyrrolo[3,4-b]pyrrol-1-yl]-methyl}-2-oxo-oxazolidin-3-yl}-4H-benzo[1,4]thiazin-3-one According to procedure H the title compound was obtained from intermediates 55.i and 93.ii), and isolated as a pale yellow foam (14 mg, 9%).

MS (ESI, m/z): 533.3 [M+H$^+$].

Example 94

(R)-3-(2,3-Dihydro-benzo[1,4]dioxin-6-yl)-5-{[(3aR*,6aR*)-5-(6-methoxy-[1,5]naphthyridin-4-yl)-hexahydro-pyrrolo[3,4-b]pyrrol-1-yl]-methyl}-oxazolidin-2-one According to procedure H the title compound was obtained from intermediates 93.ii) and 47.i) and isolated as a pale yellow foam (18 mg, 17%).

$^1$H NMR (CDCl$_3$) δ: 8.86 (m, 1H), 8.39 (d, J=5.3 Hz, 1H), 8.14 (d, J=9.1 Hz, 1H), 7.15 (d, J=8.5 Hz, 1H), 6.97 (m, 2H), 6.51 (m, 2H), 4.64 (m, 1H), 4.26 (d, J=12.3 Hz, 1H), 3.99 (m, 4H), 3.87 (m, 2H), 3.72 (m, 1H), 3.40 (s, 2H), 3.31 (m, 2H), 2.90 (m, 3H), 2.60 (m, 1H), 2.21 (m, 1H), 1.86 (m, 2H).

MS (ESI, m/z): 504.6 [M+H$^+$].

Example 95

(S)-3-(2,3-Dihydro-benzo[1,4]dioxin-6-yl)-5-[(3aR*, 6aR*)-5-(6-methoxy-[1,5]naphthyridin-4-yl)-hexahydro-pyrrolo[3,4-b]pyrrole-1-carbonyl]-oxazolidin-2-one According to procedure K, the title compound was obtained from intermediates 93.ii and 2.i) and isolated as a pale yellow foam (95 mg, 59%).

$^1$H NMR (CDCl$_3$) δ: 8.37 (m, 1H), 8.09 (m, 1H), 7.02 (m, 3H), 6.85 (m, 1H), 6.48 (dd, J=5.3, 2.1 Hz, 1H), 5.09 (m, 1H), 4.61 (m, 2H), 4.36 (m, 1H), 4.23 (s, 4H), 4.10-3.91 (m, 8H), 3.79 (m, 1H), 3.12 (m, 1H), 2.18 (m, 2H).

MS (ESI, m/z): 518.4 [M+H$^+$].

Example 96

6-{(R)-5-[4-(6-Methoxy-[1,5]naphthyridin-4-yl)-piperazin-1-ylmethyl]-2-oxo-oxazolidin-3-yl}-4H-benzo[1,4]oxazin-3-one According to procedure H and starting from intermediate 8.i) and intermediate 45.vi the title compound was isolated as a pale yellow foam (79 mg, 55%).

MS (ESI, m/z): 491.1 [M+H$^+$].

Example 97

6-{(R)-5-[4-(3-Fluoro-6-methoxy-[1,5]naphthyridin-4-yl)-piperazin-1-ylmethyl]-2-oxo-oxazolidin-3-yl}-4H-benzo[1,4]oxazin-3-one 97.i) 7-Fluoro-2-methoxy-8-piperazin-1-yl-[1,5]naphthyridine A mixture of 8-bromo-7-fluoro-2-methoxy-[1,5]naphthyridine (2.45 g, 9.5 mmol) and piperazine (4.1 g, 47.6 mmol, 5 eq) in 1-pentanol (10 ml) was heated at 80° C. overnight. The mixture was cooled to rt and the precipitate filtered off (piperazine hydrobromide). The filtrate was concentrated in vacuo (bath temperature 70° C.). The residue was purified by chromatography on SiO$_2$ (EA/MeOH 4:1 to 1:1) to afford the title intermediate as a slightly yellow solid (1.24 g, 50%)

MS (ESI, m/z): 263.6 [M+H$^+$].

97.ii 6-{(R)-5,4-(3-Fluoro-6-methoxy-[1,5]naphthyridin-4-yl)-piperazin-1-ylmethyl]-2-oxo-oxazolidin-3-yl}-4H-benzo[1,4]oxazin-3-one According to procedure H the title compound was obtained from intermediates 97.i) and 45.vi) and isolated as an off-white foam (31 mg, 21%).

$^1$H NMR (CDCl$_3$) δ: 8.47 (d, J=4.4 Hz, 1H), 8.09 (m, 2H), 7.46 (d, J=2.3 Hz, 1H), 6.99 (m, 2H), 6.82 (dd, J=8.8, 2.6 Hz, 1H), 4.84 (m, 1H), 4.59 (s, 2H), 4.06 (m, 4H), 3.84 (m, 1H), 3.74 (m, 4H), 2.82 (m, 6H).

MS (ESI, m/z): 509.1 [M+H$^+$].

Example 98

6-{(R)-5-[4-(3-Fluoro-6-methoxy-[1,5]naphthyridin-4-yl)-piperazin-1-ylmethyl]-2-oxo-oxazolidin-3-yl}-4H-benzo[1,4]thiazin-3-one According to procedure I and starting from intermediate 97.i) and intermediate 48.v), the title compound was isolated as a pale yellow foam (56 mg, 60%).

$^1$H NMR (CDCl$_3$) δ: 8.48 (d, J=4.4 Hz, 1H), 8.11 (d, J=9.4 Hz, 1H), 7.88 (s, 1H), 7.43 (d, J=2.3 Hz, 1H), 7.30 (d, J=8.5 Hz, 1H), 6.99 (m, 2H), 4.85 (m, 1H), 4.09 (t, J=8.5 Hz, 1H), 4.03 (s, 3H), 3.86 (dd, J=8.8, 7.0 Hz, 1H), 3.75 (m, 4H), 3.42 (s, 2H), 2.83 (m, 6H).

MS (ESI, m/z): 524.9 [M+H$^+$].

Example 99

(R)-3-(2,3-Dihydro-benzo[1,4]dioxin-6-yl)-5-(4-quinolin-4-yl-piperazin-1-ylmethyl)-oxazolidin-2-one 99.i) 4-[(R)-3-(2,3-Dihydro-benzo[1,4]dioxin-6-yl)-2-oxo-oxazolidin-5-ylmethyl]-piperazine-1-carboxylic acid tert-butyl ester A solution of piperazine-1-carboxylic acid tert-butyl ester (commercial; 1.40 g, 7.6 mmol) in dry MeOH (25 mL) was treated with MgSO$_4$ (1.9 g). (R)-Epichlorohydrin (1.47 mL, 18.9 mmol) was added dropwise and the mixture was heated at 35° C. for 2 h and was then stirred at rt overnight. The mixture was filtered over Celite and concentrated under reduced pressure. The residue was taken up in DCM and washed with water. The org. phase was dried over MgSO$_4$ and concentrated under reduced pressure to afford the crude 4-((R)-3-chloro-2-hydroxy-propyl)-piperazine-1-carboxylic acid tert-butyl ester. To a solution of the above intermediate chlorohydrin (2.10 g, 7.53 mmol) and (2,3-dihydro-benzo[1,4]dioxin-6-yl)-carbamic acid benzyl ester (2.15 g, 1 eq, prepared according to WO2007107965) in DMF (30 mL) was added LiOtBu (10.3 mL, 2.2M in THF) at rt. The mixture was stirred at rt over night and subsequently at 50° C. for 5 h. The mixture was partitioned between EA and 0.5M HCl. The aq. phase was basified (NH$_4$OH) and extracted with EA. The org. layer was dried over MgSO$_4$ and concentrated under reduced pressure to afford the title compound as a colorless solid (1.15 g, 36%).
MS (ESI, m/z): 420.2 [M+H$^+$].

99.ii) (R)-3-(2,3-Dihydro-benzo[1,4]dioxin-6-yl)-5-piperazin-1-ylmethyl-oxazolidin-2-one According to procedure E the title compound was obtained from intermediate 99.0 and isolated as colorless solid (854 mg, 97%).
MS (ESI, m/z): 320.3 [M+H$^+$].

99.iii) (R)-3-(2,3-Dihydro-benzo[1,4]dioxin-6-yl)-5-(4-quinolin-4-yl-piperazin-1-ylmethyl)-oxazolidin-2-one According to procedure F and starting from intermediate 99.0 and 4-chloro-quinoline (commercial) the title compound was isolated as a yellow solid (36 mg, 38%).
MS (ESI, m/z): 447.3 [M+H$^+$].

Example 100

[(S)-3-(3-Fluoro-4-methyl-phenyl)-2-oxo-oxazolidin-5-ylmethyl]-4-(6-methoxy-[1,5]naphthyridin-4-yl)-piperazin-2-one or [(R)-3-(3-Fluoro-4-methyl-phenyl)-2-oxo-oxazolidin-5-ylmethyl]-4-(6-methoxy-[1,5]naphthyridin-4-yl)-piperazin-2-one 100.i) 4-(6-Methoxy-[1,5]-naphthyridin-4-yl)-piperazin-2-one According to procedure F and starting from 8-bromo-2-methoxy-[1,5]naphthyridine and t-oxo-piperazine and using 1-pentanol instead of NMP as reaction solvent the title compound was isolated as a brown solid (410 mg, 10%).
$^1$H NMR (CDCl$_3$) δ: 8.56 (d, J=5.3 Hz, 1H), 8.19 (d, J=9.1 Hz, 1H), 7.11 (d, J=9.1 Hz, 1H), 6.81 (d, J=5.3 Hz, 1H), 6.28 (br. s, 1H), 4.26 (s, 2H), 4.12 (m, 2H), 4.03 (s, 3H), 3.69 (m, 2H).
MS (ESI, m/z): 259.4 [M+H$^+$].

100.i) 4-(6-Methoxy-[1,5]-naphthyridin-4-yl)-1-(S)-1-oxiranylmethyl-piperazin-2-one or 4-(6-methoxy-[1,5]naphthyridin-4-yl)-1-(R)-1-oxiranylmethyl-piperazin-2-one To a mixture of intermediate 100.i) (394 mg, 1.53 mmol), (R)-epichlorohydrine (0.72 mL, 6 equiv) and benzyltriethylammonium chloride (3.5 mg) were added NaOH (85 mg) and water (0.085 mL). The mixture was heated at 50° C. for 1 h. After cooling to rt, water was added and the mixture was extracted with EA. The org. layer was dried over MgSO$_4$, evaporated under reduced pressure and the residue was chromatographed over SiO$_2$ (DCM-MeOH—NH$_4$OH 1000-50-4) to afford the title intermediate as a pale yellow solid (181 mg, 38%).
MS (ESI, m/z): 315.5 [M+H$^+$].

100.iii) 1-[(R)-3-(3-Fluoro-4-methyl-phenylamino)-2-hydroxy-propyl]-4-(6-methoxy-[1,5]-naphthyridin-4-yl)-piperazin-2-one or 1-[(S)-3-(3-Fluoro-4-methyl-phenylamino)-2-hydroxy-propyl]-4-(6-methoxy-[1,5]-naphthyridin-4-yl)-piperazin-2-one A solution of intermediate 100.ii) (26 mg, 0.083 mmol) and 3-fluoro-4-methylaniline (10.4 mg, 0.083 mmol) in EtOH/water 9:1 (0.5 mL) was heated at 80° C. for 3 h. The mixture was concentrated under reduced pressure and the residue was chromatographed over SiO$_2$ (DCM/MeOH/NH$_4$OH 1000:50:4) to afford the title intermediate as a colorless oil (10 mg, 3%).
MS (ESI, m/z): 440.5 [M+H$^+$].

100.iv) [(S)-3-(3-Fluoro-4-methyl-phenyl)-2-oxo-oxazolidin-5-ylmethyl]-4-(6-methoxy-[1,5]naphthyridin-4-yl)-piperazin-2-one or [(R)-3-(3-fluoro-4-methyl-phenyl)-2-oxo-oxazolidin-5-ylmethyl]-4-(6-methoxy-[1,5]naphthyridin-4-yl)-piperazin-2-one According to procedure B, the title compound was obtained from intermediate 100.iii) and CDI isolated as a colorless oil (10 mg, 94%).
MS (ESI, m/z): 466.2 [M+H$^+$].

Example 101

6-{(R)-5-[4-(6-Methoxy-[1,5]naphthyridin-4-yl)-3-oxo-piperazin-1-ylmethyl]-2-oxo-oxazolidin-3-yl}-4H-benzo[1,4]thiazin-3-one 101.i) 4-(6-Methoxy-[1,5]naphthyridin-4-yl)-3-oxo-piperazine-1-carboxylic acid tert-butyl ester A glass vial was charged with 1-Boc-3-oxo-piperazine (commercial; 503 mg, 2.5 mmol), CuI (40 mg, 0.21 mmol) and K$_3$PO$_4$ (888 mg, 4.2 mmol), evacuated and backfilled with argon. Trans-1,2-diaminocyclohexane (24 mg, 0.21 mmol), 8-bromo-2-methoxy-[1,5]naphthyridine (500 mg, 2.1 mmol) and dioxane (2 mL) were added under a flow of argon. The tube was sealed and the mixture was heated at 110° C. for 18 h. The resulting suspension was filtered through a pad of SiO$_2$ (EA). The filtrate was concentrated under reduced pressure and the residue was chromatographed over SiO$_2$ (DCM-MeOH—NH$_4$OH 1000-50-4) to afford the title intermediate as a pale yellow oil (87 mg, 12%).
$^1$H NMR (CDCl$_3$) δ: 8.75 (d, J=4.7 Hz, 1H), 8.18 (d, J=9.1 Hz, 1H), 7.47 (d, J=4.7 Hz, 1H), 7.09 (d, J=9.1 Hz, 1H), 4.31 (s, 2H), 3.96 (s, 3H), 3.86 (s, 4H), 1.46 (s, 9H).
MS (ESI, m/z): 359.3 [M+H$^+$].

101.ii) 1-(6-Methoxy-[1,5]naphthyridin-4-yl)-piperazin-2-one

According to procedure E, the title intermediate was obtained from intermediate 101.i) and isolated as a yellow solid (59 mg, 94%).
MS (ESI, m/z): 259.2 [M+H$^+$].

101.iii) 6-{(R)-5,4-(6-Methoxyl 1,5]naphthyridin-4-yl)-3-oxo-piperazin-1-ylmethyl]-2-oxo-oxazolidin-3-yl}-4H-benzo[1,4]thiazin-3-one According to procedure I the title compound was obtained from intermediates 101.0 and 48.v) and isolated as a colorless solid (41 mg, 36%).
MS (ESI, m/z): 521.3 [M+H$^+$].

Example 102

(R)-3-(2,3-Dihydro-benzo[1,4]dioxin-6-yl)-5-{[(RS)-1-(6-methoxy-[1,5]naphthyridin-4-yl)-piperidin-3-ylamino]-methyl}-oxazolidin-2-one

102.i) (3RS)-[1-(6-Methoxy-[1,5]-naphthyridin-4-yl)-piperidin-3-yl]-carbamic acid tert-butyl ester According to procedure F and starting from 8-bromo-2-methoxy-[1,5]naphthyridine and (RS)-piperidin-3-yl-carbamic acid tert-butyl ester (commercial) and using 1-pentanol instead of NMP as reaction solvent, the title compound was isolated as an orange oil (2.44 g, 68%).
$^1$H NMR (CDCl$_3$) δ: 8.43 (d, J=5.3 Hz, 1H), 8.11 (d, J=9.1 Hz, 1H), 7.15 (d, J=9.1 Hz, 1H), 6.95 (d, J=5.3 Hz, 1H), 6.84 (d, J=7.9 Hz, 1H), 4.31 (m, 1H), 4.03 (m, 1H), 3.96 (s, 3H), 3.65 (m, 1H), 3.33 (m, 1H), 3.13 (m, 1H), 2.88 (m, 1H), 1.80 (m, 3H), 1.34 (m, 9H).

102.ii) (3RS)-1-(6-Methoxy-[1,5]-naphthyridin-4-yl)-piperidin-3-ylamine

According to procedure E, the title intermediate was obtained from intermediate 102.i) and isolated as brown oil (1.45 g, 88%).
MS (ESI, m/z): 259.4 [M+H$^+$].

102.iii) (R)-3-(2,3-Dihydro-benzo[1,4]dioxin-6-yl)-5-{[(RS)-1-(6-methoxy-[1,5]-naphthyridin-4-yl)-piperidin-3-ylamino]-methyl}-oxazolidin-2-one According to procedure H, the title compound was obtained from intermediate 102.ii) and 47.i) and isolated as yellow solid (45 mg, 43%).
MS (ESI, m/z): 492.2 [M+H$^+$].

Example 103

6-{(R)-5-[4-(3-Fluoro-6-methoxy-[1,5]naphthyridin-4-yl)-[1,4]diazepan-1-ylmethyl]-2-oxo-oxazolidin-3-yl}-4H-benzo[1,4]oxazin-3-one

103.i) 4-(3-Fluoro-6-methoxy-[1,5]naphthyridin-4-yl)-[1,4]diazepane-1-carboxylic acid benzyl ester According to procedure F and starting from [1,4]diazepane-1-carboxylic acid benzyl ester (commercial) and 8-bromo-7-fluoro-2-methoxy-[1,5]naphthyridine, the title compound was isolated as a brown oil (1.62 g, 51%).
MS (ESI, m/z): 411.1 [M+H$^+$].

103.ii) 8-[1,4]-Diazepan-1-yl-7-fluoro-2-methoxy-[1,5]naphthyridine

According to procedure G, the title intermediate was obtained from intermediate 103.i) and isolated as a yellow solid (530 mg, 49%).
MS (ESI, m/z): 277.3 [M+H$^+$].

103.iii) 6-{(R)-5,4-(3-Fluoro-6-methoxy-[1,5]naphthyridin-4-yl)-[1,4]diazepan-1-ylmethyl]-2-oxo-oxazolidin-3-yl}-4H-benzo[1,4]oxazin-3-one According to procedure H, the title compound was obtained from intermediate 103.ii) and 45.vi) and isolated as an off-white foam (36 mg, 24%).
$^1$H NMR (CDCl$_3$) δ: 8.73 (s, 1H), 8.44 (d, J=5.3 Hz, 1H), 8.10 (d, J=9.1 Hz, 1H), 6.96 (m, 4H), 4.68 (m, 1H), 4.59 (s, 2H), 4.25 (m, 1H), 4.05-3.80 (m, 4H), 4.01 (s, 3H), 3.64 (m, 1H), 2.99 (m, 5H), 2.80 (dd, J=13.8, 6.4 Hz, 1H), 2.02 (m, 2H).
MS (ESI, m/z): 523.1 [M+H$^+$].

Example 104

6-{(R)-5-[4-(3-Fluoro-6-methoxy-[1,5]naphthyridin-4-yl)-[1,4]diazepan-1-ylmethyl]-2-oxo-oxazolidin-3-yl}-4H-benzo[1,4]thiazin-3-one According to procedure I the title compound was obtained from intermediates 103.ii) and 48.v) and isolated as pale yellow foam (54 mg, 39%).
MS (ESI, m/z): 539.0 [M+H$^+$].

Example 105

6-{(R)-5-[4-(6-Methoxy-[1,5]naphthyridin-4-yl)-[1,4]diazepan-1-ylmethyl]-2-oxo-oxazolidin-3-yl}-4H-benzo[1,4]oxazin-3-one

105.i) 4-(6-Methoxy-[1,5]naphthyridin-4-yl)-[1,4]diazepane-1-carboxylic acid benzyl ester According to procedure F and starting from [1,4]diazepane-1-carboxylic acid benzyl ester and 8-bromo-2-methoxy-[1,5]naphthyridine the title compound was isolated as a brown oil (4.18 g, 62%).
MS (ESI, m/z): 393.3 [M+H$^+$].

105.ii) 8-[1,4]-Diazepan-1-yl-2-methoxy-[1,5]naphthyridine

According to procedure G, the title intermediate obtained from intermediate 105.i) and was isolated as a brown oil (2.68 g, 98%).
MS (ESI, m/z): 259.6 [M+H$^+$].

105.iii) 6-{(R)-5,4-(6-Methoxy-[1,5]naphthyridin-4-yl)-[1,4]diazepan-1-ylmethyl]-2-oxo-oxazolidin-3-yl}-4H-benzo[1,4]oxazin-3-one According to procedure H, the title compound was obtained from intermediate 105.0 and 45.vi isolated as pale yellow foam (62 mg, 42%).
$^1$H NMR (CDCl$_3$) δ: 10.49 (br. s, 1H), 8.42 (d, J=5.6 Hz, 1H), 8.15 (d, J=9.1 Hz, 1H), 7.40 (dd, J=8.8, 2.3 Hz, 1H), 7.04 (d, J=9.1 Hz, 1H), 6.86 (d, J=8.8 Hz, 1H), 6.73 (d, J=5.6 Hz, 1H), 5.84 (d, J=2.3 Hz, 1H), 4.93 (m, 1H), 4.60 (s, 2H), 4.36 (m, 2H), 3.97 (m, 1H), 3.95 (s, 3H), 3.66 (m, 1H), 3.28 (t, J=9.1 Hz, 1H), 2.96 (m, 6H), 2.48 (m, 1H), 1.92 (m, 2H).
MS (ESI, m/z): 505.4 [M+H$^+$].

Example 106

6-{(R)-5-[4-(6-Methoxy-[1,5]naphthyridin-4-yl)-[1,4]diazepan-1-ylmethyl]-2-oxo-oxazolidin-3-yl}-4H-benzo[1,4]thiazin-3-one According to procedure H, the title compound was obtained from intermediates 105.ii) and 55.i) and isolated as pale yellow foam (39 mg, 27%).
MS (ESI, m/z): 521.3 [M+H$^+$].

Example 107

(R)-3-(2,3-Dihydro-benzo[1,4]dioxin-6-yl)-5-[4-(6-methoxy-[1,5]naphthyridin-4-yl)-[1,4]diazepan-1-ylmethyl]-oxazolidin-2-one According to procedure H the title compound was obtained from intermediates 105.ii) and 47.i) and isolated as pale yellow foam (44 mg, 29%).

MS (ESI, m/z): 492.3 [M+H$^+$].

Example 108

(R)-3-(3-Fluoro-4-methyl-phenyl)-5-[4-(6-methoxy-[1,5]naphthyridin-4-yl)-[1,4]diazepan-1-ylmethyl]-oxazolidin-2-one According to procedure H, the title compound was obtained from intermediates 105.ii) and 46.ii) and isolated as yellow foam (23 mg, 21%).

$^1$H NMR (CDCl$_3$) δ: 8.35 (d, J=5.3 Hz, 1H), 8.11 (d, J=9.1 Hz, 1H), 7.30 (m, 1H), 7.08 (m, 3H), 6.63 (d, J=5.6 Hz, 1H), 4.69 (m, 1H), 4.15 (m, 2H), 3.93 (m, 7H), 3.70 (dd, J=8.8, 6.7 Hz, 1H), 3.11 (m, 2H), 2.89 (m, 3H), 2.23 (d, J=1.8 Hz, 3H), 2.07 (m, 2H).

MS (ESI, m/z): 466.3 [M+H$^+$].

Example 109

(S)-3-(2,3-Dihydro-benzo[1,4]dioxin-6-yl)-5-[4-(6-methoxy-[1,5]naphthyridin-4-yl)-[1,4]diazepane-1-carbonyl]-oxazolidin-2-one According to procedure J, the title compound was obtained from intermediates 105.ii) and 2.i) and isolated as beige foam (97 mg, 62%).

MS (ESI, m/z): 506.2 [M+H$^+$].

Example 110

(RS)-3-(6,7-Dihydro-[1,4]dioxino[2,3-c]pyridazin-3-yl)-5-[4-(6-methoxy-[1,5]naphthyridin-4-yl)-piperazin-1-ylmethyl]-oxazolidin-2-one A mixture of intermediate 43.iii) (0.1 g, 0.29 mmol), Cs$_2$CO$_3$ (0.116 g), tris(dibenzylidenacetone)dipalladium(0) chloroform complex (15 mg) and BINAP (27 mg) in dioxane (4.5 mL) was sonicated for 10 min. The mixture turned from red to orange. 3-Chloro-6,7-dihydro-[1,4]dioxino[2,3-c]pyridazine (0.1 g, 0.58 mmol, WO07/071,936)) was added and the mixture heated at 100° C. over night. The mixture was cooled and partitioned between water and EA. The org. extracts were washed with sat. NH$_4$Cl solution, dried over MgSO$_4$ and concentrated under reduced pressure. The residue was purified by CC (EA/MeOH 9:1+1% NH$_4$OH) and triturated with ether and filtered to give the title compound (0.09 g, 64% yield) as a colourless solid.

$^1$H NMR (DMSO-d6) δ: 8.44 (d, J=5.3 Hz, 1H), 8.11 (d, J=9.1 Hz, 1H), 7.74 (s, 1H), 7.14 (d, J=9.1 Hz, 1H), 6.91 (d, J=5.3 Hz, 1H), 4.93 (m, 1H), 4.47 (m, 2H), 4.39 (m, 2H), 4.28 (m, 1H), 3.91 (m, 4H), 3.60 (m, 4H), 2.76 (m, 6H),

MS (ESI, m/z): 480.4 [M+H$^+$].

Example 111

(RS)-7-{5-[4-(6-Methoxy-[1,5]naphthyridin-4-yl)-piperazin-1-ylmethyl]-2-oxo-oxazolidin-3-yl}-1H-quinolin-2-one A mixture of intermediate 43.iii) (0.15 g, 0.45 mmol), palladium (II) acetate (0.01 g), K$_3$PO$_4$ (0.19 g), DPEphos (49 mg) and 7-bromo-1H-quinolin-2-one (0.1 g, 0.45 mmol) in dioxane (2 ml) was degassed and heated at 100° C. overnight. The mixture was partitioned between EA (20 ml) and water (20 ml). The org. phase was washed with brine, dried over MgSO$_4$ and concentrated. The product (0.02 g, 9% yield) was isolated after CC (EA/MeOH 19:1, 9:1, 4:1+1% NH$_4$OH) as an off-white solid.

$^1$H NMR (DMSO-d6) δ: 11.63 (s, 1H), 8.45 (d, J=5.3 Hz, 1H), 8.13 (d, J=9.1 Hz, 1H), 7.82 (d, J=9.7 Hz, 1H), 7.64 (d, J=8.8 Hz, 1H), 7.58 (d, J=2.1 Hz, 1H), 7.39 (dd, J=8.8, 2.1 Hz, 1H), 7.17 (d, J=9.1 Hz, 1H), 6.94 (d, J=5.3 Hz, 1H), 6.37 (d, J=9.7 Hz, 1 H), 4.93 (m, 1H), 4.19 (t, J=8.8 Hz, 1H), 3.94 (m, 4H), 3.83 (dd, J=8.8, 7.3 Hz, 1H), 3.65 (s, 4H), 2.79 (m, 6H).

MS (ESI, m/z): 487.6 [M+H$^+$].

Example 112

(R)-3-(2,3-Dihydro-benzo[1,4]dioxin-6-yl)-5-({[(S)-1-(6-methoxy-[1,5]naphthyridin-4-yl)-pyrrolidin-3-yl]-methyl-amino}-methyl)-oxazolidin-2-one According to procedure M and starting from compound 41.iii), the title compound was isolated as a colorless solid (4 mg, 48%).

MS (ESI, m/z): 492.1 [M+H$^+$].

Example 113

(RS)-6-{5-[4-(6-Methoxy-[1,5]naphthyridin-4-yl)-piperazin-1-ylmethyl]-2-oxo-oxazolidin-3-yl}-4H-pyrido[3,2-b][1,4]oxazin-3-one A mixture of intermediate 43.iii) (0.15 g, 0.45 mmol), palladium (II) acetate (0.01 g), K$_3$PO$_4$ (0.19 g), DPEphos (49 mg) and 6-bromo-4H-pyrido[3,2-b][1,4]oxazin-3-one (0.123 g, 0.54 mmol) in dioxane (2 ml) was degassed and heated at 100° C. overnight. The mixture was partitioned between EA (20 ml) and water (20 ml). The org. phase was washed with brine, dried over MgSO$_4$ and concentrated under reduced pressure. The product (0.054 g, 25% yield) was isolated after CC (EA/MeOH 19:1, 9:1, 4:1+1% NH$_4$OH) and crystallization from ether as an off-white solid.

$^1$H NMR (DMSO-d6) δ: 11.16 (br, 1H), 8.44 (d, J=5.0 Hz, 1H), 8.12 (d, J=8.8 Hz, 1H), 7.58 (m, 1H), 7.40 (d, J=8.5 Hz, 1H), 7.15 (d, J=9.1 Hz, 1H), 6.92 (d, J=5.3 Hz, 1H), 4.87 (m, 1H), 4.58 (s, 2H), 4.19 (d, J=1.2 Hz, 1H), 3.94 (s, 3H), 3.83 (m, 1H), 3.59 (m, 4H), 2.75 (m, 6H)

MS (ESI, m/z): 492.1 [M+H$^+$].

Example 114

6-((R)-5-{2-[4-(6-Methoxy-[1,5]naphthyridin-4-yl)-piperazin-1-yl]-2-oxo-ethyl}-2-oxo-oxazolidin-3-yl)-4H-benzo[1,4]thiazin-3-one 114.i) (3R)-3-Hydroxy-4-(3-oxo-3,4-dihydro-2H-benzo[1,4]thiazin-6-ylamino)-butyric acid tert-butyl ester The title intermediate was prepared according to Procedure A starting from (R)-oxiranyl-acetic acid tert-butyl ester (0.5 g, 3.2 mmol, prepared according to *JACS,* 2000, 122, 11090) and 6-amino-4H-benzo[1,4]thiazin-3-one (0.577 g, 3.2 mmol) and isolated as a beige solid (0.98 g, 90% yield).
MS (ESI, m/z): 339.4 [M+H⁺].

114.ii) (R)-[2-oxo-3-(3-oxo-3,4-dihydro-2H-benzo [1,4]thiazin-6-yl)-oxazolidin-5-yl]-acetic acid tert-butyl ester The title intermediate was prepared according to Procedure B starting from intermediate 114.i) (0.98 g, 2.9 mmol) and isolated after chromatography on SiO₂ (hept/EA 1:1, 1:2, EA) and trituration with ether as an off-white solid (0.35 g, 33%).
¹H NMR (DMSO-d6) δ: 10.54 (s, 1H), 7.29 (m, 2H), 7.11 (dd, J=8.5, 2.3 Hz, 1H), 4.91 (m, 1H), 4.11 (t, J=8.8 Hz, 1H), 3.73 (m, 1H), 3.42 (s, 2H), 2.80 (m, 2H), 1.39 (s, 9H).
MS (ESI, m/z): 365.2 [M+H⁺].

114.iii) [(R)-2-oxo-3-(3-oxo-3,4-dihydro-2H-benzo [1,4]thiazin-6-yl)-oxazolidin-5-yl]-acetic acid A solution of intermediate 114.ii) (0.26 g, 0.7 mmol) in DCM (2.5 mL) was treated with triethylsilane (0.127 mL) and TFA (2.5 mL). The mixture was stirred at rt for 4 h and water was added. The resulting precipitate was filtered and washed with water and dried at HV to give the title intermediate (0.15 g, 70% yield) as a colourless solid.
¹H NMR (DMSO-d6) δ: 12.54 (s, 1H), 10.52 (s, 1H), 7.28 (m, 2H), 7.10 (dd, J=8.8, 2.3 Hz, 1H), 4.92 (m, 1H), 4.11 (t, J=8.8 Hz, 1H), 3.73 (m, 1H), 3.41 (s, 2H), 2.81 (m, 2H).

114.iv) 6-((R)-5-{2-[4-(6-Methoxy-[1,5]-naphthyridin-4-yl)-piperazin-1-yl]-2-oxo-ethyl}-2-oxo-oxazolidin-3-yl)-4H-benzo[1,4]thiazin-3-one A solution of intermediate 114.iii) (0.055 g, 0.178 mmol) and intermediate 8.i) (0.043 g, 0.178 mmol) in DMF (1.5 mL) was treated with DIPEA (0.088 mL, 3 eq) and dropwise with a solution of propylphosphonic anhydride solution (50% in EA, 0.116 ml). The mixture was stirred at rt for 5 h, partitioned between EA (15 mL) and water (15 mL). The org. phase was washed with water and brine, dried over MgSO₄ and concentrated. The residue was triturated with EA/MeOH, filtered and dried under HV to give 0.044 g (46% yield) of a yellowish solid.
¹H NMR (DMSO-d6) δ: 10.51 (br, 1H), 8.46 (m, 1H), 8.13 (d, J=8.5 Hz, 1H), 7.28 (m, 2H), 7.17 (m, 2H), 6.94 (d, J=5.0 Hz, 1H), 4.17 (d, J=0.6 Hz, 1H), 3.98 (m, 4H), 3.66 (m, 10H), 3.40 (s, 2H).
MS (ESI, m/z): 535.5 [M+H⁺].

Example 115

N-[1-(6-Methoxy-[1,5]naphthyridin-4-yl)-azetidin-3-yl]-2-[(R)-2-oxo-3-(3-oxo-3,4-dihydro-2H-benzo[1,4]thiazin-6-yl)-oxazolidin-5-yl]-acetamide A solution of intermediate 114.iii) (0.055 g, 0.178 mmol) and intermediate 50.ii) 0.041 g, 0.178 mmol) in DMF (1.5 mL) was treated with DIPEA (0.088 mL, 3 eq) and dropwise with a solution of propylphosphonic anhydride solution (50% in EA, 0.116 ml). The mixture was stirred at rt for 5 h, partitioned between EA (15 mL) and water (15 mL). The org. phase was washed with water and brine, dried over MgSO₄ and concentrated. The residue was triturated with EA/MeOH, filtered and dried under HV to give 0.033 g (36% yield) of a yellowish solid.
MS (ESI, m/z): 521.3 [M+H⁺].

Example 116

(S)-3-(2,3-Dihydro-benzo[1,4]dioxin-6-yl)-2-oxo-oxazolidine-5-carboxylic acid[1-(6-methoxy-[1,5] naphthyridin-4-yl)-azetidin-3-yl]-amide In analogy to example 114.iv) and starting from intermediate 50.ii) (60 mg, 0.258 mmol), intermediate 2.i) (69 mg, 1 eq), the residue was purified by CC (DCM/MeOH/NH₄OH 1000:50:4) to afford the title compound as a colorless solid (47 mg, 38%).
MS (ESI, m/z): 447.9 [M+H⁺].

Example 117

6-[(R)-5-({[(RS)-1-(6-Methoxy-[1,5]naphthyridin-4-yl)-pyrrolidin-3-ylmethyl]-methyl-amino}-methyl)-2-oxo-oxazolidin-3-yl]-4H-benzo[1,4]thiazin-3-one According to procedure M and starting from compound 80.iii), the title compound was isolated as a colorless solid (7 mg, 85%).
MS (ESI, m/z): 535.6 [M+H⁺].

Example 118

(S)-3-(2,3-Dihydro-benzo[1,4]dioxin-6-yl)-5-({[1-(6-methoxy-[1,5]naphthyridin-4-yl)-azetidin-3-ylmethyl]-methyl-amino}-methyl)-oxazolidin-2-one According to procedure M and starting from compound 1.v), the title compound was isolated as a colorless solid (7 mg, 68%).
¹H NMR (CDCl₃) δ: 8.33 (d, J=5.3 Hz, 1H), 8.04 (d, J=9.1 Hz, 1H), 7.02 (m, 3H), 6.85 (m, 1H), 6.20 (d, J=5.3 Hz, 1H), 4.72 (m, 1H), 4.55 (m, 2H), 4.25 (m, 4H), 4.05 (m, 6H), 3.73 (dd, J=8.5, 6.7 Hz, 1H), 2.97 (m, 1H), 2.77 (m, 4H), 2.38 (s, 3H).
MS (ESI, m/z): 492.3 [M+H⁺].

Example 119

6-((R)-5-{[1-(6-Methoxy-[1,5]naphthyridin-4-yl)-piperidin-4-ylamino]-methyl}-2-oxo-oxazolidin-3-yl)-4H-benzo[1,4]thiazin-3-one

119.i) [1-(6-Methoxy-[1,5]-naphthyridin-4-yl)-piperidin-4-yl]-carbamic acid benzyl ester According to procedure F and starting from 8-bromo-2-methoxy-[1,5]naphthyridine and piperidin-4-yl-carbamic acid benzyl ester the title compound was isolated as a pale yellow foam (806 mg, 60%).
MS (ESI, m/z): 393.4 [M+H⁺].

119.ii) 1-(6-Methoxy-[1,5]naphthyridin-4-yl)-piperidin-4-ylamine

According to procedure G and starting from intermediate 119.i) the title compound was isolated as a yellow oil (559 mg, 100%).
MS (ESI, m/z): 259.4 [M+H⁺].

119.iii) 6-((R)-5-{[1-(6-Methoxy-[1,5]naphthyridin-4-yl)-piperidin-4-ylamino]-methyl}-2-oxo-oxazolidin-3-yl)-4H-benzo[1,4]thiazin-3-one According to procedure I and starting from intermediate 119.0 and intermediate 48.v) the title compound was isolated as a yellow foam (34 mg, 25%).
MS (ESI, m/z): 521.3 [M+H⁺].

Example 120

6-((R)-5-{[1-(6-Methoxy-[1,5]naphthyridin-4-yl)-piperidin-4-ylamino]-methyl}-2-oxo-oxazolidin-3-yl)-4H-benzo[1,4]oxazin-3-one According to procedure H and starting from intermediate 119.0 and intermediate 45.0 the title compound was isolated as a yellow foam (22 mg, 15%).
$^1$H NMR (CDCl$_3$) δ: 8.51 (d, J=5.3 Hz, 1H), 8.34 (s, 1H), 8.14 (d, J=9.1 Hz, 1H), 7.48 (d, J=2.6 Hz, 1H), 7.06 (d, J=9.1 Hz, 1H), 6.95 (m, 1H), 6.81 (m, 2H), 4.78 (m, 1H), 4.58 (s, 2H), 4.27 (m, 2H), 4.02 (m, 4H), 3.88 (m, 1H), 3.04 (m, 4H), 2.81 (m, 1H), 2.08 (m, 2H), 1.65 (m, 3H).
MS (ESI, m/z): 505.4 [M+H$^+$].

Example 121

(R)-3-(3-Fluoro-4-methyl-phenyl)-5-{[1-(6-methoxy-[1,5]naphthyridin-4-yl)-piperidin-4-ylamino]-methyl}-oxazolidin-2-one According to procedure I and starting from intermediate 119.ii) and intermediate 46.iii) the title compound was isolated as a yellow foam (24 mg, 17%).
$^1$H NMR (CDCl$_3$) δ: 8.51 (d, J=5.0 Hz, 1H), 8.14 (d, J=9.1 Hz, 1H), 7.37 (dd, J=11.4, 1.2 Hz, 1H), 7.15 (m, 2H), 7.06 (d, J=9.1 Hz, 1H), 6.83 (d, J=5.0 Hz, 1H), 4.78 (m, 1H), 4.28 (m, 2H), 4.04 (m, 4H), 3.88 (dd, J=8.5, 6.7 Hz, 1H), 3.04 (m, 4H), 2.81 (m, 1H), 2.24 (d, J=1.8 Hz, 3H), 2.08 (m, 2H), 1.67 (m, 3H).
MS (ESI, m/z): 466.2 [M+H$^+$].

Example 122

6-((R)-5-{[1-(3-Fluoro-6-methoxy-[1,5]naphthyridin-4-yl)-piperidin-4-ylamino]-methyl}-2-oxo-oxazolidin-3-yl)-4H-benzo[1,4]thiazin-3-one 122.i) [1-(3-Fluoro-6-methoxy-[1,5]naphthyridin-4-yl)-piperidin-4-yl]-carbamic acid benzyl ester An oven-dried vial was charged with 8-bromo-7-fluoro-2-methoxy-[1,5]naphthyridine (797 mg, 3.40 mmol), palladium(II) acetate (31 mg, 0.136 mmol), DPEphos (146 mg, 0.272 mmol), K$_3$PO$_4$ (1.81 g, 8.50 mmol) and piperidin-4-yl-carbamic acid benzyl ester (875 mg, 3.40 mmol). The resulting mixture was purged with argon for several min. Dioxane (11 mL) was then added via syringe and the resulting suspension was purged with argon for 3 min. The mixture was then heated at 85° C. overnight. The solvent was removed in vacuo and the residue was extracted with EA/water. The org. layer was washed with brine, dried over MgSO$_4$ and concentrated. To the resulting solid TBME and a few drops of DCM and MeOH were added and the mixture was sonicated for 5 min and filtered to afford the title intermediate as a pale yellow foam (293 mg, 21%).
MS (ESI, m/z): 411.1 [M+H$^+$].

122.ii) 1-(3-Fluoro-6-methoxy-[1,5]naphthyridin-4-yl)-piperidin-4-ylamine

According to procedure G and starting from intermediate 122.i) the title compound was isolated as a yellow oil (191 mg, 97%).
MS (ESI, m/z): 277.1 [M+H$^+$].

122.iii) 6-((R)-5-{[1-(3-Fluoro-6-methoxy-[1,5]naphthyridin-4-yl)-piperidin-4-ylamino]-methyl}-2-oxo-oxazolidin-3-yl)-4H-benzo[1,4]thiazin-3-one According to procedure I and starting from intermediate 122.0 and intermediate 48.v) the title compound was isolated as a yellow foam (34 mg, 25%).
MS (ESI, m/z): 539.0 [M+H$^+$].

Example 123

6-((R)-5-{[1-(3-Fluoro-6-methoxy-[1,5]naphthyridin-4-yl)-piperidin-4-ylamino]-methyl}-2-oxo-oxazolidin-3-yl)-4H-benzo[1,4]oxazin-3-one According to procedure H and starting from intermediate 122.ii) and intermediate 45.vi) the title compound was isolated as a yellow foam (16 mg, 9%).
$^1$H NMR (CDCl$_3$) δ: 8.47 (d, J=4.4 Hz, 1H), 8.10 (m, 2H), 7.47 (d, J=2.6 Hz, 1H), 6.98 (m, 2H), 6.81 (dd, J=8.8, 2.6 Hz, 1H), 4.79 (m, 1H), 4.59 (s, 2H), 4.05 (m, 5H), 3.89 (m, 1H), 3.34 (m, 2H), 3.11 (m, 1H), 2.99 (m, 1H), 2.77 (m, 1H), 2.03 (m, 2H), 1.60 (m, 3H).
MS (ESI, m/z): 523.1 [M+H$^+$].

Example 124

6-[(R)-5-({[1-(3-Fluoro-6-methoxy-[1,5]naphthyridin-4-yl)-piperidin-4-yl]-methyl-amino}-methyl)-2-oxo-oxazolidin-3-yl]-4H-benzo[1,4]thiazin-3-one According to procedure M and starting from compound 122.iii), the title compound was isolated as a pale yellow foam (15 mg, 97%).
MS (ESI, m/z): 553.2 [M+H$^+$].

Example 125

6-{(R)-5-[4-Hydroxy-4-(6-methoxy-quinolin-4-yl)-piperidin-1-ylmethyl]-2-oxo-oxazolidin-3-yl}-4H-benzo[1,4]thiazin-3-one 125.i) 4-(6-Methoxy-quinolin-4-yl)-piperidin-4-ol This intermediate was prepared starting from 4-bromo-6-methoxy-quinoline (1.19 g, 5 mmol) and following the procedure of Example 3 steps i) and ii) and isolated as a yellowish oil (0.354 g; 28% over two steps).
$^1$H NMR (DMSO-d6) δ: 8.65 (d, J=4.4 Hz, 1H), 8.30 (d, J=2.9 Hz, 1H), 7.91 (d, J=9.1 Hz, 1H), 7.39 (m, 2H), 5.32 (s, 1H), 3.85 (s, 3H), 3.07 (m, 2H), 2.79 (m, 2H), 1.98 (m, 4H).
MS (ESI, m/z): 259.3 [M+H$^+$].

125.ii) 6-{(R)-5,4-Hydroxy-4-(6-methoxy-quinolin-4-yl)-piperidin-1-ylmethyl]-2-oxo-oxazolidin-3-yl}-4H-benzo[1,4]thiazin-3-one According to procedure I and starting from intermediate 125.i) (0.046 g, 0.18 mmol) and intermediate 48.v), the title compound was isolated as a yellow foam (20 mg, 21%).
$^1$H NMR (DMSO-d6) δ: 10.53 (s, 1H), 8.65 (d, J=4.7 Hz, 1H), 8.27 (d, J=2.9 Hz, 1H), 7.92 (d, J=9.1 Hz, 1H), 7.44 (d, J=4.7 Hz, 1H), 7.35 (m, 2H), 7.30 (m, 1H), 7.11 (dd, J=8.5, 2.3 Hz, 1H), 4.85 (m, 1H), 4.08 (m, 1H), 3.84 (s, 3H), 3.74 (dd, J=8.8, 7.0 Hz, 1H), 3.40 (s, 2H), 2.75 (m, 6H), 2.09 (m, 4H).
MS (ESI, m/z): 521.3 [M+H$^+$].

Example 126

6-{(R)-5-[4-(3-Fluoro-6-methoxy-[1,5]naphthyridin-4-yl)-4-hydroxy-piperidin-1-ylmethyl]-2-oxo-oxazolidin-3-yl}-4H-benzo[1,4]thiazin-3-one

126.i) 4-(3-Fluoro-6-methoxy-[1,5]naphthyridin-4-yl)-piperidin-4-ol

This intermediate was prepared starting from 8-bromo-7-fluoro-2-methoxy-[1,5]naphthyridine (1.28 g, 5 mmol) and following the procedure of Example 3 steps 3.i) and 3.ii), and isolated as a yellowish oil (0.41 g; 29% over two steps).
MS (ESI, m/z): 278.4 [M+H$^+$].

126.ii) 6-{(R)-5,4-(3-Fluoro-6-methoxy-[1,5]naphthyridin-4-yl)-4-hydroxy-piperidin-1-ylmethyl]-2-oxo-oxazolidin-3-yl}-4H-benzo[1,4]thiazin-3-one According to procedure I and starting from intermediate 126.ii) (0.05 g, 0.18 mmol) and intermediate 48.v), the title compound was isolated as a yellow foam (30 mg, 31%).
$^1$H NMR (DMSO-d6) δ: 10.53 (s, 1H), 8.76 (d, J=3.5 Hz, 1H), 8.35 (d, J=9.1 Hz, 1H), 7.32 (m, 4H), 7.13 (dd, J=8.8, 2.3 Hz, 1H), 4.86 (m, 1H), 4.05 (m, 5H), 3.74 (m, 1H), 3.42 (s, 2H), 2.74 (m, 6H), 2.41 (m, 2H), 2.05 (m, 2H),
MS (ESI, m/z): 540.1 [M+H$^+$].

Example 127

6-[(R)-5-({[1-(3-Fluoro-6-methoxy-[1,5]naphthyridin-4-yl)-azetidin-3-yl]-methyl-amino}-methyl)-2-oxo-oxazolidin-3-yl]-4H-benzo[1,4]oxazin-3-one According to procedure M and starting from compound 45.vii), the title compound was isolated as a colorless solid (23 mg, 70%).
$^1$H NMR (CDCl$_3$) δ: 9.24 (s, 1H), 8.29 (d, J=4.1 Hz, 1H), 8.01 (d, J=9.1 Hz, 1H), 7.42 (d, J=2.3 Hz, 1H), 6.89 (m, 2H), 6.76 (dd, J=8.8, 2.3 Hz, 1H), 4.78 (m, 3H), 4.51 (m, 4H), 4.02 (t, J=8.8 Hz, 1H), 3.92 (s, 3H), 3.76 (dd, J=8.5, 7.0 Hz, 1H), 3.58 (m, 1H), 2.73 (dd, J=8.5, 6.4 Hz, 2H), 2.35 (s, 3H).
MS (ESI, m/z): 508.9 [M+H$^+$].

Example 128

6-[(R)-5-({(2-Hydroxy-ethyl)-[1-(6-methoxy-[1,5]naphthyridin-4-yl)-azetidin-3-yl]-amino}-methyl)-2-oxo-oxazolidin-3-yl]-4H-benzo[1,4]thiazin-3-one To a stirred solution of compound 48.vi) (34 mg, 0.07 mmol) and (tert-butyldimethylsilyloxy)acetaldehyde (0.064 mL, 4.4 eq) in DCE (1.2 mL) and MeOH (0.1 mL) was added sodium triacetoxy borohydride (76 mg, 5.2 eq). The reaction mixture was stirred at rt overnight. The mixture was poured into 0.1M HCl and washed with ether. The aq. layer was basified with NH$_4$OH and extracted with DCM. The combined organic layers were dried over MgSO$_4$, filtered and evaporated under reduced pressure. The residue was taken up in 1:1 TFA-water (2 mL) and stirred for 30 min at rt. The solution was concentrated to dryness and the residue basified with NH$_4$OH. The mixture was extracted several times with DCM-MeOH (9:1). The combined org. layers were dried over MgSO$_4$, filtered and evaporated under reduced pressure. The residue was purified by CC (DCM-MeOH—NH$_4$OH 1000-50-4-->1000-100-8) to afford the title compound as a colorless solid (9 mg, 24%).
$^1$H NMR (DMSO-d6) δ: 10.53 (s, 1H), 8.25 (d, J=5.6 Hz, 1H), 8.01 (d, J=9.1 Hz, 1H), 7.30 (m, 2H), 7.09 (m, 2H), 6.33 (d, J=5.3 Hz, 1H), 4.81 (m, 1H), 4.51 (m, 2H), 4.05 (m, 2H), 3.91 (m, 4H), 3.71 (m, 1H), 3.50 (d, 2H), 3.42 (s, 2H), 3.15 (d, J=5.3 Hz, 2H), 2.95 (m, 2H), 2.72 (m, 2H).
MS (ESI, m/z): 537.1 [M+H$^+$].

Example 129

6-[(R)-5-({[(RS)-3-Hydroxy-1-(6-methoxy-[1,5]naphthyridin-4-yl)-pyrrolidin-3-ylmethyl]-amino}-methyl)-2-oxo-oxazolidin-3-yl]-4H-benzo[1,4]thiazin-3-one

129.i) (RS)-3-(Benzylamino-methyl)-3-hydroxy-pyrrolidine-1-carboxylic acid tert-butyl ester Benzyl amine (1.7 mL, 1.1 eq) was added to a solution of rac-1-oxa-5-aza-spiro[2.4]heptane-5-carboxylic acid tert-butyl ester (commercial, 2.80 g, 14.05 mmol) in MeOH (25 mL) and the mixture was heated at reflux for 2 h. The resulting solution was concentrated under reduced pressure and the residue was purified by CC (DCM-MeOH—NH$_4$OH 1000:50:4) to afford the title compound as colourless oil (4.29 g, 100%).
MS (ESI, m/z): 307.5 [M+H$^+$].

129.ii) (RS)-3-(Benzylamino-methyl)-pyrrolidin-3-ol

According to procedure E and starting from intermediate 129.i), the title compound was isolated as yellow oil (2.91 g, 79%).
MS (ESI, m/z): 207.1 [M+H$^+$].

129.iii) (RS)-3-(Benzylamino-methyl)-1-(6-methoxy-[1,5]naphthyridin-4-yl)-pyrrolidin-3-ol According to procedure F and starting from 8-bromo-2-methoxy-[1,5]naphthyridine (commercial) and intermediate 129.ii), the desired intermediate was isolated as a brown oil (1.14 g, 64%).
MS (ESI, m/z): 365.1 [M+H$^+$].

129.iv) (RS)-3-Aminomethyl-1-(6-methoxy-[1,5]naphthyridin-4-yl)-pyrrolidin-3-ol A solution of intermediate 129.iii) (370 mg, 1.02 mmol) in MeOH (10 mL) and AcOH (0.06 mL, 1 eq) was hydrogenated over Pd(OH)$_2$ (80 mg) for 2 d. The catalyst was filtered off and the filtrate was concentrated. NH$_4$OH was added and the mixture extracted with DCM-MeOH 9:1 (3×). The combined org. layers were washed with brine, dried over MgSO$_4$, filtered and concentrated under reduced pressure. The residue was purified by CC (DCM/MeOH/NH$_4$OH 1000:100:8) to afford the title intermediate as off-white solid (136 mg, 49%).
MS (ESI, m/z): 275.4 [M+H$^+$].

129.v) 6-[(R)-5-({[(RS)-3-Hydroxy-1-(6-methoxy-[1,5]naphthyridin-4-yl)-pyrrolidin-3-ylmethyl]-amino}-methyl)-2-oxo-oxazolidin-3-yl]-4H-benzo[1,4]thiazin-3-one According to procedure I and starting from intermediate 129.iv) and intermediate 48.v), the title compound was isolated as off-white solid (3 mg, 2%).
$^1$H NMR (CDCl$_3$) δ: 8.76 (s, 1H), 8.12 (m, 1H), 8.01 (d, J=8.8 Hz, 1H), 7.52 (m, 1H), 7.23 (m, 1H), 6.89 (m, 1H), 6.93

(m, 1H), 6.16 (t, J=7.6 Hz, 1H), 4.80 (m, 1H), 3.95 (m, 6H), 3.90 (s, 3H), 3.37 (d, J=3.8 Hz, 2H), 3.04 (m, 4H), 2.10 (m, 2H), 1.94 (m, 2H).
MS (ESI, m/z): 537.3 [M+H$^+$].

Example 130

(S)-3-(3-Fluoro-4-methyl-phenyl)-2-oxo-oxazolidine-5-carboxylic acid

[1-(6-methoxy-[1,5]naphthyridin-4-yl)-azetidin-3-ylmethyl]-amide

According to procedure N and starting from intermediate 1.ii) and intermediate 62.i), the title compound was isolated as an off-white solid (3 mg, 3%).
$^1$H NMR (CDCl$_3$) δ: (d, J=4.98 Hz, 1H), 8.15 (d, J=9.08 Hz, 1H), 7.31 (s, 1H), 7.27 (m, 1H), 7.08 (m, 3H), 6.21 (m, 1H), 5.03 (m, 1H), 4.23 (m, 4H), 3.98 (m, 3H), 3.71 (t, J=6.4, Hz, 2H), 3.65 (m, 2H), 3.04 (m, 1H), 2.24 (s, 3H).
MS (ESI, m/z): 466.1 [M+H$^+$].

Example 131

6-((R)-5-{[1-(6-Methoxy-2-methyl-quinolin-4-yl)-azetidin-3-ylamino]-methyl}-2-oxo-oxazolidin-3-yl)-4H-benzo[1,4]thiazin-3-one 131.i) Trifluoro-methanesulfonic acid 6-methoxy-2-methyl-quinolin-4-yl ester To an ice-chilled solution 6-methoxy-2-methyl-quinolin-4-ol (commercial, 1.7 g, 9 mmol) in DCM/DMF 2:1 (30 mL) and TEA (2.1 mL) was added portionwise phenyl bis (trifluoromethanesulfonimide) (6.4 g, 18 mmol). The suspension was stirred at 40° C. overnight. DCM was evaporated under reduced pressure and the residue was partitioned between sat. NaHCO$_3$ and EA. The phases were separated and the aq phase was extracted twice with EA. The combined org. extracts were washed with water and brine, dried over MgSO$_4$ and concentrated under reduced pressure. The residue was purified by CC (EA/Hept 1:1) to afford the title intermediate as yellow oil (1.2 g, 42%).
MS (ESI, m/z): 322.2 [M+H$^+$].

131.ii) 1-(6-Methoxy-2-methyl-quinolin-4-yl)-azetidin-3-yl]-carbamic acid benzyl ester According to procedure F and starting from 131.i) and azetidin-3-yl-carbamic acid benzyl ester, the desired intermediate was isolated as yellow oil (165 mg, 23%).
MS (ESI, m/z): 378.1 [M+H$^+$].

131.iii) 1-(6-Methoxy-2-methyl-quinolin-4-yl)-azetidin-3-ylamine

According to procedure G and starting form intermediate 131.ii) the desired intermediate was isolated as yellow oil (165 mg, 23%).
MS (ESI, m/z): 244.3 [M+H$^+$].

131.iv) 6-((R)-5-{[1-(6-Methoxy-2-methyl-quinolin-4-yl)-azetidin-3-ylamino]-methyl}-2-oxo-oxazolidin-3-yl)-4H-benzo[1,4]thiazin-3-one According to procedure I and starting from intermediate 131.iii) and intermediate 48.v), the title compound was isolated as a colorless solid (11 mg, 12%).

$^1$H NMR (CDCl$_3$) δ: 8.86 (s, 1H), 7.83 (m, 1H), 7.51 (d, J=2.1 Hz, 1H), 7.23 (m, 2H), 7.13 (m, 1H), 6.81 (dd, J=8.8, 2.3 Hz, 1H), 6.08 (s, 1H), 4.68 (m, 1H), 4.52 (m, 2H), 3.91 (m, 8H), 3.30 (s, 2H), 3.03 (m, 1H), 2.87 (m, 1H), 2.55 (s, 3H), 1.98 (m, 1H).
MS (ESI, m/z): 506.2 [M+H$^+$].

Example 132

6-{(R)-5-[4-Hydroxy-4-(6-methoxy-quinolin-4-yl)-piperidin-1-ylmethyl]-2-oxo-oxazolidin-3-yl}-4H-benzo[1,4]oxazin-3-one 132.i) 4-Hydroxy-4-(6-methoxy-quinolin-4-yl)-piperidine-1-carboxylic acid tert-butyl ester The title intermediate was prepared starting from 4-bromo-6-methoxyquinoline (CAS 42881-66-3, 1.19 g, 5 mmol) following the procedure of example 3 step i and obtained as brownish foam (0.567 g, 32% yield).
$^1$H NMR (DMSO d6) δ: 8.65 (d, J=4.7 Hz, 1H), 8.23 (d, J=2.6 Hz, 1H), 8.23 (d, J=2.6 Hz, 1H), 7.93 (d, J=9.1 Hz, 1H), 7.40 (m, 2H), 5.60 (s, 1H), 3.85 (s, 2H), 3.80 (s, 3H), 3.29 (br, 2H), 2.02 (m, 4H), 1.40 (s, 9H).
MS (ESI, m/z): 359.3 [M+H$^+$].

132.ii) 4-(6-Methoxy-quinolin-4-yl)-piperidin-4-ol

The BOC group of intermediate 132.i) (0.567 g, 1.58 mmol) was removed according to procedure E and the title intermediate was isolated as brown foam (0.354 g, 87% yield).
$^1$H NMR (DMSO d6) δ: 8.65 (d, J=4.4 Hz, 1H), 8.30 (d, J=2.9 Hz, 1H), 7.91 (d, J=9.1 Hz, 1H), 7.39 (m, 2H), 5.32 (s, 1H), 3.85 (s, 3H), 3.09 (m, 2H), 2.79 (m, 2H), 1.97 (m, 4H).
MS (ESI, m/z): 259.3 [M+H$^+$].

132.iii) 6-{(R)-5,4-Hydroxy-4-(6-methoxy-quinolin-4-yl)-piperidin-1-ylmethyl]-2-oxo-oxazolidin-3-yl}-4H-benzo[1,4]oxazin-3-one The title compound was obtained starting from intermediate 132.ii) (0.129 g, 0.5 mmol) and intermediate 45 vi) (0.17 g, 0.5 mmol) according to procedure H. The desired title compound was isolated after CC (DCM/MeOH 9:1+1% NH$_4$OH) as brownish foam (0.065 g, 26% yield).
1H NMR (DMSO d6) δ: 10.69 (s, 1H), 8.65 (d, J=4.7 Hz, 1H), 8.27 (d, J=2.9 Hz, 1H), 7.92 (d, J=9.1 Hz, 1H), 7.44 (d, J=4.7 Hz, 1H), 7.35 (m, 2H), 6.94 (s, 2H), 5.36 (s, 1H), 4.84 (m, 1H), 4.52 (s, 2H), 4.06 (m, 2H), 3.84 (s, 3H), 3.73 (m, 1H), 2.74 (m, 4H), 2.07 (m, 4H).
MS (ESI, m/z): 505.4 [M+H$^+$].

Example 133

(R)-5-({[1-(6-Methoxy-[1,5]naphthyridin-4-yl)-azetidin-3-yl]-methyl-amino}-methyl)-3-phenyl-oxazolidin-2-one 133.i) (1-Benzhydryl-azetidin-3-yl)-methyl-amine To a solution of methanesulfonic acid 1-benzhydryl-azetidin-3-yl ester (commercial, 40 g, 126 mmol) in i-PrOH (440 mL) was added methylamine (41% in water, 320 mL). The mixture was heated in a 1.6 L-Parr reactor for 3.5 h at 75° C. (1.5-2 bar). After cooling to rt the solution was concentrated, diluted with water and extracted with DCM. The combined org. phases were washed with brine, dried over MgSO₄ and concentrated. The residue was suspended in TBME (150 mL) and treated with AcOH (7.28 mL, 126 mmol). The mixture was stirred for 1 h at rt and the resulting crystals were filtered, washed with TBME and dried under HV to afford the title intermediate as its AcOH salt (15.07 g, 38%).

MS (ESI, m/z): 253.3 [M+H⁺].

133.ii) (1-Benzhydryl-azetidin-3-yl)-methyl-carbamic acid benzyl ester

According to procedure C and starting from intermediate 133.i) the title compound was isolated as a pale yellow oil (10.6 g, 100%).

MS (ESI, m/z): 387.3 [M+H⁺].

133.iii) Azetidin-3-yl-methyl-carbamic acid benzyl ester

A solution of intermediate 133.ii) (3.7 g, 9.6 mmol) in DCM (20 mL), cooled to 0° C., was treated with 1-chloroethylchloroformate (1.46 mL, 1.4 eq) and allowed to warm to rt. The reaction mixture was stirred at rt overnight and then concentrated. The residue was dissolved in MeOH (20 mL) and stirred at rt for 2 h. The solution was concentrated and the solid residue was triturated with EA, filtered and washed with EA to give the title intermediate as its HCl salt (1.36 g, 55%).

MS (ESI, m/z): 221.2 [M+H⁺].

133.iv) [1-(6-Methoxy-[1,5]naphthyridin-4-yl)-azetidin-3-yl]-methyl-carbamic acid benzyl ester According to procedure F and starting from trifluoromethanesulfonic acid 6-methoxy-[1,5]naphthyridin-4-yl ester (prepared according to WO2000040554) and intermediate 133.iii), the desired intermediate was isolated as brown oil (6.27 g, 100%).

MS (ESI, m/z): 379.2 [M+H⁺].

133.v) [1-(6-Methoxy-[1, 5]naphthyridin-4-yl)-azetidin-3-yl]-methyl-amine

According to procedure G and starting from intermediate 133.iv) the desired intermediate was isolated as a pale yellow solid (2.7 g, 67%).

MS (ESI, m/z): 245.3 [M+H⁺].

133.vi) (R)-1-Chloro-3-{[1-(6-methoxy-[1,5]naphthyridin-4-yl)-azetidin-3-yl]-methyl-amino}-propan-2-ol (R)-epichlorohydrin (0.88 mL, 2.5 eq) was added dropwise to a suspension of intermediate 133.v) (1.09 g, 4.46 mmol) and MgSO₄ (1.25 g) in MeOH (15 mL) and the mixture was warmed at 40° C. for 6 h. The mixture was taken up in EA and washed with water. The organic phase was dried over MgSO₄ and concentrated to give the title intermediate as a light yellow solid (1.18 g, 79%).

MS (ESI, m/z): 337.3 [M+H⁺].

133.vii) (R)-5-({[1-(6-Methoxy-1,5]naphthyridin-4-yl)-azetidin-3-yl]-methyl-amino}-methyl)-3-phenyl-oxazolidin-2-one LiOtBu (2.2M in THF, 0.2 mL, 3 eq) was added to a solution of intermediate 133.vi) (50 mg, 0.15 mmol) and phenyl-carbamic acid benzyl ester (34 mg, 0.15 mmol) in DMF (1 mL) and the mixture was left at rt for 1 week after which the solution was diluted with EA, washed with water and concentrated. The residue was purified by CC (DCM/MeOH/NH₄OH 1000:25:2) to afford the title compound as pale yellow foam (28 mg, 45%).

¹H NMR (CDCl₃) δ: 8.36 (d, J=5.0 Hz, 1H), 8.05 (d, J=9.1 Hz, 1H), 7.54 (m, 2H), 7.36 (m, 2H), 7.14 (m, 1H), 7.01 (d, J=9.1 Hz, 1H), 6.26 (d, J=5.0 Hz, 1H), 4.79 (m, 1H), 4.56 (m, 2H), 4.24 (m, 2H), 4.09 (t, J=8.8 Hz, 1H), 3.97 (s, 3H), 3.85 (dd, J=9.1, 7.0 Hz, 1H), 3.64 (m, 1H), 2.78 (m, 2H), 2.39 (m, 3H).

MS (ESI, m/z): 420.3 [M+H⁺].

The following examples were prepared from intermediate 133.vi) using the appropriate carbamic acid benzyl ester in analogy to Example 133:

| Example | Chemical name | Yield | MS (ESI) [M + H⁺] |
|---|---|---|---|
| 134 | (R)-3-(4-Difluoromethoxy-phenyl)-5-({[1-(6-methoxy-[1,5]naphthyridin-4-yl)-azetidin-3-yl]-methyl-amino}-methyl)-oxazolidin-2-one | 33% | 486.2 |
| 135 | (R)-5-({[1-(6-Methoxy-[1,5]naphthyridin-4-yl)-azetidin-3-yl]-methyl-amino}-methyl)-3-(4-methyl-3-trifluoromethyl-phenyl)-oxazolidin-2-one | 41% | 502.3 |
| 136 | (R)-3-(3-Chloro-4-fluoro-phenyl)-5-({[1-(6-methoxy-[1,5]naphthyridin-4-yl)-azetidin-3-yl]-methyl-amino}-methyl)-oxazolidin-2-one | 34% | 472.4 |
| 137 | (R)-3-(4-Ethyl-phenyl)-5-({[1-(6-methoxy-[1,5]naphthyridin-4-yl)-azetidin-3-yl]-methyl-amino}-methyl)-oxazolidin-2-one | 45% | 448.5 |
| 138 | (R)-3-(3,4-Dimethyl-phenyl)-5-({[1-(6-methoxy-[1,5]naphthyridin-4-yl)-azetidin-3-yl]-methyl-amino}-methyl)-oxazolidin-2-one | 40% | 448.3 |
| 139 | (R)-5-({[1-(6-Methoxy-[1,5]naphthyridin-4-yl)-azetidin-3-yl]-methyl-amino}-methyl)-3-(4-propyl-phenyl)-oxazolidin-2-one | 38% | 462.1 |
| 140 | (R)-3-(3-Dimethylamino-phenyl)-5-({[1-(6-methoxy-[1,5]naphthyridin-4-yl)-azetidin-3-yl]-methyl-amino}-methyl)-oxazolidin-2-one | 30% | 463.2 |
| 141 | (R)-3-(4-Bromo-3-fluoro-phenyl)-5-({[1-(6-methoxy-[1,5]naphthyridin-4-yl)-azetidin-3-yl]-methyl-amino}-methyl)-oxazolidin-2-one | 23% | 518.0 |

| Example | Chemical name | Yield | MS (ESI) [M + H⁺] |
|---|---|---|---|
| 142 | (R)-3-(3-Bromo-4-methyl-phenyl)-5-({[1-(6-methoxy-[1,5]naphthyridin-4-yl)-azetidin-3-yl]-methyl-amino}-methyl)-oxazolidin-2-one | 39% | 514.1 |
| 143 | (R)-3-(4-Bromo-3-methyl-phenyl)-5-({[1-(6-methoxy-[1,5]naphthyridin-4-yl)-azetidin-3-yl]-methyl-amino}-methyl)-oxazolidin-2-one | 29% | 514.1 |
| 144 | (R)-3-Benzothiazol-6-yl-5-({[1-(6-methoxy-[1,5]naphthyridin-4-yl)-azetidin-3-yl]-methyl-amino}-methyl)-oxazolidin-2-one | 35% | 476.9 |
| 145 | (R)-3-Benzo[1,3]dioxol-5-yl-5-({[1-(6-methoxy-[1,5]naphthyridin-4-yl)-azetidin-3-yl]-methyl-amino}-methyl)-oxazolidin-2-one | 25% | 464.2 |
| 146 | (R)-3-Benzothiazol-5-yl-5-({[1-(6-methoxy-[1,5]naphthyridin-4-yl)-azetidin-3-yl]-methyl-amino}-methyl)-oxazolidin-2-one | 35% | 477.0 |
| 147 | (R)-3-(3-Fluoro-phenyl)-5-({[1-(6-methoxy-[1,5]naphthyridin-4-yl)-azetidin-3-yl]-methyl-amino}-methyl)-oxazolidin-2-one | 28% | 438.3 |

Example 148

1-(6-Methoxy-[1,5]naphthyridin-4-yl)-azetidine-3-carboxylic acid [(R)-3-(3-fluoro-4-methyl-phenyl)-2-oxo-oxazolidin-5-ylmethyl]-amide

148.i) [(R)-3-(3-Fluoro-4-methyl-phenyl)-2-oxo-oxazolidin-5-ylmethyl]-carbamic acid tert-butyl ester According to procedure C and starting from 3-fluoro-4-methylaniline (commercial) the corresponding Cbz-protected intermediate was obtained in quantitative yields. LiOtBu (2.2M in THF, 6.8 mL, 3 eq) was added to a solution of the latter (1.3 g, 5.0 mmol) and (R)-oxiranylmethyl-carbamic acid tert-butyl ester (commercial, 0.87 g, 5.0 mmol) in DMF (10 mL). The mixture was stirred at rt over the weekend after which the solution was diluted with EA, washed with water and concentrated. The residue was purified by CC (Hept-EA 2:1) to afford the title intermediate as a colorless oil (1.32 g, 81%).

MS (ESI, m/z): 324.3 [M+H⁺].

148.ii) 3-{[(R)-3-(3-Fluoro-4-methyl-phenyl)-2-oxo-oxazolidin-5-ylmethyl]-carbamoyl}-azetidine-1-carboxylic acid tert-butyl ester According to procedure E and starting from intermediate 148.i) the corresponding free amine was obtained as a colorless solid (300 mg, 46%). According to procedure N the latter was reacted with azetidine-1,3-dicarboxylic acid mono-tert-butyl ester (commercial) affording the title intermediate as yellow solid (340 mg, 94%).

MS (ESI, m/z): 408.3 [M+H⁺].

148.iii) Azetidine-3-carboxylic acid [(R)-3-(3-fluoro-4-methyl-phenyl)-2-oxo-oxazolidin-5-ylmethyl]-amide According to procedure E and starting with intermediate 148.ii) the title intermediate was isolated as a colorless solid (192 mg, 80%).

MS (ESI, m/z): 308.3 [M+H⁺].

148.iv) Azetidine-3-carboxylic acid [(R)-3-(3-fluoro-4-methyl-phenyl)-2-oxo-oxazolidin-5-ylmethyl]-amide According to procedure F and starting from intermediate 148.iii) and trifluoromethanesulfonic acid 6-methoxy-[1,5]naphthyridin-4-yl ester (prepared according to WO2000040554), the title intermediate was isolated as off-white foam (49 mg, 65%).

¹H NMR (CDCl₃) δ: 8.34 (d, J=5.3 Hz, 1H), 8.04 (d, J=9.1 Hz, 1H), 7.34 (dd, J=12.0, 2.1 Hz, 1H), 7.03 (m, 3H), 6.28 (m, 1H), 6.19 (d, J=5.3 Hz, 1H), 4.80 (m, 1H), 4.59 (m, 2H), 4.04 (t, J=9.1 Hz, 1H), 3.93 (s, 3H), 3.84 (dd, J=9.4, 6.2 Hz, 1H), 3.74 (dd, J=6.4, 4.4 Hz, 2H), 2.19 (d, J=2.1 Hz, 3H).

MS (ESI, m/z): 466.2 [M+H⁺].

Example 149

(RS)-3-(3-Fluoro-4-methyl-phenyl)-5-(2-{[1-(6-methoxy-[1,5]naphthyridin-4-yl)-azetidin-3-ylmethyl]-amino}-ethyl)-oxazolidin-2-one

149.i) (RS)-4-(tert-Butyl-dimethyl-silanyloxy)-1-(3-fluoro-4-methyl-phenylamino)-butan-2-ol LiClO₄ (6.31 g, 60 mmol) was added to a solution of (RS)-tert-butyl-dimethyl-(2-oxiranyl-ethoxy)-silane (4 g, 20 mmol, prepared according to *Heterocycles* (1987), 25(1), 329-32) in MeCN (60 mL). 3-Fluoro-4-methylaniline (2.28 g, 18 mmol) was added and the mixture was stirred at 50° C. for 5 h. The solvent was removed under reduced pressure and the residue was purified by CC (DCM/MeOH/NH₄OH 1000:25:2) to afford the title intermediate as brown oil (5.56 g, 86%).

MS (ESI, m/z): 328.4 [M+H⁺].

149.ii) (RS)-5-[2-(tert-Butyl-dimethyl-silanyloxy)-ethyl]-3-(3-fluoro-4-methyl-phenyl)-oxazolidin-2-one According to procedure B and starting from intermediate 149.i) the title intermediate was isolated as off-white solid (1.22 g, 45%).

MS (ESI, m/z): 354.2 [M+H⁺].

149.iii) (RS)-3-(3-Fluoro-4-methyl-phenyl)-5-(2-hydroxy-ethyl)-oxazolidin-2-one A solution of intermediate 149.ii) (1.20 g, 3.40 mmol) in THF (8 mL) was treated with TBAF solution (1M in THF, 1 eq.). The solution was stirred at 0° C. for 2 h, after which water and EA were added. The aq. phase was extracted with EA. The combined org. layers were washed with brine, dried over MgSO$_4$, filtered and concentrated under reduced pressure. The residue was triturated with EA-DCM-MeOH-ether to afford the title intermediate as colorless solid (478 mg, 59%).

MS (ESI, m/z): 240.1.1 [M+H$^+$].

149.iv) (RS)-Methanesulfonic acid 2-[3-(3-fluoro-4-methyl-phenyl)-2-oxo-oxazolidin-5-yl]-ethyl ester MsCl (0.19 mL, 2.4 mmol) was added dropwise to a ice cooled solution of intermediate 149.iii) (470 mg, 2.0 mmol) in anhydrous DCM (12 mL) and DIPEA (0.93 mL, 5.6 mmol). The resulting mixture was stirred at 0° C. for 1 h. Water was added and the mixture was extracted with DCM and the combined org. layers were washed with water. The yellow residue was purified by CC (DCM/MeOH/NH$_4$OH 1000:50:4) to afford the title intermediate as beige solid (600 mg, 96%).

MS (ESI, m/z): 318.2 [M+H$^+$].

149.v) (RS)-3-(3-Fluoro-4-methyl-phenyl)-5-(2-[1-(6-methoxy-[1,5]naphthyridin-4-yl)-azetidin-3-ylmethyl]-amino}-ethyl)-oxazolidin-2-one According to procedure H and starting from intermediate 1.0 and intermediate 149.iv), the title compound was isolated as off-white solid (34 mg, 18%).

$^1$H NMR (CDCl$_3$) δ: 8.30 (d, J=5.3 Hz, 1H), 8.12 (d, J=9.1 Hz, 1H), 7.33 (dd, J=2.3, 12.0, 1.2 Hz, 1H), 7.13 (m, 2H), 7.01 (d, J=9.1 Hz, 2H), 6.21 (d, J=5.3 Hz, 1H), 4.79 (m, 1H), 4.60 (m, 2H), 4.18 (m, 2H), 4.07 (t, J=8.8 Hz, 1H), 3.98 (m, 3H), 3.68 (m, 1H), 3.48 (m, 3H), 2.92 (m, 3H), 2.24 (m, 2H), 1.99 (m, 2H).

MS (ESI, m/z): 466.2 [M+H$^+$].

Example 150

6-[(R)-5-({[1-(6-Methoxy-[1,5]naphthyridin-4-yl)-azetidin-3-yl]-methyl-amino}-methyl)-2-oxo-oxazolidin-3-yl]-4H-pyrido[3,2-b][1,4]oxazin-3-one

150.i) ((S)-2-Hydroxy-3-[1-(6-methoxy-[1,5]naphthyridin-4-yl)-azetidin-3-yl]-methyl-amino}-propyl)-carbamic acid benzyl ester According to procedure A and starting from intermediate 133.v) and (S)-oxiranylmethyl-carbamic acid benzyl ester (commercial), the title compound was isolated as yellow oil (1.06 g, 53%).

MS (ESI, m/z): 452.3 [M+H$^+$].

150.ii) (S)-5-({[1-(6-Methoxy-[1,5]naphthyridin-4-yl)-azetidin-3-yl]-methyl-amino}-methyl)-oxazolidin-2-one NaH (55% in mineral oil, 113 mg, 2.35 mmol) was added to a solution of intermediate 150.ii) (1.06 g, 2.35 mmol) in DMF (12 mL) and the mixture was stirred at rt for 2 h. Water was added and the mixture was extracted with EA. The combined org. phases were washed with water and brine, dried over MgSO$_4$ and concentrated. The residue was purified by CC (DCM/MeOH/NH$_4$OH 1000:50:4) to afford the title intermediate as yellow foam (0.25 g, 31%).

MS (ESI, m/z): 344.6 [M+H$^+$].

150.iii) 6-[(R)-5-({[1-(6-Methoxy-[1,5]naphthyridin-4-yl)-azetidin-3-yl]-methyl-amino}-methyl)-2-oxo-oxazolidin-3-yl]-4H-pyrido[3,2-b][1,4]oxazin-3-one According to procedure L and starting from intermediate 150.ii) and 6-bromo-4H-benzo[1,4]oxazin-3-one (prepared according to WO2007118130), the title compound was isolated as pale yellow solid (21 mg, 29%).

$^1$H NMR (DMSO-d6) δ: 11.18 (s, 1H), 8.25 (d, J=5.0 Hz, 1H), 8.01 (d, J=9.1 Hz, 1H), 7.58 (m, 1H), 7.40 (d, J=8.8 Hz, 1H), 7.08 (d, J=9.1 Hz, 1H), 6.33 (d, J=5.3 Hz, 1H), 4.84 (m, 1H), 4.57 (s, 2H), 4.15 (m, 2H), 3.87 (m, 3H), 3.55 (s, 2H), 3.28 (s, 3H), 2.70 (m, 2H), 2.26 (s, 3H).

MS (ESI, m/z): 492.1 [M+H$^+$].

Example 151

6-{(R)-5-[(1S,4S)-5-(6-Methoxy-[1,5]naphthyridin-4-yl)-2,5-diaza-bicyclo[2.2.1]hept-2-ylmethyl]-2-oxo-oxazolidin-3-yl}-4H-benzo[1,4]oxazin-3-one

151.i) (1S,4S)-546-Methoxy-[1,5]naphthyridin-4-yl)-2,5-diaza-bicyclo[2.2.1]heptane-2-carboxylic acid tert-butyl ester According to procedure F and starting from 8-bromo-2-methoxy-[1,5]naphthyridine (commercial) and (1S,4S)-2,5-diaza-bicyclo[2.2.1]heptane-2-carboxylic acid tert-butyl ester (commercial), the desired intermediate was isolated as brown oil (0.46 g, 62%).

MS (ESI, m/z): 357.2 [M+H$^+$].

151.ii) 8-(1S,4S)-2,5-Diaza-bicyclo[2.2.1]hept-2-yl-2-methoxy-[1,5]naphthyridine According to procedure E and starting from intermediate 151.i) the desired intermediate was isolated as brown oil (309 mg, 93%).

MS (ESI, m/z): 257.4 [M+H$^+$].

151.iii) 6-{(R)-5-[(1S,4S)-5-(6-Methoxy-[1,5]-naphthyridin-4-yl)-2,5-diaza-bicyclo[2.2.1]hept-2-ylmethyl]-2-oxo-oxazolidin-3-yl}-4H-benzo[1,4]oxazin-3-one According to procedure H and starting from intermediate 151.0 and intermediate 45.vi), the title compound was isolated as yellow foam (16 mg, 14%).

$^1$H NMR (CDCl$_3$) δ: 8.37 (s, 1H), 8.32 (d, J=5.6 Hz, 1H), 8.14 (d, J=9.1 Hz, 1H), 7.42 (d, J=2.3 Hz, 1H), 7.03 (d, J=9.1 Hz, 1H), 6.91 (m, 1H), 6.78 (dd, J=8.8, 2.6 Hz, 1H), 6.41 (d, J=5.6 Hz, 1H), 4.66 (m, 1H), 4.57 (m, 2H), 3.85 (m, 9H), 3.16 (dd, J=9.4, 2.1 Hz, 1H), 3.03 (m, 2H), 2.85 (dd, J=13.5, 4.7 Hz, 1H), 1.98 (m, 2H).

MS (ESI, m/z): 503.5 [M+H$^+$].

Example 152

6-{(R)-5-[(1S,4S)-5-(6-Methoxy-[1,5]naphthyridin-4-yl)-2,5-diaza-bicyclo[2.2.1]hept-2-ylmethyl]-2-oxo-oxazolidin-3-yl}-4H-benzo[1,4]thiazin-3-one According to procedure I and starting from intermediate 151.0 and intermediate 48.v), the title compound was isolated as yellow foam (37 mg, 35%).
$^1$H NMR (CDCl$_3$) δ: 8.45 (s, 1H), 8.32 (d, J=5.6 Hz, 1H), 8.11 (d, J=8.8 Hz, 1H), 7.39 (d, J=2.3 Hz, 1H), 7.24 (m, 1H), 7.03 (d, J=9.1 Hz, 1H), 6.93 (dd, J=8.5, 2.3 Hz, 1H), 6.40 (d, J=5.6 Hz, 1H), 4.67 (dd, J=4.7, 4.7, 1.8, 1.2 Hz, 1H), 3.92 (m, 7H), 3.70 (s, 2H), 3.39 (s, 2H), 3.15 (m, 1H), 3.02 (m, 2H), 2.85 (m, 1H), 1.97 (s, 2H).
MS (ESI, m/z): 519.5 [M+H$^+$].

Example 153

(R)-3-(6,7-Dihydro-[1,4]dioxino[2,3-c]pyridazin-3-yl)-5-({[1-(6-methoxy-[1,5]naphthyridin-4-yl)-azetidin-3-yl]-methyl-amino}-methyl)-oxazolidin-2-one According to procedure L and starting from intermediate 150.0 and 3-chloro-6,7-dihydro-[1,4]dioxino[2,3-c]pyridazine (commercial), the title compound was isolated as yellow foam (10 mg, 24%).
$^1$H NMR (CDCl$_3$) δ: 8.32 (d, J=5.3 Hz, 1H), 8.14 (d, J=9.1 Hz, 1H), 8.00 (s, 1H), 7.02 (d, J=9.1 Hz, 1H), 6.26 (d, J=5.3 Hz, 1H), 4.83 (m, 1H), 4.46 (m, 8H), 4.09 (dd, J=10.8, 7.6 Hz, 1H), 3.97 (m, 3H), 3.67 (m, 2H), 2.81 (m, 2H), 2.42 (s, 3H).
MS (ESI, m/z): 480.4 [M+H$^+$].

Example 154

(R)-3-(3-Fluoro-4-methyl-phenyl)-5-({[1-(6-methoxy-[1,5]naphthyridin-4-yl)-azetidin-3-ylmethyl]-amino}-methyl)-oxazolidin-2-one According to procedure I and starting from intermediate 1.ii) and intermediate 46.iii), the title compound was isolated as yellow foam (36 mg, 28%).
$^1$H NMR (CDCl$_3$) δ: 8.30 (d, J=5.3 Hz, 1H), 8.03 (d, J=9.1 Hz, 1H), 7.34 (dd, J=12.6, 2.3 Hz, 1H), 7.11 (m, 2H), 6.97 (d, J=9.1 Hz, 1H), 6.17 (d, J=5.3 Hz, 1H), 4.75 (m, 1H), 4.53 (m, 2H), 4.12 (m, 2H), 3.99 (t, J=8.5 Hz, 1H), 3.94 (s, 3H), 3.82 (dd, J=8.5, 6.7 Hz, 1H), 3.07 (d, J=3.8 Hz, 1H), 3.00 (m, 4H), 2.89 (m, 3H).
MS (ESI, m/z): 452.2 [M+H$^+$].

Example 155

7-Fluoro-6-((R)-5-{[1-(3-fluoro-6-methoxy-[1,5]naphthyridin-4-yl)-azetidin-3-ylamino]-methyl}-2-oxo-oxazolidin-3-yl)-4H-benzo[1,4]thiazin-3-one

155.i) 6-(3-Chloro-2-hydroxy-propylamino)-7-fluoro-4H-benzo[1,4]thiazin-3-one A solution of 6-amino-7-fluoro-4H-benzo[1,4]thiazin-3-one (1 g, 5 mmol, Bioscience, Biotechnology, and Biochemistry 1994, 58, 788) and (S)-epichlorohydrin (0.467 g, 5 mmol) in EtOH/H$_2$O (9:1, 20 mL) was heated at 80° C. for 3 d. The volatiles were removed under reduced pressure and the residue was crystallized from MeOH to give a brown solid (0.83 g, 57%).
MS (ESI, m/z): 291.2 [M+H$^+$].

155.i). 6-(5-Chloromethyl-2-oxo-oxazolidin-3-yl)-7-fluoro-4H-benzo[1,4]thiazin-3-one A solution of intermediate 155.i) (0.83 g, 2 mmol) in THF (20 mL) was treated with CDI (0.39 g, 1.2 eq). The mixture was heated at 50° C. for 3 d, NaH (0.03 g) was added and the mixture stirred at 50° C. for 1 h. The mixture was partitioned between EA and water. The organic phase was washed with water and brine, dried over MgSO$_4$ and concentrated. The residue was purified by CC (EA/MeOH 19:1, 9:1) to give the title intermediate (0.38 g, 60% yield).
MS (ESI, m/z): 317.1 [M+H$^+$].

155.iii) 6-(5-Iodomethyl-2-oxo-oxazolidin-3-yl)-7-fluoro-4H-benzo[1,4]thiazin-3-one A hot saturated solution of intermediate 155.ii) (0.38 g, 1.2 mmol) in 2-butanone (3 mL) was treated with NaI (0.36 g, 2 eq). The mixture was heated at reflux for 2 d. The resulting suspension was poured on water and the precipitate filtered off and purified by CC (EA, EA/MeOH 19:1) to give the desired intermediate (0.38 g, 80% yield) as a beige solid.
MS (ESI, m/z): 409.1 [M+H$^+$].

155.iv) 7-Fluoro-6-((R)-5-{[1-(3-fluoro-6-methoxy-[1,5]naphthyridin-4-yl)-azetidin-3-ylamino]-methyl}-2-oxo-oxazolidin-3-yl)-4H-benzo[1,4]thiazin-3-one Intermediate 155.iii) (0.115 g, 0.28 mmol) and intermediate 45.ii) (0.07 g, 0.28 mmol) were coupled according to procedure I. The title product was isolated after CC (EA/MeOH 19:1, 9:1) as a beige solid (0.03 g, 20% yield).
MS (ESI, m/z): 529.1 [M+H$^+$].

Example 156

6-((R)-5-{[1-(6-Methoxy-quinolin-4-yl)-azetidin-3-ylamino]-methyl}-2-oxo-oxazolidin-3-yl)-4H-benzo[1,4]oxazin-3-one According to procedure H and starting from intermediate 49.0 and intermediate 45.vi) the title compound was isolated as a beige solid (21 mg, 10%).
$^1$H NMR (DMSO-d6) δ: 10.70 (s, 1H), 8.29 (d, J=5.3 Hz, 1H), 8.15 (s, 1H), 7.74 (d, J=9.1 Hz, 1H), 7.27 (m, 2H), 6.93 (m, 2H), 6.27 (d, J=5.3 Hz, 1H), 4.68 (m, 1H), 4.52 (m, 4H), 4.05-3.75 (m, 8H), 2.87 (d, J=5.3 Hz, 2H). (ESI, m/z): 476.1 [M+H$^+$].

Example 157

6-((R)-5-{[1-(3-Methoxy-quinolin-5-yl)-azetidin-3-ylamino]-methyl}-2-oxo-oxazolidin-3-yl)-4H-benzo[1,4]thiazin-3-one

157.i) 1-(3-Methoxy-quinolin-5-yl)-azetidin-3-ylamine

Starting from 5-bromo-3-methoxyquinoline (WO 2007/107965) and azetidin-3-yl-carbamic acid benzyl ester (commercial) the title compound was prepared according to procedure L followed by procedure G and was isolated as a pale yellow solid (122 mg, 63% over two steps).
MS (ESI, m/z): 230.3 [M+H$^+$].

157.ii) 6-((R)-5-{[1-(3-Methoxy-quinolin-5-yl)-azetidin-3-ylamino]-methyl}-2-oxo-oxazolidin-3-yl)-4H-benzo[1,4]thiazin-3-one According to procedure I and starting from intermediate 157.i) and intermediate 48.v) the title compound was isolated as a pale yellow solid (20 mg, 16%).
$^1$H NMR (CDCl$_3$) δ: 8.93 (br. s, 1H), 8.63 (m, 1H), 7.57 (m, 1H), 7.43 (m, 3H), 7.21 (d, J=8.5 Hz, 1H), 6.83 (dd, J=8.8, 2.3 Hz, 1H), 6.59 (d, J=7.6 Hz, 1H), 4.70 (m, 1H), 4.34 (m, 2H), 3.84 (m, 8H), 3.32 (s, 2H), 3.04 (m, 1H), 2.89 (dd, J=12.9, 5.6 Hz, 1H), 1.87 (m, 1H).
MS (ESI, m/z): 492.0 [M+H$^+$].

Example 158

6-((R)-5-{[1-(2-Methoxy-quinolin-8-yl)-azetidin-3-ylamino]-methyl}-2-oxo-oxazolidin-3-yl)-4H-benzo[1,4]thiazin-3-one 158.i) 6-[(R)-5-(Azetidin-3-ylaminomethyl)-2-oxo-oxazolidin-3-yl]-4H-benzo[1,4]thiazin-3-one Starting from 3-amino-azetidine-1-carboxylic acid tert-butyl ester (commercial) and intermediate 48.v) the title compound was prepared according to procedure I followed by procedure E and was isolated as a pale yellow solid (980 mg, 25% over two steps).
MS (ESI, m/z): 335.1 [M+H$^+$].

158.ii) 6-((R)-5-{[1-(2-Methoxy-quinolin-8-yl)-azetidin-3-ylamino]-methyl}-2-oxo-oxazolidin-3-yl)-4H-benzo[1,4]thiazin-3-one According to procedure L and starting from intermediate 158.i) and 8-bromo-2-methoxyquinoline (WO 2007/081597) the title compound was isolated as a pale yellow solid (43 mg, 23%).
$^1$H NMR (CDCl$_3$) δ: 8.32 (s, 1H), 7.90 (d, J=8.8 Hz, 1H), 7.45 (d, J=2.3 Hz, 1H), 7.23 (m, 2H), 7.12 (m, 1H), 6.91 (dd, J=8.5, 2.3 Hz, 1H), 6.84 (d, J=8.8 Hz, 1H), 6.55 (dd, J=7.6, 1.5 Hz, 1H), 4.76 (m, 1H), 4.58 (m, 2H), 3.94 (m, 8H), 3.37 (s, 2H), 3.08 (m, 1H), 2.96 (m, 1H), 1.78 (m, 1H). (ESI, m/z): 492.1 [M+H$^+$].

Example 159

6-((R)-5-{[1-(7-Fluoro-2-methoxy-quinolin-8-yl)-azetidin-3-ylamino]-methyl}-2-oxo-oxazolidin-3-yl)-4H-benzo[1,4]thiazin-3-one According to procedure L and starting from intermediate 158.i) and 8-bromo-7-fluoro-2-methoxyquinoline (WO 2008/003690) the title compound was isolated as a colorless solid (33 mg, 16%).
MS (ESI, m/z): 510.1 [M+H$^+$].

Example 160

6-((R)-5-{[1-(6-Fluoro-quinolin-4-yl)-azetidin-3-ylamino]-methyl}-2-oxo-oxazolidin-3-yl)-4H-benzo[1,4]thiazin-3-one According to procedure F and starting from intermediate 158.i) and 4-bromo-6-fluoroquinoline (commercial) the title compound was isolated as a dark orange solid (26 mg, 9%).
$^1$H NMR (CDCl$_3$) δ: 8.20 (s, 1H), 7.84 (d, J=9.1 Hz, 1H), 7.44 (d, J=2.3 Hz, 1H), 7.26 (m, 1H), 7.03 (m, 2H), 6.92 (dd, J=8.5, 2.3 Hz, 1H), 6.77 (d, J=8.8 Hz, 1H), 4.79 (m, 3H), 4.22 (m, 2H), 4.05 (m, 1H), 3.98 (s, 3H), 3.90 (dd, J=8.5, 7.0 Hz, 1H), 3.76 (m, 1H), 3.38 (s, 2H), 3.06 (m, 1H), 2.94 (dd, J=12.9, 5.6 Hz, 1H), 1.74 (br. s, 1H).
MS (ESI, m/z): 480.1 [M+H$^+$].

Example 161

4-(3-{[(R)-2-oxo-3-(3-oxo-3,4-dihydro-2H-benzo[1,4]thiazin-6-yl)-oxazolidin-5-ylmethyl]amino}-azetidin-1-yl)-quinoline-6-carbonitrile According to procedure F and starting from intermediate 158.i) and 4-bromo-6-cyanoquinoline (commercial) the title compound was isolated as a dark orange solid (63 mg, 22%).
MS (ESI, m/z): 487.4 [M+H$^+$].

Example 162

6-[(R)-5-({[1-(2-Methoxy-quinolin-8-yl)-azetidin-3-ylmethyl]-amino}-methyl)-2-oxo-oxazolidin-3-yl]-4H-benzo[1,4]thiazin-3-one 162.i) 6-((R)-5-{[(Azetidin-3-ylmethyl)-amino]-methyl}-2-oxo-oxazolidin-3-yl)-4H-benzo[1,4]thiazin-3-one Starting from 3-aminomethyl-azetidine-1-carboxylic acid tert-butyl ester (commercial) and intermediate 48.v) the title compound was prepared according to procedure I followed by procedure E and was isolated as a dark orange solid (338 mg, 20% over two steps).
MS (ESI, m/z): 349.1 [M+H$^+$].

162.ii) 6-[(R)-5-({[1-(2-Methoxy-quinolin-8-yl)-azetidin-3-ylmethyl]-amino}-methyl)-2-oxo-oxazolidin-3-yl]-4H-benzo[1,4]thiazin-3-one According to procedure L and starting from intermediate 162.0 and 8-bromo-2-methoxyquinoline (WO 2007/081597) the title compound was isolated as a yellow solid (5 mg, 3%).
MS (ESI, m/z): 506.3 [M+H$^+$].

Example 163

6-[(R)-5-({[1-(3-Methoxy-quinolin-5-yl)-azetidin-3-ylmethyl]-amino}-methyl)-2-oxo-oxazolidin-3-yl]-4H-benzo[1,4]thiazin-3-one According to procedure L and starting from intermediate 162.0 and 5-bromo-3-methoxyquinoline (WO 2007/107965) the title compound was isolated as a yellow solid (13 mg, 8%).
MS (ESI, m/z): 506.2 [M+H$^+$].

Example 164

6-((S)-5-{[(S)-1-(3-Fluoro-6-methoxy-[1,5]naphthyridin-4-yl)-pyrrolidin-3-ylamino]methyl}-2-oxo-oxazolidin-3-yl)-4H-benzo[1,4]thiazin-3-one According to procedure I and starting from intermediate 64.ii) and the enantiomeric antipode of intermediate 48.v) the title compound was isolated as a pale yellow solid (59 mg, 42%).
MS (ESI, m/z): 525.0 [M+H$^+$].

Example 165

6-((S)-5-{[1-(6-Methoxy-[1,5]naphthyridin-4-yl)-piperidin-4-ylamino]-methyl}-2-oxo-oxazolidin-3-yl)-4H-benzo[1,4]thiazin-3-one According to procedure I and starting from intermediate 119.ii) and the enantiomeric antipode of intermediate 48.v) the title compound was isolated as a pale yellow solid (43 mg, 31%).

MS (ESI, m/z): 521.3 [M+H$^+$].

Example 166

6-{(S)-5-[4-(6-Methoxy-[1,5]naphthyridin-4-yl)-[1,4]diazepan-1-ylmethyl]-2-oxo-oxazolidin-3-yl}-4H-benzo[1,4]thiazin-3-one According to procedure I and starting from intermediate 105.ii) and the enantiomeric antipode of intermediate 48.v) the title compound was isolated as a pale yellow solid (69 mg, 50%).

MS (ESI, m/z): 521.3 [M+H$^+$].

Example 167

6-[(R)-5-({[(R)-1-(6-Methoxy-[1,5]naphthyridin-4-yl)-pyrrolidin-3-ylmethyl]amino}-methyl)-2-oxo-oxazolidin-3-yl]-4H-benzo[1,4]oxazin-3-one 167.i) [(R)-1-(6-Methoxy-[1,5]naphthyridin-4-yl)-pyrrolidin-3-yl]-methylamine Starting from (S)-pyrrolidin-3-ylmethyl-carbamic acid tert-butyl ester (commercial) and trifluoromethanesulfonic acid 6-methoxy-[1,5]naphthyridin-4-yl ester (WO 2002/008224) the title compound was prepared according to procedure F followed by procedure E and was isolated as a yellow oil (399 mg, 32% over two steps).

MS (ESI, m/z): 259.5 [M+H$^+$].

167.ii) 6-[(R)-5-({[(R)-1-(6-Methoxy-[1,5]naphthyridin-4-yl)-pyrrolidin-3-ylmethyl]-amino}-methyl)-2-oxo-oxazolidin-3-yl]-4H-benzo[1,4]oxazin-3-one According to procedure H and starting from intermediate 167.i) and intermediate 45. vi) the title compound was isolated as a pale yellow solid (50 mg, 26%).

MS (ESI, m/z): 505.4 [M+H$^+$].

Example 168

6-[(R)-5-({[(S)-1-(6-Methoxy-[1,5]naphthyridin-4-yl)-pyrrolidin-3-ylmethyl]-amino}-methyl)-2-oxo-oxazolidin-3-yl]-4H-benzo[1,4]oxazin-3-one According to procedure H and starting from the enantiomeric antipode of intermediate 167.i) and intermediate 45.vi) the title compound was isolated as an off-white solid (41 mg, 21%).

MS (ESI, m/z): 505.4 [M+H$^+$].

Example 169

(R)-5-{[(S)-1-(3-Fluoro-6-methoxy-[1,5]naphthyridin-4-yl)-pyrrolidin-3-ylamino]-methyl}-3-(4-methoxy-phenyl)-oxazolidin-2-one 169.i) (S)-5-Hydroxymethyl-3-(4-methoxy-phenyl)-oxazolidin-2-one Starting from (4-methoxy-phenyl)-carbamic acid benzyl ester (prepared from 4-methoxy-aniline and CbzCl according to procedure C) and (S)-glycidyl butyrate and following the procedure described for the preparation of intermediate 1.iii), the title compound was obtained as a grey solid (469 mg, 54%).

MS (ESI, m/z): 224.2 [M+H$^+$].

169.ii) Methanesulfonic acid (S)-3-(4-methoxy-phenyl)-2-oxo-oxazolidin-5-ylmethyl ester A solution of intermediate 169.i) (460 mg, 2.06 mmol) in anhydrous DCM (8 mL) and DIPEA (0.42 mL, 2.47 mmol) was cooled to 0° C. and Ms-Cl (0.18 mL, 2.27 mmol) was added dropwise. The resulting mixture was stirred at 0° C. for 1 h. Water was added and the mixture was extracted with DCM and the combined org. layers were washed with water. The yellow residue was triturated with EA/ether to afford the title intermediate as a grey solid (426 mg, 69%).

MS (ESI, m/z): 301.8 [M+H$^+$].

169.iii) (R)-5-{[(S)-1-(3-Fluoro-6-methoxy-[1,5]naphthyridin-4-yl)-pyrrolidin-3-ylamino]-methyl}-3-(4-methoxy-phenyl)-oxazolidin-2-one According to procedure H and starting from 169.ii) and intermediate 64.ii) the title compound was isolated as a pale yellow solid (56 mg, 42%).

MS (ESI, m/z): 468.1 [M+H$^+$].

Example 170

(R)-3-(4-Ethoxy-phenyl)-5-{[(S)-1-(3-fluoro-6-methoxy-[1,5]naphthyridin-4-yl)-pyrrolidin-3-ylamino]-methyl}-oxazolidin-2-one 170.i) Methanesulfonic acid (S)-3-(4-ethoxy-phenyl)-2-oxo-oxazolidin-5-ylmethyl ester According to the preparation of intermediate 169.ii) and starting the synthetic sequence with (4-ethoxy-phenyl)-carbamic acid benzyl ester (prepared from 4-ethoxy-aniline and CbzCl according to procedure C) the title intermediate was obtained as a grey solid (489 mg, 78%).

MS (ESI, m/z): 316.0 [M+H$^+$].

170.ii) (R)-3-(4-Ethoxy-phenyl)-5-{[(S)-1-(3-fluoro-6-methoxy-[1,5]-naphthyridin-4-yl)-pyrrolidin-3-ylamino]-methyl}-oxazolidin-2-one According to procedure H and starting from 170.i) and intermediate 64.0 the title compound was isolated as a pale yellow solid (62 mg, 45%).

MS (ESI, m/z): 482.3 [M+H$^+$].

Example 171

(R)-3-(4-Difluoromethoxy-phenyl)-5-{[(S)-1-(3-fluoro-6-methoxy-[1,5]naphthyridin-4-yl)-pyrrolidin-3-ylamino]-methyl}-oxazolidin-2-one 171.i) Methanesulfonic acid (S)-3-(4-difluoromethoxy-phenyl)-2-oxo-oxazolidin-5-ylmethyl ester According to the preparation of intermediate 169.ii) and starting the synthetic sequence with (4-difluoromethoxy-phenyl)-carbamic acid benzyl ester (prepared from 4-difluoromethoxy-aniline and CbzCl according to procedure C) the title intermediate was obtained as a yellow solid (293 mg, 68%).
MS (ESI, m/z): 338.3 [M+H$^+$].

171.ii) (R)-3-(4-Difluoromethoxy-phenyl)-5-{[(S)-1-(3-fluoro-6-methoxy-[1,5]-naphthyridin-4-yl)-pyrrolidin-3-ylamino]-methyl}-oxazolidin-2-one According to procedure H and starting from 171.i) and intermediate 64.ii) the title compound was isolated as a pale yellow solid (23 mg, 16%).
MS (ESI, m/z): 504.4 [M+H$^+$].

Example 172

6-((R)-5-{[(S)-1-(6-Methoxy-quinolin-4-yl)-pyrrolidin-3-ylamino]-methyl}-2-oxo-oxazolidin-3-yl)-4H-benzo[1,4]thiazin-3-one 172.i) (S)-1-(6-Methoxy-quinolin-4-yl)-pyrrolidin-3-ylamine Starting from (S)-pyrrolidin-3-yl-carbamic acid tert-butyl ester (commercial) and 4-bromo-6-methoxy-quinoline (commercial) the title compound was prepared according to procedure F followed by procedure E and was isolated as a brown oil (801 mg, 78% over two steps).
MS (ESI, m/z): 244.4 [M+H$^+$].

172.ii) 6-((R)-5-{[(S)-1-(6-Methoxy-quinolin-4-yl)-pyrrolidin-3-ylamino]-methyl}-2-oxo-oxazolidin-3-yl)-4H-benzo[1,4]thiazin-3-one According to procedure I and starting from intermediate 172.i) and intermediate 48.v) the title compound was isolated as a dark yellow solid (36 mg, 22%).
MS (ESI, m/z): 506.0 [M+H$^+$].

Example 173

6-[(R)-5-({[(S)-1-(6-Methoxy-quinolin-4-yl)-pyrrolidin-3-ylmethyl]-amino}-methyl)-2-oxo-oxazolidin-3-yl]-4H-benzo[1,4]thiazin-3-one 173.i) [(S)-1-(6-Methoxy-quinolin-4-yl)-pyrrolidin-3-yl]-methylamine Starting from (S)-pyrrolidin-3-ylmethyl-carbamic acid tert-butyl ester (commercial) and 4-bromo-6-methoxy-quinoline (commercial) the title compound was prepared according to procedure F followed by procedure E and was isolated as a yellow solid (730 mg, 69% over two steps).
MS (ESI, m/z): 258.4 [M+H$^+$].

173.ii) 6-[(R)-5-({[(S)-1-(6-Methoxy-quinolin-4-yl)-pyrrolidin-3-ylmethyl]-amino}-methyl)-2-oxo-oxazolidin-3-yl]-4H-benzo[1,4]thiazin-3-one According to procedure I and starting from intermediate 173.i) and intermediate 48.v) the title compound was isolated as a dark yellow solid (7 mg, 12%).
MS (ESI, m/z): 520.4 [M+H$^+$].

Example 174

(R)-5-{[1-(6-Methoxy-[1,5]naphthyridin-4-yl)-azetidin-3-ylamino]-methyl}-3-(4-methoxy-phenyl)-oxazolidin-2-one According to procedure H and starting from 169.ii) and intermediate 50.0 the title compound was isolated as a pale yellow solid (43 mg, 33%).
MS (ESI, m/z): 436.2 [M+H$^+$].

Example 175

(R)-3-(4-Ethoxy-phenyl)-5-{[1-(6-methoxy-[1,5]naphthyridin-4-yl)-azetidin-3-ylamino]-methyl}-oxazolidin-2-one According to procedure H and starting from 170.i) and intermediate 50.0 the title compound was isolated as a colorless solid (30 mg, 22%).
MS (ESI, m/z): 450.2 [M+H$^+$].

Example 176

(R)-3-(4-Difluoromethoxy-phenyl)-5-{[1-(6-methoxy-[1,5]naphthyridin-4-yl)-azetidin-3-ylamino]-methyl}-oxazolidin-2-one According to procedure H and starting from 171i) and intermediate 50.0 the title compound was isolated as a colorless solid (22 mg, 18%).
MS (ESI, m/z): 472.4 [M+H$^+$].

Example 177

6-((R)-5-{[(R)-1-(6-Fluoro-quinolin-4-yl)-pyrrolidin-3-ylamino]-methyl}-2-oxo-oxazolidin-3-yl)-4H-benzo[1,4]thiazin-3-one 177.i) (R)-1-(6-Fluoro-quinolin-4-yl)-pyrrolidin-3-ylamine Starting from 4-bromo-6-fluoroquinoline (commercial) and (R)-pyrrolidin-3-yl-carbamic acid tert-butyl ester (commercial) the title compound was prepared according to procedure F followed by procedure E and was isolated as a yellow solid (212 mg, 43% over two steps).
MS (ESI, m/z): 232.4 [M+H$^+$].

177.ii) 6-((R)-5-{[(R)-1-(6-Fluoro-quinolin-4-yl)-pyrrolidin-3-ylamino]-methyl}-2-oxo-oxazolidin-3-yl)-4H-benzo[1,4]thiazin-3-one According to procedure I and starting from intermediate 177.i) and intermediate 48.v) the title compound was isolated as a yellow solid (2 mg, 1%).
MS (ESI, m/z): 494.1 [M+H$^+$].

Example 178

4-((R)-3-{[(R)-2-oxo-3-(3-oxo-3,4-dihydro-2H-benzo[1,4]thiazin-6-yl)-oxazolidin-5-ylmethyl]-amino}-pyrrolidin-1-yl)-quinoline-6-carbonitrile 178.i) 4-((R)-3-Amino-pyrrolidin-1-yl)-quinoline-6-carbonitrile Starting from 4-bromo-6-cyanoquinoline (commercial) and (R)-pyrrolidin-3-yl-carbamic acid tert-butyl ester (commercial) the title compound was prepared according to procedure F followed by procedure E and was isolated as a yellow solid (330 mg, 65% over two steps).
MS (ESI, m/z): 239.1 [M+H$^+$].

178.ii) 4-((R)-3-{[(R)-2-oxo-3-(3-oxo-3,4-dihydro-2H-benzo[1,4]thiazin-6-yl)-oxazolidin-5-ylmethyl]-amino}-pyrrolidin-1-yl)-quinoline-6-carbonitrile According to procedure I and starting from intermediate 178.i) and intermediate 48.v) the title compound was isolated as a yellow solid (21 mg, 12%).
MS (ESI, m/z): 501.3 [M+H$^+$].

Example 179

6-((R)-5-{[1-(6-Fluoro-quinolin-4-yl)-piperidin-4-ylamino]-methyl}-2-oxo-oxazolidin-3-yl)-4H-benzo[1,4]thiazin-3-one 179.i) 1-(6-Fluoro-quinolin-4-yl)-piperidin-4-ylamine Starting from 4-bromo-6-fluoroquinoline (commercial) and piperidin-4-yl-carbamic acid tert-butyl ester (commercial) the title compound was prepared according to procedure F followed by procedure E and was isolated as a yellow solid (223 mg, 40% over two steps).
MS (ESI, m/z): 246.5 [M+H$^+$].

179.ii) 6-((R)-5-{[1-(6-Fluoro-quinolin-4-yl)-piperidin-4-ylamino]-methyl}-2-oxo-oxazolidin-3-yl)-4H-benzo[1,4]thiazin-3-one According to procedure I and starting from intermediate 179.i) and intermediate 48.v) the title compound was isolated as a yellow solid (15 mg, 9%).
MS (ESI, m/z): 508.1 [M+H$^+$].

Example 180

4-(4-{[(R)-2-oxo-3-(3-oxo-3,4-dihydro-2H-benzo[1,4]thiazin-6-yl)-oxazolidin-5-ylmethyl]-amino}-piperidin-1-yl)-quinoline-6-carbonitrile 180.i) 4-(4-Amino-piperidin-1-yl)-quinoline-6-carbonitrile Starting from 4-bromo-6-cyanoquinoline (commercial) and piperidin-4-yl-carbamic acid tert-butyl ester (commercial) the title compound was prepared according to procedure F followed by procedure E and was isolated as a yellow solid (382 mg, 69% over two steps).
MS (ESI, m/z): 253.0 [M+H$^+$].

180.ii) 4-(4-{[(R)-2-Oxo-3-(3-oxo-3,4-dihydro-2H-benzo[1,4]thiazin-6-yl)-oxazolidin-5-ylmethyl]-amino}-piperidin-1-yl)-quinoline-6-carbonitrile According to procedure I and starting from intermediate 180.i) and intermediate 48.v) the title compound was isolated as a yellow solid (16 mg, 9%).
MS (ESI, m/z): 515.4 [M+H$^+$].

Example 181

6-((R)-5-{[(3S,4S)-4-Methoxy-1-(6-methoxy-[1,5]naphthyridin-4-yl)-pyrrolidin-3-ylamino]-methyl}-2-oxo-oxazolidin-3-yl)-4H-benzo[1,4]oxazin-3-one 181.i) (3S,4S)-4-Azido-pyrrolidin-3-ol A solution of (3S,4S)-1-(3-azido-4-trimethylsilanyloxy-pyrrolidin-1-yl)-2,2,2-trifluoro-ethanone (5.8 g, 19.57 mmol, prepared according to J. Org. Chem. 1997, 62, 4197) in MeOH (200 mL) was treated with K$_2$CO$_3$ (2.7 g, 1 eq) and the mixture stirred at rt for 4 h. concentrated in vacuo and purified by CC (DCM/MeOH 4:1+1% NH$_4$OH) to give the title intermediate (2 g, 80% yield) as a brownish oil.
$^1$H NMR (DMSO d6) δ: 4.06 (m, 2H), 3.24 (m, J=12.3, 5.6 Hz, 1H), 3.09 (dd, J=12.0, 5.0 Hz, 1H), 2.92 (dd, J=12.3, 2.6 Hz, 1H), 2.82 (dd, J=12.0, 2.6 Hz, 1H).

181.ii) (3S,4S)-4-Azido-1-(6-methoxy-[1,5]naphthyridin-4-yl)-pyrrolidin-3-ol

8-Bromo-2-methoxy-[1,5]naphthyridine (3.73 g, 15.6 mmol) and intermediate 181.i) (2 g, 15.6 mmol) were coupled according to procedure F. The title intermediate was isolated after CC (EA/MeOH 9:1+1% NH$_4$OH) as a beige solid (0.9 g, 20% yield).
MS (ESI, m/z): 287.2 [M+H$^+$].

181.iii) 8-((3S,4S)-3-Azido-4-methoxy-pyrrolidin-1-yl)-2-methoxy-[1,5]naphthyridine A solution of intermediate 181.ii) (0.9 g, 3.1 mmol) in dry DMF (25 mL) was treated sequentially with NaH dispersion (0.15 g, 1.2 eq, 60% purity) and methyl iodide (0.294 mL, 1.5 eq) and the mixture was stirred at rt for 1 h. The mixture was partitioned between EA and water. The org. phase was washed with water and brine, dried over MgSO$_4$ and concentrated. The title intermediate was isolated after CC (EA/MeOH 9:1) as a yellowish oil (0.5 g, 53% yield).
MS (ESI, m/z): 301.2 [M+H$^+$].

181.iv) (3S,4S)-4-Methoxy-1-(6-methoxy-[1,5]naphthyridin-4-yl)-pyrrolidin-3-ylamine A solution of intermediate 181.iii) (0.5 g, 1.7 mmol) in EtOH was hydrogenated over Pd(OH)$_2$ (0.1 eq) and 1 bar of H$_2$ for 3.5 h. The catalyst was filtered off and the volatiles removed under reduced pressure to yield the title intermediate as a yellow oil (0.37 g, 81% yield).
MS (ESI, m/z): 275.3 [M+H$^+$].

181.v) 6-((R)-5-{[(3S,4S)-4-Methoxy-1-(6-methoxy-[1,5]naphthyridin-4-yl)-pyrrolidin-3-ylamino]-methyl}-2-oxo-oxazolidin-3-yl)-4H-benzo[1,4]oxazin-3-one Intermediate 181.iv) (0.175 g, 0.64 mmol) and intermediate 45.vi) (0.22 g, 1 eq) were coupled according to procedure H. The title compound was isolated after CC (EA/MeOH 9:1+1% NH₄OH) as a yellowish foam (0.025 g, 7.5% yield) MS (ESI, m/z): 521.3 [M+H⁺].

Example 182

6-((R)-5-{[(3S,4S)-4-Methoxy-1-(6-methoxy-[1,5]naphthyridin-4-yl)-pyrrolidin-3-ylamino]-methyl}-2-oxo-oxazolidin-3-yl)-4H-benzo[1,4]thiazin-3-one Intermediate 181.iv) (0.175 g, 0.64 mmol) and intermediate 48.v) (0.25 g, 1 eq) were coupled according to procedure I. The title compound was isolated after CC (EA/MeOH 9:1, 4:1+1% NH₄OH) as a beige foam (0.085 g, 25% yield) MS (ESI, m/z): 537.3 [M+H⁺].

Example 183

(R)-5-{[1-(6-Methoxy-[1,5]naphthyridin-4-yl)-piperidin-4-ylamino]-methyl}-3-(4-methoxy-phenyl)-oxazolidin-2-one According to procedure H and starting from 169.ii) and intermediate 119.ii) the title compound was isolated as a pale yellow solid (40 mg, 30%).
MS (ESI, m/z): 464.3 [M+H⁺].

Example 184

(R)-3-(4-Ethoxy-phenyl)-5-{[1-(6-methoxy-[1,5]naphthyridin-4-yl)-piperidin-4-ylamino]-methyl}-oxazolidin-2-one According to procedure H and starting from 170.i) and intermediate 119.ii) the title compound was isolated as a colorless solid (50 mg, 36%).
MS (ESI, m/z): 477.9 [M+H⁺].

Example 185

(R)-3-(4-Difluoromethoxy-phenyl)-5-{[1-(6-methoxy-[1,5]naphthyridin-4-yl)-piperidin-4-ylamino]-methyl}-oxazolidin-2-one According to procedure H and starting from 171.i) and intermediate 119.ii) the title compound was isolated as a colorless solid (26 mg, 19%).
MS (ESI, m/z): 500.2 [M+H⁺].

Example 186

6-[(R)-5-({[1-(6-Methoxy-quinolin-4-yl)-azetidin-3-ylmethyl]-amino}-methyl)-2-oxo-oxazolidin-3-yl]-4H-benzo[1,4]thiazin-3-one According to procedure F and starting from intermediate 162.i) and 4-chloro-6-methoxy-quinoline (commercial) the title compound was isolated as a pale yellow solid (3 mg, 3%).
MS (ESI, m/z): 506.1 [M+H⁺].

Pharmacological Properties of the Invention Compounds
In Vitro Assays
Experimental Methods:

These assays have been performed following the description given in "Methods for dilution Antimicrobial Susceptibility Tests for Bacteria that Grow Aerobically, 4th ed.; Approved standard: NCCLS Document M7-A4; National Committee for Clinical Laboratory Standards Villanova, Pa., USA, 1997". Minimal inhibitory concentrations (MICs; mg/l) were determined in cation-adjusted Mueller-Hinton Broth by a microdilution method following NCCLS guidelines (National Committee for Clinical Laboratory Standards. Methods for Dilution Antimicrobial Susceptibility). The pH of the test medium was 7.2-7.3.

Results:

All Example compounds were tested against several Gram positive and Gram negative bacteria.

Antibacterial test results are given in the table hereafter (MIC in mg/l).

| Compound of Example | S aureus A798 | Compound of Example | S aureus A798 | Compound of Example | S aureus A798 |
|---|---|---|---|---|---|
| 1 | 0.25 | 2 | 4 | 3 | <=0.031 |
| 4 | <=0.031 | 5 | <=0.031 | 6 | <=0.031 |
| 7 | <=0.031 | 8 | <=0.031 | 9 | <=0.031 |
| 10 | 0.25 | 11 | 0.063 | 12 | <=0.031 |
| 13 | <=0.031 | 14 | 2 | 15 | 0.25 |
| 16 | 0.25 | 17 | <=0.031 | 18 | <=0.031 |
| 19 | <=0.031 | 20 | <=0.031 | 21 | 0.25 |
| 22 | <=0.031 | 23 | 2 | 24 | 0.25 |
| 25 | <=0.031 | 26 | <=0.031 | 27 | <=0.031 |
| 28 | 1 | 29 | <=0.031 | 30 | 0.125 |
| 31 | <=0.031 | 32 | <=0.031 | 33 | 4 |
| 34 | 0.125 | 35 | <=0.031 | 36 | <=0.031 |
| 37 | 0.063 | 38 | 0.063 | 39 | <=0.031 |
| 40 | 0.125 | 41 | <=0.031 | 42 | <=0.031 |
| 43 | 1 | 44 | 0.5 | 45 | <=0.031 |
| 46 | <=0.031 | 47 | <=0.031 | 48 | <=0.031 |
| 49 | <=0.031 | 50 | <=0.031 | 51 | <=0.031 |
| 52 | <=0.031 | 53 | <=0.031 | 54 | <=0.031 |
| 55 | <=0.031 | 56 | <=0.031 | 57 | <=0.031 |
| 58 | <=0.031 | 59 | <=0.031 | 60 | <=0.031 |
| 61 | <=0.031 | 62 | <=0.031 | 63 | 0.25 |
| 64 | <=0.031 | 65 | <=0.031 | 66 | <=0.031 |
| 67 | 0.063 | 68 | 0.063 | 69 | <=0.031 |
| 70 | <=0.031 | 71 | <=0.031 | 72 | <=0.031 |
| 73 | <=0.031 | 74 | 0.5 | 75 | <=0.031 |
| 76 | <=0.031 | 77 | 0.25 | 78 | <=0.031 |
| 79 | 0.25 | 80 | <=0.031 | 81 | 0.125 |
| 82 | <=0.031 | 83 | 0.25 | 84 | <=0.031 |
| 85 | 0.25 | 86 | <=0.031 | 87 | <=0.031 |
| 88 | 0.125 | 89 | <=0.031 | 90 | 4 |
| 91 | <=0.031 | 92 | 0.25 | 93 | <=0.031 |
| 94 | 2 | 95 | 0.125 | 96 | <=0.031 |
| 97 | <=0.031 | 98 | <=0.031 | 99 | <=0.031 |
| 100 | 0.063 | 101 | 0.5 | 102 | 4 |
| 103 | <=0.031 | 104 | <=0.031 | 105 | <=0.031 |
| 106 | <=0.031 | 107 | <=0.031 | 108 | 0.25 |
| 109 | <=0.031 | 110 | 8 | 111 | 0.125 |
| 112 | <=0.031 | 113 | <=0.031 | 114 | <=0.031 |
| 115 | 1 | 116 | <=0.031 | 117 | <=0.031 |
| 118 | 0.25 | 119 | <=0.031 | 120 | <=0.031 |
| 121 | <=0.031 | 122 | <=0.031 | 123 | <=0.031 |
| 124 | <=0.031 | 125 | <=0.031 | 126 | <=0.031 |
| 127 | <=0.031 | 128 | <=0.031 | 129 | 0.063 |
| 130 | 0.25 | 131 | <=0.031 | 132 | 0.063 |
| 133 | 2 | 134 | <=0.031 | 135 | <=0.031 |
| 136 | 0.25 | 137 | <=0.031 | 138 | <=0.031 |
| 139 | <=0.031 | 140 | 0.25 | 141 | <=0.031 |
| 142 | <=0.031 | 143 | <=0.031 | 144 | 0.063 |
| 145 | 0.125 | 146 | 0.063 | 147 | 0.25 |
| 148 | 0.5 | 149 | 0.063 | 150 | <=0.031 |
| 151 | 0.063 | 152 | 0.063 | 153 | 4 |
| 154 | 0.063 | 155 | <=0.031 | 156 | <=0.031 |
| 157 | <=0.031 | 158 | <=0.031 | 159 | <=0.031 |
| 160 | <=0.031 | 161 | <=0.031 | 162 | <=0.031 |
| 163 | <=0.031 | 164 | <=0.031 | 165 | <=0.031 |
| 166 | <=0.031 | 167 | <=0.031 | 168 | <=0.031 |
| 169 | 0.5 | 170 | 0.25 | 171 | 0.063 |
| 172 | <=0.031 | 173 | <=0.031 | 174 | <=0.031 |
| 175 | <=0.031 | 176 | <=0.031 | 177 | 0.125 |
| 178 | 0.063 | 179 | <=0.031 | 180 | <=0.031 |
| 181 | 0.25 | 182 | <=0.031 | 183 | 0.25 |
| 184 | 0.5 | 185 | 0.5 | 186 | <=0.031 |

The invention claimed is:
1. A method for treating a bacterial infection caused by *Staphylococcus aureus* comprising the step of administering to a patient in need thereof a therapeutically effective amount of a compound of formula (I) or a pharmaceutically acceptable salt thereof,

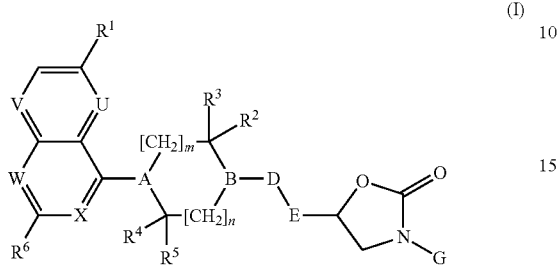

wherein
$R^1$ represents hydrogen, alkoxy, halogen or cyano;
one or two of U, V, W, and X represent(s) N and the remaining each represent CH, or, in the case of X, represent $CR^a$;
$R^a$ represents hydrogen or halogen;
$R^6$ represents hydrogen or $(C_1$-$C_4)$alkyl;
  A represents N, B represents N, D represents a bond, E represents $CH_2$ or CO, $R^2$, $R^3$, $R^4$ and $R^5$ each represent H, m represents the integer 2, and n represents the integer 1; or
  A represents N; B represents N; D represents a bond; E represents $CH_2$ or *—$COCH_2$— wherein the asterisk indicates the bond which is attached to B; $R^2$, $R^3$, $R^4$ and $R^5$ each represent H, or $R^4$ and $R^5$ represent H and $R^2$ and $R^3$ together with the carbon atom to which they are attached to form a carbonyl group, or $R^2$ and $R^3$ represent H and $R^4$ and $R^5$ together with the carbon atom to which they are attached to form a carbonyl group, or $R^2$ and $R^4$ represent H and $R^3$ and $R^5$ together form a methylene bridge; and m and n each represent the integer 1; or
  A represents N, B represents C(OH), D represents a bond, E represents $CH_2$, $R^2$, $R^3$, $R^4$ and $R^5$ each represent H, and m and n each represent the integer 1; or
  A represents N, B represents CH, D represents $NR^b$, E represents $CH_2$, $R^2$, $R^3$, $R^4$ and $R^5$ each represent H, $R^b$ represents H or $(C_1$-$C_4)$alkyl, and m and n each represent the integer 1; or
  A represents N, B represents CH, D represents NH, E represents $CH_2$, $R^2$, $R^3$, $R^4$ and $R^5$ each represent H, m represents the integer 2, and n represents the integer 0; or
  A represents C(OH), B represents N, D represents a bond, E represents $CH_2$, $R^2$, $R^3$, $R^4$ and $R^5$ each represent H, and m and n each represent the integer 1; or
  A represents N; B represents CH; D represents $NR^c$; E represents $CH_2$, CO or $CH_2CH_2$; $R^2$, $R^3$, $R^4$ and $R^5$ each represent H and $R^c$ represents H or $(C_1$-$C_4)$alkyl, or $R^c$, $R^3$, $R^4$ and $R^5$ each represent H and $R^2$ represents hydroxy, $(C_1$-$C_4)$alkoxy, $(C_1$-$C_4)$alkoxy-carbonyl, or carboxy, or $R^3$, $R^4$ and $R^5$ each represent H and $R^c$ forms together with $R^2$ an ethane-1,2-diyl bridge; m represents the integer 1, and n represents the integer 0; or
  A represents N; B represents CH; D represents *—CH($R^d$)—N($R^e$)— wherein the asterisk indicates the bond which is attached to B; E represents $CH_2$ or CO; $R^d$, $R^2$, $R^3$, $R^4$ and $R^5$ each represent H and $R^e$ represents H or $(C_1$-$C_4)$alkyl, or, r, $R^3$, $R^4$ and $R^5$ each represent H and $R^d$ and $R^2$ together form a bond, or $R^d$, $R^2$, $R^3$ and $R^5$ each represent H and $R^e$ and $R^4$ together form a methylene bridge, or $R^d$, $R^e$, $R^3$, $R^4$ and $R^5$ each represent H and $R^2$ represents hydroxy; m represents the integer 1, and n represents the integer 0; or
  A represents N, B represents CH, D represents *—CONH— wherein the asterisk indicates the bond which is attached to B, E represents $CH_2$, $R^2$, $R^3$, $R^4$ and $R^5$ each represent H, m represents the integer 1, and n represents the integer 0; or
  A represents N, B represents CH, D represents NH, E represents $CH_2$ or CO, $R^2$, $R^3$ and $R^5$ each represent H and $R^4$ represents hydroxymethyl, m represents the integer 0, and n represents the integer 1; or
  A represents N, B represents C(OH), D represents *—$CH_2$—NH— wherein the asterisk indicates the bond which is attached to B, E represents $CH_2$, $R^2$, $R^3$, $R^4$ and $R^5$ each represent H, m represents the integer 1, and n represents the integer 0; or
  A represents N, B represents CH, D represents *—CO—NH— wherein the asterisk indicates the bond which is attached to B, E represents $CH_2$, $R^2$, $R^3$, $R^4$ and $R^5$ each represent H, and m and n each represent the integer 0; or
  A represents N, B represents CH, D represents *—$CH_2$—N($R^f$)— wherein the asterisk indicates the bond which is attached to B, E represents $CH_2$, $CH_2CH_2$ or CO, $R^2$, $R^3$, $R^4$ and $R^5$ each represent H, $R^f$ represents H or $(C_1$-$C_4)$alkyl, and m and n each represent the integer 0; or
  A represents N; B represents CH; D represents $NR^g$; E represents $CH_2$, $CH_2CH_2$, CO or *—$COCH_2$— wherein the asterisk indicates the bond which is attached to B; $R^2$, $R^3$, $R^4$ and $R^5$ each represent H; $R^g$ represents H, $(C_1$-$C_4)$alkyl or $(C_2$-$C_4)$alkyl which is mono- or di-substituted with hydroxy; and m and n each represent the integer 0;
G represents phenyl which is unsubstituted, mono-substituted in position 3 or 4, or disubstituted in positions 3 and 4, wherein each substituent is independently $(C_1$-$C_4)$alkyl, $(C_1$-$C_4)$alkoxy, fluoroalkyl, fluoroalkoxy, cyano, halogen or $NR^{N1}R^{N2}$ or
G represents pyridin-2-yl which is mono-substituted in position 5, wherein the substituent is $(C_1$-$C_4)$alkyl or fluoroalkyl; or
G represents 6,7-dihydro-[1,4]dioxino[2,3-c]pyridazin-3-yl; or
G represents:

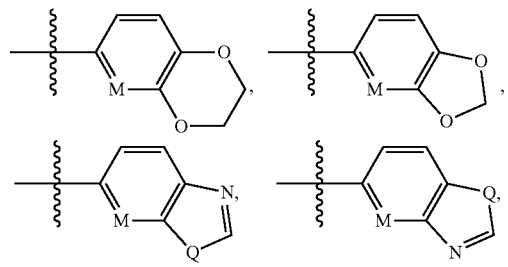

-continued

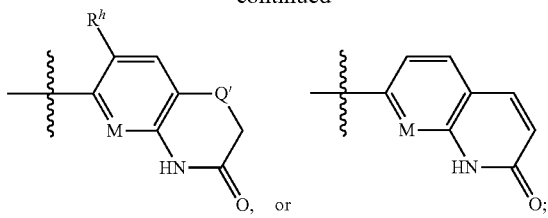

wherein
$R^h$ represents hydrogen or fluorine;
M represents CH or N; and Q and Q' independently represent O or S; and
$R^{N1}$ and $R^{N2}$ independently represent $(C_1-C_4)$alkyl, or together with the nitrogen that carries them form a pyrrolidine ring.

2. The method of claim 1, wherein
$R^6$ represents hydrogen;
- A represents N, B represents N, D represents a bond, E represents $CH_2$ or CO, $R^2$, $R^3$, $R^4$ and $R^5$ each represent H, m represents the integer 2, and n represents the integer 1; or
- A represents N; B represents N; D represents a bond; E represents $CH_2$ or *—$COCH_2$— wherein the asterisk indicates the bond which is attached to B; $R^2$, $R^3$, $R^4$ and $R^5$ each represent H, or $R^4$ and $R^5$ represent H and $R^2$ and $R^3$ together with the carbon atom to which they are attached to form a carbonyl group, or $R^2$ and $R^3$ represent H and $R^4$ and $R^5$ together with the carbon atom to which they are attached to form a carbonyl group; and m and n each represent the integer 1; or
- A represents N, B represents C(OH), D represents a bond, E represents $CH_2$, $R^2$, $R^3$, $R^4$ and $R^5$ each represent H, and m and n each represent the integer 1; or
- A represents N, B represents CH, D represents $NR^b$, E represents $CH_2$, $R^2$, $R^3$, $R^4$ and $R^5$ each represent H, $R^b$ represents H or $(C_1-C_4)$alkyl, and m and n each represent the integer 1; or
- A represents N, B represents CH, D represents NH, E represents $CH_2$, $R^2$, $R^3$, $R^4$ and $R^5$ each represent H, m represents the integer 2, and n represents the integer 0; or
- A represents C(OH), B represents N, D represents a bond, E represents $CH_2$, $R^2$, $R^3$, $R^4$ and $R^5$ each represent H, and m and n each represent the integer 1; or
- A represents N; B represents CH; D represents $NR^c$; E represents $CH_2$, CO or $CH_2CH_2$; $R^2$, $R^3$, $R^4$ and $R^5$ each represent H and $R^c$ represents H or $(C_1-C_4)$alkyl, or $R^c$, $R^3$, $R^4$ and $R^5$ each represent H and $R^2$ represents hydroxy, $(C_1-C_4)$alkoxy, $(C_1-C_4)$alkoxy-carbonyl, or carboxy, or $R^3$, $R^4$ and $R^5$ each represent H and $R^c$ forms together with $R^2$ an ethane-1,2-diyl bridge; m represents the integer 1, and n represents the integer 0; or
- A represents N; B represents CH; D represents *—CH($R^d$)—N($R^e$)— wherein the asterisk indicates the bond which is attached to B; E represents $CH_2$ or CO; $R^d$, $R^2$, $R^3$, $R^4$ and $R^5$ each represent H and $R^e$ represents H or $(C_1-C_4)$alkyl, or $R^e$, $R^3$, $R^4$ and $R^5$ each represent H and $R^d$ and $R^2$ together form a bond, or $R^d$, $R^2$, $R^3$ and $R^5$ each represent H and $R^e$ and $R^4$ together form a methylene bridge, or $R^d$, $R^e$, $R^3$, $R^4$ and $R^5$ each represent H and $R^2$ represents hydroxy; m represents the integer 1, and n represents the integer 0; or
- A represents N, B represents CH, D represents *—CONH— wherein the asterisk indicates the bond which is attached to B, E represents $CH_2$, $R^2$, $R^3$, $R^4$ and $R^5$ each represent H, m represents the integer 1, and n represents the integer 0; or
- A represents N, B represents CH, D represents NH, E represents $CH_2$ or CO, $R^2$, $R^3$ and $R^5$ each represent H and $R^4$ represents hydroxymethyl, m represents the integer 0, and n represents the integer 1; or
- A represents N, B represents CH, D represents *—$CH_2$—N($R^f$)— wherein the asterisk indicates the bond which is attached to B, E represents $CH_2$ or CO, $R^2$, $R^3$, $R^4$ and $R^5$ each represent H, $R^f$ represents H or $(C_1-C_4)$alkyl, and m and n each represent the integer 0; or
- A represents N; B represents CH; D represents $NR^g$; E represents $CH_2$, $CH_2CH_2$, CO or *—$COCH_2$— wherein the asterisk indicates the bond which is attached to B; $R^2$, $R^3$, $R^4$ and $R^5$ each represent H; $R^g$ represents H, $(C_1-C_4)$alkyl or 2-hydroxyethyl; and m and n each represent the integer 0; and G represents phenyl which is unsubstituted, mono-substituted in position 3 or 4, or disubstituted in positions 3 and 4, wherein each substituent is independently $(C_1-C_4)$alkyl, $(C_1-C_4)$alkoxy, fluoroalkyl, fluoroalkoxy, cyano, halogen or —$NR^{N1}R^{N2}$; or G represents pyridin-2-yl which is mono-substituted in position 5, wherein the substituent is $(C_1-C_4)$alkyl or fluoroalkyl; or G represents 6,7-dihydro-[1,4]dioxino[2,3-c]pyridazin-3-yl; or G represents:

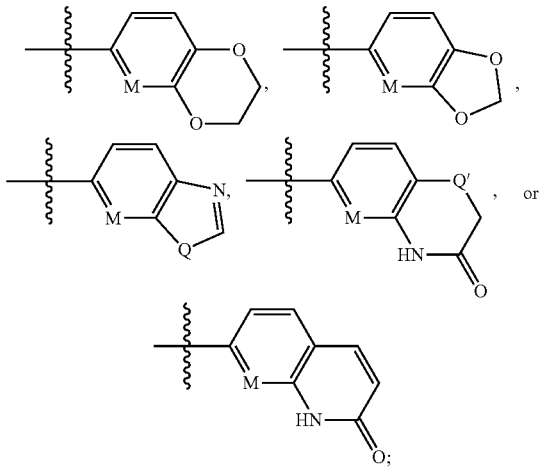

wherein
M represents CH or N; and Q and Q' independently represent O or S.

3. The method of claim 1, wherein the compound of formula $(I_{P1})$,

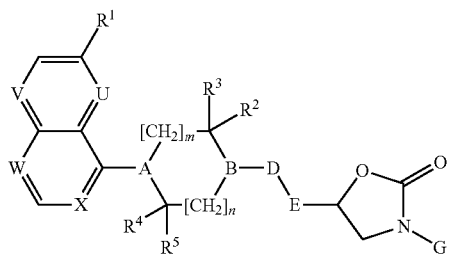

(I_{P1})

wherein

R¹ represents alkoxy, halogen or cyano;

one or two of U, V, W, and X represent(s) N and the remaining each represent CH, or, in the case of X, represent CR^a;

R^a represents hydrogen or halogen;

A represents N, B represents N, D represents a bond, E represents CH₂, R², R³, R⁴ and R⁵ each represent H, and m and n each represent the integer 1; or A represents N, B represents C(OH), D represents a bond, E represents CH₂, R², R³, R⁴ and R⁵ each represent H, and m and n each represent the integer 1; or A represents C(OH), B represents N, D represents a bond, E represents CH₂, R², R³, R⁴ and R⁵ each represent H, and m and n each represent the integer 1; or A represents N, B represents CH, D represents *—CH₂—NH— wherein the asterisk indicates the bond which is attached to B, E represents CH₂ or CO, R², R³, R⁴ and R⁵ each represent H, and m and n each represent the integer 0; or A represents N, B represents CH, D represents NH, E represents CH₂, R², R³, R⁴ and R⁵ each represent H, m represents the integer 1, and n represents the integer 0;

G represents phenyl which is unsubstituted, mono-substituted in position 3 or 4, or disubstituted in positions 3 and 4, wherein each substituent is independently (C₁-C₄)alkyl, (C₁-C₄)alkoxy, fluoroalkyl, fluoroalkoxy, cyano, halogen or —NR^{N1}R^{N2}; or G represents pyridin-2-yl which is mono-substituted in position 5, wherein the substituent is (C₁-C₄)alkyl and or fluoroalkyl; or G represents:

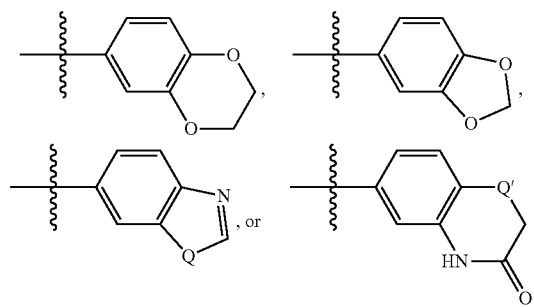

wherein

Q and Q' independently represent O or S; and

R^{N1} and R^{N2} independently represent (C₁-C₄)alkyl, or together with the nitrogen that carries them form a pyrrolidine ring.

4. The method of claim 1, wherein the compound of formula (I) is:

(S)-3-(2,3-Dihydro-benzo[1,4]dioxin-6-yl)-5-({[1-(6-methoxy-[1,5]naphthyridin-4-yl)-azetidin-3-ylmethyl]-amino}-methyl)-oxazolidin-2-one ;

(S)-3-(2,3-Dihydro-benzo[1,4]dioxin-6-yl)-2-oxo-oxazolidine-5-carboxylic acid [1-(6-methoxy-[1,5]naphthyridin-4-yl)-azetidin-3-ylmethyl]-amide;

3-(2,3-Dihydro-benzo[1,4]dioxin-6-yl)-5-[4-hydroxy-4-(6-methoxy-[1,5]naphthyridin-4-yl)-piperidin-1-ylmethyl]-oxazolidin-2-one;

3-(2,3-Dihydro-benzo[1,4]dioxin-6-yl)-5-[4-hydroxy-1-(6-methoxy-quinazolin-4-yl)-piperidin-4-ylmethyl]-oxazolidin-2-one;

3-(2,3-Dihydro-benzo[1,4]dioxin-6-yl)-5-[4-hydroxy-1-(6-methoxy-[1,5]naphthyridin-4-yl)-piperidin-4-ylmethyl]-oxazolidin-2-one;

3-(2,3-Dihydro-benzo[1,4]dioxin-6-yl)-5-[4-(6-methoxy-quinazolin-4-yl)-piperazin-1-ylmethyl]-oxazolidin-2-one;

6-{5-[4-(6-Methoxy-quinazolin-4-yl)-piperazin-1-ylmethyl]-2-oxo-oxazolidin-3-yl}-4H-benzo[1,4]thiazin-3-one;

3-(2,3-Dihydro-benzo[1,4]dioxin-6-yl)-5-[4-(6-methoxy-[1,5]naphthyridin-4-yl)-piperazin-1-ylmethyl]-oxazolidin-2-one;

(R)-3-(2,3-Dihydro-benzo[1,4]dioxin-6-yl)-5-[4-(6-methoxy-[1,5]naphthyridin-4-yl)-piperazin-1-ylmethyl]-oxazolidin-2-one;

(R)-5-[4-(6-Methoxy-[1,5]naphthyridin-4-yl)-piperazin-1-ylmethyl]-3-(3-trifluoromethoxy-phenyl)-oxazolidin-2-one;

(R)-5-[4-(6-Methoxy-[1,5]naphthyridin-4-yl)-piperazin-1-ylmethyl]-3-(4-trifluoromethoxy-phenyl)-oxazolidin-2-one;

(R)-5-[4-(6-Methoxy-[1,5]naphthyridin-4-yl)-piperazin-1-ylmethyl]-3-phenyl-oxazolidin-2-one ;

(R)-3-(4-Bromo-3-fluoro-phenyl)-5-[4-(6-methoxy-[1,5]naphthyridin-4-yl)-piperazin-1-ylmethyl]-oxazolidin-2-one;

(R)-3-(3,4-Dimethoxy-phenyl)-5-[4-(6-methoxy-[1,5]naphthyridin-4-yl)-piperazin-1-ylmethyl]-oxazolidin-2-one;

(R)-3-(4-Fluoro-phenyl)-5-[4-(6-methoxy-[1,5]naphthyridin-4-yl)-piperazin-1-ylmethyl]-oxazolidin-2-one;

(R)-5-[4-(6-Methoxy-[1,5]naphthyridin-4-yl)-piperazin-1-ylmethyl]-3-(3-trifluoromethyl-phenyl)-oxazolidin-2-one;

(R)-3-(3-Chloro-4-fluoro-phenyl)-5-[4-(6-methoxy-[1,5]naphthyridin-4-yl)-piperazin-1-ylmethyl]-oxazolidin-2-one;

(R)-5-[4-(6-Methoxy-[1,5]naphthyridin-4-yl)-piperazin-1-ylmethyl]-3-(4-methyl-3-trifluoromethyl-phenyl)-oxazolidin-2-one;

(R)-3-Benzothiazol-6-yl-5-[4-(6-methoxy-[1,5]naphthyridin-4-yl)-piperazin-1-ylmethyl]-oxazolidin-2-one;

(R)-3-(4-Difluoromethoxy-phenyl)-5-[4-(6-methoxy-[1,5]naphthyridin-4-yl)-piperazin-1-ylmethyl]-oxazolidin-2-one;

3-{[(R)-5-[4-(6-Methoxy-[1,5]naphthyridin-4-yl)-piperazin-1-ylmethyl]-2-oxo-oxazolidin-3-yl}-benzonitrile;

6-{(R)-5-[4-(6-Methoxy-[1,5]naphthyridin-4-yl)-piperazin-1-ylmethyl]-2-oxo-oxazolidin-3-yl}-4H-benzo[1,4]thiazin-3-one;

(R)-5-[4-(6-Methoxy-[1,5]naphthyridin-4-yl)-piperazin-1-ylmethyl]-3-(4-pyrrolidin-1-yl-phenyl)-oxazolidin-2-one;

(R)-5-[4-(6-Methoxy-[1,5]naphthyridin-4-yl)-piperazin-1-ylmethyl]-3-(3-methoxy-phenyl)-oxazolidin-2-one;

(R)-5-[4-(6-Methoxy-[1,5]naphthyridin-4-yl)-piperazin-1-ylmethyl]-3-(4-propyl-phenyl)-oxazolidin-2-one;
(R)-3-(4-Ethyl-phenyl)-5-[4-(6-methoxy-[1,5]naphthyridin-4-yl)-piperazin-1-ylmethyl]-oxazolidin-2-one;
(R)-3-(3,4-Dimethyl-phenyl)-5-[4-(6-methoxy-[1,5]naphthyridin-4-yl)-piperazin-1-ylmethyl]-oxazolidin-2-one;
(R)-3-(3-Chloro-4-methoxy-phenyl)-5-[4-(6-methoxy-[1,5]naphthyridin-4-yl)-piperazin-1-ylmethyl]-oxazolidin-2-one;
(R)-3-(3,4-Difluoro-phenyl)-5-[4-(6-methoxy-[1,5]naphthyridin-4-yl)-piperazin-1-ylmethyl]-oxazolidin-2-one;
(R)-3-(4-Fluoro-3-methyl-phenyl)-5-[4-(6-methoxy-41,5]naphthyridin-4-yl)-piperazin-1-ylmethyl]-oxazolidin-2-one;
(R)-3-(4-Bromo-3-methyl-phenyl)-5-[4-(6-methoxy-4[,5]naphthyridin-4-yl)-piperazin-1-ylmethyl]-oxazolidin-2-one;
(R)-3-(3-Bromo-4-methyl-phenyl)-5-[4-(6-methoxy-[1,5]naphthyridin-4-yl)-piperazin-1-ylmethyl]-oxazolidin-2-one;
(R)-5-[4-(6-Methoxy-[1,5]naphthyridin-4-yl)-piperazin-1-ylmethyl]-3-(4-methoxy-3-trifluoromethyl-phenyl)-oxazolidin-2-one;
(R)-3-(3-Dimethylamino-phenyl)-5-[4-(6-methoxy-[1,5]naphthyridin-4-yl)-piperazin-1-ylmethyl]-oxazolidin-2-one;
(R)-3-Benzo[1,3]dioxol-5-yl-5-[4-(6-methoxy-[1,5]naphthyridin-4-yl)-piperazin-1-ylmethyl]-oxazolidin-2-one;
(R)-3-(3-Fluoro-4-methyl-phenyl)-5-[4-(6-methoxy-[1,5]naphthyridin-4-yl)-piperazin-1-ylmethyl]-oxazolidin-2-one;
(S)-3-(2,3-Dihydro-benzo[1,4]dioxin-6-yl)-5-[4-(6-methoxy-[1,5]naphthyridin-4-yl)-piperazin-1-ylmethyl]-oxazolidin-2-one;
(S)-3-(3-Fluoro-4-methyl-phenyl)-5-[4-(6-methoxy-[1,5]naphthyridin-4-yl)-piperazin-1-ylmethyl]-oxazolidin-2-one;
6-{(S)-5-[4-(6-Methoxy-[1,5]naphthyridin-4-yl)-piperazin-1-ylmethyl]-2-oxo-oxazolidin-3-yl}-4H-benzo[1,4]thiazin-3-one;
(S)-3-(3-Fluoro-phenyl)-5-[4-(6-methoxy-[1,5]naphthyridin-4-yl)-piperazin-1-ylmethyl]-oxazolidin-2-one;
(R)-3-(2,3-Dihydro-benzo[1,4]dioxin-6-yl)-5-[(S)-1-(6-methoxy-[1,5]naphthyridin-4-yl)-pyrrolidin-3-ylamino]-methyl}-oxazolidin-2-one;
(R)-3-(2,3-Dihydro-benzo[1,4]dioxin-6-yl)-5-[(R)-1-(6-methoxy-[1,5]naphthyridin-4-yl)-pyrrolidin-3-ylamino]-methyl}-oxazolidin-2-one;
5-[4-(6-Methoxy-[1,5]naphthyridin-4-yl)-piperazin-1-ylmethyl]-3-(5-methyl-pyridin-2-yl)-oxazolidin-2-one;
5-[4-(6-Methoxy-[1,5]naphthyridin-4-yl)-piperazin-1-ylmethyl]-3-(5-trifluoromethyl-pyridin-2-yl)-oxazolidin-2-one;
6-((R)-5-{[1-(3-Fluoro-6-methoxy-[1,5]naphthyridin-4-yl)-azetidin-3-ylamino]-methyl}-2-oxo-oxazolidin-3-yl)-4H-benzo[1,4]oxazin-3-one;
(R)-5-{[1-(3-Fluoro-6-methoxy-[1,5]naphthyridin-4-yl)-azetidin-3-ylamino]-methyl}-3-(3-fluoro-4-methyl-phenyl)-oxazolidin-2-one;
(R)-3-(2,3-Dihydro-benzo[1,4]dioxin-6-yl)-5-[1-(3-fluoro-6-methoxy-[1,5]naphthyridin-4-yl)-azetidin-3-ylamino]-methyl}-oxazolidin-2-one;
6-((R)-5-{[1-(3-Fluoro-6-methoxy-[1,5]naphthyridin-4-yl)-azetidin-3-ylamino]-methyl}-2-oxo-oxazolidin-3-yl)-4H-benzo[1,4]thiazin-3-one;
6-((R)-5-{[1-(6-Methoxy-quinolin-4-yl)-azetidin-3-ylamino]-methyl}-2-oxo-oxazolidin-3-yl)-4H-benzo[1,4]thiazin-3-one;
(R)-3-(3-Fluoro-4-methyl-phenyl)-5-{[1-(6-methoxy-[1,5]naphthyridin-4-yl)-azetidin-3-ylamino]-methyl}-oxazolidin-2-one;
(R)-3-(2,3-Dihydro-benzo[1,4]dioxin-6-yl)-5-{[1-(6-methoxy-[1,5]naphthyridin-4-yl)-azetidin-3-ylamino]-methyl}-oxazolidin-2-one;
6-((R)-5-{[1-(6-Methoxy-[1,5]naphthyridin-4-yl)-azetidin-3-ylamino]-methyl}-2-oxo-oxazolidin-3-yl)-4H-benzo[1,4]oxazin-3-one;
6-((R)-5-{[1-(6-Methoxy-[1,5]naphthyridin-4-yl)-azetidin-3-ylamino]-methyl}-2-oxo-oxazolidin-3-yl)-4H-benzo[1,4]thiazin-3-one;
6-((R)-5-{[1-(6-Methoxy-quinazolin-4-yl)-azetidin-3-ylamino]-methyl}-2-oxo-oxazolidin-3-yl)-4H-benzo[1,4]oxazin-3-one;
6-((R)-5-{[1-(6-Methoxy-quinazolin-4-yl)-azetidin-3-ylamino]-methyl}-2-oxo-oxazolidin-3-yl)-4H-benzo[1,4]thiazin-3-one;
6-[(R)-5-({[1-(6-Methoxy-[1,5]naphthyridin-4-yl)-azetidin-3-yl]-methyl-amino}-methyl)-2-oxo-oxazolidin-3-yl]-4H-benzo[1,4]thiazin-3-one;
6-((S)-5-{[1-(6-Methoxy-[1,5]naphthyridin-4-yl)-azetidin-3-ylamino]-methyl}-2-oxo-oxazolidin-3-yl)-4H-benzo[1,4]thiazin-3-one;
6-(5-{2-[1-(6-Methoxy-[1,5]naphthyridin-4-yl)-azetidin-3-ylamino]-ethyl}-2-oxo-oxazolidin-3-yl)-4H-benzo[1,4]thiazin-3-one;
6-[(S)-5-({[1-(6-Methoxy-[1,5]naphthyridin-4-yl)-azetidin-3-ylmethyl]-amino}-methyl)-2-oxo-oxazolidin-3-yl]-4H-benzo[1,4]thiazin-3-one;
(S)-3-(2,3-Dihydro-benzo[1,4]dioxin-6-yl)-2-oxo-oxazolidine-5-carboxylic acid [(S)-1-(6-methoxy-[1,5]naphthyridin-4-yl)-pyrrolidin-3-yl]-amide;
(S)-3-(2,3-Dihydro-benzo[1,4]dioxin-6-yl)-2-oxo-oxazolidine-5-carboxylic acid [(R)-1-(6-methoxy-[1,5]naphthyridin-4-yl)-pyrrolidin-3-yl]amide;
(S)-3-(3-Fluoro-4-methyl-phenyl)-2-oxo-oxazolidine-5-carboxylic acid [(R)-1-(6-methoxy-[1,5]naphthyridin-4-yl)-pyrrolidin-3-yl]-amide;
(S)-3-(3-Fluoro-4-methyl-phenyl)-2-oxo-oxazolidine-5-carboxylic acid [(S)-1-(6-methoxy-[1,5]naphthyridin-4-yl)-pyrrolidin-3-yl]amide;
6-((R)-5-{[(S)-1-(3-Fluoro-6-methoxy-[1,5]naphthyridin-4-yl)-pyrrolidin-3-ylamino]-methyl}-2-oxo-oxazolidin-3-yl)-4H-benzo[1,4]oxazin-3-one;
6-((R)-5-{[(S)-1-(3-Fluoro-6-methoxy-[1,5]naphthyridin-4-yl)-pyrrolidin-3-ylamino]-methyl}-2-oxo-oxazolidin-3-yl)-4H-benzo[1,4]thiazin-3-one;
(R)-3-(2,3-Dihydro-benzo[1,4]dioxin-6-yl)-5-[(S)-1-(3-fluoro-6-methoxy-[1,5]naphthyridin-4-yl)-pyrrolidin-3-ylamino]-methyl}-oxazolidin-2-one;
(R)-3-(3-Fluoro-4-methyl-phenyl)-5-{[(S)-1-(6-methoxy-[1,5]naphthyridin-4-yl)-pyrrolidin-3-ylamino]-methyl}-oxazolidin-2-one;
(R)-3-(3-Fluoro-4-methyl-phenyl)-5-[(R)-1-(6-methoxy-[1,5]naphthyridin-4-yl)-pyrrolidin-3-ylamino]-methyl}-oxazolidin-2-one;
6-((R)-5-{[(S)-1-(6-Methoxy-[1,5]naphthyridin-4-yl)-pyrrolidin-3-ylamino]-methyl}-2-oxo-oxazolidin-3-yl)-4H-benzo[1,4]oxazin-3-one;
6-((R)-5-{[(S)-1-(6-Methoxy-[1,5]naphthyridin-4-yl)-pyrrolidin-3-ylamino]-methyl}-2-oxo-oxazolidin-3-yl)-4H-benzo[1,4]thiazin-3-one;

6-((R)-5-[(R)-1-(6-Methoxy-[1,5]naphthyridin-4-yl)-pyr-rolidin-3-ylamino]-methyl}-2-oxo-oxazolidin-3-yl)-4H-benzo[1,4]thiazin-3-one;

6-((R)-5-[(R)-1-(6-Methoxy-[1,5]naphthyridin-4-yl)-pyr-rolidin-3-ylamino]-methyl}-2-oxo-oxazolidin-3-yl)-4H-benzo[1,4]oxazin-3-one;

(3R*,4S*)-1-(6-Methoxy-[1,5]naphthyridin-4-yl)-4-{[(S)-2-oxo-3-(3-oxo-3,4-dihydro-2H-benzo[1,4]thiazin-6-yl)-oxazolidin-5-ylmethyl]-amino}-pyrrolidine-3-carboxylic acid ethyl ester;

(3R*,4S*)-1-(6-Methoxy-[1,5]naphthyridin-4-yl)-4-{[(R)-2-oxo-3-(3-oxo-3,4-dihydro-2H-benzo[1,4]thiazin-6-yl)-oxazolidin-5-ylmethyl]amino}-pyrrolidine-3-carboxylic acid;

6-((R)-5-{[(3R*,4R*)-4-Methoxy-1-(6-methoxy-[1,5]naphthyridin-4-yl)-pyrrolidin-3-ylamino]-methyl}-2-oxo-oxazolidin-3-yl)-4H-benzo[1,4]thiazin-3-one;

6-((R)-5-{[(3R*,4R*)-4-Hydroxy-1-(6-methoxy-[1,5]naphthyridin-4-yl)-pyrrolidin-3-ylamino]-methyl}-2-oxo-oxazolidin-3-yl)-4H-benzo[1,4]thiazin-3-one;

(R)-3-(2,3-Dihydro-benzo[1,4]dioxin-6-yl)-5-{[(3R*,4R*)-4-hydroxy-1-(6-methoxy-[1,5]naphthyridin-4-yl)-pyrrolidin-3-ylamino]-methyl}-oxazolidin-2-one;

(S)-3-(2,3-Dihydro-benzo[1,4]dioxin-6-yl)-2-oxo-oxazolidine-5-carboxylic acid [(3R,5S)-5-hydroxymethyl-1-(6-methoxy-[1,5]naphthyridin-4-yl)-pyrrolidin-3-yl]-amide;

6-((R)-5-{[(3R,5S)-5-Hydroxymethyl-1-(6-methoxy-[1,5]naphthyridin-4-yl)-pyrrolidin-3-ylamino]-methyl}-2-oxo-oxazolidin-3-yl)-4H-benzo[1,4]thiazin-3-one;

6-[(R)-5-({[1-(6-Methoxy-[1,5]naphthyridin-4-yl)-pyrrolidin-3-ylmethyl]-amino-methyl)-2-oxo-oxazolidin-3-yl]-4H-benzo[1,4]thiazin-3-one;

(S)-3-(2,3-Dihydro-benzo[1,4]dioxin-6-yl)-2-oxo-oxazolidine-5-carboxylic acid [1-(6-methoxy-[1,5]naphthyridin-4-yl)-pyrrolidin-3-ylmethyl]-amide;

(S)-3-(3-Fluoro-4-methyl-phenyl)-2-oxo-oxazolidine-5-carboxylic acid [1-(6-methoxy-[1,5]naphthyridin-4-yl)-pyrrolidin-3-ylmethyl]-amide;

6-[(R)-5-({[4-Hydroxy-1-(6-methoxy-[1,5]naphthyridin-4-yl)-pyrrolidin-3-ylmethyl]-amino}-methyl)-2-oxo-oxazolidin-3-yl]-4H-benzo[1,4]thiazin-3-one;

1-(6-Methoxy-[1,5]naphthyridin-4-yl)-pyrrolidine-3-carboxylic acid [(R)-3-(3-fluoro-4-methyl-phenyl)-2-oxo-oxazolidin-5-ylmethyl]-amide;

1-(6-Methoxy-[1,5]naphthyridin-4-yl)-pyrrolidine-3-carboxylic acid [(R)-3-(2,3-dihydro-benzo[1,4]dioxin-6-yl)-2-oxo-oxazolidin-5-ylmethyl]-amide;

6-(5-{2-[(S)-1-(6-Methoxy-[1,5]naphthyridin-4-yl)-pyrrolidin-3-ylamino]-ethyl}-2-oxo-oxazolidin-3-yl)-4H-benzo[1,4]thiazin-3-one;

6-(5-{2-[(R)-1-(6-Methoxy-[1,5]naphthyridin-4-yl)-pyrrolidin-3-ylamino]-ethyl}-2-oxo-oxazolidin-3-yl)-4H-benzo[1,4]thiazin-3-one;

(R)-3-(3-Fluoro-4-methyl-phenyl)-5-[(1a,5a,6a)-3-(6-methoxy-[1,5]naphthyridin-4-yl)-3-aza-bicyclo[3.1.0]hex-6-ylamino]-methyl}-oxazolidin-2-one;

6-((R)-5-{[(1a,5a,6a)-3-(6-Methoxy-[1,5]naphthyridin-4-yl)-3-aza-bicyclo[3.1.0]hex-6-ylamino]-methyl}-2-oxo-oxazolidin-3-yl)-4H-benzo[1,4]thiazin-3-one;

(R)-3-(2,3-Dihydro-benzo[1,4]dioxin-6-yl)-5-{[(3aR*,6aR*)-1-(6-methoxy-[1,5]naphthyridin-4-yl)-hexahydro-pyrrolo[3,4-b]pyrrol-5-yl]-methyl}-oxazolidin-2-one;

6-{(R)-5-[(3aR*,6aR*)-1-(6-Methoxy-[1,5]naphthyridin-4-yl)-hexahydro-pyrrolo[3,4-b]pyrrol-5-yl]-methyl}-2-oxo-oxazolidin-3-yl]-4H-benzo[1,4]thiazin-3-one;

(S)-3-(2,3-Dihydro-benzo[1,4]dioxin-6-yl)-5-[(3aR*,6aR*)-1-(6-methoxy-[1,5]naphthyridin-4-yl)-hexahydro-pyrrolo[3,4-b]pyrrole-5-carbonyl]-oxazolidin-2-one;

6-{(R)-5-{[(3aR*,6aR*)-5-(6-Methoxy-[1,5]naphthyridin-4-yl)-hexahydro-pyrrolo[3,4-b]pyrrol-1-yl]-methyl}-2-oxo-oxazolidin-3-yl}-4H-benzo[1,4]thiazin-3-one ;

(R)-3-(2,3-Dihydro-benzo[1,4]dioxin-6-yl)-5-{[(3aR*,6aR*)-5-(6-methoxy-[1,5]naphthyridin-4-yl)-hexahydro-pyrrolo[3,4-b]pyrrol-1-yl]-methyl}-oxazolidin-2-one;

(S)-3-(2,3-Dihydro-benzo[1,4]dioxin-6-yl)-5-[(3aR*,6aR*)-5-(6-methoxy-[1,5]naphthyridin-4-yl)-hexahydro-pyrrolo[3,4-b]pyrrole-1-carbonyl]-oxazolidin-2-one;

6-{(R)-5-[4-(6-Methoxy-[1,5]naphthyridin-4-yl)-piperazin-1-ylmethyl]-2-oxo-oxazolidin-3-yl}-4H-benzo[1,4]oxazin-3-one;

6-{(R)-5-[4-(3-Fluoro-6-methoxy-[1,5]naphthyridin-4-yl)-piperazin-1-ylmethyl]-2-oxo-oxazolidin-3-yl]-4H-benzo[1,4]oxazin-3-one;

6-{(R)-5-[4-(3-Fluoro-6-methoxy-[1,5]naphthyridin-4-yl)-piperazin-1-ylmethyl]-2-oxo-oxazolidin-3-yl}-4H-benzo[1,4]thiazin-3-one;

(R)-3-(2,3-Dihydro-benzo[1,4]dioxin-6-yl)-5-(4-quinolin-4-yl-piperazin-1-ylmethyl)-oxazolidin-2-one;

[3-(3-Fluoro-4-methyl-phenyl)-2-oxo-oxazolidin-5-ylmethyl]-4-(6-methoxy-[1,5]naphthyridin-4-yl)-piperazin-2-one ;

6-{(R)-5-[4-(6-Methoxy-[1,5]naphthyridin-4-yl)-3-oxo-piperazin-1-ylmethyl]-2-oxo-oxazolidin-3-yl}-4H-benzo[1,4]thiazin-3-one;

(R)-3-(2,3-Dihydro-benzo[1,4]dioxin-6-yl)-5-{[1-(6-methoxy-[1,5]naphthyridin-4-yl)-piperidin-3-ylamino]-methyl}-oxazolidin-2-one;

6-{(R)-5-[4-(3-Fluoro-6-methoxy-[1,5]naphthyridin-4-yl)-[1,4]diazepan-1-ylmethyl]-2-oxo-oxazolidin-3-yl}-4H-benzo[1,4]oxazin-3-one;

6-{(R)-5-[4-(3-Fluoro-6-methoxy-[1,5]naphthyridin-4-yl)-[1,4]diazepan-1-ylmethyl]-2-oxo-oxazolidin-3-yl}-4H-benzo[1,4]thiazin-3-one;

6-{(R)-5-[4-(6-Methoxy-[1,5]naphthyridin-4-yl)-[1,4]diazepan-1-ylmethyl]-2-oxo-oxazolidin-3-yl}-4H-benzo[1,4]oxazin-3-one;

6-{(R)-5-[4-(6-Methoxy-[1,5]naphthyridin-4-yl)-[1,4]diazepan-1-ylmethyl]-2-oxo-oxazolidin-3-yl}-4H-benzo[1,4]thiazin-3-one;

(R)-3-(2,3-Dihydro-benzo[1,4]dioxin-6-yl)-5-[4-(6-methoxy-[1,5]naphthyridin-4-yl)-[1,4]diazepan-1-ylmethyl]-oxazolidin-2-one;

(R)-3-(3-Fluoro-4-methyl-phenyl)-5-[4-(6-methoxy-[1,5]naphthyridin-4-yl)-[1,4]diazepan-1-ylmethyl]-oxazolidin-2-one;

(S)-3-(2,3-Dihydro-benzo[1,4]dioxin-6-yl)-5-[4-(6-methoxy-[1,5]naphthyridin-4-yl)-[1,4]diazepane-1-carbonyl]-oxazolidin-2-one;

3-(6,7-Dihydro-[1,4]dioxino[2,3-c]pyridazin-3-yl)-5-[4-(6-methoxy-[1,5]naphthyridin-4-yl)-piperazin-1-ylmethyl]-oxazolidin-2-one;

3-(6,7-Dihydro-[1,4]dioxino[2,3-c]pyridazin-3-yl)-5-[4-(6-methoxy-[1,5]naphthyridin-4-yl)-piperazin-1-ylmethyl]-oxazolidin-2-one;

(R)-3-(2,3-Dihydro-benzo[1,4]dioxin-6-yl)-5-({[(S)-1-(6-methoxy-[1,5]naphthyridin-4-yl)-pyrrolidin-3-yl]-methyl-amino}-methyl)-oxazolidin-2-one;

6-{5-[4-(6-Methoxy-[1,5]naphthyridin-4-yl)-piperazin-1-ylmethyl]-2-oxo-oxazolidin-3-yl}-4H-pyrido[3,2-b][1,4]oxazin-3-one;

6-((R)-5-{2-[4-(6-Methoxy-[1,5]naphthyridin-4-yl)-piperazin-1-yl]-2-oxo-ethyl}-2-oxo-oxazolidin-3-yl)-4H-benzo[1,4]thiazin-3-one;

N-[1-(6-Methoxy-[1,5]naphthyridin-4-yl)-azetidin-3-yl]-2-[(R)-2-oxo-3-(3-oxo-3,4-dihydro-2H-benzo[1,4]thiazin-6-yl)-oxazolidin-5-yl]-acetamide;

(S)-3-(2,3-Dihydro-benzo[1,4]dioxin-6-yl)-2-oxo-oxazolidine-5-carboxylic acid [1-(6-methoxy-[1,5]naphthyridin-4-yl)-azetidin-3-yl]-amide;

6-[(R)-5-({[1-(6-Methoxy-[1,5]naphthyridin-4-yl)-pyrrolidin-3-ylmethyl]-methyl-amino}-methyl)-2-oxo-oxazolidin-3-yl]-4H-benzo[1,4]thiazin-3-one;

(S)-3-(2,3-Dihydro-benzo[1,4]dioxin-6-yl)-5-({[1-(6-methoxy-[1,5]naphthyridin-4-yl)-azetidin-3-ylmethyl]-methyl-amino}-methyl)-oxazolidin-2-one;

6-((R)-5-{[1-(6-Methoxy-[1,5]naphthyridin-4-yl)-piperidin-4-ylamino]-methyl}-2-oxo-oxazolidin-3-yl)-4H-benzo[1,4]thiazin-3-one;

6-((R)-5-{[1-(6-Methoxy-[1,5]naphthyridin-4-yl)-piperidin-4-ylamino]-methyl}-2-oxo-oxazolidin-3-yl)-4H-benzo[1,4]oxazin-3-one;

(R)-3-(3-Fluoro-4-methyl-phenyl)-5-{[1-(6-methoxy-[1,5]naphthyridin-4-yl)-piperidin-4-ylamino]-methyl}-oxazolidin-2-one;

6-((R)-5-{[1-(3-Fluoro-6-methoxy-[1,5]naphthyridin-4-yl)-piperidin-4-ylamino]-methyl}-2-oxo-oxazolidin-3-yl)-4H-benzo[1,4]thiazin-3-one;

6-((R)-5-{[1-(3-Fluoro-6-methoxy-[1,5]naphthyridin-4-yl)-piperidin-4-ylamino]-methyl}-2-oxo-oxazolidin-3-yl)-4H-benzo[1,4]oxazin-3-one;

6-[(R)-5-({[1-(3-Fluoro-6-methoxy-[1,5]naphthyridin-4-yl)-piperidin-4-yl]-methyl-amino}-methyl)-2-oxo-oxazolidin-3-yl]-4H-benzo[1,4]thiazin-3-one;

6-{(R)-5-[4-Hydroxy-4-(6-methoxy-quinolin-4-yl)-piperidin-1-ylmethyl]-2-oxo-oxazolidin-3-yl}-4H-benzo[1,4]thiazin-3-one;

6-{(R)-5-[4-(3-Fluoro-6-methoxy-[1,5]naphthyridin-4-yl)-4-hydroxy-piperidin-1-ylmethyl]-2-oxo-oxazolidin-3-yl}-4H-benzo[1,4]thiazin-3-one;

6-[(R)-5-({[1-(3-Fluoro-6-methoxy-[1,5]naphthyridin-4-yl)-azetidin-3-yl]-methyl-amino}-methyl)-2-oxo-oxazolidin-3-yl]-4H-benzo[1,4]oxazin-3-one;

6-[(R)-5-({(2-Hydroxy-ethyl)-[1-(6-methoxy-[1,5]naphthyridin-4-yl)-azetidin-3-yl]-amino}-methyl)-2-oxo-oxazolidin-3-yl]-4H-benzo[1,4]thiazin-3-one;

6-[(R)-5-({[3-Hydroxy-1-(6-methoxy-[1,5]naphthyridin-4-yl)-pyrrolidin-3-ylmethyl]-amino}-methyl)-2-oxo-oxazolidin-3-yl]-4H-benzo[1,4]thiazin-3-one;

(S)-3-(3-Fluoro-4-methyl-phenyl)-2-oxo-oxazolidine-5-carboxylic acid [1-(6-methoxy-[1,5]naphthyridin-4-yl)-azetidin-3-ylmethyl]-amide;

6-((R)-5-{[1-(6-Methoxy-2-methyl-quinolin-4-yl)-azetidin-3-ylamino]-methyl}-2-oxo-oxazolidin-3-yl)-4H-benzo[1,4]thiazin-3-one;

6-{(R)-5-[4-Hydroxy-4-(6-methoxy-quinolin-4-yl)-piperidin-1-ylmethyl]-2-oxo-oxazolidin-3-yl}-4H-benzo[1,4]oxazin-3-one;

(R)-5-([1-(6-Methoxy-[1,5]naphthyridin-4-yl)-azetidin-3-yl]-methyl-amino}-methyl)-3-phenyl-oxazolidin-2-one;

(R)-3-(4-Difluoromethoxy-phenyl)-5-({[1-(6-methoxy-[1,5]naphthyridin-4-yl)-azetidin-3-yl]-methyl-amino}-methyl)-oxazolidin-2-one;

(R)-5-({[1-(6-Methoxy-[1,5]naphthyridin-4-yl)-azetidin-3-yl]-methyl-amino}-methyl)-3-(4-methyl-3-trifluoromethyl-phenyl)-oxazolidin-2-one;

(R)-3-(3-Chloro-4-fluoro-phenyl)-5-({[1-(6-methoxy-[1,5]naphthyridin-4-yl)-azetidin-3-yl]-methyl-amino-methyl}-oxazolidin-2-one;

(R)-3-(4-Ethyl-phenyl)-5-({[1-(6-methoxy-[1,5]naphthyridin-4-yl)-azetidin-3-yl]-methyl-amino}-methyl)-oxazolidin-2-one;

(R)-3-(3,4-Dimethyl-phenyl)-5-({[1-(6-methoxy-[1,5]naphthyridin-4-yl)-azetidin-3-yl]-methyl-amino}-methyl)-oxazolidin-2-one;

(R)-5-({[1-(6-Methoxy-[1,5]naphthyridin-4-yl)-azetidin-3-yl]-methyl-amino}-methyl)-3-(4-propyl-phenyl)-oxazolidin-2-one;

(R)-3-(3-Dimethylamino-phenyl)-5-({[1-(6-methoxy-[1,5]naphthyridin-4-yl)-azetidin-3-yl]-methyl-amino}-methyl)-oxazolidin-2-one;

(R)-3-(4-Bromo-3-fluoro-phenyl)-5-({[1-(6-methoxy-[1,5]naphthyridin-4-yl)-azetidin-3-yl]-methyl-amino}-methyl)-oxazolidin-2-one;

(R)-3-(3-Bromo-4-methyl-phenyl)-5-({[1-(6-methoxy-[1,5]naphthyridin-4-yl)-azetidin-3-yl]-methyl-amino}-methyl)-oxazolidin-2-one;

(R)-3-(4-Bromo-3-methyl-phenyl)-5({[1-(6-methoxy-[1,5]naphthyridin-4-yl)-azetidin-3-yl]-methyl-amino}-methyl)-oxazolidin-2-one;

(R)-3-Benzothiazol-6-yl-5-({[1-(6-methoxy-[1,5]naphthyridin-4-yl)-azetidin-3yl]-methyl-amino}-methyl)-oxazolidin-2-one;

(R)-3-Benzo[1,3]dioxol-5-yl-5-({[1-(6-methoxy-[1,5]naphthyridin-4-yl)-azetidin-3-yl]-methyl-amino}-methyl)-oxazolidin-2-one;

(R)-3-Benzothiazol-5-yl-5({[1-(6-methoxy-[1,5]naphthyridin-4-yl)-azetidin-3-yl]-methyl-amino}-methyl)-oxazolidin-2-one;

(R)-3-(3-Fluoro-phenyl)-5({[1-(6-methoxy-[1,5]naphthyridin-4-yl)-azetidin-3-yl]-methyl-amino}-methyl)-oxazolidin-2-one;

1-(6-Methoxy-[1,5]naphthyridin-4-yl)-azetidine-3-carboxylic acid [(R)-3-(3-fluoro-4-methyl-phenyl)-2-oxo-oxazolidin-5-ylmethyl]-amide;

3-(3-Fluoro-4-methyl-phenyl)-5-(2-{[1-(6-methoxy-[1,5]naphthyridin-4-yl)-azetidin-3-ylmethyl]-amino 1-ethyl)-oxazolidin-2-one;

6-[(R)-5-({[1-(6-Methoxy-[1,5]naphthyridin-4-yl)-azetidin-3-yl]-methyl-amino}-methyl)-2-oxo-oxazolidin-3-yl]-4H-pyrido[3,2-b][1,4]oxazin-3-one;

6-{(R)-5-[(1S,4S)-5-(6-Methoxy-[1,5]naphthyridin-4-yl)-2,5-diaza-bicyclo[2.2.1]hept-2-ylmethyl]-2-oxo-oxazolidin-3-yl}-4H-benzo[1,4]oxazin-3-one;

6-{(R)-5-[(1S,4S)-5-(6-Methoxy-[1,5]naphthyridin-4-yl)-2,5-diaza-bicyclo[2.2.1]hept-2-ylmethyl]-2-oxo-oxazolidin-3-yl}-4H-benzo[1,4]thiazin-3-one;

(R)-3-(6,7-Dihydro-[1,4]dioxino[2,3-c]pyridazin-3-yl)-5-([1-(6-methoxy-[1,5]naphthyridin-4-yl)-azetidin-3-yl]-methyl-amino}-methyl)-oxazolidin-2-one;

(R)-3-(3-Fluoro-4-methyl-phenyl)-5-({[1-(6-methoxy-[1,5]naphthyridin-4-yl)-azetidin-3-ylmethyl]-amino}-methyl)-oxazolidin-2-one;

7-Fluoro-6-((R)-5-{[1-(3-fluoro-6-methoxy-[1,5]naphthyridin-4-yl)-azetidin-3-ylamino]-methyl}-2-oxo-oxazolidin-3-yl)-4H-benzo[1,4]thiazin-3-one;

6-((R)-5-{[1-(6-Methoxy-quinolin-4-yl)-azetidin-3-ylamino]-methyl}-2-oxo-oxazolidin-3-yl)-4H-benzo[1,4]oxazin-3-one;

6-((R)-5-{[1-(3-Methoxy-quinolin-5-yl)-azetidin-3-ylamino]-methyl}-2-oxo-oxazolidin-3-yl)-4H-benzo[1,4]thiazin-3-one;
6-((R)-5-{[1-(2-Methoxy-quinolin-8-yl)-azetidin-3-ylamino]-methyl}-2-oxo-oxazolidin-3-yl)-4H-benzo[1,4]thiazin-3-one;
6-((R)-5-={1-(7-Fluoro-2-methoxy-quinolin-8-yl)-azetidin-3-ylamino]-methyl}-2-oxo-oxazolidin-3-yl)-4H-benzo[1,4]thiazin-3-one;
6-((R)-5-{[1-(6-Fluoro-quinolin-4-yl)-azetidin-3-ylamino]-methyl}-2-oxo-oxazolidin-3-yl)-4H-benzo[1,4]thiazin-3-one;
4-(3-{[(R)-2-oxo-3-(3-oxo-3,4-dihydro-2H-benzo[1,4]thiazin-6-yl)-oxazolidin-5-ylmethyl]-amino}-azetidin-1-yl)-quinoline-6-carbonitrile;
6-[(R)-5-({[1-(2-Methoxy-quinolin-8-yl)-azetidin-3-ylmethyl]-amino}-methyl)-2-oxo-oxazolidin-3-yl]-4H-benzo[1,4]thiazin-3-one;
6-[(R)-5-({[1-(3-Methoxy-quinolin-5-yl)-azetidin-3-ylmethyl]-amino}-methyl)-2-oxo-oxazolidin-3-yl]-4H-benzo[1,4]thiazin-3-one;
6-((S)-5-{[(S)-1-(3-Fluoro-6-methoxy-[1,5]naphthyridin-4-yl)-pyrrolidin-3-ylamino]-methyl}-2-oxo-oxazolidin-3-yl)-4H-benzo[1,4]thiazin-3-one;
6-((S)-5-{[1-(6-Methoxy-[1,5]naphthyridin-4-yl)-piperidin-4-ylamino]-methyl}-2-oxo-oxazolidin-3-yl)-4H-benzo[1,4]thiazin-3-one;
6-{(S)-5-[4-(6-Methoxy-[1,5]naphthyridin-4-yl)-[1,4]diazepan-1-ylmethyl]-2-oxo-oxazolidin-3-yl}-4H-benzo[1,4]thiazin-3-one;
6-[(R)-5-({[(R)-1-(6-Methoxy-[1,5]naphthyridin-4-yl)-pyrrolidin-3-ylmethyl]-amino}-methyl)-2-oxo-oxazolidin-3-yl]-4H-benzo[1,4]oxazin-3-one;
6-[(R)-5-({[(S)-1-(6-Methoxy-[1,5]naphthyridin-4-yl)-pyrrolidin-3-ylmethyl]-amino}-methyl)-2-oxo-oxazolidin-3-yl]-4H-benzo[1,4]oxazin-3-one;
(R)-5-{[(S)-1-(3-Fluoro-6-methoxy-[1,5]naphthyridin-4-yl)-pyrrolidin-3-ylamino]-methyl}-3-(4-methoxy-phenyl)-oxazolidin-2-one;
(R)-3-(4-Ethoxy-phenyl)-5-{[(S)-1-(3-fluoro-6-methoxy-[1,5]naphthyridin-4-yl)-pyrrolidin-3-ylamino]-methyl}-oxazolidin-2-one;
(R)-3-(4-Difluoromethoxy-phenyl)-5-{[(S)-1-(3-fluoro-6-methoxy-[1,5]naphthyridin-4-yl)-pyrrolidin-3-ylamino]-methyl}-oxazolidin-2-one;
6-((R)-5-{[(S)-1-(6-Methoxy-quinolin-4-yl)-pyrrolidin-3-ylamino]-methyl}-2-oxo-oxazolidin-3-yl)-4H-benzo[1,4]thiazin-3-one ;
6-[(R)-5-({[(S)-1-(6-Methoxy-quinolin-4-yl)-pyrrolidin-3-ylmethyl]-amino}-methyl)-2-oxo-oxazolidin-3-yl]-4H-benzo[1,4]thiazin-3-one;
(R)-5-{[1-(6-Methoxy-[1,5]naphthyridin-4-yl)-azetidin-3-ylamino]-methyl}-3-(4-methoxy-phenyl)-oxazolidin-2-one ;
(R)-3-(4-Ethoxy-phenyl)-5-{[1-(6-methoxy-[1,5]naphthyridin-4-yl)-azetidin-3-ylamino]-methyl}-oxazolidin-2-one;
(R)-3-(4-Difluoromethoxy-phenyl)-5-{[1-(6-methoxy-[1,5]naphthyridin-4-yl)-azetidin-3-ylamino]-methyl}-oxazolidin-2-one;
6-((R)-5-{[(R)-1-(6-Fluoro-quinolin-4-yl)-pyrrolidin-3-ylamino]-methyl}-2-oxo-oxazolidin-3-yl)-4H-benzo[1,4]thiazin-3-one;
4-((R)-3-{[(R)-2-Oxo-3-(3-oxo-3,4-dihydro-2H-benzo[1,4]thiazin-6-yl)-oxazolidin-5-ylmethyl]-amino}-pyrrolidin-1-yl)-quinoline-6-carbonitrile;
6-((R)-5-{[1-(6-Fluoro-quinolin-4-yl)-piperidin-4-ylamino]-methyl}-2-oxo-oxazolidin-3-yl)-4H-benzo[1,4]thiazin-3-one;
4-(4-{[(R)-2-Oxo-3-(3-oxo-3,4-dihydro-2H-benzo[1,4]thiazin-6-yl)-oxazolidin-5-ylmethyl]-amino}-piperidin-1-yl)-quinoline-6-carbonitrile;
6-((R)-5-[(3S,4S)-4-Methoxy-1-(6-methoxy-[1,5]naphthyridin-4-yl)-pyrrolidin-3-ylamino]-methyl}-2-oxo-oxazolidin-3-yl)-4H-benzo[1,4]oxazin-3-one;
(R)-5-{[1-(6-Methoxy-[1,5]naphthyridin-4-yl)-piperidin-4-ylamino]-methyl}-3-(4-methoxy-phenyl)-oxazolidin-2-one;
(R)-3-(4-Ethoxy-phenyl)-5-{[1-(6-methoxy-[1,5]naphthyridin-4-yl)-piperidin-4-ylamino]-methyl}-oxazolidin-2-one;
(R)-3-(4-Difluoromethoxy-phenyl)-5-{[1-(6-methoxy-[1,5]naphthyridin-4-yl)-piperidin-4-ylamino]-methyl}-oxazolidin-2-one; or
6-[(R)-5-({[1-(6-Methoxy-quinolin-4-yl)-azetidin-3-ylmethyl]-amino}-methyl)-2-oxo-oxazolidin-3-yl]-4H-benzo[1,4]thiazin-3-one.

5. A compound of formula ($I_N$), ($I_N$)

wherein
$R^1$ represents hydrogen, alkoxy, halogen or cyano;
one or two of U, V, W, and X represent(s) N and the remaining each represent CH, or, in the case of X, represent $CR^a$;
$R^a$ represents hydrogen or halogen;
$R^6$ represents hydrogen or $(C_1-C_4)$alkyl;
A represents N;
B represents N, D represents a bond, E represents $CH_2$ or CO, $R^2$, $R^3$, $R^4$ and $R^5$ each represent H, m represents the integer 2, and n represents the integer 1; or
B represents N; D represents a bond; E represents $CH_2$ or *—$COCH_2$— wherein the asterisk indicates the bond which is attached to B; $R^2$, $R^3$, $R^4$ and $R^5$ each represent H, or $R^4$ and $R^5$ represent H and $R^2$ and $R^3$ together with the carbon atom to which they are attached to form a carbonyl group, or $R^2$ and $R^3$ represent H and $R^4$ and $R^5$ together with the carbon atom to which they are attached to form a carbonyl group, or $R^2$ and $R^4$ represent H and $R^3$ and $R^5$ together form a methylene bridge; and m and n each represent the integer 1; or
B represents C(OH), D represents a bond, E represents $CH_2$, $R^2$, $R^3$, $R^4$ and $R^5$ each represent H, and m and n each represent the integer 1; or
B represents CH, D represents $NR^b$, E represents $CH_2$, $R^2$, $R^3$, $R^4$ and $R^5$ each represent H, $R^b$ represents H or $(C_1-C_4)$alkyl, and m and n each represent the integer 1; or B represents CH, D represents NH, E represents CH$_2$, R$^2$, R$^3$, R$^4$ and R$^5$ each represent H, m represents the integer 2, and n represents the integer 0; or B represents CH; D represents NR$^c$; E represents CH$_2$, CO or CH$_2$CH$_2$; R$^2$, R$^3$, R$^4$ and R$^5$ each represent H and R$^c$ represents H or (C$_1$-C$_4$)alkyl, or R$^c$, R$^3$, R$^4$ and R$^5$ each represent H and R$^2$ represents hydroxy, (C$_1$-C$_4$)alkoxy, (C$_1$-C$_4$)alkoxy-carbonyl, or carboxy, or R$^3$, R$^4$ and R$^5$ each represent H and R$^c$ forms together with R$^2$ an ethane-1,2-diyl bridge; m represents the integer 1, and n represents the integer 0; or B represents CH; D represents *—CH(R$^d$)—N(R$^e$)— wherein the asterisk indicates the bond which is attached to B; E represents CH$_2$ or CO; R$^d$, R and R$^5$ each represent H and R$^e$ represents H or (C$_1$-C$_4$)alkyl, or R$^e$, R$^3$, R$^4$ and R$^5$ each represent H and R$^d$ and R$^2$ together form a bond, or R$^d$, R$^2$, R$^3$ and R$^5$ each represent H and R$^e$ and R$^4$ together form a methylene bridge, or R$^d$, R$^e$, R$^3$, R$^4$ and R$^5$ each represent H and R$^2$ represents hydroxy; m represents the integer 1, and n represents the integer 0; or B represents CH, D represents *—CONH— wherein the asterisk indicates the bond which is attached to B, E represents CH$_2$, R$^2$, R$^3$, R$^4$ and R$^5$ each represent H, m represents the integer 1, and n represents the integer 0; or B represents CH, D represents NH, E represents CH$_2$ or CO, R$^2$, R$^3$ and R$^5$ each represent H and R$^4$ represents hydroxymethyl, m represents the integer 0, and n represents the integer 1; or B represents C(OH), D represents *—CH$_2$—NH— wherein the asterisk indicates the bond which is attached to B, E represents CH$_2$, R$^2$, R$^3$, R$^4$ and R$^5$ each represent H, m represents the integer 1, and n represents the integer 0; or B represents CH, D represents *—CO—NH— wherein the asterisk indicates the bond which is attached to B, E represents CH$_2$, R$^2$, R$^3$, R$^4$ and R$^5$ each represent H, and m and n each represent the integer 0; or B represents CH, D represents *—CH$_2$—N(R$^f$)— wherein the asterisk indicates the bond which is attached to B, E represents CH$_2$, CH$_2$CH$_2$ or CO, R$^2$, R$^3$, R$^4$ and R$^5$ each represent H, R$^f$ represents H or (C$_1$-C$_4$)alkyl, and m and n each represent the integer 0; or B represents CH; D represents NR$^g$; E represents CH$_2$, CH$_2$CH$_2$, CO or *—COCH$_2$— wherein the asterisk indicates the bond which is attached to B; R$^2$, R$^3$, R$^4$ and R$^5$ each represent H; R$^g$ represents H, (C$_1$-C$_4$)alkyl or (C$_2$-C$_4$)alkyl which is mono- or di-substituted with hydroxy; and m and n each represent the integer 0;

G represents phenyl which is unsubstituted, mono-substituted in position 3 or 4, or disubstituted in positions 3 and 4, wherein each substituent is independently (C$_1$-C$_4$)alkyl, (C$_1$-C$_4$)alkoxy, fluoroalkyl, fluoroalkoxy, cyano, halogen or —NR$^{N1}$R$^{N2}$; or G represents pyridin-2-yl which is mono-substituted in position 5, wherein the substituent is (C$_1$-C$_4$)alkyl or fluoroalkyl; or G represents 6,7-dihydro-[1,4]dioxino[2,3-c]pyridazin-3-yl; or G represents:

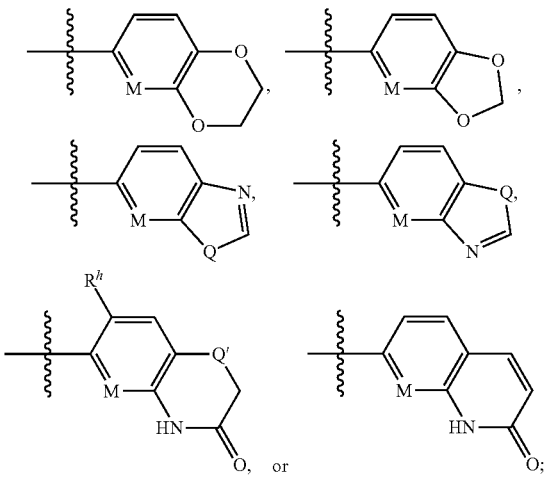

R$^h$ represents hydrogen or fluorine;
M represents CH or N; and Q and Q' independently represent O or S; and
R$^{N1}$ and R$^{N2}$ independently represent (C$_1$-C$_4$)alkyl, or together with the nitrogen that carries them form a pyrrolidine ring;
or a salt of said compound.

6. The compound of claim 5, wherein
R$^6$ represents hydrogen;
B represents N, D represents a bond, E represents CH$_2$ or CO, R$^2$, R$^3$, R$^4$ and R$^5$ each represent H, m represents the integer 2, and n represents the integer 1; or B represents N; D represents a bond; E represents CH$_2$ or *—COCH$_2$— wherein the asterisk indicates the bond which is attached to B; R$^2$, R$^3$, R$^4$ and R$^5$ each represent H, or R$^4$ and R$^5$ represent H and R$^2$ and R$^3$ together with the carbon atom to which they are attached to form a carbonyl group, or R$^2$ and R$^3$ represent H and R$^4$ and R$^5$ together with the carbon atom to which they are attached to form a carbonyl group; and m and n each represent the integer 1; or B represents C(OH), D represents a bond, E represents CH$_2$, R$^2$, R$^3$, R$^4$ and R$^5$ each represent H, and m and n each represent the integer 1; or B represents CH, D represents NR$^b$, E represents CH$_2$, R$^2$, R$^3$, R$^4$ and R$^5$ each represent H, R$^b$ represents H or (C$_1$-C$_4$)alkyl, and m and n each represent the integer 1; or B represents CH, D represents NH, E represents CH$_2$, R$^2$, R$^3$, R$^4$ and R$^5$ each represent H, m represents the integer 2, and n represents the integer 0; or B represents CH; D represents NR$^c$; E represents CH$_2$, CO or CH$_2$CH$_2$; R$^2$, R$^3$, R$^4$ and R$^5$ each represent H and R$^c$ represents H or (C$_1$-C$_4$)alkyl, or R$^c$, R$^3$, R$^4$ and R$^5$ each represent H and R$^2$ represents hydroxy, (C$_1$-C$_4$)alkoxy, (C$_1$-C$_4$)alkoxy-carbonyl, or carboxy, or R$^3$, R$^4$ and R$^5$ each represent H and R$^c$ forms together with R$^2$ an ethane-1,2-diyl bridge; m represents the integer 1, and n represents the integer 0; or B represents CH; D represents *—CH(R$^d$)—N(R$^e$)— wherein the asterisk indicates the bond which is attached to B; E represents CH$_2$ or CO; R$^d$, R$^2$, R$^3$, R$^4$ and R$^5$ each represent H and R$^e$ represents H or (C$_1$-C$_4$)alkyl, or R$^e$, R$^3$, R$^4$ and R$^5$ each represent H and R$^d$ and $R^2$ methylene bridge, or $R^d$, $R^e$, $R^3$, $R^4$ and $R^5$ each represent H and $R^2$ represents hydroxy; m represents the integer 1, and n represents the integer 0; or B represents CH, D represents *—CONH— wherein the asterisk indicates the bond which is attached to B, E represents $CH_2$, $R^2$, $R^3$, $R^4$ and $R^5$ each represent H, m represents the integer 1, and n represents the integer 0; or B represents CH, D represents NH, E represents $CH_2$ or CO, $R^2$, $R^3$ and $R^5$ each represent H and $R^4$ represents hydroxymethyl, m represents the integer 0, and n represents the integer 1; or B represents CH, D represents *—$CH_2$—N($R^f$)— wherein the asterisk indicates the bond which is attached to B, E represents $CH_2$, $CH_2CH_2$ or CO, $R^2$, $R^3$, $R^4$ and $R^5$ each represent H, $R^f$ represents H or ($C_1$-$C_4$)alkyl, and m and n each represent the integer 0; or B represents CH; D represents $NR^g$; E represents $CH_2$, $CH_2CH_2$, CO or *—$COCH_2$— wherein the asterisk indicates the bond which is attached to B; $R^2$, $R^3$, $R^4$ and $R^5$ each represent H; $R^g$ represents H, ($C_1$-$C_4$)alkyl or 2-hydroxyethyl; and m and n each represent the integer 0; and G represents phenyl which is unsubstituted, mono-substituted in position 3 or 4, or disubstituted in positions 3 and 4, wherein each substituent is independently ($C_1$-$C_4$)alkyl, ($C_1$-$C_4$)alkoxy, fluoroalkyl, fluoroalkoxy, cyano, halogen or —$NR^{N1}R^{N2}$; or G represents pyridin-2-yl which is mono-substituted in position 5, wherein the substituent is ($C_1$-$C_4$)alkyl or fluoroalkyl; or G represents 6,7-dihydro-[1,4]dioxino[2,3-c]pyridazin-3-yl; or G represents:

wherein
M represents CH or N; and Q and Q' independently represent O or S;

or a salt of said compound.

7. The compound of claim 5, which is also a compound of formula ($I_{N-P1}$), ($I_{N-P1}$)

wherein
$R^1$ represents alkoxy, halogen or cyano;
one or two of U, V, W, and X represent(s) N and the remaining each represent CH, or, in the case of X, represent $CR^a$;
$R^a$ represents hydrogen or halogen;
A represents N;
  B represents N, D represents a bond, E represents $CH_2$, $R^2$, $R^3$, $R^4$ and $R^5$ each represent H, and m and n each represent the integer 1; or
  B represents C(OH), D represents a bond, E represents $CH_2$, $R^2$, $R^3$, $R^4$ and $R^5$ each represent H, and m and n each represent the integer 1; or
  B represents CH, D represents *—$CH_2$—NH— wherein the asterisk indicates the bond which is attached to B, E represents $CH_2$ or CO, $R^2$, $R^3$, $R^4$ and $R^5$ each represent H, and m and n each represent the integer 0; or
  B represents CH, D represents NH, E represents $CH_2$, $R^2$, $R^3$, $R^4$ and $R^5$ each represent H, m represents the integer 1, and n represents the integer 0;
G represents phenyl which is unsubstituted, mono-substituted in position 3 or 4, or disubstituted in positions 3 and 4, wherein each substituent is independently ($C_1$-$C_4$)alkyl, ($C_1$-$C_4$)alkoxy, fluoroalkyl, fluoroalkoxy, cyano, halogen or —$NR^{N1}R^{N2}$; or
G represents pyridin-2-yl which is mono-substituted in position 5, wherein the substituent is ($C_1$-$C_4$)alkyl or fluoroalkyl; or
G represents:

wherein
Q and Q' independently represent O or S; and
$R^{N1}$ and $R^{N2}$ independently represent ($C_1$-$C_4$)alkyl, or together with the nitrogen that carries them form a pyrrolidine ring;

or a salt of said compound.

8. The compound of claim 5, wherein two of U, W, and X represent N and the remaining and V each represent CH, or, in the case of X, represent CR$^a$; wherein R$^a$ represents hydrogen or fluorine; or a salt of said compound.

9. The compound of claim 5, wherein A represents N; and
B represents N, D represents a bond, E represents CH$_2$ or CO, R$^2$, R$^3$, R$^4$ and R$^5$ each represent H, m represents the integer 2, and n represents the integer 1; or B represents N; D represents a bond; E represents CH$_2$ or *—COCH$_2$— wherein the asterisk indicates the bond which is attached to B; R$^2$, R$^3$, R$^4$ and R$^5$ each represent H; and m and n each represent the integer 1; or B represents C(OH), D represents a bond, E represents CH$_2$, R$^2$, R$^3$, R$^4$ and R$^5$ each represent H, and m and n each represent the integer 1; or B represents CH, D represents NR$^b$, E represents CH$_2$, R$^2$, R$^3$, R$^4$ and R$^5$ each represent H, R$^b$ represents H or (C$_1$-C$_4$)alkyl, and m and n each represent the integer 1; or B represents CH; D represents NR$^c$; E represents CH$_2$, CO or CH$_2$CH$_2$; R$^2$, R$^3$, R$^4$ and R$^5$ each represent H and R$^c$ represents H or (C$_1$-C$_4$)alkyl, or R$^3$, R$^4$ and R$^5$ each represent H and R$^c$ forms together with R$^2$ an ethane-1,2-diyl bridge; m represents the integer 1, and n represents the integer 0; or B represents CH; D represents *—CH(R$^d$)—N(R$^e$)— wherein the asterisk indicates the bond which is attached to B; E represents CH$_2$ or CO; R$^d$, R$^2$, R$^3$, R$^4$ and R$^5$ each represent H and R$^e$ represents H or (C$_1$-C$_4$)alkyl, or R$^e$, R$^3$, R$^4$ and R$^5$ each represent H and R$^d$ and R$^2$ together form a bond; m represents the integer 1, and n represents the integer 0; or B represents CH, D represents *—CONH— wherein the asterisk indicates the bond which is attached to B, E represents CH$_2$, R$^2$, R$^3$, R$^4$ and R$^5$ each represent H, m represents the integer 1, and n represents the integer 0; or B represents CH, D represents *—CH$_2$—N(R$^f$)— wherein the asterisk indicates the bond which is attached to B, E represents CH$_2$, CH$_2$CH$_2$ or CO, R$^2$, R$^3$, R$^4$ and R$^5$ each represent H, R$^f$ represents H or (C$_1$-C$_4$)alkyl, and m and n each represent the integer 0; or B represents CH; D represents NR$^g$; E represents CH$_2$, CH$_2$CH$_2$ or CO; R$^2$, R$^3$, R$^4$ and R$^5$ each represent H; R$^g$ represents H, (C$_1$-C$_4$)alkyl or 2-hydroxyethyl; and m and n each represent the integer 0;

or a salt of said compound.

10. The compound of claim 5, wherein R$^2$, R$^3$, R$^4$ and R$^5$ each represent H;
or a salt of said compound.

11. The compound of claim 5, wherein E represents CH$_2$ or CH$_2$CH$_2$;
or a salt of said compound.

12. The compound of claim 5, wherein m represents the integer 0 or 1 and n represents the integer 0;
or a salt of said compound.

13. The compound of claim 5, wherein G represents phenyl which is mono-substituted in position 4, or disubstituted in positions 3 and 4, wherein each substituent is independently (C$_1$-C$_3$)alkyl, (C$_1$-C$_3$) alkoxy, fluoroalkyl, fluoroalkoxy or halogen;
or a salt of said compound.

14. The compound of claim 5, wherein G represents 6,7-dihydro-[1,4]dioxino[2,3-c]pyridazin-3-yl; or G represents:

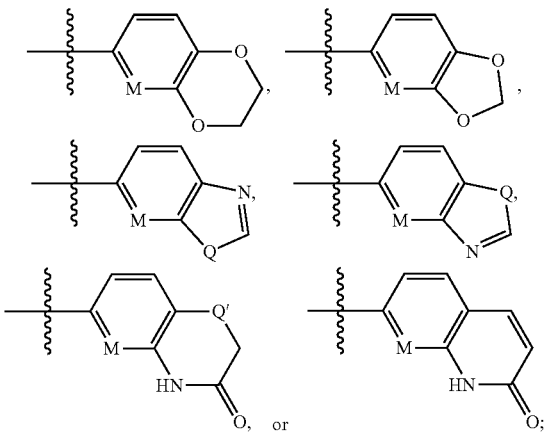

M represents CH or N; and Q and Q' independently represent O or S;
or a salt of said compound.

15. The compound of claim 5, wherein G represents 2,3-dihydro-benzo[1,4]dioxin-6-yl, 3-oxo-3,4-dihydro-2H-benzo[1,4]oxazin-6-yl, 3-oxo-3,4-dihydro-2H-benzo[1,4] thiazin-6-yl, 3-oxo-3,4-dihydro-2H-pyrido[3,2-b][1,4] oxazin-6-yl or 2-oxo-1,2-dihydro-quinolin-7-yl;
or a salt of said compound.

16. The compound of claim 6, wherein said compound is:
(S)-3-(2,3-Dihydro-benzo[1,4]dioxin-6-yl)-5-({[1-(6-methoxy-[1,5]naphthyridin-4-yl)-azetidin-3-ylm-ethyl]-amino}-methyl)-oxazolidin-2-one;
(S)-3-(2,3-Dihydro-benzo[1,4]dioxin-6-yl)-2-oxo-oxazolidine-5-carboxylic acid [1-(6-methoxy-[1,5]naphthyridin-4-yl)-azetidin-3-ylmethyl]-amide;
3-(2,3-Dihydro-benzo[1,4]dioxin-6-yl)-5-[4-hydroxy-1-(6-methoxy-quinazolin-4-yl)-piperidin-4-ylmethyl]-oxazolidin-2-one;
3-(2,3-Dihydro-benzo[1,4]dioxin-6-yl)-5-[4-hydroxy-1-(6-methoxy-[1,5]naphthyridin-4-yl)-piperidin-4-ylm-ethyl]-oxazolidin-2-one;
3-(2,3-Dihydro-benzo[1,4]dioxin-6-yl)-5-[4-(6-methoxy-quinazolin-4-yl)-piperazin-1-ylmethyl]-oxazolidin-2-one;
6-{5-[4-(6-Methoxy-quinazolin-4-yl)-piperazin-1-ylm-ethyl]-2-oxo-oxazolidin-3-yl}-4H-benzo[14]thiazin-3-one.
3-(2,3-Dihydro-benzo[1,4]dioxin-6-yl)-5-[4-(6-methoxy-[1,5]naphthyridin-4-yl)-piperazin-1-ylmethyl]-oxazo-lidin-2-one;
(R)-3-(2,3-Dihydro-benzo[1,4]dioxin-6-yl)-5-[4-(6-methoxy-[1,5]naphthyridin-4-yl)-piperazin-1-ylm-ethyl]-oxazolidin-2-one;
(R)-5-[4-(6-Methoxy-[1,5]naphthyridin-4-yl)-piperazin-1-ylmethyl]-3-(3-trifluoromethoxy-phenyl)-oxazoli-din-2-one;
(R)-5-[4-(6-Methoxy-[1,5]naphthyridin-4-yl)-piperazin-1-ylmethyl]-3-(4-trifluoromethoxy-phenyl)-oxazoli-din-2-one;
(R)-5-[4-(6-Methoxy-[1,5]naphthyridin-4-yl)-piperazin-1-ylmethyl]-3-phenyl-oxazolidin-2-one;
(R)-3-(4-Bromo-3-fluoro-phenyl)-5-[4-(6-methoxy-[1,5] naphthyridin-4-yl)-piperazin-1-ylmethyl]-oxazolidin-2-one;

(R)-3-(3,4-Dimethoxy-phenyl)-5-[4-(6-methoxy-[1,5]naphthyridin-4-yl)-piperazin-1-ylmethyl]-oxazolidin-2-one;
(R)-3-(4-Fluoro-phenyl)-5-[4-(6-methoxy-[1,5]naphthyridin-4-yl)-piperazin-1-ylmethyl]-oxazolidin-2-one ;
(R)-5-[4-(6-Methoxy-[1,5]naphthyridin-4-yl)-piperazin-1-ylmethyl]-3-(3-trifluoromethyl-phenyl)-oxazolidin-2-one;
(R)-3-(3-Chloro-4-fluoro-phenyl)-5-[4-(6-methoxy-[1,5]naphthyridin-4-yl)-piperazin-1-ylmethyl]-oxazolidin-2-one;
(R)-5-[4-(6-Methoxy-[1,5]naphthyridin-4-yl)-piperazin-1-ylmethyl]-3-(4-methyl-3-trifluoromethyl-phenyl)-oxazolidin-2-one;
(R)-3-Benzothiazol-6-yl-5-[4-(6-methoxy-[1,5]naphthyridin-4-yl)-piperazin-1-ylmethyl]-oxazolidin-2-one;
(R)-3-(4-Difluoromethoxy-phenyl)-5-[-4-(6-methoxy-[1,5]naphthyridin-4-yl)-piperazin-1-ylmethyl]-oxazolidin-2-one;
3-{(R)-5-[4-(6-Methoxy-[1,5]naphthyridin-4-yl)-piperazin-1-ylmethyl]-2-oxo-oxazolidin-3-yl}-benzonitrile;
6-{(R)-5-[4-(6-Methoxy-[1,5]naphthyridin-4-yl)-piperazin-1-ylmethyl]-2-oxo-oxazolidin-3-yl}-4H-benzo[1,4]thiazin-3-one;
(R)-5-[4-(6-Methoxy-[1,5]naphthyridin-4-yl)-piperazin-1-ylmethyl]-3-(4-pyrrolidin-1-yl-phenyl)-oxazolidin-2-one;
(R)-5-[4-(6-Methoxy-[1,5]naphthyridin-4-yl)-piperazin-1-ylmethyl]-3-(3-methoxy-phenyl)-oxazolidin-2-one;
(R)-5-[4-(6-Methoxy-[1,5]naphthyridin-4-yl)-piperazin-1-ylmethyl]-3-(4-propyl-phenyl)-oxazolidin-2-one;
(R)-3-(4-Ethyl-phenyl)-5-[4-(6-methoxy-[1,5]naphthyridin-4-yl)-piperazin-1-ylmethyl]-oxazolidin-2-one;
(R)-3-(3,4-Dimethyl-phenyl)-5-[4-(6-methoxy-[1,5]naphthyridin-4-yl)-piperazin-1-ylmethyl]-oxazolidin-2-one;
(R)-3-(3-Chloro-4-methoxy-phenyl)-5-[4-(6-methoxy-[1,5]naphthyridin-4-yl)-piperazin-1-ylmethyl]-oxazolidin-2-one;
(R)-3-(3,4-Difluoro-phenyl)-5-[4-(6-methoxy-[1,5]naphthyridin-4-yl)-piperazin-1-ylmethyl]-oxazolidin-2-one;
(R)-3-(4-Fluoro-3-methyl-phenyl)-5-[4-(6-methoxy-[1,5]naphthyridin-4-yl)-piperazin-1-ylmethyl]-oxazolidin-2-one;
(R)-3-(4-Bromo-3-methyl-phenyl)-5-[4-(6-methoxy-[1,5]naphthyridin-4-yl)-piperazin-1-ylmethyl]-oxazolidin-2-one;
(R)-3-(3-Bromo-4-methyl-phenyl)-5-[4-(6-methoxy-[1,5]naphthyridin-4-yl)-piperazin-1-ylmethyl]-oxazolidin-2-one;
(R)-5-[4-(6-Methoxy-[1,5]naphthyridin-4-yl)-piperazin-1-ylmethyl]-3-(4-methoxy-3-trifluoromethyl-phenyl)-oxazolidin-2-one;
(R)-3-(3-Dimethylamino-phenyl)-5-[4-(6-methoxy-[1,5]naphthyridin-4-yl)-piperazin-1-ylmethyl]-oxazolidin-2-one;
(R)-3-Benzo[1,3]-dioxol-5-yl-5[4-(6-methoxy-[1,5]naphthyridin-4-yl)-piperazin-1-ylmethyl]-oxazolidin-2-one;
(R)-3-(3-Fluoro-4-methyl-phenyl)-5-[4-(6-methoxy-[1,5]naphthyridin-4-yl)-piperazin-1-ylmethyl]-oxazolidin-2-one;
(S)-3-(2,3-Dihydro-benzo[1,4]dioxin-6-yl)-5-[-4-(6-methoxy-[1,5]naphthyridin-4-yl)-piperazin-1-ylmethyl]-oxazolidin-2-one;
(S)-3-(3-Fluoro-4-methyl-phenyl)-5-[4-(6-methoxy-[1,5]naphthyridin-4-yl)-piperazin-1-ylmethyl]-oxazolidin-2-one;
6-{(S)-5-[4-(6-Methoxy-[1,5]naphthyridin-4-yl)-piperazin-1-ylmethyl]-2-oxo-oxazolidin-3-yl}-4H-benzo[1,4]thiazin-3-one;
(S)-3-(3-Fluoro-phenyl)-5-[4-(6-methoxy-[1,5]naphthyridin-4-yl)-piperazin-1-ylmethyl]-oxazolidin-2-one;
(R)-3-(2,3-Dihydro-benzo[1,4]dioxin-6-yl)-5-{[(S)-1-(6-methoxy-[1,5]naphthyridin-4-yl)-pyrrolidin-3-ylamino]-methyl}-oxazolidin-2-one;
(R)-3-(2,3-Dihydro-benzo[1,4]dioxin-6-yl)-5-{[(R)-1-(6-methoxy-[1,5]naphthyridin-4-yl)-pyrrolidin-3-ylamino]-methyl}-oxazolidin-2-one;
5-[4-(6-Methoxy-[1,5]naphthyridin-4-yl)-piperazin-1-ylmethyl]-3-(5-methyl-pyridin-2-yl)-oxazolidin-2-one;
5-[4-(6-Methoxy-[1,5]naphthyridin-4-yl)-piperazin-1-ylmethyl]-3-(5-trifluoromethyl-pyridin-2-yl)-oxazolidin-2-one;
6-((R)-5-{[1-(3-Fluoro-6-methoxy-[1,5]naphthyridin-4-yl)-azetidin-3-ylamino]-methyl}-2-oxo-oxazolidin-3-yl)-4H-benzo[1,4]oxazin-3-one;
(R)-5-{[1-(3-Fluoro-6-methoxy-[1,5]naphthyridin-4-yl)-azetidin-3-ylamino]-methyl}-3-(3-fluoro-4-methyl-phenyl)-oxazolidin-2-one;
(R)-3-(2,3-Dihydro-benzo[1,4]dioxin-6-yl)-5-{[1-(3-fluoro-6-methoxy-[1,5]naphthyridin-4-yl)-azetidin-3-ylamino]-methyl}-oxazolidin-2-one;
6-((R)-5-{[1-(3-Fluoro-6-methoxy-[1,5]naphthyridin-4-yl)-azetidin-3-ylamino]-methyl}-2-oxo-oxazolidin-3-yl)-4H-benzo[1,4]thiazin-3-one;
6-((R)-5-{[1-(6-Methoxy-quinolin-4-yl)-azetidin-3-ylamino]-methyl}-2-oxo-oxazolidin-3-yl)-4H-benzo[1,4]thiazin-3-one;
(R)-3-(3-Fluoro-4-methyl-phenyl)-5-{[1-(6-methoxy-[1,5]naphthyridin-4-yl)-azetidin-3-ylamino]-methyl}-oxazolidin-2-one;
(R)-3-(2,3-Dihydro-benzo[1,4]dioxin-6-yl)-5-{[1-(6-methoxy-[1,5]naphthyridin-4-yl)-azetidin-3-ylamino]-methyl}-oxazolidin-2-one;
6-((R)-5-{[1-(6-Methoxy-[1,5]naphthyridin-4-yl)-azetidin-3-ylamino]-methyl}-2-oxo-oxazolidin-3-yl)-4H-benzo[1,4]oxazin-3-one;
6-((R)-5-{[1-(6-Methoxy-[1,5]naphthyridin-4-yl)-azetidin-3-ylamino]-methyl}-2-oxo-oxazolidin-3-yl)-4H-benzo[1,4]thiazin-3-one;
6-((R)-5-{[1-(6-Methoxy-quinazolin-4-yl)-azetidin-3-ylamino]-methyl}-2-oxo-oxazolidin-3-yl)-4H-benzo[1,4]oxazin-3-one;
6-((R)-5-{[1-(6-Methoxy-quinazolin-4-yl)-azetidin-3-ylamino]-methyl}-2-oxo-oxazolidin-3-yl)-4H-benzo[1,4]thiazin-3-one;
6-[(R)-5-{[1-(6-Methoxy-[1,5]naphthyridin-4-yl)-azetidin-3-yl]-methyl-amino}-methyl)-2-oxo-oxazolidin-3-yl]-4H-benzo[1,4]thiazin-3-one;
6-((S)-5-{[1-(6-Methoxy-[1,5]naphthyridin-4-yl)-azetidin-3-ylamino]-methyl 1-2-oxo-oxazolidin-3-yl)-4H-benzo[1,4]thiazin-3-one;
6-(5-{2-[1-(6-Methoxy-[1,5]naphthyridin-4-yl)-azetidin-3-ylamino]-ethyl}-2-oxo-oxazolidin-3-yl)-4H-benzo[1,4]thiazin-3-one;
6-[(S)-5-({[1-(6-Methoxy-[1,5]naphthyridin-4-yl)-azetidin-3-ylmethyl]-amino}-methyl)-2-oxo-oxazolidin-3-yl]-4H-benzo[1,4]thiazin-3-one;
(S)-3-(2,3-Dihydro-benzo[1,4]dioxin-6-yl)-2-oxo-oxazolidine-5-carboxylic acid[(S)-1-(6-methoxy-[1,5]naphthyridin-4-yl)-pyrrolidin-3-yl]-amide;
(S)-3-(2,3-Dihydro-benzo[1,4]dioxin-6-yl)-2-oxo-oxazolidine-5-carboxylic acid[(R)-1-(6-methoxy-[1,5]naphthyridin-4-yl)-pyrrolidin-3-yl]-amide;

(S)-3-(3-Fluoro-4-methyl-phenyl)-2-oxo-oxazolidine-5-carboxylic acid 1(R)-1-(6-methoxy-[1,5]naphthyridin-4-yl)-pyrrolidin-3-yl]-amide;

(S)-3-(3-Fluoro-4-methyl-phenyl)-2-oxo-oxazolidine-5-carboxylic acid[(S)-1-(6-methoxy-[1,5]naphthyridin-4-yl)-pyrrolidin-3-yl]-amide;

6-((R)-5-{[(S)-1-(3-Fluoro-6-methoxy-[1,5]naphthyridin-4-yl)-pyrrolidin-3-ylamino]-methyl 1-2-oxo-oxazolidin-3-yl)-4H-benzo[1,4]oxazin-3-one;

6-((R)-5-{[(S)-1-(3-Fluoro-6-methoxy-[1,5]naphthyridin-4-yl)-pyrrolidin-3-ylamino]-methyl 1-2-oxo-oxazolidin-3-yl)-4H-benzo[1,4]thiazin-3-one;

(R)-3-(2,3-Dihydro-benzo[1,4]dioxin-6-yl)-5-[(S)-1-(3-fluoro-6-methoxy-[1,5]naphthyridin-4-yl)-methyl}-oxazolidin-2-one;

(R)-3-(3-Fluoro-4-methyl-phenyl)-5-{[(S)-1-(6-methoxy-[1,5]naphthyridin-4-yl)-pyrrolidin-3-ylamino]-methyl}-oxazolidin-2-one;

(R)-3-(3-Fluoro-4-methyl-phenyl)-5-{[(R)-1-(6-methoxy-[1,5]naphthyridin-4-yl)-pyrrolidin-3-ylamino]-methyl}-oxazolidin-2-one;

6-((R)-5-{[(S)-1-(6-Methoxy-[1,5]naphthyridin-4-yl)-pyrrolidin-3-ylamino]-methyl}-2-oxo-oxazolidin-3-yl)-4H-benzo[1,4]oxazin-3-one;

6-((R)-5-{[(S)-1-(6-Methoxy-[1,5]naphthyridin-4-yl)-pyrrolidin-3-ylamino]-methyl}-2-oxo-oxazolidin-3-yl)-4H-benzo[1,4]thiazin-3-one;

6-((R)-5-{[(R)-1-(6-Methoxy-[1,5]naphthyridin-4-yl)-pyrrolidin-3-ylamino]-methyl}-2-oxo-oxazolidin-3-yl)-4H-benzo[1,4]thiazin-3-one;

6-((R)-5-{[(R)-1-(6-Methoxy-[1,5]naphthyridin-4-yl)-pyrrolidin-3-ylamino]-methyl}-2-oxo-oxazolidin-3-yl)-4H-benzo[1,4]oxazin-3-one;

(3R*,4S*)-1-(6-Methoxy-[1,5]naphthyridin-4-yl)-4-{[(S-2-oxo-3-(3-oxo-3,4-dihydro-2H-benzo[1,4]thiazin-6-yl)-oxazolidin-5-ylmethyl]-amino}-pyrrolidine-3-carboxylic acid ethyl ester;

(3R*,4S*)-1-(6-Methoxy-[1,5]naphthyridin-4-yl)-4-{[(R)-2-oxo-3-(3-oxo-3,4-dihydro-2H-benzo[1,4]thiazin-6-yl)-oxazolidin-5-ylmethyl]-amino}-pyrrolidine-3-carboxylic acid;

6-((R)-5-{[(3R*,4R*)-4-Methoxy-1-(6-methoxy-[1,5]naphthyridin-4-yl)-pyrrolidin-3-ylamino]-methyl}-2-oxo-oxazolidin-3-yl)-4H-benzo[1,4]thiazin-3-one;

6-((R)-5-{[(3R*,4R*)-4-Hydroxy-1-(6-methoxy-[1,5]naphthyridin-4-yl)-pyrrolidin-3-ylamino]-methyl}-2-oxo-oxazolidin-3-yl)-4H-benzo[1,4]thiazin-3-one;

(R)-3-(2,3-Dihydro-benzol[1,4]dioxin-6-yl)-5-{[(3R*,4R*)-4-hydroxy-1-(6-methoxy-[1,5]naphthyridin-4-yl)-pyrrolidin-3-ylamino]-methyl}-oxazolidin-2-one ;

(S)-3-(2,3-Dihydro-benzo[1,4]dioxin-6-yl)-2-oxo-oxazolidine-5-carboxylic acid[1-(3R,5S)-5-hydroxymethyl-1-(6-methoxy-[1,5]naphthyridin-4-yl)-pyrrolidin-3-yl]-amide;

6-((R)-5-{[(3R,5S)-5-Hydroxymethyl-1-(6-methoxy-[1,5]naphthyridin-4-yl)-pyrrolidin-3-ylamino]-methyl}-2-oxo-oxazolidin-3-yl)-4H-benzo[1,4]thiazin-3-one;

6-((R)-5-({[1-(6-Methoxy-[1,5]naphthyridin-4-yl)-pyrrolidin-3-ylmethyl]-amino}-methyl)-2-oxo-oxazolidin-3-yl)-4H-benzol-[1,4]thiazin-3-one;

(S)-3-(2,3-Dihydro-benzo[1,4]dioxin-6-yl)-2-oxo-oxazolidine-5-carboxylic acid[1-(6-methoxy-[1,5]naphthyridin-4-yl)-pyrrolidin-3-ylmethyl]-amide;

(S)-3-(3-Fluoro-4-methyl-phenyl)-2-oxo-oxazolidine-5-carboxylic acid[1-(6-methoxy-[1,5]naphthyridin-4-yl)-pyrrolidin-3-ylmethyl]-amide;

6-((R)-5-({[4-Hydroxy-1-(6-methoxy-[1,5]naphthyridin-4-yl)-pyrrolidin-3-ylmethyl]-amino}-methyl)-2-oxo-oxazolidin-3-yl)-4H-benzo[1,4]thiazin-3-one;

1-(6-Methoxy-[1,5]naphthyridin-4-yl)-pyrrolidine-3-carboxylic acid[(R)-3-(3-fluoro-4-methyl-phenyl)-2-oxo-oxazolidin-5-ylmethyl]-amide;

1-(6-Methoxy-[1,5]naphthyridin-4-yl)-pyrrolidine-3-carboxylic acid[(R)-3-(2,3-dihydro-benzo[1,4]dioxin-6-yl)-2-oxo-oxazolidin-5-ylmethyl]-amide;

6-(5-{2-[(S)-1-(6-Methoxy-[1,5]naphthyridin-4-yl)-pyrrolidin-3-ylamino]-ethyl}-2-oxo-oxazolidin-3-yl)-4H-benzo[1,4]thiazin-3-one;

6-(5-{2-[(R)-1-(6-Methoxy-[1,5]naphthyridin-4-yl)-pyrrolidin-3-ylamino]-ethyl}-2-oxo-oxazolidin-3-yl)-4H-benzo[1,4]thiazin-3-one;

(R)-3-(3-Fluoro-4-methyl-phenyl)-5-{[(1a,5a,6a)-3-(6-methoxy-[1,5]naphthyridin-4-yl)-3-aza-bicyclo[3.1.0]hex-6-ylamino]-methyl}-oxazolidin-2-one;

6-((R)-5-{[(1a,5a,6a)-3-(6-Methoxy-[1,5]naphthyridin-4-yl)-3-aza-bicyclo[3.1.0]hex-6-ylamino]-methyl}-2-oxo-oxazolidin-3-yl)-4H-benzo[1,4]thiazin-3-one;

(R)-3-(2,3-Dihydro-benzo[1,4]dioxin-6-yl)-5-{[(3aR*,6aR*)-1-(6-methoxy-[1,5]naphthyridin-4-yl)-hexahydro-pyrrolo[3,4-b]pyrrol-5-yl]-methyl}-oxazolidin-2-one;

6-}(R)-5-{[(3aR*,6aR*)-1-(6-Methoxy-[1,5]naphthyridin-4-yl)-hexahydro-pyrrolo[3,4-b]pyrrol-5-yl]-methyl}-2-oxo-oxazolidin-3-yl]-4H-benzo[1,4]thiazin-3-one;

(S)-3-(2,3-Dihydro-benzo[1,4]dioxin-6-yl)-5-1(3aR*,6aR*)-1-(6-methoxy-[1,5]naphthyridin-4-yl)-hexahydro-pyrrolo[3,4-b]pyrrole-5-carbonyl]-oxazolidin-2-one;

6-{(R)-5-{[(3aR*,6aR*)-5-(6-Methoxy-[1,5]naphthyridin-4-yl)-hexahydro-pyrrolo[3,4-b]pyrrol-1-yl]-methyl}-2-oxo-oxazolidin-3-yl}-4H-benzo[-1,4]thiazin-3-one;

(R)-3-(2,3-Dihydro-benzo[1,4]dioxin-6-yl)-5-{[(3aR*,6aR*)-5-(6-methoxy-[1,5]naphthyridin-4-yl)-hexahydro-pyrrolo[3,4-b]pyrrol-1-yl]-methyl}-oxazolidin-2-one ;

(S)-3-(2,3-Dihydro-benzo[1,4]dioxin-6-yl)-5-[(3aR*,6aR*)-5-(6-methoxy-[1,5]naphthyridin-4-yl)-hexahydro-pyrrolo[3,4-b]pyrrole-1-carbonyl]-oxazolidin-2-one;

6-{(R)-5-[4-(6-Methoxy-[1,5]naphthyridin-4-yl)-piperazin-1-ylmethyl]-2-oxo-oxazolidin-3-yl}-4H-benzo[1,4]oxazin-3-one;

6-{(R)-5-[4-(3-Fluoro-6-methoxy-[1,5]naphthyridin-4-yl)-piperazin-1-ylmethyl]-2-oxo-oxazolidin-3-yl}-4H-benzo[1,4]oxazin-3-one;

6-{(R)-5-[4-(3-Fluoro-6-methoxy-[1,5]naphthyridin-4-yl)-piperazin-1-ylmethyl]-2-oxo-oxazolidin-3-yl}-4H-benzo[1,4]thiazin-3-one;

(R)-3-(2,3-Dihydro-benzo[1,4]dioxin-6-yl)-5-(4-quinolin-4-yl-piperazin-1-ylmethyl)-oxazolidin-2-one;

[3-(3-Fluoro-4-methyl-phenyl)-2-oxo-oxazolidin-5-ylmethyl]-4-(6-methoxy-[1,5]naphthyridin-4-yl)-piperazin-2-one;

6-{(R)-5-[4-(6-Methoxy-[1,5]naphthyridin-4-yl)-3-oxo-piperazin-1-ylmethyl]-2-oxo-oxazolidin-3-yl}-4H-benzo[1,4]thiazin-3-one;

(R)-3-(2,3-Dihydro-benzo[1,4]dioxin-6-yl)-5-{[1-(6-methoxy-[1,5]naphthyridin-4-yl)-piperidin-3-ylamino]-methyl}-oxazolidin-2-one;

6-{(R)-5-[4-(3-Fluoro-6-methoxy-[1,5]naphthyridin-4-yl)-[1,4]diazepan-1-ylmethyl]-2-oxo-oxazolidin-3-yl}-4H-benzo[1,4]oxazin-3-one;
6-{(R)-5-[4-(3-Fluoro-6-methoxy-[1,5]naphthyridin-4-yl)-[1,4]diazepan-1-ylmethyl]-2-oxo-oxazolidin-3-yl}-4H-benzo[1,4]thiazin-3-one;
6-{(R)-5-[4-(6-Methoxy-[1,5]naphthyridin-4-yl)-[1,4]diazepan-1-ylmethyl]-2-oxo-oxazolidin-3-yl}-4H-benzo[1,4]oxazin-3-one;
6-[(R)-5-[4-(6-Methoxy-[1,5]naphthyridin-4-yl)-[1,4]diazepan-1-ylmethyl]-2-oxo-oxazolidin-3-yl}-4H-benzo[1,4]thiazin-3-one;
(R)-3-(2,3-Dihydro-benzo[1,4]dioxin-6-yl)-5-[4-(6-methoxy-[1,5]naphthyridin-4-yl)-[1,4]diazepan-1-ylmethyl]-oxazolidin-2-one;
(R)-3-(3-Fluoro-4-methyl-phenyl)-5-[4-(6-methoxy-[1,5]naphthyridin-4-yl)-[1,4]diazepan-1-ylmethyl]-oxazolidin-2-one;
(S)-3-(2,3-Dihydro-benzo[1,4]dioxin-6-yl)-5-[4-(6-methoxy-[1,5]naphthyridin-4-yl)-[1,4]diazepane-1-carbonyl]-oxazolidin-2-one;
3-(6,7-Dihydro-[1,4]dioxino[2,3-c]pyridazin-3-yl)-5-[4-(6-methoxy-[1,5]naphthyridin-4-yl)-piperazin-1-ylmethyl]-oxazolidin-2-one;
3-(6,7-Dihydro[1,4]dioxino[2,3-c]pyridazin-3-yl)-5-[4-(6-methoxy-[1,5]naphthyridin-4-yl)-piperazin-1-ylmethyl]-oxazolidin-2-one;
(R)-3-(2,3-Dihydro-benzo[1,4]dioxin-6-yl)-5-({[(S)-1-(6-methoxy-[1,5]naphthyridin-4-yl)-pyrrolidin-3-yl]-methyl-amino}-methyl)-oxazolidin-2-one;
6-{5-[4-(6-Methoxy-[1,5]naphthyridin-4-yl)-piperazin-1-ylmethyl]-2-oxo-oxazolidin-3-yl}-4H-pyrido[3,2-b][1,4]oxazin-3-one;
6-((R)-5-{2-[4-(6-Methoxy-[1,5]naphthyridin-4-yl)-piperazin-1-yl]-2-oxo-ethyl}-2-oxo-oxazolidin-3-yl)-4H-benzo[1,4]thiazin-3-one;
N-[1-(6-Methoxy-[1,5]naphthyridin-4-yl)-azetidin-3-yl]-2-[(R)-2-oxo-3-(3-oxo-3,4-dihydro-2H-benzo[1,4]thiazin-6-yl)-oxazolidin-5-yl]-acetamide;
(S)-3-(2,3-Dihydro-benzo[1,4]dioxin-6-yl)-2-oxo-oxazolidine-5-carboxylic acid[1-(6-methoxy-[1,5]naphthyridin-4-yl)-azetidin-3-yl]-amide;
6-[(R)-5-({[1-(6-Methoxy-[1,5]naphthyridin-4-yl)-pyrrolidin-3-ylmethyl]-methyl-amino}-methyl)-2-oxo-oxazolidin-3-yl]-4H-benzo[1,4]thiazin-3-one;
(S)-3-(2,3-Dihydro-benzo[1,4]dioxin-6-yl)-5-({[1-(6-methoxy-[1,5]naphthyridin-4-yl)-azetidin-3-ylmethyl]-methyl-amino}-methyl)-oxazolidin-2-one;
6-((R)-5-{[1-(6-Methoxy-[1,5]naphthyridin-4-yl)-piperidin-4-ylamino]-methyl}-2-oxo-oxazolidin-3-yl)-4H-benzo[1,4]thiazin-3-one;
6-((R)-5-{[1-(6-Methoxy-[1,5]naphthyridin-4-yl)-piperidin-4-ylamino]-methyl}-2-oxo-oxazolidin-3-yl)-4H-benzo[1,4]oxazin-3-one;
(R)-3-(3-Fluoro-4-methyl-phenyl)-5-{[1-(6-methoxy-[1,5]naphthyridin-4-yl)-piperidin-4-ylamino]-methyl}-oxazolidin-2-one;
6-((R)-5-{[1-(3-Fluoro-6-methoxy-[1,5]naphthyridin-4-yl)-piperidin-4-ylamino]-methyl}-2-oxo-oxazolidin-3-yl)-4H-benzo[1,4]thiazin-3-one;
6-((R)-5-({[1-(3-Fluoro-6-methoxy-[1,5]naphthyridin-4-yl)-piperidin-4-ylamino]-methyl}-2-oxo-oxazolidin-3-yl)-4H-benzo[1,4]oxazin-3-one;
6-[(R)-5-({[1-(3-Fluoro-6-methoxy-[1,5]naphthyridin-4-yl)-piperidin-4-yl]-methyl-amino}-methyl)-2-oxo-oxazolidin-3-yl]-4H-benzo[1,4]thiazin-3-one;
6-[(R)-5-({[1-(3-Fluoro-6-methoxy-[1,5]naphthyridin-4-yl)-azetidin-3-yl]-methyl-amino}-methyl)-2-oxo-oxazolidin-3-yl]-4H-benzo[1,4]oxazin-3-one;
6-[(R)-5-({(2-Hydroxy-ethyl)-[1-(6-methoxy-[1,5]naphthyridin-4-yl)-azetidin-3-yl]-amino}-methyl)-2-oxo-oxazolidin-3-yl]-4H-benzo[1,4]thiazin-3-one;
6-[(R)-5-({[3-Hydroxy-1-(6-methoxy-[1,5]naphthyridin-4-yl)-pyrrolidin-3-ylmethyl]-amino}-methyl)-2-oxo-oxazolidin-3-yl]-4H-benzo[1,4]thiazin-3-one;
(S)-3-(3-Fluoro-4-methyl-phenyl)-2-oxo-oxazolidine-5-carboxylic acid[1-(6-methoxy-1,5naphthyridin-4-yl)-azetidin-3-ylmethyl]-amide;
6-((R)-5-{[1-(6-Methoxy-2-methyl-quinolin-4-yl)-azetidin-3-ylamino]-methyl}-2-oxo-oxazolidin-3-yl)-4H-benzo[1,4]thiazin-3-one;
(R)-5-({[1-(6-Methoxy-[1,5]naphthyridin-4-yl)-azetidin-3-yl]-methyl-amino}-methyl)-3-phenyl-oxazolidin-2-one;
(R)-3-(4-Difluoromethoxy-phenyl)-5-({[1-(6-methoxy-[1,5]naphthyridin-4-yl)-azetidin-3-yl]-methyl-amino}-methyl)-oxazolidin-2-one;
(R)-5-({[1-(6-Methoxy-[1,5]naphthyridin-4-yl)-azetidin-3-yl]-methyl-amino}-methyl)-3-(4-methyl-3-trifluoromethyl-phenyl)-oxazolidin-2-one;
(R)-3-(3-Chloro-4-fluoro-phenyl)-5-({[1-(6-methoxy-[1,5]naphthyridin-4-yl)-azetidin-3-yl]-methyl-amino}-methyl)-oxazolidin-2-one;
(R)-3-(4-Ethyl-phenyl)-5-({[1-(6-methoxy-[1,5]naphthyridin-4-yl)-azetidin-3-yl]-methyl-amino}-methyl)-oxazolidin-2-one;
(R)-3-(3,4-Dimethyl-phenyl)-5-({[1-(6-methoxy-[1,5]naphthyridin-4-yl)-azetidin-3-yl]-methyl-amino}-methyl)-oxazolidin-2-one;
(R)-5-({[1-(6-Methoxy-[1,5]naphthyridin-4-yl)-azetidin-3-yl]-methyl-amino}-methyl)-3-(4-propyl-phenyl)-oxazolidin-2-one;
(R)-3-(3-Dimethylamino-phenyl)-5-({[1-(6-methoxy-[1,5]naphthyridin-4-yl)-azetidin-3-yl]-methyl-amino}-methyl)-oxazolidin-2-one;
(R)-3-(4-Bromo-3-fluoro-phenyl)-5-({[1-(6-methoxy-[1,5]naphthyridin-4-yl)-azetidin-3-yl]-methyl-amino}-methyl)-oxazolidin-2-one;
(R)-3-(3-Bromo-4-methyl-phenyl)-5-({[1-(6-methoxy-[1,5]naphthyridin-4-yl)-azetidin-3-yl]-methyl-amino}-methyl)-oxazolidin-2-one;
(R)-3-(4-Bromo-3-methyl-phenyl)-5-({[1-(6-methoxy-[1,5]naphthyridin-4-yl)-azetidin-3-yl]-methyl-amino}-methyl)-oxazolidin-2-one;
(R)-3-Benzothiazol-6-yl-5-({[1-(6-methoxy-[1,5]naphthyridin-4-yl)-azetidin-3-yl]-methyl-amino}-methyl)-oxazolidin-2-one;
(R)-3-Benzo[1,3]dioxol-5-yl-5-({[1-6-methoxy-[1,5]naphthyridin-4-yl)-azetidin-3-yl]-methyl-amino}-methyl)-oxazolidin-2-one;
(R)-3-Benzothiazol-5-yl-5-({[1-(6-methoxy-[1,5]naphthyridin-4-yl)-azetidin-3-yl]-methyl-amino}-methyl)-oxazolidin-2-one;
(R)-3-(3-Fluoro-phenyl)-5-({[1-(6-methoxy-[1,5]naphthyridin-4-yl)-azetidin-3-yl]-methyl-amino}-methyl)-oxazolidin-2-one;
1-(6-Methoxy-[1,5]naphthyridin-4-yl)-azetidine-3-carboxylic acid[(R)-3-(3-fluoro-4-methyl-phenyl)-2-oxo-oxazolidin-5-ylmethyl]-amide;
3-(3-Fluoro-4-methyl-phenyl)-5-(2-{[1-(6-methoxy-[1,5]naphthyridin-4-yl)-azetidin-3-ylmethyl]-amino}-ethyl)-oxazolidin-2-one;

6-[(R)-5-({[1-(6-Methoxy-[1,5]naphthyridin-4-yl)-azetidin-3-yl]-methyl-amino}-methyl)-2-oxo-oxazolidin-3-yl]-4H-pyrido3,2-b][1,4]oxazin-3-one;

6-{(R)-5[(1S,4S)-5-(6-Methoxy-[1,5]naphthyridin-4-yl)-2,5-diaza-bicyclo[1]hept-2-ylmethyl]-2-oxo-oxazolidin-3-yl}-4H-benzo[1,4]oxazin-3-one;

6-{(R)-5[(1S,4S)-5-(6-Methoxy-[1,5]naphthyridin-4-yl)-2,5-diaza-bicyclo[2.2.1]hept-2-ylmethyl]-2-oxo-oxazolidin-3-yl}-4H-benzo[1,4]thiazin-3-one;

(R)-3-(6,7-Dihydro-[1,4]dioxino[2,3-c]pyridazin-3-yl)-5-({[1-(6-methoxy-[1,5]naphthyridin-4-yl)-azetidin-3-yl]-methyl-amino}-methyl)-oxazolidin-2-one;

(R)-3-(3-Fluoro-4-methyl-phenyl)-5-({[1-(6-methoxy-[1,5]naphthyridin-4-yl)-azetidin-3-ylmethyl]-amino}-methyl)-oxazolidin-2-one;

7-Fluoro-6-((R)-5-{[1-(3-fluoro-6-methoxy-[1,5]naphthyridin-4-yl)-azetidin-3-ylamino]-methyl}-2-oxo-oxazolidin-3-yl)-4H-benzo[1,4]thiazin-3-one;

6-((R)-5-{[1-(6-Methoxy-quinolin-4-yl)-azetidin-3-ylamino]-methyl}-2-oxo-oxazolidin-3-yl)-4H-benzo[1,4]oxazin-3-one;

6-((R)-5-{[1-(3-Methoxy-quinolin-5-yl)-azetidin-3-ylamino]-methyl}-2-oxo-oxazolidin-3-yl)-4H-benzo[1,4]thiazin-3-one;

6-((R)-5-{[1-(2-Methoxy-quinolin-8-yl)-azetidin-3-ylamino]-methyl}-2-oxo-oxazolidin-3-yl)-4H-benzo[1,4]thiazin-3-one;

6-((R)-5-{[1-(7-Fluoro-2-methoxy-quinolin-8-yl)-azetidin-3-ylamino]-methyl}-2-oxo-oxazolidin-3-yl)-4H-benzo[1,4]thiazin-3-one;

6-((R)-5-{[1-(6-Fluoro-quinolin-4-yl)-azetidin-3-ylamino]-methyl}-2-oxo-oxazolidin-3-yl)-4H-benzo[1,4]thiazin-3-one;

4-(3-{[(R)-2-oxo-3-(3-oxo-3,4-dihydro-2H-benzo[1,4]thiazin-6-yl)-oxazolidin-5-ylmethyl]-amino}-azetidin-1-yl)-quinoline-6-carbonitrile;

6-[(R)-5-({[1-(2-Methoxy-quinolin-8-yl)-azetidin-3-ylmethyl]-amino}-methyl)-2-oxo-oxazolidin-3-yl]-4H-benzo[1,4]thiazin-3-one;

6-[(R)-5-({[1-(3-Methoxy-quinolin-5-yl)-azetidin-3-ylmethyl]-amino}-methyl)-2-oxo-oxazolidin-3-yl]-4H-benzo[1,4]thiazin-3-one;

6-((S)-5-{[(S)-1-(3-Fluoro-6-methoxy-[1,5]naphthyridin-4-yl)-pyrrolidin-3-ylamino]-methyl}-2-oxo-oxazolidin-3-yl)-4H-benzo[1,4]thiazin-3-one;

6-((S)-5-{[1-(6-Methoxy-[1,5]naphthyridin-4-yl)-piperidin-4-ylamino]-methyl}-2-oxo-oxazolidin-3-yl)-4H-benzo[1,4]thiazin-3-one;

6-[(S)-5-{[4-(6-Methoxy-[1,5]naphthyridin-4-yl)-[1,4]diazepan-1-ylmethyl]-2-oxo-oxazolidin-3-yl}-4H-benzo[1,4]thiazin-3-one;

6-[(R)-5-({[1(R)-1-(6-Methoxy-[1,5]naphthyridin-4-yl)-pyrrolidin-3-ylmethyl]-amino}-methyl)-2-oxo-oxazolidin-3-yl]-4H-benzo[1,4]oxazin-3-one;

6-[(R)-5-({[(S)-1-(6-Methoxy-[1,5]naphthyridin-4-yl)-pyrrolidin-3-ylmethyl]-amino}-methyl)-2-oxo-oxazolidin-3-yl]-4H-benzo[1,4]oxazin-3-one;

(R)-5-{[(S)-1-(3-Fluoro-6-methoxy-[1,5]naphthyridin-4-yl)-pyrrolidin-3-ylamino]-methyl}-3-(4-methoxy-phenyl)-oxazolidin-2-one;

(R)-3-(4-Ethoxy-phenyl)-5-{[(S)-1-(3-fluoro-6-methoxy-[1,5]naphthyridin-4-yl)-pyrrolidin-3-ylamino]-methyl}-oxazolidin-2-one;

(R)-3-(4-Difluoromethoxy-phenyl)-5-{[(S)-1-(3-fluoro-6-methoxy-[1,5]naphthyridin-4-yl)-pyrrolidin-3-ylamino]-methyl}-oxazolidin-2-one;

6-((R)-5-{[(S)-1-(6-Methoxy-quinolin-4-yl)-pyrrolidin-3-ylamino]-methyl}-2-oxo-oxazolidin-3-yl)-4H-benzo[1,4]thiazin-3-one;

6-[(R)-5-({[(S)-1-(6-Methoxy-quinolin-4-yl)-pyrrolidin-3-ylmethyl]-amino}-methyl)-2-oxo-oxazolidin-3-yl]-4H-benzo[1,4]thiazin-3-one;

(R)-5-{[1-(6-Methoxy-[1,5]naphthyridin-4-yl)-azetidin-3-ylamino]-methyl}-3-(4-methoxy-phenyl)-oxazolidin-2-one;

(R)-3-(4-Ethoxy-phenyl)-5-{[1-(6-methoxy-[1,]naphthyridin-4-yl)-azetidin-3-ylamino]-methyl}-oxazolidin-2-one;

(R)-3-(4-Difluoromethoxy-phenyl)-5-{[1-(6-methoxy-[1,5]naphthyridin-4-yl)-azetidin-3-ylamino]-methyl}-oxazolidin-2-one;

6-((R)-5-{[(R)-1-(6-Fluoro-quinolin-4-yl)-pyrrolidin-3-ylamino]-methyl}-2-oxo-oxazolidin-3-yl)-4H-benzo[1,4]thiazin-3-one;

4-((R)-3-{[(R)-2-oxo-3-(3-oxo-3,4-dihydro-2H-benzo[1,4]thiazin-6-yl)-oxazolidin-5-ylmethyl]-amino}-pyrrolidin-1-yl)-quinoline-6-carbonitrile;

6-((R)-5-{[1-(6-Fluoro-quinolin-4-yl)-piperidin-4-ylamino]-methyl}-2-oxo-oxazolidin-3-yl)-4H-benzo[1,4]thiazin-3-one;

4-(4-{[(R)-2-oxo-3-(3-oxo-3,4-dihydro-2H-benzo[1,4]thiazin-6-yl)-oxazolidin-5-ylmethyl]-amino}-piperidin-1-yl)-quinoline-6-carbonitrile;

6-((R)-5-{[(3S,4S)-4-Methoxy-1-(6-methoxy-[1,5]naphthyridin-4-yl)-pyrrolidin-3-ylamino]-methyl}-2-oxo-oxazolidin-3-yl)-4H-benzo[1,4]oxazin-3-one;

(R)-5-{[1-(6-Methoxy-[1,5]naphthyridin-4-yl)-piperidin-4-ylamino]-methyl}-3-(4-methoxy-phenyl)-oxazolidin-2-one;

(R)-3-(4-Ethoxy-phenyl)-5-{[1-(6-methoxy-[1,5]naphthyridin-4-yl)-piperidin-4-ylamino]-methyl}-oxazolidin-2-one;

(R)-3-(4-Difluoromethoxy-phenyl)-5-{[1-(6-methoxy-[1,5]naphthyridin-4-yl)-piperidin-4-ylamino]-methyl}-oxazolidin-2-one; or 6-[(R)-5-{[-(6-Methoxy-quinolin-4-yl)-azetidin-3-ylmethyl]-amino}-methyl)-2-oxo-oxazolidin-3-yl]-4H-benzo[1,4]thiazin-3-one or a salt of said compound.

17. A pharmaceutical composition comprising the compound of claim 5, or a pharmaceutically acceptable salt thereof, and at least one therapeutically inert excipient.

18. A method for treating a bacterial infection caused by *Staphylococcus aureus* comprising the step of administering to a patient in need thereof a therapeutically effective amount of the compound of claim 5, or a pharmaceutically acceptable salt thereof.

19. A method for treating a bacterial infection caused by *Staphylococcus aureus* comprising the step of administering to a patient in need thereof a therapeutically effective amount of a compound of formula (I), or a pharmaceutically acceptable salt thereof, wherein the compound of formula (I) is also a compound of formula $(I_N)$ according to of claims 16.

* * * * *